(12) United States Patent
Barlaam et al.

(10) Patent No.: US 11,352,369 B2
(45) Date of Patent: *Jun. 7, 2022

(54) PYRIDINE AND PYRIMIDINE DERIVATIVES

(71) Applicant: ASTRAZENECA AB, Sodertalje (SE)

(72) Inventors: Bernard Barlaam, Cambridge (GB); Christopher De Savi, Wilmington, DE (US); Janet Hawkins, Cambridge (GB); Alexander Hird, Wilmington, DE (US); Michelle Lamb, Wilmington, DE (US); Kurt Pike, Cambridge (GB); Melissa Vasbinder, Wilmington, DE (US)

(73) Assignee: ASTRAZENECA AB, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 16/931,786

(22) Filed: Jul. 17, 2020

(65) Prior Publication Data

US 2021/0171541 A1  Jun. 10, 2021

Related U.S. Application Data

(60) Continuation of application No. 15/833,277, filed on Dec. 6, 2017, now Pat. No. 10,717,746, which is a division of application No. 15/193,826, filed on Jun. 27, 2016, now Pat. No. 9,845,331.

(60) Provisional application No. 62/185,852, filed on Jun. 29, 2015.

(51) Int. Cl.
| | | |
|---|---|---|
| *C07D 498/04* | (2006.01) | |
| *C07D 487/04* | (2006.01) | |
| *C07D 471/04* | (2006.01) | |
| *A61P 35/00* | (2006.01) | |

(52) U.S. Cl.
CPC ............ *C07D 498/04* (2013.01); *A61P 35/00* (2018.01); *C07D 471/04* (2013.01); *C07D 487/04* (2013.01); *C07B 2200/13* (2013.01)

(58) Field of Classification Search
CPC ............... C07D 498/04; C07D 487/04; C07D 471/04
See application file for complete search history.

(56) References Cited

U.S. PATENT DOCUMENTS

| | | |
|---|---|---|
| 2010/0184780 A1 | 7/2010 | Schauerte et al. |
| 2010/0184789 A1 | 7/2010 | Wabnitz et al. |
| 2010/0249149 A1 | 9/2010 | Allgeier et al. |
| 2011/0113038 A1 | 6/2011 | Barsanti et al. |
| 2011/0224225 A1 | 9/2011 | Ulrich et al. |
| 2011/0251178 A1* | 10/2011 | Mattes ................ C07D 487/04 514/214.02 |
| 2012/0157433 A1 | 6/2012 | Pfister et al. |
| 2013/0331407 A1 | 12/2013 | Schauerte et al. |
| 2013/0338147 A1 | 12/2013 | Wabnitz et al. |
| 2014/0275004 A1 | 9/2014 | Florjancic et al. |
| 2014/0275027 A1 | 9/2014 | Gong et al. |
| 2014/0275153 A1 | 9/2014 | Lai et al. |

FOREIGN PATENT DOCUMENTS

| | | |
|---|---|---|
| WO | 2008132138 A1 | 11/2008 |
| WO | 2012066065 A1 | 5/2012 |
| WO | 2012101063 A1 | 8/2012 |
| WO | 2012101064 A1 | 8/2012 |
| WO | 2014139328 A1 | 9/2014 |
| WO | 2014151444 A1 | 9/2014 |
| WO | 2014160017 A1 | 10/2014 |

OTHER PUBLICATIONS

Golub et al., Science, vol. 286, Oct. 15, 1999, pp. 531-537.*
Cidado, Justin et al., "AZD4573 Is a Highly Selective CDK9 Inhibitor That Suppresses MCL-1 and Induces Apoptosis in Hematologic Cancer Cells", Clinical Cancer Research, 2019, pp. OF1-OF13.
Iron, Adriana E. et al., 2018, "Discovery of Mcl-1-specific inhibitor AZD5991 and preclinical activity in multiple myeloma and acute myeloid leukemia",Nature Communications, pp. 1-14.

* cited by examiner

*Primary Examiner* — Samira J Jean-Louis

(57) ABSTRACT

Provided are a series of novel pyridine or pyrimidine derivatives which inhibit CDK9 and may be useful for the treatment of hyperproliferative diseases. In particular the compounds are of use in the treatment of proliferative disease such as cancer including hematological malignancies such as acute myeloid leukemia, multiple myeloma, chronic lymphocytic leukemia, diffuse large B cell lymphoma, Burkitt's lymphoma, follicular lymphoma and solid tumors such as breast cancer, lung cancer, neuroblastoma and colon cancer.

19 Claims, 8 Drawing Sheets

PYRIDINE AND PYRIMIDINE DERIVATIVES

The present invention relates to certain pyridine or pyrimidine derivatives for use in the treatment of certain diseases in particular to proliferative disease such as cancer and in the preparation of medicaments for use in the treatment of proliferative disease, to novel pyridine or pyrimidine derivatives and to processes for their preparation, as well as pharmaceutical compositions containing them as active ingredient.

Cyclin-dependent protein kinases (CDKs) represent a family of serine/threonine protein kinases that become active upon binding to a cyclin regulatory partner. CDK/cyclin complexes were first identified as regulators of cell cycle progression. More recently however, CDK/cyclin complexes have also been implicated in transcription and mRNA processing. CDK9/PTEFb (positive transcription elongation factor b) phosphorylates the carboxyl-terminal domain (CTD) of the large subunit of RNA polymerase II (RNAP II), predominantly Ser-2, regulating elongation of transcription. Inhibition of CDK9 and transcriptional repression results in the rapid depletion of short lived mRNA transcripts and associated proteins including Mcl1 and c-myc, leading to induction of apoptosis in tumor cells hyper dependent on these survival proteins. Targeting transcriptional CDKs including CDK9, therefore, represents a therapeutic strategy for treating tumor types hyper dependent on these labile pro-survival proteins including, but not limited to, hematological malignancies such as acute myeloid leukemia, multiple myeloma, chronic lymphocytic leukemia, diffuse large B cell lymphoma, Burkitt's lymphoma, follicular lymphoma and solid tumors such as breast cancer, lung cancer, neuroblastoma and colon cancer. CDK9 inhibitors may also have therapeutic utility in other disease indications including cardiology, virology, inflammation and pain.

Disclosed herein are a series of novel pyridine or pyrimidine derivatives which inhibit CDK9 and may be useful for the treatment of hyperproliferative diseases. In particular the compounds are of use in the treatment of proliferative disease such as cancer including hematological malignancies such as acute myeloid leukemia, multiple myeloma, chronic lymphocytic leukemia, diffuse large B cell lymphoma, Burkitt's lymphoma, follicular lymphoma and solid tumors such as breast cancer, lung cancer, neuroblastoma and colon cancer.

DESCRIPTION OF THE INVENTION

Figure 1:
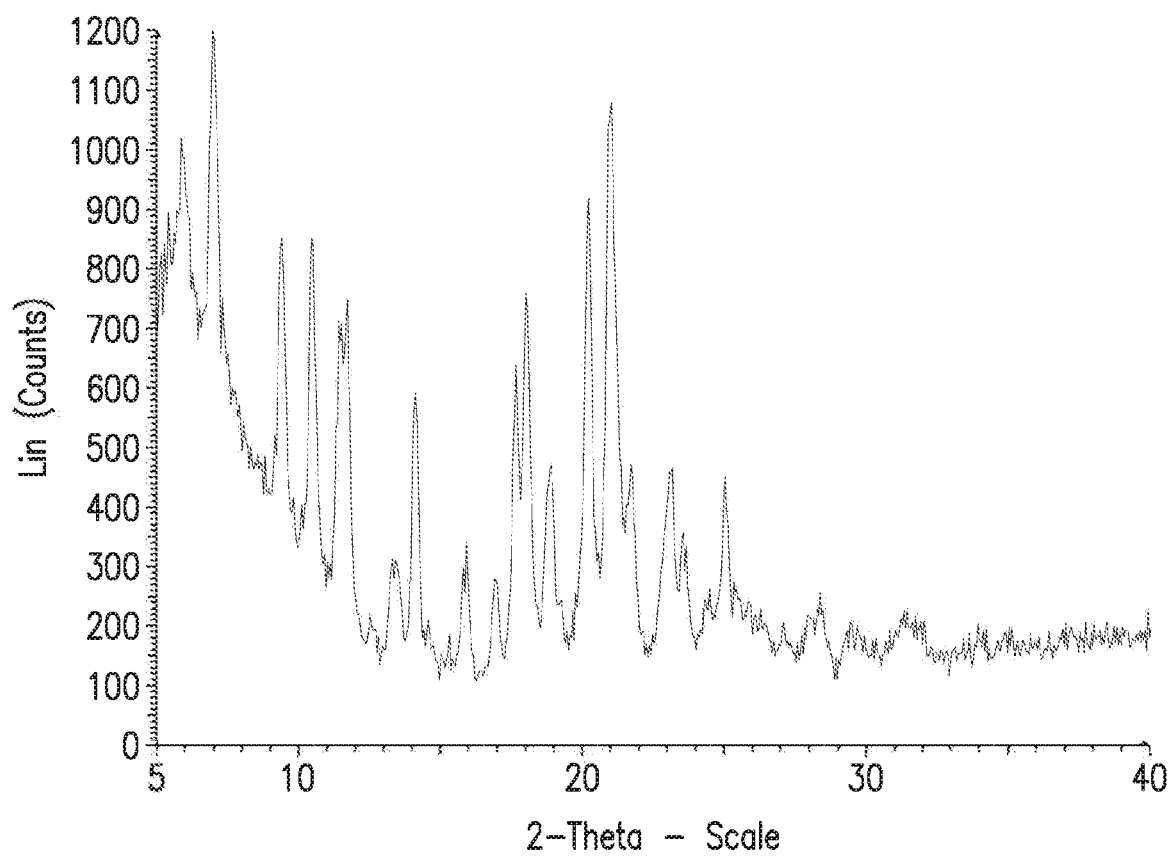
FIG. 1 is a representative X-ray powder diffractogram of Form A of (1S,3R)-3-acetamido-N-(5-chloro-4-(5,5-dimethyl-5,6-dihydro-4H-pyrrolo[1,2-b]pyrazol-3-yl)pyridin-2-yl)cyclohexanecarboxamide (Example 14).

According to one aspect of the present invention is provided compounds of Formula I:

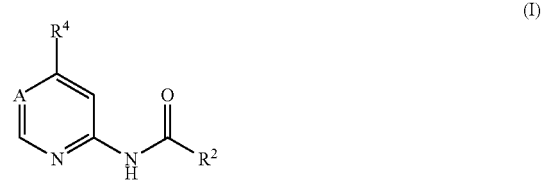

Wherein:

A is $C(R^5)$ or N;

$R^5$ is H, $C_{1-3}$ alkyl, CN or halogen;

$R^2$ is 3-7 membered heterocycloalkyl or 3-7 membered cycloalkyl;

optionally substituted with one to three substituents independently selected from the group consisting of $R^{10}$, $OR^{10}$, $SR^{10}$, $S(O)R^{10}$, $S(O)_2R^{10}$, $C(O)R^{10}$, $C(O)OR^{10}$, $OC(O)R^{10}$, $OC(O)OR^{10}$), $NH_2$, $NHR^{10}$, $N(R^{10})_2$, $NHC(O)H$, $NHC(O)R^{10}$, $NR^{10}C(O)H$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NH_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHS(O)_2R^{10}$, $C(O)NR^{10}S(O)_2R^{10}$, $S(O)_2NH_2$, $S(O)_2NH\ R^{10}$, $S(O)_2N(R^{10})_2$, $S(O)_2NHC(O)OR^{10}$, $S(O)_2NR^{10}C(O)OR^{10}$, $C(O)H$, $C(O)OH$, OH, CN, $NO_2$, F, Cl, Br and I; wherein one or more ring $CH_2$ groups can optionally be replaced by a corresponding number of —C(O) groups, one or more ring sulfur or nitrogen atoms may be optionally oxidized to form S-oxides or N-oxides;

$R^{10}$, at each occurrence, is independently selected from the group consisting of a 3 to 6 membered cycloalkyl or heterocycloalkyl group, $C_{1-6}$ alkyl, —O—$C_{1-6}$ alkyl, $C_{1-6}$ alkyl-O— $C_{1-6}$ alkyl, $NH_2$, $C(O)NH_2$, $C(O)H$, $C(O)OH$, OH, CN, $NO_2$, F, Cl, Br and I; wherein two $R^{10}$ groups together with the atoms to which they are attached may form a 3 to 6 membered cycloalkyl or heterocycloalkyl group; and each aforementioned $R^{10}$ alkyl, cycloalkyl and heterocycloalkyl group may be further substituted with one or two substituents independently selected from CN, OH, halogen, $C_{1-3}$ alkyl, —O—$C_{1-3}$ alkyl, $NH_2$, $NH$—$C_{1-3}$ alkyl, and $NHC(O)$—$C_{1-3}$ alkyl. $R^4$ is

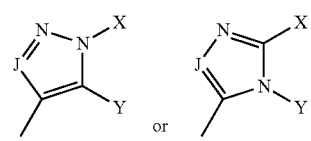

or wherein X and Y together with the atoms to which they are attached, form a 5 to 7 membered heterocycloalkyl ring which, in addition to the bridge nitrogen, may contain one or two heteroatoms selected from N, O, and S which ring may be saturated or partially saturated; wherein one or two ring $CH_2$ groups can optionally be replaced by a corresponding number of —C(O) groups, one or more ring sulfur or nitrogen atoms which may be optionally oxidized to form S-oxides or N-oxides and wherein the ring may be substituted on a ring carbon by one or two $R^{10}$ substituents or on a ring nitrogen by an $R^{12}$ substituent;

J is N or $CR^{11}$;

$R^{11}$ is H, $C_{1-3}$ alkyl; and $R^{12}$ is at each occurrence independently selected from the group consisting of a 3 to 6 membered cycloalkyl or heterocycloalkyl group, $C_{1-6}$ alkyl, $C_{1-6}$ alkyl-O—$C_{1-6}$ alkyl, $C(O)NH_2$, C(O)H; wherein $R^{12}$ alkyl, cycloalkyl and heterocycloalkyl group may be further substituted with one or two substituents independently selected from CN, OH, and halogen, $C_{1-3}$ alkyl, $NH_2$, and NH—$C_{1-3}$ alkyl, NHC(O)—$C_{1-3}$ alkyl, or pharmaceutical acceptable salts thereof.

Compounds of Formula (I) are useful for their ability to inhibit CDK9 activity and are accordingly also useful in the treatment of diseases or medical conditions mediated alone or in part by CDK9.

Compounds of Formula (I) may be useful for the treatment of hyperproliferative diseases. In particular the compounds are of use in the treatment of proliferative disease such as cancer, including hematological malignancies such as, but not limited to acute myeloid leukemia, multiple myeloma, chronic lymphocytic leukemia, diffuse large B cell lymphoma, Burkitt's lymphoma, follicular lymphoma and solid tumors such as, but not limited to, breast cancer, lung cancer (including but not limited to non-small cell lung cancer (NSCLC)) including the non-squamous and squamous subtypes, neuroblastoma and colon cancer.

The invention also relates to processes for the manufacture of said compounds, to pharmaceutical compositions containing them, and to their use in the manufacture of medicaments for use in the production of an anti-proliferation effect in warm-blooded animals such as man. Also in accordance with the present invention there are provided methods of using said compounds or pharmaceutically acceptable salts thereof in the treatment of cancer.

In order that the present invention can be more readily understood, certain terms are first defined. Additional definitions are set forth throughout the detailed description.

The foregoing written specification is considered to be sufficient to enable one skilled in the art to practice the embodiments. The foregoing description and Examples detail certain embodiments and describes the best mode contemplated by the inventors. It will be appreciated, however, that no matter how detailed the foregoing may appear in text, the embodiments may be practiced in many ways and the claims include any equivalents thereof.

Before describing the present invention in detail, it is to be understood that this invention is not limited to specific compositions or process steps, as such can vary. As used in this specification and the appended claims, the singular forms "a", "an" and "the" include plural referents unless the context clearly dictates otherwise. The terms "a" (or "an"), as well as the terms "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range.

It is understood that wherever aspects are described herein with the language "comprising," otherwise analogous aspects described in terms of "consisting of" and/or "consisting essentially of" are also provided.

The terms "inhibit," "block," and "suppress" are used interchangeably herein and refer to any statistically significant decrease in biological activity, including full blocking of the activity.

For example, "inhibition" can refer to a decrease of about 10%, 20%, 30%, 40%, 50%, 60%, 70%, 80%, 90% or 100% in biological activity.

Cellular proliferation can be assayed using art recognized techniques which measure rate of cell division, and/or the fraction of cells within a cell population undergoing cell division, and/or rate of cell loss from a cell population due to terminal differentiation or cell death (e.g., thymidine incorporation).

The term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

The term "pharmaceutical composition" refers to a preparation which is in such form as to permit the biological activity of the active ingredient, and which contains no additional components which are unacceptably toxic to a subject to which the composition would be administered. Such composition can be sterile.

Terms such as "treating" or "treatment" or "to treat" or "alleviating" or "to alleviate" refer to both (1) therapeutic measures that cure, slow down, lessen symptoms of, and/or halt progression of a diagnosed pathologic condition or disorder and (2) prophylactic or preventative measures that prevent and/or slow the development of a targeted pathologic condition or disorder. Thus, those in need of treatment include those already with the disorder; those prone to have the disorder; and those in whom the disorder is to be prevented. In certain aspects, a subject is successfully "treated" for cancer according to the methods of the present disclosure if the patient shows, e.g., total, partial, or transient remission of a certain type of cancer.

The terms "cancer", "tumor", "cancerous", and "malignant" refer to or describe the physiological condition in mammals that is typically characterized by unregulated cell growth. Examples of cancers include but are not limited to, hematological malignancies such as acute myeloid leukemia, multiple myeloma, chronic lymphocytic leukemia, diffuse large B cell lymphoma, Burkitt's lymphoma, follicular lymphoma and solid tumors such as breast cancer, lung cancer, neuroblastoma and colon cancer.

The term "cytotoxic agent" as used herein is defined broadly and refers to a substance that inhibits or prevents the function of cells and/or causes destruction of cells (cell death), and/or exerts anti-neoplastic/anti-proliferative effects. For example, cytotoxic agent prevents directly or indirectly the development, maturation, or spread of neoplastic tumor cells. The term includes also such agents that cause a cytostatic effect only and not a mere cytotoxic effect. The term includes chemotherapeutic agents as specified below, as well as other HER2 antagonists, anti-angiogenic agents, tyrosine kinase inhibitors, protein kinase A inhibitors, members of the cytokine family, radioactive isotopes, and toxins such as enzymatically active toxins of bacterial, fungal, plant or animal origin.

The term "chemotherapeutic agent" is a subset of the term "cytotoxic agent" comprising natural or synthetic chemical compounds.

In accordance with the methods of the present disclosure, compounds of the present disclosure may be administered to a patient to promote a positive therapeutic response with respect to cancer. The term "positive therapeutic response" with respect to cancer treatment refers to an improvement in the symptoms associated with the disease.

For example, an improvement in the disease can be characterized as a complete response. The term "complete response" refers to an absence of clinically detectable disease with normalization of any previously test results. Alternatively, an improvement in the disease can be categorized as being a partial response. A "positive therapeutic response" encompasses a reduction or inhibition of the progression and/or duration of cancer, the reduction or amelioration of the severity of cancer, and/or the amelioration of one or more symptoms thereof resulting from the administration of compounds of the present disclosure.

In specific aspects, such terms refer to one, two or three or more results following the administration of compounds of the instant disclosure:
 (1) a stabilization, reduction or elimination of the cancer cell population;
 (2) a stabilization or reduction in cancer growth;
 (3) an impairment in the formation of cancer;
 (4) eradication, removal, or control of primary, regional and/or metastatic cancer;
 (5) a reduction in mortality;
 (6) an increase in disease-free, relapse-free, progression-free, and/or overall survival, duration, or rate;
 (7) an increase in the response rate, the durability of response, or number of patients who respond or are in remission;
 (8) a decrease in hospitalization rate,
 (9) a decrease in hospitalization lengths,
 (10) the size of the cancer is maintained and does not increase or increases by less than 10%, preferably less than 5%, preferably less than 4%, preferably less than 2%, and
 (11) an increase in the number of patients in remission.
 (12) a decrease in the number of adjuvant therapies (e.g., chemotherapy or hormonal therapy) that would otherwise be required to treat the cancer.

Clinical response can be assessed using screening techniques such as PET, magnetic resonance imaging (MRI) scan, x-radiographic imaging, computed tomographic (CT) scan, flow cytometry or fluorescence-activated cell sorter (FACS) analysis, histology, gross pathology, and blood chemistry, including but not limited to changes detectable by ELISA, RIA, chromatography, and the like. In addition to these positive therapeutic responses, the subject undergoing therapy can experience the beneficial effect of an improvement in the symptoms associated with the disease.

In this specification the prefix $C_{x-y}$ as used in terms such as $C_{x-y}$ alkyl and the like (where x and y are integers) indicates the numerical range of carbon atoms that are present in the group; for example, $C_{1-4}$alkyl includes $C_1$alkyl (methyl), $C_2$alkyl (ethyl), $C_3$alkyl (propyl and isopropyl) and $C_4$alkyl (butyl, 1-methylpropyl, 2-methylpropyl, and t-butyl).

Unless specifically stated, the bonding atom of a group may be any suitable atom of that group; for example, propyl includes prop-1-yl and prop-2-yl.

As used herein, the phrase "optionally substituted," indicates that substitution is optional and therefore it is possible for the designated group to be either substituted or unsubstituted. In the event a substitution is desired, any number of hydrogens on the designated group may be replaced with a selection from the indicated substituents, provided that the normal valency of the atoms on a particular substituent is not exceeded, and that the substitution results in a stable compound.

In one aspect, when a particular group is designated as being optionally substituted with "one or more" substituents, the particular group may be unsubstituted. In another aspect, the particular group may bear one substituent. In another aspect, the particular substituent may bear two substituents. In still another aspect, the particular group may bear three substituents. In yet another aspect, the particular group may bear four substituents. In a further aspect, the particular group may bear one or two substituents. In still a further aspect, the particular group may be unsubstituted, or may bear one or two substituents.

As used herein the term "alkyl" refers to both straight and branched chain saturated hydrocarbon radicals having the specified number of carbon atoms. References to individual alkyl groups such as "propyl" are specific for the straight chain version only and references to individual branched chain alkyl groups such as "isopropyl" are specific for the branched chain version only. In one aspect, "alkyl" may be "$C_{1-4}$alkyl." In another aspect, "alkyl" and "$C_{1-4}$ alkyl" may be "$C_{1-3}$ alkyl." In another aspect, "alkyl," "$C_{1-4}$alkyl," and "$C_{1-3}$alkyl," may be methyl. An analogous convention applies to other generic terms, for example "alkenyl" and "alkynyl".

"Cycloalkyl" is a monocyclic, saturated or partially unsaturated alkyl ring containing 3 to 7 carbon atoms. Illustrative examples of cycloalkyl include cyclopropyl, cyclobutyl, cyclopentyl, cyclohexyl and cycloheptyl.

"Heterocycloalkyl" is a saturated or partially saturated monocyclic ring containing 3 to 7 ring atoms of which 1, 2, 3 or 4 ring atoms are chosen from nitrogen, sulphur or oxygen, which ring may be carbon or nitrogen linked, wherein a —$CH_2$— group can optionally be replaced by a —C(O)—; wherein a ring nitrogen or sulphur atom is optionally oxidised to form the N-oxide or S-oxide(s) (i.e. sulfoxide and sulfone); wherein a ring —NH is optionally substituted by acetyl, formyl, methyl or mesyl; and wherein a ring is optionally substituted by one or more halo. Illustrative examples of "5- or 6-membered heterocycloalkyl" include, imidazolinyl, pyrazolidinyl, piperazinyl, piperidinyl, pyrrolidinyl, oxazinyl, morpholinyl, hexahydropyrimidinyl, and thiomorpholinyl.

Suitable values for any R group ($R^1$ to $R^{12}$) or any part or substituent for such groups include:

for $C_{1-4}$alkyl: methyl, ethyl, propyl, isopropyl, butyl, 2-methylpropyl and tert-butyl;

for $C_{1-6}$alkyl: $C_{1-4}$ alkyl, pentyl, 2,2-dimethylpropyl, 3-methylbutyl and hexyl;

for $C_{3-7}$ cycloalkyl: cyclopropyl, cyclobutyl, cyclopentyl cyclohexyl, and cycloheptyl;

for halo or halogen: fluoro, chloro, bromo and iodo;

for heterocycloalkyl: pyrrolidinyl, piperidinyl, N-acetylpiperidinyl, N-methylpiperidinyl, N-formylpiperazinyl, N-mesylpiperazinyl, homopiperazinyl, piperazinyl, azetidinyl, oxetanyl, morpholinyl, pyranyl, dihydro-2H-pyranyl, tetrahydrofuranyl, 2,5-dioximidazolidinyl, and 2,2-dimethyl-1,3-dioxolanyl It should be noted that examples given for terms used in the description are not limiting.

As used herein, the phrase "effective amount" means an amount of a compound or composition which is sufficient enough to significantly and positively modify the symptoms and/or conditions to be treated (e.g., provide a positive clinical response). The effective amount of an active ingredient for use in a pharmaceutical composition will vary with the particular condition being treated, the severity of the condition, the duration of the treatment, the nature of concurrent therapy, the particular active ingredient(s) being employed, the particular pharmaceutically-acceptable excipient(s)/carrier(s) utilized, and like factors within the knowledge and expertise of the attending physician.

In particular, an effective amount of a compound of Formula (I) for use in the treatment of cancer is an amount sufficient to symptomatically relieve in a warm-blooded animal such as man, the symptoms of cancer and myeloproliferative diseases, to slow the progression of cancer and myeloproliferative diseases, or to reduce in patients with symptoms of cancer and myeloproliferative diseases the risk of getting worse.

As used herein, the phrase "leaving group" is intended to refer to groups readily displaceable by a nucleophile such as an amine nucleophile, and alcohol nucleophile, or a thiol nucleophile. Examples of suitable leaving groups include halo, such as chloro and bromo, and sulfonyloxy group, such as methanesulfonyloxy and toluene-4-sulfonyloxy.

As used herein, the term "pharmaceutically acceptable" refers to those compounds, materials, compositions, and/or dosage forms which are, within the scope of sound medical judgement, suitable for use in contact with the tissues of human beings and animals without excessive toxicity, irritation, allergic response, or other problem or complication, commensurate with a reasonable benefit/risk ratio.

As used herein, the term "protecting group" is intended to refer to those groups used to prevent selected reactive groups (such as carboxy, amino, hydroxy, and mercapto groups) from undergoing undesired reactions.

Illustrative examples of suitable protecting groups for a hydroxy group include, but are not limited to acyl groups; alkanoyl groups such as acetyl; aroyl groups, such as benzoyl; silyl groups, such as trimethylsilyl; and arylmethyl groups, such as benzyl. The deprotection conditions for the above hydroxy protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively a silyl group such as trimethylsilyl may be removed, for example, by fluoride or by aqueous acid; or an arylmethyl group such as a benzyl group may be removed, for example, by hydrogenation in the presence of a catalyst such as palladium-on-carbon.

Illustrative examples of suitable protecting groups for an amino group include, but are not limited to acyl groups; alkanoyl groups such as acetyl; alkoxycarbonyl groups, such as methoxycarbonyl, ethoxycarbonyl, and t-butoxycarbonyl; arylmethoxycarbonyl groups, such as benzyloxycarbonyl; and aroyl groups, such benzoyl. The deprotection conditions for the above amino protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulfuric, phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid, for example boron trichloride. A suitable alternative protecting group for a primary amino group is, for example, a phthaloyl group, which may be removed by treatment with an alkylamine, for example dimethylaminopropylamine or 2-hydroxyethylamine, or with hydrazine.

The protecting groups may be removed at any convenient stage in the synthesis using conventional techniques well known in the chemical art, or they may be removed during a later reaction step or work-up.

With reference to substituent "R" for illustrative purposes, the following substituent definitions refer to the indicated structure:

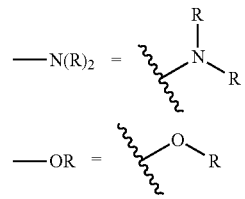

Within the present invention it is to be understood that a compound of formula (I) or a salt thereof may exhibit the phenomenon of tautomerism and that the formulae drawings within this specification can represent only one of the possible tautomeric forms. It is to be understood that the invention encompasses any tautomeric form which has CDK9 inhibitory activity and is not to be limited merely to any one tautomeric form utilised within the formulae drawings.

It is also to be understood that certain compounds of formula (I) and salts thereof can exist in solvated as well as unsolvated forms such as, for example, hydrated forms. It is to be understood that the invention encompasses all such solvated forms which have CDK9 inhibitory activity.

The compounds of formula (I) may also be provided as in vivo hydrolysable esters. An in vivo hydrolysable ester of a compound of formula (I) containing carboxy or hydroxy group is, for example a pharmaceutically acceptable ester which is cleaved in the human or animal body to produce the parent acid or alcohol. Such esters can be identified by administering, for example, intravenously to a test animal, the compound under test and subsequently examining the test animal's body fluid.

Suitable pharmaceutically acceptable esters for carboxy include $C_{1-6}$ alkoxymethyl esters for example methoxymethyl, $C_{1-6}$alkanoyloxymethyl esters for example pivaloyloxymethyl, phthalidyl esters, $C_{3-8}$cycloalkcarbonyloxy-$C_{1-6}$alkyl esters for example 1-cyclohexylcarbonyloxyethyl, (1,3-dioxolen-2-one)ylmethyl esters for example (5-methyl-1,3-dioxolen-2-one)ylmethyl, and $C_{1-6}$ alkoxycarbonyloxyethyl esters for example 1-methoxycarbonyloxyethyl; and may be formed at any carboxy group in the compounds of this invention.

Suitable pharmaceutically acceptable esters for hydroxy include inorganic esters such as phosphate esters (including phosphoramidic cyclic esters) and α-acyloxyalkyl ethers and related compounds which as a result of the in vivo hydrolysis of the ester breakdown to give the parent hydroxy groups. Examples of α-acyloxyalkyl ethers include acetoxymethoxy and 2,2-dimethylpropionyloxymethoxy. A selection of in vivo hydrolysable ester forming groups for hydroxy include $C_{1-10}$alkanoyl, for example acetyl, benzoyl, phenylacetyl, substituted benzoyl and phenylacetyl; $C_{1-10}$alkoxycarbonyl (to give alkyl carbonate esters), for example ethoxycarbonyl; di-$C_{1-4}$alkylcarbamoyl and N-(di-$C_{1-4}$alkylaminoethyl)-N—$C_{1-4}$alkylcarbamoyl (to give carbamates); di-$C_{1-4}$alkylaminoacetyl and carboxyacetyl. Examples of ring substituents on phenylacetyl and benzoyl include aminomethyl, $C_{1-4}$alkylaminomethyl and di-($C_{1-4}$alkyl)aminomethyl, and morpholino or piperazino linked from a ring nitrogen atom via a methylene linking group to the 3- or 4-position of the benzoyl ring. Other interesting in vivo hydrolysable esters include, for example, $R^A C(O)$-$OC_{1-6}$alkyl-CO—, wherein $R^A$ is for example, benzyloxy-$C_{1-4}$alkyl, or phenyl. Suitable substituents on a phenyl group in such esters include, for example, 4-$C_{1-4}$alkylpiperazino-$C_{1-4}$alkyl, piperazino-$C_{1-4}$alkyl and morpholino-$C_{1-4}$alkyl.

Compounds of Formula (I) may form stable pharmaceutically acceptable acid or base salts, and in such cases administration of a compound as a salt may be appropriate. Examples of acid addition salts include acetate, adipate, ascorbate, benzoate, benzenesulfonate, bicarbonate, bisulfate, butyrate, camphorate, camphorsulfonate, choline, citrate, cyclohexyl sulfamate, diethylenediamine, ethanesulfonate, fumarate, glutamate, glycolate, hemisulfate, 2-hydroxyethyl-sulfonate, heptanoate, hexanoate, hydrochloride, hydrobromide, hydroiodide, hydroxymaleate, lactate, malate, maleate, methanesulfonate, meglumine, 2-naphthalenesulfonate, nitrate, oxalate, pamoate, persulfate, phenylacetate, phosphate, diphosphate, picrate, pivalate, propionate, quinate, salicylate, stearate, succinate, sulfamate, sulfanilate, sulfate, tartrate, tosylate (p-toluenesulfonate), trifluoroacetate, and undecanoate. Examples of base salts include ammonium salts; alkali metal salts such as sodium, lithium and potassium salts; alkaline earth metal salts such as aluminum, calcium and magnesium salts; salts with organic bases such as dicyclohexylamine salts and N-methyl-D-glucamine; and salts with amino acids such as arginine, lysine, ornithine, and so forth. Also, basic nitrogen-containing groups may be quaternized with such agents as: lower alkyl halides, such as methyl, ethyl, propyl, and butyl halides; dialkyl sulfates such as dimethyl, diethyl, dibutyl; diamyl sulfates; long chain halides such as decyl, lauryl, myristyl and stearyl halides; arylalkyl halides such as benzyl bromide and others. Non-toxic physiologically-acceptable salts are preferred, although other salts may be useful, such as in isolating or purifying the product.

The salts may be formed by conventional means, such as by reacting the free base form of the product with one or more equivalents of the appropriate acid in a solvent or medium in which the salt is insoluble, or in a solvent such as water, which is removed in vacuo or by freeze drying or by exchanging the anions of an existing salt for another anion on a suitable ion-exchange resin.

Compounds of Formula (I) have chiral centers, and thus exist as stereoisomers. It is to be understood that the invention encompasses all such stereoisomers, including enantiomers and diastereoisomers. Insofar as compounds of Formula (I) may exist in optically active or racemic forms, the invention includes in its definition any such optically active or racemic form which possesses the above-mentioned activity. The present invention encompasses all such stereoisomers having activity as herein defined.

The synthesis of optically active forms may be carried out by standard techniques of organic chemistry well known in the art, for example by synthesis from optically active starting materials or by resolution of a racemic form. Racemates may be separated into individual enantiomers using known procedures (see, for example, Advanced Organic Chemistry: 3rd Edition: author J March, p 104-107). A suitable procedure involves formation of diastereomeric derivatives by reaction of the racemic material with a chiral auxiliary, followed by separation, for example by chromatography, of the diastereomers and then cleavage of the auxiliary species. Similarly, the above-mentioned activity may be evaluated using the standard laboratory techniques referred to hereinafter.

Thus, throughout the specification, where reference is made to the compound of Formula (I), it is to be understood that the term compound includes stereoisomers, mixtures of stereoisomers, and polymorphs that inhibit CDK9 activity in a human or animal.

Stereoisomers may be separated using conventional techniques, e.g. chromatography or fractional crystallisation. The enantiomers may be isolated by separation of a racemate for example by fractional crystallisation, resolution or HPLC. The diastereoisomers may be isolated by separation by virtue of the different physical properties of the diastereoisomers, for example, by fractional crystallisation, HPLC or flash chromatography. Alternatively particular stereoisomers may be made by chiral synthesis from chiral starting materials under conditions which will not cause racemisation or epimerisation, or by derivatisation, with a chiral reagent.

When a specific stereoisomer is provided (whether provided by separation, by chiral synthesis, or by other methods) it is favorably provided substantially isolated from other stereoisomers of the same compound. In one aspect, a mixture containing a particular stereoisomer of a compound of Formula (I) may contain less than 30%, particularly less than 20%, and more particularly less than 10% by weight of other stereoisomer(s) of the same compound. In another aspect, a mixture containing a particular stereoisomer of a compound of Formula (I) may contain less than 6%, particularly less than 3%, and more particularly less than 2% by weight of other stereoisomer(s) of the compound. In another aspect, a mixture containing a particular stereoisomer of a compound of Formula (I) may contain less than 1%, particularly less than 0.5%, and more particularly less than 0.3%, and still more particularly less than 0.1% by weight of other stereoisomer(s) of the compound. Where the absolute configuration of isolated stereoisomers is not determined, stereoisomers may be differentiated by a method of preparation or separation. For example, isolated stereoisomers may be differentiated by their elution time and denoted, for example, isomer 1, isomer 2, etc.

In accordance with the present invention compounds of the invention occur in a number of structurally different forms. It is an object of the present invention to provide a substantially pure crystal forms in some aspects of the invention.

Some structural forms of the invention may provide advantages. For instance, some forms of compound of the invention may be easier to handle and store. Other forms of the compound of the invention may be easier to characterize because it exists in a well defined state. Additionally, the compound of the invention may be easier to synthesize in a reproducible manner and thereby easier to handle in a full scale production.

When a specific polymorphic form is provided, it is favorably provided substantially isolated from other polymorphic forms of the same compound. In one aspect, a mixture containing a particular polymorphic form of a compound of Formula (I) may contain less than 30%, particularly less than 20%, and more particularly less than 10% by weight of other polymorphic forms of the same compound. In another aspect, a mixture containing a particular polymorphic form of a compound of Formula (I) may contain less than 6%, particularly less than 3%, and more particularly less than 2% by weight of other polymorphic forms of the compound. In another aspect, a mixture containing a particular polymorphic form of a compound of Formula (I) may contain less than 1%, particularly less than 0.5%, and more particularly less than 0.3%, and still more particularly less than 0.1% by weight of other polymorphic forms of the compound.

The compounds of the invention may be characterized by the positions and intensities of the major peaks in the X-ray powder diffractogram, but may also be characterized by conventional FT-IR spectroscopy. These may be used to distinguish one crystal form from other crystal forms of the compound. The compounds of the invention are characterized by being highly crystalline, i.e. having a higher crystallinity than other forms. With the expression "any other form" is meant anhydrates, hydrates, solvates, and polymorphs or amorphous forms thereof disclosed in the prior art. Examples of any other forms of compounds include, but are not limited to, anhydrates, monohydrates, dihydrates, sesquihydrates, trihydrates, alcoholates, such as methanolates and ethanolates, and polymorphs or amorphous forms thereof.

The compound of the invention may also be characterized by its unit cell. The compound of the invention prepared according to the present invention may be analyzed by XRPD, a technique which is known per se.

The amount of water in the compound can be determined by thermogravimetric analysis, a technique which is known per se.

Additional embodiments of the invention are as follows. These additional embodiments relate to compounds of Formula (I) and pharmaceutically acceptable salts thereof. Such specific substituents may be used, where appropriate, with any of the definitions, claims or embodiments defined hereinbefore or hereinafter.

A

In one aspect, A is $C(R^5)$.

$R^5$

In one aspect of the present invention $R^5$ is halogen.
In one aspect of the present invention $R^5$ is chloro.
In one aspect of the present invention $R^5$ is fluoro.
In one aspect of the present invention $R^5$ is cyano.

$R^2$

In one aspect $R^2$ is 3-7 membered cycloalkyl.

In another aspect $R^2$ 1 S 3-7 membered cycloalkyl substituted with $NHCOR^{10}$ or $R^{10}$.
In another aspect $R^2$ is cyclohexyl substituted with $NHCOR^{10}$.
In another aspect $R^2$ is cyclopropyl substituted with $R^{10}$.
In another aspect $R^2$ is 3-7 membered heterocycloalkyl.
In another aspect $R^2$ is 3-7 membered heterocycloalkyl substituted with $NHCOR^{10}$.
In another aspect $R^2$ is piperidinyl.
In another aspect $R^2$ is cyclobutyl.
In another aspect $R^2$ is cyclobutyl substituted with $R^{10}$.

$R^4$

In one aspect $R^4$ is

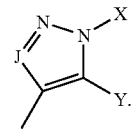

In another aspect $R^4$ is

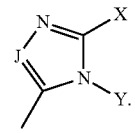

J

In one aspect J is $C(R^{11})$ and $R^{11}$ is H.

X and Y

In one aspect X and Y together with the atoms to which they are attached form a 6 membered heterocycloalkyl ring.
In one aspect X and Y together with the atoms to which they are attached form a 6 membered heterocycloalkyl ring containing an additional heteroatom which is oxygen.
In one aspect X and Y together with the atoms to which they are attached form a 6 membered heterocycloalkyl ring containing an additional heteroatom which is nitrogen.
In one aspect X and Y together with the atoms to which they are attached form a 6 membered heterocycloalkyl ring in which one $CH_2$ is substituted with two methyl groups.
In one aspect X and Y together with the atoms to which they are attached form a 5 membered heterocycloalkyl ring.
In one aspect X and Y together with the atoms to which they are attached form a 5 membered heterocycloalkyl ring in which one $CH_2$ is substituted with two methyl groups.
In one aspect X and Y together with the atoms to which they are attached form a 7 membered heterocycloalkyl ring.
In one aspect X and Y together with the atoms to which they are attached form a 7 membered heterocycloalkyl ring in which one $CH_2$ is substituted with two methyl groups.

In one aspect
A is $C(R^5)$;
$R^2$ is 3-7 membered cycloalkyl;
$R^4$ is

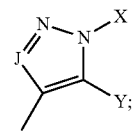

and
X and Y together with the atoms to which they are attached form a 6 membered heterocycloalkyl ring.
In one aspect
A is C(R$^5$);
R$^5$ is halogen;
R$^2$ is 3-7 membered cycloalkyl;
R$^4$ is

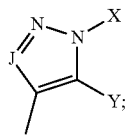

and
X and Y together with the atoms to which they are attached form a 6 membered heterocycloalkyl ring.
In one aspect
A is C(R$^5$);
R$^5$ is chloro;
R$^2$ is 3-7 membered cycloalkyl;
R$^4$ is

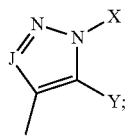

and
X and Y together with the atoms to which they are attached form a 6 membered heterocycloalkyl ring.
In one aspect
A is C(R$^5$);
R$^5$ is chloro;
R$^2$ is cyclohexyl;
R$^4$ is

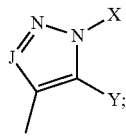

and
X and Y together with the atoms to which they are attached form a 6 membered heterocycloalkyl ring.
In one aspect
A is C(R$^5$);
R$^5$ is chloro;
R$^2$ is cyclohexyl substituted with NHC(O)R$^{10}$;
R$^4$ is

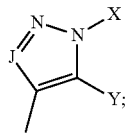

and
X and Y together with the atoms to which they are attached form a 6 membered heterocycloalkyl ring.
In one aspect
A is C(R$^5$);
R$^5$ is chloro;
R$^2$ is cyclohexyl substituted with NHC(O)R$^{10}$;
R$^{10}$ is C$_{1-6}$ alkyl;
R$^4$ is

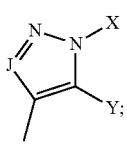

J is C(R$^{11}$) and R$^{11}$ is H;
and
X and Y together with the atoms to which they are attached form a 6 membered heterocycloalkyl ring.
In one aspect
A is C(R$^5$);
R$^2$ is 3-7 membered cycloalkyl;
R$^4$ is

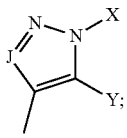

and
X and Y together with the atoms to which they are attached form a 5 membered heterocycloalkyl ring.
A is C(R$^5$);
R$^5$ is halogen;
R$^2$ is cyclohexyl;
R$^4$ is

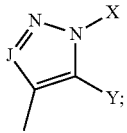

and
X and Y together with the atoms to which they are attached form a 5 membered heterocycloalkyl ring.
In one aspect
A is C(R$^5$);
R$^5$ is chloro;
R$^2$ is cyclohexyl;
R$^4$ is

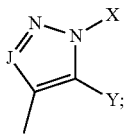

and
X and Y together with the atoms to which they are attached form a 5 membered heterocycloalkyl ring.

In one aspect
A is C(R⁵);
R⁵ is chloro;
R² is cyclohexyl substituted with NHC(O)R¹⁰;
R⁴ is

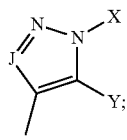

and
X and Y together with the atoms to which they are attached form a 5 membered heterocycloalkyl ring.
In one aspect
A is C(R⁵);
R⁵ is chloro;
R² is cyclohexyl substituted with NHC(O)R¹⁰;
R¹⁰ is C$_{1-6}$ alkyl;
R⁴ is

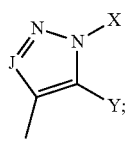

J is C(R¹¹) and R¹¹ is H;
and
X and Y together with the atoms to which they are attached form a 5 membered heterocycloalkyl ring.
In one aspect
A is C(R⁵);
R⁵ is chloro;
R² is cyclohexyl substituted with NHC(O)R¹⁰;
R¹⁰ is C$_{1-6}$ alkyl;
R⁴ is

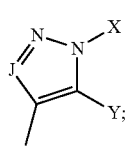

J is C(R¹¹) and R¹¹ is H
and
X and Y together with the atoms to which they are attached form a piperidinyl ring.
In one aspect
A is C(R⁵);
R⁵ is chloro;
R² is cyclohexyl substituted with NHC(O)R¹⁰;
is C$_{1-6}$ alkyl;
R⁴ is

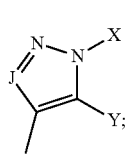

J is C(R¹¹) and R¹¹ is H
and
X and Y together with the atoms to which they are attached form a piperidinyl ring wherein one ring carbon may be substituted by one or two R¹⁰ substituents.
In one aspect
A is C(R⁵);
R⁵ is chloro;
R¹⁰ is cyclohexyl substituted with NHC(O)R¹⁰;
is C$_{1-6}$ alkyl;
R⁴ is

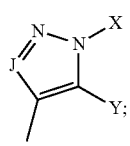

J is C(R₅) and R₅ is H
and
X and Y together with the atoms to which they are attached form a piperazinyl ring.
In one aspect
A is C(R⁵);
R⁵ is chloro;
R² is cyclohexyl substituted with NHC(O)R¹⁰;
is C$_{1-6}$ alkyl;
R⁴ is

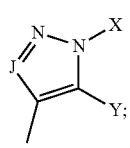

J is C(R₅) and R₅ is H
and
X and Y together with the atoms to which they are attached form a morpholinyl ring.
In one aspect
A is C(R⁵);
R⁵ is chloro;
R² is cyclohexyl substituted with NHC(O)R¹⁰;
R¹⁰ is C$_{1-6}$ alkyl;
R⁴ is

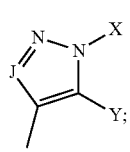

J is C(R₅) and R₅ is H
and
X and Y together with the atoms to which they are attached form a pyrrolidinyl wherein one CH₂ is substituted with two methyl groups.
A is C(R⁵);
R² is 3-7 membered cycloalkyl;

$R^4$ is

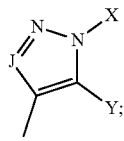

and

X and Y together with the atoms to which they are attached form a 7 membered heterocycloalkyl ring.

In one aspect
A is $C(R^5)$;
$R^5$ is halogen;
$R^2$ is 3-7 membered cycloalkyl;
$R^4$ is

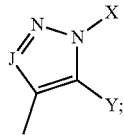

and

X and Y together with the atoms to which they are attached form a 7 membered heterocycloalkyl ring.

In one aspect
A is $C(R^5)$;
$R^5$ is chloro;
$R^2$ is 3-7 membered cycloalkyl;
$R^4$ is

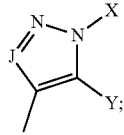

and

X and Y together with the atoms to which they are attached form a 7 membered heterocycloalkyl ring.

In one aspect
A is $C(R^5)$;
$R^5$ is chloro;
$R^2$ is cyclohexyl;
$R^4$ is

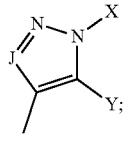

and

X and Y together with the atoms to which they are attached form a 7 membered heterocycloalkyl ring.

In one aspect
A is $C(R^5)$;
$R^5$ is chloro;
$R^2$ is cyclohexyl substituted with $NHC(O)R^{10}$;

$R^4$ is

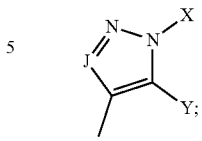

and

X and Y together with the atoms to which they are attached form a 7 membered heterocycloalkyl ring.

In one aspect
A is $C(R^5)$;
$R^5$ is chloro;
$R^2$ is cyclohexyl substituted with $NHC(O)R^{10}$;
$R^{10}$ is $C_{1-6}$ alkyl;
$R^4$ is

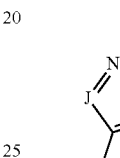

J is $C(R^{11})$ and $R^{11}$ is H;
and
X and Y together with the atoms to which they are attached form a 7 membered heterocycloalkyl ring.

In another aspect of the invention there is provided a compound selected from:

(R)—N-(5-chloro-4-(5,6,7,8-tetrahydroimidazo[1,2-a]pyridin-3-yl)pyridin-2-yl)piperidine-3-carboxamide;

(1S,3R)-3-acetamido-N-(5-chloro-4-(4,5,6,7-tetrahydropyrazolo[1,5-a]pyridin-3-yl)pyridin-2-yl)cyclohexanecarboxamide;

(1S,3R)-3-acetamido-N-(4-(4,5,6,7-tetrahydropyrazolo[1,5-a]pyridin-3-yl)pyridin-2-yl)cyclohexanecarboxamide;

Cis-N-(5-chloro-4-(4,5,6,7-tetrahydropyrazolo[1,5-a]pyridin-3-yl)pyridin-2-yl)-3-hydroxycyclobutanecarboxamide;

(R)—N-(5-chloro-4-(4,5,6,7-tetrahydropyrazolo[1,5-a]pyridin-3-yl)pyridin-2-yl)piperidine-3-carboxamide;

cis-3-hydroxy-N-(4-(4,5,6,7-tetrahydropyrazolo[1,5-a]pyridin-3-yl)pyridin-2-yl)cyclobutanecarboxamide;

(1S,3R)-3-acetamido-N-(5-chloro-4-(5,6,7,8-tetrahydroimidazo[1,2-a]pyridin-3-yl)pyridin-2-yl)cyclohexanecarboxamide;

(1S,3R)-3-acetamido-N-(5-chloro-4-(6,7-dihydro-5H-pyrazolo[5,1-b][1,3]oxazin-3-yl)pyridin-2-yl)cyclohexanecarboxamide; (1R,3S)-3-acetamido-N-(5-chloro-4-(4,5,6,7-tetrahydropyrazolo[1,5-a]pyridin-3-yl)pyridin-2-yl)cyclohexanecarboxamide;

(1S,3R)-3-acetamido-N-(5-chloro-4-(5,6-dihydro-4H-pyrrolo[1,2-b]pyrazol-3-yl)pyridin-2-yl)cyclohexanecarboxamide;

(1S,3R)-3-acetamido-N-(5-chloro-4-(6,7-dihydro-4H-pyrazolo[5,1-c][1,4]oxazin-3-yl)pyridin-2-yl)cyclohexanecarboxamide;

(1S,3R)-3-acetamido-N-(5-chloro-4-(6,7-dihydro-5H-pyrrolo[1,2-a]imidazol-3-yl)pyridin-2-yl)cyclohexanecarboxamide;

(1S,3R)-3-acetamido-N-(5-chloro-4-(5-methyl-4,5,6,7-tetrahydropyrazolo[1,5-a]pyrazin-3-yl)pyridin-2-yl)cyclohexanecarboxamide;

(1S,3R)-3-acetamido-N-(5-chloro-4-(5,5-dimethyl-5,6-dihydro-4H-pyrrolo[1,2-b]pyrazol-3-yl)pyridin-2-yl)cyclohexanecarboxamide;

(1S,3R)-3-acetamido-N-(5-chloro-4-(4,5,6,7-tetrahydropyrazolo[1,5-a]pyrimidin-3-yl)pyridin-2-yl)cyclohexanecarboxamide;

(1S,3R)-3-acetamido-N-(4-(5,5-dimethyl-5,6-dihydro-4H-pyrrolo[1,2-b]pyrazol-3-yl)pyridin-2-yl)cyclohexanecarboxamide;

(1S,3R)—N-(4-(5,5-dimethyl-5,6-dihydro-4H-pyrrolo[1,2-b]pyrazol-3-yl)pyridin-2-yl)-3-(1-hydroxycyclopropanecarboxamido)cyclohexanecarboxamide;

N-((1R,3S)-3-((4-(5,5-dimethyl-5,6-dihydro-4H-pyrrolo[1,2-b]pyrazol-3-yl)pyridin-2-yl)carbamoyl)cyclohexyl)oxetane-3-carboxamide;

N-((1R,3S)-3-((5-chloro-4-(5,5-dimethyl-5,6-dihydro-4H-pyrrolo[1,2-b]pyrazol-3-yl)pyridin-2-yl)carbamoyl)cyclohexyl)oxetane-3-carboxamide;

(1S,3R)—N-(5-chloro-4-(5,5-dimethyl-5,6-dihydro-4H-pyrrolo[1,2-b]pyrazol-3-yl)pyridin-2-yl)-3-((S)-2-hydroxypropanamido)cyclohexanecarboxamide;

(1S,3R)—N-(5-chloro-4-(5,5-dimethyl-5,6-dihydro-4H-pyrrolo[1,2-b]pyrazol-3-yl)pyridin-2-yl)-3-(1-hydroxycyclopropanecarboxamido)cyclohexanecarboxamide;

(1S,3R)-3-acetamido-N-(5-chloro-4-(6,6-dimethyl-6,7-dihydro-5H-pyrrolo[1,2-a]imidazol-3-yl)pyridin-2-yl)cyclohexanecarboxamide;

(R)—N-((1R,3S)-3-((5-chloro-4-(5,5-dimethyl-5,6-dihydro-4H-pyrrolo[1,2-b]pyrazol-3-yl)pyridin-2-yl)carbamoyl)cyclohexyl)tetrahydrofuran-3-carboxamide;

(S)—N-((1R,3S)-3-((5-chloro-4-(5,5-dimethyl-5,6-dihydro-4H-pyrrolo[1,2-b]pyrazol-3-yl)pyridin-2-yl)carbamoyl)cyclohexyl)tetrahydrofuran-3-carboxamide;

(1S,3R)-3-acetamido-N-(4-(5,5-dimethyl-5,6-dihydro-4H-pyrrolo[1,2-b]pyrazol-3-yl)-5-fluoropyridin-2-yl)cyclohexanecarboxamide;

cis-N-(4-(5,5-dimethyl-5,6-dihydro-4H-pyrrolo[1,2-b]pyrazol-3-yl)pyridin-2-yl)-3-hydroxycyclobutanecarboxamide;

cis-N-(5-chloro-4-(5,5-dimethyl-5,6-dihydro-4H-pyrrolo[1,2-b]pyrazol-3-yl)pyridin-2-yl)-3-hydroxycyclobutanecarboxamide;

(1S,3R)-3-acetamido-N-(6-(4,5,6,7-tetrahydropyrazolo[1,5-a]pyridin-3-yl)pyrimidin-4-yl)cyclohexanecarboxamide;

trans-3-hydroxy-N-(6-(4,5,6,7-tetrahydropyrazolo[1,5-a]pyridin-3-yl)pyrimidin-4-yl)cyclobutanecarboxamide;

(1S,3R)-3-acetamido-N-(6-(5,5-dimethyl-5,6-dihydro-4H-pyrrolo[1,2-b]pyrazol-3-yl)pyrimidin-4-yl)cyclohexanecarboxamide;

(1S,3R)—N-(5-chloro-4-(4,5,6,7-tetrahydropyrazolo[1,5-a]pyridin-3-yl)pyridin-2-yl)-3-(2-cyanoacetamido)cyclohexanecarboxamide;

tert-butyl ((1R,3S)-3-((5-chloro-4-(4,5,6,7-tetrahydropyrazolo[1,5-a]pyridin-3-yl)pyridin-2-yl)carbamoyl)cyclohexyl)carbamate;

(1S,3R)-3-amino-N-(5-chloro-4-(4,5,6,7-tetrahydropyrazolo[1,5-a]pyridin-3-yl)pyridin-2-yl)cyclohexanecarboxamide;

(1S,3R)—N-(5-chloro-4-(4,5,6,7-tetrahydropyrazolo[1,5-a]pyridin-3-yl)pyridin-2-yl)-3-(1-hydroxycyclopropanecarboxamido)cyclohexanecarboxamide;

(R)—N-((1R,3S)-3-((5-chloro-4-(4,5,6,7-tetrahydropyrazolo[1,5-a]pyridin-3-yl)pyridin-2-yl)carbamoyl)cyclohexyl)tetrahydrofuran-3-carboxamide;

N-((1R,3S)-3-((5-chloro-4-(4,5,6,7-tetrahydropyrazolo[1,5-a]pyridin-3-yl)pyridin-2-yl)carbamoyl)cyclohexyl)-3-methyloxetane-3-carboxamide;

(S)—N-((1R,3S)-3-((5-chloro-4-(4,5,6,7-tetrahydropyrazolo[1,5-a]pyridin-3-yl)pyridin-2-yl)carbamoyl)cyclohexyl)tetrahydrofuran-2-carboxamide;

(R)—N-((1R,3S)-3-((5-chloro-4-(4,5,6,7-tetrahydropyrazolo[1,5-a]pyridin-3-yl)pyridin-2-yl)carbamoyl)cyclohexyl)tetrahydrofuran-2-carboxamide;

(1S,3R)—N-(5-chloro-4-(4,5,6,7-tetrahydropyrazolo[1,5-a]pyridin-3-yl)pyridin-2-yl)-3-((S)-2-hydroxypropanamido)cyclohexanecarboxamide;

(S)—N-((1R,3S)-3-((5-chloro-4-(4,5,6,7-tetrahydropyrazolo[1,5-a]pyridin-3-yl)pyridin-2-yl)carbamoyl)cyclohexyl)tetrahydrofuran-3-carboxamide;

(1S,3R)-3-acetamido-N-(5-cyano-4-(5,5-dimethyl-5,6-dihydro-4H-pyrrolo[1,2-b]pyrazol-3-yl)pyridin-2-yl)cyclohexanecarboxamide;

Isomer 1 of (1S,3R)-3-acetamido-N-(5-chloro-4-(5-methyl-5,6-dihydro-4H-pyrrolo[1,2-b]pyrazol-3-yl)pyridin-2-yl)cyclohexanecarboxamide;

Isomer 2 of (1S,3R)-3-acetamido-N-(5-chloro-4-(5-methyl-5,6-dihydro-4H-pyrrolo[1,2-b]pyrazol-3-yl)pyridin-2-yl)cyclohexanecarboxamide;

(1R,3S)-3-acetamido-N-(5-chloro-4-(5,5-dimethyl-5,6-dihydro-4H-pyrrolo[1,2-b]pyrazol-3-yl)pyridin-2-yl)cyclohexanecarboxamide;

(1S,3R)-3-acetamido-N-(4-(5,5-dimethyl-4,5,6,7-tetrahydropyrazolo[1,5-a]pyridin-3-yl)pyridin-2-yl)cyclohexanecarboxamide;

(S)—N-((1R,3S)-3-((5-chloro-4-(5,5-dimethyl-5,6-dihydro-4H-pyrrolo[1,2-b]pyrazol-3-yl)pyridin-2-yl)carbamoyl)cyclohexyl)tetrahydrofuran-2-carboxamide;

(R)—N-((1R,3S)-3-((5-chloro-4-(5,5-dimethyl-5,6-dihydro-4H-pyrrolo[1,2-b]pyrazol-3-yl)pyridin-2-yl)carbamoyl)cyclohexyl)tetrahydrofuran-2-carboxamide;

(1S,3R)-3-acetamido-N-(4-(5,5-dimethyl-5,6-dihydro-4H-pyrrolo[1,2-b]pyrazol-3-yl)-5-methylpyridin-2-yl)cyclohexanecarboxamide;

(1S,3R)-3-acetamido-N-(5-chloro-4-(5,5-dimethyl-5,6-dihydro-4H-pyrrolo[1,2-b]pyrazol-3-yl)pyridin-2-yl)cyclopentanecarboxamide;

(1S,3R)-3-acetamido-N-(5-chloro-4-(4,5,6,7-tetrahydro-[1,2,3]triazolo[1,5-a]pyridin-3-yl)pyridin-2-yl)cyclohexanecarboxamide;

(1S,3R)-3-acetamido-N-(4-(6,6-dimethyl-6,7-dihydro-5H-pyrrolo[1,2-a]imidazol-3-yl)-5-fluoropyridin-2-yl)cyclohexanecarboxamide;

(1S,3R)-3-acetamido-N-(4-(5,5-dimethyl-4,5,6,7-tetrahydropyrazolo[1,5-a]pyridin-3-yl)-5-fluoropyridin-2-yl)cyclohexanecarboxamide;

(1S,3R)-3-amino-N-(4-(5,5-dimethyl-4,5,6,7-tetrahydropyrazolo[1,5-a]pyridin-3-yl)-5-fluoropyridin-2-yl)cyclohexanecarboxamide;

(1S,3R)—N-(5-chloro-4-(5,5-dimethyl-5,6-dihydro-4H-pyrrolo[1,2-b]pyrazol-3-yl)pyridin-2-yl)-3-(3-hydroxypropanamido)cyclohexanecarboxamide;

(1S,3R)—N-(5-chloro-4-(5,5-dimethyl-5,6-dihydro-4H-pyrrolo[1,2-b]pyrazol-3-yl)pyridin-2-yl)-3-(cis-3-hydroxycyclobutanecarboxamido)cyclohexanecarboxamide (1S,3R)-3-amino-N-(4-(5,5-dimethyl-5,6-dihydro-4H-pyrrolo[1,2-b]pyrazol-3-yl)-5-fluoropyridin-2-yl)cyclohexane-1-carboxamide;

(1S,3R)—N-(4-(5,5-dimethyl-5,6-dihydro-4H-pyrrolo[1,2-b]pyrazol-3-yl)-5-fluoropyridin-2-yl)-3-(1-hydroxycyclopropanecarboxamido)cyclohexanecarboxamide;

(1S,3R)—N-(5-chloro-4-(6,6-dimethyl-6,7-dihydro-5H-pyrrolo[1,2-a]imidazol-3-yl)pyridin-2-yl)-3-(1-hydroxycyclopropanecarboxamido)cyclohexanecarboxamide;

N-((1R,3S)-3-((5-chloro-4-(6,6-dimethyl-6,7-dihydro-5H-pyrrolo[1,2-a]imidazol-3-yl)pyridin-2-yl)carbamoyl)cyclohexyl)oxetane-3-carboxamide;

cis-N-(5-chloro-4-(6,6-dimethyl-6,7-dihydro-5H-pyrrolo[1,2-a]imidazol-3-yl)pyridin-2-yl)-3-hydroxycyclobutanecarboxamide;

Isomer 1 of trans-3-acetamido-N-(5-chloro-4-(5,5-dimethyl-5,6-dihydro-4H-pyrrolo[1,2-b]pyrazol-3-yl)pyridin-2-yl)cyclohexanecarboxamide;

Isomer 2 of trans-3-acetamido-N-(5-chloro-4-(5,5-dimethyl-5,6-dihydro-4H-pyrrolo[1,2-b]pyrazol-3-yl)pyridin-2-yl)cyclohexanecarboxamide;

Isomer 1 of trans-3-acetamido-N-(5-chloro-4-(4,5,6,7-tetrahydropyrazolo[1,5-a]pyridin-3-yl)pyridin-2-yl)cyclohexanecarboxamide;

Isomer 2 of trans-3-acetamido-N-(5-chloro-4-(4,5,6,7-tetrahydropyrazolo[1,5-a]pyridin-3-yl)pyridin-2-yl)cyclohexanecarboxamide;

(1S,3R)-3-acetamido-N-(5-fluoro-4-(4,5,6,7-tetrahydropyrazolo[1,5-a]pyridin-3-yl)pyridin-2-yl)cyclohexanecarboxamide;

Isomer 1 of (1S,3R)-3-acetamido-N-(5-chloro-4-(5-methyl-4,5,6,7-tetrahydropyrazolo[1,5-a]pyridin-3-yl)pyridin-2-yl)cyclohexanecarboxamide;

Isomer 2 of (1S,3R)-3-acetamido-N-(5-chloro-4-(5-methyl-4,5,6,7-tetrahydropyrazolo[1,5-a]pyridin-3-yl)pyridin-2-yl)cyclohexanecarboxamide;

(1S,3R)-3-acetamido-N-(5-chloro-4-(5,6,7,8-tetrahydro-4H-pyrazolo[1,5-a]azepin-3-yl)pyridin-2-yl)cyclohexanecarboxamide;

N-((1R,3S)-3-((5-chloro-4-(4,5,6,7-tetrahydropyrazolo[1,5-a]pyridin-3-yl)pyridin-2-yl)carbamoyl)cyclohexyl)oxetane-3-carboxamide;

Isomer 1 of (1S,3R)-3-acetamido-N-(5-chloro-4-(6-methyl-4,5,6,7-tetrahydropyrazolo[1,5-a]pyridin-3-yl)pyridin-2-yl)cyclohexanecarboxamide;

Isomer 2 of (1S,3R)-3-acetamido-N-(5-chloro-4-(6-methyl-4,5,6,7-tetrahydropyrazolo[1,5-a]pyridin-3-yl)pyridin-2-yl)cyclohexanecarboxamide;

Isomer 1 of (1S,3R)-3-acetamido-N-(5-chloro-4-(6-methoxy-4,5,6,7-tetrahydropyrazolo[1,5-a]pyridin-3-yl)pyridin-2-yl)cyclohexanecarboxamide;

Isomer 2 of (1S,3R)-3-acetamido-N-(5-chloro-4-(6-methoxy-4,5,6,7-tetrahydropyrazolo[1,5-a]pyridin-3-yl)pyridin-2-yl)cyclohexanecarboxamide;

Isomer 1 of (1S,3R)-3-acetamido-N-(5-chloro-4-(5-methoxy-4,5,6,7-tetrahydropyrazolo[1,5-a]pyridin-3-yl)pyridin-2-yl)cyclohexanecarboxamide;

Isomer 2 of (1S,3R)-3-acetamido-N-(5-chloro-4-(5-methoxy-4,5,6,7-tetrahydropyrazolo[1,5-a]pyridin-3-yl)pyridin-2-yl)cyclohexanecarboxamide;

(1S,3R)-3-acetamido-N-(5-fluoro-4-(5,6,7,8-tetrahydro-4H-pyrazolo[1,5-a]azepin-3-yl)pyridin-2-yl)cyclohexanecarboxamide;

(1S,3R)—N-(4-(5,5-dimethyl-5,6-dihydro-4H-pyrrolo[1,2-b]pyrazol-3-yl)-5-methylpyridin-2-yl)-3-(2-hydroxyacetamido)cyclohexanecarboxamide;

N-((1R,3S)-3-((4-(5,5-dimethyl-5,6-dihydro-4H-pyrrolo[1,2-b]pyrazol-3-yl)-5-methylpyridin-2-yl)carbamoyl)cyclohexyl)oxetane-3-carboxamide;

(1S,3R)-3-acetamido-N-(5-methyl-4-(4,5,6,7-tetrahydropyrazolo[1,5-a]pyridin-3-yl)pyridin-2-yl)cyclohexanecarboxamide;

(1S,3R)-3-acetamido-N-(5-chloro-4-(7-hydroxy-4,5,6,7-tetrahydropyrazolo[1,5-a]pyridin-3-yl)pyridin-2-yl)cyclohexanecarboxamide;

(1S,3R)-3-acetamido-N-(5-chloro-4-(5-(4-hydroxybutyl)-1H-pyrazol-4-yl)pyridin-2-yl)cyclohexanecarboxamide;

Isomer 1 of (1S,3R)-3-acetamido-N-(5-chloro-4-(4-hydroxy-5,5-dimethyl-5,6-dihydro-4H-pyrrolo[1,2-b]pyrazol-3-yl)pyridin-2-yl)cyclohexanecarboxamide;

Isomer 2 of (1S,3R)-3-acetamido-N-(5-chloro-4-(4-hydroxy-5,5-dimethyl-5,6-dihydro-4H-pyrrolo[1,2-b]pyrazol-3-yl)pyridin-2-yl)cyclohexanecarboxamide;

(1R,3S)-3-acetamido-N-(4-(5,5-dimethyl-5,6-dihydro-4H-pyrrolo[1,2-b]pyrazol-3-yl)-5-fluoropyridin-2-yl)cyclohexanecarboxamide;

(1S,3R)-3-acetamido-N-(5-chloro-4-(5-(3-hydroxy-2,2-dimethylpropyl)-1H-pyrazol-4-yl)pyridin-2-yl)cyclohexane-1-carboxamide;

(1S,3R)-3-acetamido-N-(5-chloro-4-(6-hydroxy-5,5-dimethyl-5,6-dihydro-4H-pyrrolo[1,2-b]pyrazol-3-yl)pyridin-2-yl)cyclohexane-1-carboxamide;

(1R,3R)-3-acetamido-N-(4-(5,5-dimethyl-5,6-dihydro-4H-pyrrolo[1,2-b]pyrazol-3-yl)-5-fluoropyridin-2-yl)cyclohexane-1-carboxamide; and (1S,3S)-3-acetamido-N-(4-(5,5-dimethyl-5,6-dihydro-4H-pyrrolo[1,2-b]pyrazol-3-yl)-5-fluoropyridin-2-yl)cyclohexane-1-carboxamide.

The compounds of Formula (I) are useful for their ability to inhibit CDK9 activity. The compounds are also useful for the treatment of cancer in a patient. In accordance with those aspects of the invention compounds of Formula I, or a pharmaceutically acceptable salt thereof, may be administered to a patient suffering from a cancer such as hematological malignancies including acute myeloid leukemia, multiple myeloma, chronic lymphocytic leukemia, diffuse large B cell lymphoma, Burkitt's lymphoma, follicular lymphoma and solid tumors such as breast cancer, lung cancer, neuroblastoma and colon cancer.

The compounds of Formula (I) have been shown to inhibit CDK9 activity as demonstrated by an assay based on the assay description below. Although the pharmacological properties of the compounds of the Formula (I) may vary with structural change, typical compounds of the Formula (I) possess CDK9 inhibitory activity at $IC_{50}$ concentrations (concentrations to achieve 50% inhibition) or doses at a level below 10 μM.

CDK9 Kinase Assay

ATP Concentration at Km

Activity of CDK9 was determined in-vitro using a mobility shift assay on a Caliper LC3000 reader (Caliper/PerkinElmer), which measures fluorescence of a phosphorylated and unphosphorylated fluorescent peptide substrate and calculates a ratiometric value to determine percent turnover. Phosphorylation of the peptide in the presence and absence of the compound of interest was determined. Enzyme/substrate/adenosine triphosphate (ATP) mix (3 nM CDK9/CycT1, 6 μM ATP, 1.5 μM CDK9 peptide substrate (FITC-X-GSRTPMY-NH$_2$ (X: epsilon aminocaproic acid)), 50 mM HEPES (pH7.2), 1 mM dithiothreitol, 0.01% tween 20, 50 μg/mL bovine serum albumin, (final assay concentration)) (5 μl) was preincubated with 2 μl of compound for 15 minutes at 25° C. Reactions were initiated with 5 μl of 24 mM MgCl$_2$ (10 mM final assay concentration) in buffer (50 mM HEPES (pH7.2), 1 mM dithiothreitol, 0.01% tween 20, 50 μg/mL bovine serum albumin, (final assay concentration) and incubated at 25° C. for 90 minutes and reactions were stopped by addition of 5 μl of Stop mix consisting of 65 mM HEPES (pH7.2), 35.5 mM EDTA, 0.227% Coatin Reagent 3 (Caliper/PerkinElmer), and 0.003% Tween. Phosphorylated and unphosphorylated substrate was detected by a Caliper LC3000 reader (Caliper/PerkinElmer) in the presence of separation buffer consisting of 100 mM HEPES (pH7.2), 15.8 mM EDTA, 0.1% Coatin Reagent 3 (Caliper/PerkinElmer), 0.015% Brij-35, 5% DMSO, and 5.6 mM $MgCl_2$. CDK9 enzyme was acquired from Carna Biosciences (Catalogue number 04-110), the CDK9 peptide substrate was acquired from Intonation (Boston, Mass.; Custom-made).

$IC_{50}$ values were calculated using standard curve fitting methods, with the maximum signal being defined as the turnover from the inhibited reaction at 83.3 mM EDTA and the minimum signal being defined as the turnover from the reaction at 0.83% DMSO.

High ATP Concentration

High ATP assays were run the same way with the following modifications: the final assay concentration of CDK9 was 1.5 nM and the final assay concentration of ATP was 5 mM.

MCF7 pSer2 RNAPII MOA Assay

This is an immunofluorescence assay to determine the effect of CDK9 inhibitors on phosphorylation of RNA Polymerase II (RNAPII) at the Ser2 site in the breast cancer cell line, MCF7. On day one, 2500 MCF7 cells/well were seeded in 30 µl of growth media (RPMI+10% FBS+1% L-Glu+P/S) in 384-well black-wall clear-bottom plates, incubate plates overnight at 37° C. incubator. On the second day, the cells were treated with CDK9 inhibitors (7 point dose response ranging from 3 µM to 0.004 µM) using an ECHO liquid handler (Labcyte). After 6-hr treatment at 37° C. incubator, the cells were fixed with 30 µl/well 7.4% paraformaldehyde for 15 min at room temperature; the cells were washed twice with PBS, then permeabilized with 0.3% Triton X/PBS for 5 min at room temperature. After washing cells with PBS, the cells were incubated with 1:2000 diluted Anti-Ser2 Phospho-RNA pol II antibody (Covance MMS-129R) in 3% FBS/0.1% PBST overnight at 4° C. On the next day, the cells were washed twice with 0.1% PBST, then incubated with 1:1000 diluted Alexa Fluor 488 Goat-anti-mouse antibody (Life Technologies A-11001) and 1:4000 diluted DAPI at room temperature in dark. After one hour incubation, the cells were washed twice with 0.1% PBST, and once with PBS. The plates where sealed and read on an Acumen eX3 microplate cytometer (TTP Labtech) to assess phosphorylation level in each well. The $IC_{50}$ values were calculated using GeneData analysis software (DMSO control as maximum and 11 µM Dinaciclib control as minimum).

MV411 Caspase Activity Assay

This is a cell assay to measure the induction of caspase activity in the acute myeloid leukemia cell line, MV411 after 6-hr treatment with CDK9 inhibitors. On the first day, 3000 MV411 cells/well were seeded in 5 µl of growth media (IMDM+10% FBS+2% L-Glu+P/S) in 384-well white plates, incubate plates in 37° C. incubator overnight. On the second day, the cells were treated with CDK9 inhibitors by ECHO (10 point dose response ranging from 31.5 µM down to 0.001 µM). After 6 hour incubation in 37° C. incubator, 25 µl of Caspase-Glo 3/7 reagent (Promega) per well was added into each well, and plates were incubated at room temperature for 30 min in dark. The plates were read on an Infinite M200 microplate reader (Tecan) with a 100 ms integration time. $EC_{50}$ values were calculated using GeneData analysis software (DMSO control as Min and 11 µM Dinaciclib control as Max).

Table I provides data for the assays.

TABLE I

| Example | CDK9 ATP conc. at Km ($IC_{50}$, µM) | CDK9 High ATP conc. ($IC_{50}$, µM) | p-Ser 2 RNAPII ($IC_{50}$, µM) | MV4-11 Caspase Activity ($IC_{50}$, µM) |
| --- | --- | --- | --- | --- |
| 1 | 0.0491 | 4.5 | 1.539 | 1.777 |
| 2 | <0.003 | 0.040 | 0.13 | 0.12 |
| 3 | <0.003 | 0.21 | 0.52 | 0.44 |
| 4 | 0.003 | 0.17 | 0.22 | 0.28 |
| 5 | <0.004 | 0.27 | 0.26 | 0.16 |
| 6 | 0.008 | 0.75 | 0.46 | 0.63 |
| 7 | 0.008 | 0.69 | 1.45 | 1.181 |
| 8 | <0.003 | 0.12 | 0.69 | 0.256 |
| 9 | 0.039 | 2.5 | >3 | 4.089 |
| 10 | 0.005 | 0.217 | 0.55 | 0.333 |
| 11 | 0.011 | 1.20 | 2.7 | 1.934 |
| 12 | 0.005 | 0.35 | 0.83 | 0.701 |
| 13 | 0.006 | 0.24 | 0.82 | 0.914 |
| 14 | <0.003 | <0.004 | 0.023 | 0.014 |
| 15 | 0.005 | 0.35 | 1.3 | 0.669 |
| 16 | <0.003 | 0.028 | 0.15 | 0.10 |
| 17 | 0.004 | 0.036 | 0.207 | 0.14 |
| 18 | <0.003 | 0.014 | 0.122 | 0.071 |
| 19 | <0.003 | <0.003 | 0.013 | 0.011 |
| 20 | <0.003 | <0.003 | 0.01 | 0.014 |
| 21 | <0.003 | <0.003 | <0.007 | 0.013 |
| 22 | <0.003 | 0.011 | 0.036 | 0.054 |
| 23 | <0.003 | <0.003 | 0.006 | 0.012 |
| 24 | <0.003 | 0.004 | 0.011 | 0.015 |
| 25 | <0.003 | 0.004 | 0.025 | 0.029 |
| 26 | <0.003 | 0.093 | 0.122 | 0.152 |
| 27 | <0.003 | 0.025 | 0.044 | 0.038 |
| 28 | 0.036 | 4.714 | >3.000 | 6.599 |
| 29 | 0.063 | 7.543 | >2.631 | 7.22 |
| 30 | 0.007 | 0.606 | 1.245 | 1.054 |
| 31 | <0.003 | 0.012 | 0.036 | 0.09 |
| 31a | <0.003 | 0.016 | 0.17 | 0.177 |
| 31b | 0.036 | 2.645 | 1.8 | |
| 32 | <0.003 | 0.017 | 0.055 | 0.136 |
| 33 | <0.003 | 0.019 | 0.057 | 0.171 |
| 34 | <0.003 | 0.029 | 0.107 | 0.188 |
| 35 | <0.003 | 0.023 | 0.04 | 0.125 |
| 36 | <0.003 | 0.039 | 0.038 | 0.104 |
| 37 | <0.003 | 0.038 | 0.149 | 0.177 |
| 38 | <0.003 | 0.028 | 0.123 | 0.139 |
| 39 | <0.003 | 0.062 | 0.147 | 0.145 |
| 40 | <0.003 | 0.028 | 0.057 | 0.067 |
| 41 | <0.003 | 0.027 | 0.076 | 0.077 |
| 42 | <0.003 | 0.026 | 0.036 | 0.092 |
| 43 | 0.007 | 0.287 | 0.307 | 0.416 |
| 44 | <0.003 | 0.008 | 0.048 | 0.039 |
| 45 | <0.003 | <0.004 | 0.012 | 0.008 |
| 46 | <0.003 | <0.004 | 0.009 | 0.012 |
| 47 | <0.003 | 0.022 | 0.04 | 0.074 |
| 48 | <0.003 | 0.003 | 0.04 | 0.015 |
| 49 | 0.039 | 4.396 | >2.867 | 7.977 |
| 50 | <0.003 | 0.005 | 0.019 | 0.026 |
| 51 | <0.003 | <0.003 | 0.01 | 0.015 |
| 51a | <0.003 | 0.148 | 0.292 | 0.228 |
| 52 | <0.003 | 0.004 | | |
| 53 | <0.003 | <0.003 | 0.012 | 0.013 |
| 54 | 0.01 | 0.777 | 0.455 | 0.431 |
| 55 | <0.003 | <0.003 | 0.007 | 0.01 |
| 56 | <0.003 | 0.004 | 0.029 | 0.022 |
| 57 | <0.003 | 0.004 | 0.028 | 0.053 |
| 58 | <0.003 | 0.041 | 0.017 | 0.076 |
| 59 | 0.051 | 6.819 | >2.435 | 4.839 |
| 60 | <0.003 | 0.017 | 0.049 | 0.068 |
| 61 | 0.215 | 21.208 | >3.000 | >31.500 |
| 62 | 0.004 | 0.169 | 0.333 | 0.615 |
| 63 | <0.003 | 0.051 | 0.104 | 0.159 |
| 64 | <0.003 | 0.007 | 0.045 | 0.043 |
| 65 | <0.003 | <0.004 | 0.037 | 0.048 |
| 66 | <0.003 | 0.023 | 0.092 | 0.183 |
| 67 | <0.003 | 0.019 | 0.062 | 0.099 |
| 68 | <0.003 | 0.053 | 0.131 | 0.166 |
| 69 | 0.005 | 0.246 | 0.193 | 0.792 |

TABLE I-continued

| Example | CDK9 ATP conc. at Km (IC$_{50}$, µM) | CDK9 High ATP conc. (IC$_{50}$, µM) | p-Ser 2 RNAPII (IC$_{50}$, µM) | MV4-11 Caspase Activity (IC$_{50}$, µM) |
|---|---|---|---|---|
| 70 | <0.003 | 0.02 | 0.073 | 0.107 |
| 71 | 0.016 | 1.722 | >2.348 | 4.828 |
| 72 | 0.003 | 0.111 | 0.36 | 0.4 |
| 73 | <0.003 | 0.039 | 0.218 | 0.447 |
| 74 | <0.003 | 0.039 | 0.192 | 0.281 |
| 75 | <0.003 | 0.029 | 0.067 | 0.111 |
| 76 | <0.003 | 0.009 | 0.038 | 0.036 |
| 77 | 0.004 | 0.213 | 0.338 | 0.543 |
| 78 | <0.003 | 0.06 | 0.72 | 1.227 |
| 78a | <0.003 | 0.085 | >2.628 | 7.13 |
| 79 | <0.003 | <0.003 | 0.01 | 0.015 |
| 80 | 0.004 | 0.135 | 0.247 | 0.318 |
| 81 | 0.008 | 0.554 | 0.665 | 0.896 |
| 82 | <0.004 | 0.022 | 0.174 | 0.124 |
| 82a | 0.004 | 0.139 | >2.337 | 2.256 |
| 83 | <0.003 | 0.025 | 0.061 | 0.073 |
| 84 | 0.028 | 2.134 | >1.947 | 2.518 |

In one aspect, there is provided a compound of Formula (I), or a pharmaceutically acceptable salt thereof, for use as a medicament.

In another aspect, there is provided the use of a compound of Formula (I), or a pharmaceutically acceptable salt thereof, in the manufacture of a medicament for the treatment or prophylaxis of at least one of: hematological malignancies such as acute myeloid leukemia, multiple myeloma, chronic lymphocytic leukemia, diffuse large B cell lymphoma, Burkitt's lymphoma, follicular lymphoma and solid tumors such as breast cancer, lung cancer, neuroblastoma and colon cancer.

In another aspect, there is provided the use of a compound of Formula (I), or a pharmaceutically acceptable salt thereof, in the manufacture of a medicament for the treatment of cancer.

In another aspect, there is provided the use of a compound of Formula (I), or a pharmaceutically acceptable salt thereof, in the manufacture of a medicament for the production of an anti-proliferative and/or pro-apoptotic effect in a warm-blooded animal such as man.

In another aspect, there is provided the use of a compound of Formula (I), or a pharmaceutically acceptable salt thereof, in the manufacture of a medicament for the production of a CDK9 inhibitory effect in a warm blooded animal such as man.

In another aspect, there is provided a method for the treatment or prophylaxis of at least one of hematological malignancies such as acute myeloid leukemia, multiple myeloma, chronic lymphocytic leukemia, diffuse large B cell lymphoma, Burkitt's lymphoma, follicular lymphoma and solid tumors such as breast cancer, lung cancer, neuroblastoma and colon cancer.

In another aspect, there is provided a method for producing an anti-proliferative and/or pro-apoptotic effect in a warm-blooded animal such as man, said method comprising administering to said animal an effective amount of a compound of Formula (I), or a pharmaceutically acceptable salt thereof.

In another aspect, there is provided a method for producing a CDK9 inhibitory effect in a warm-blooded animal such as man, said method comprising administering to said animal an effective amount of a compound of Formula (I), or a pharmaceutically acceptable salt thereof.

In another aspect, there is provided a method for treating cancer in a warm-blooded animal such as man, said method comprising administering to said animal an effective amount of a compound of Formula (I), or a pharmaceutically acceptable salt thereof.

In another aspect, there is provided a compound of Formula (I), or a pharmaceutically acceptable salt thereof, for use in the treatment of at least one of: hematological malignancies such as acute myeloid leukemia, multiple myeloma, chronic lymphocytic leukemia, diffuse large B cell lymphoma, Burkitt's lymphoma, follicular lymphoma and solid tumors such as breast cancer, lung cancer, neuroblastoma and colon cancer.

In another aspect, there is provided a pharmaceutical composition comprising a compound of Formula (I), or a pharmaceutically acceptable salt thereof, and at least one pharmaceutically acceptable carrier, diluent, or excipient.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients well known in the art. Thus, compositions intended for oral use may contain, for example, one or more coloring, sweetening, flavoring and/or preservative agents.

Suitable pharmaceutically acceptable excipients for a tablet formulation include, for example, inert diluents such as lactose, sodium carbonate, calcium phosphate or calcium carbonate; granulating and disintegrating agents such as corn starch or algenic acid; binding agents such as starch; lubricating agents such as magnesium stearate, stearic acid or talc; preservative agents such as ethyl or propyl p-hydroxybenzoate; and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form or in the form of nano or micronized particles together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives such as ethyl or propyl p-hydroxybenzoate; anti-oxidants such as ascorbic acid; coloring agents; flavoring agents; and/or sweetening agents such as sucrose, saccharine or aspartame.

Oily suspensions may be formulated by suspending the active ingredient in a vegetable oil such as arachis oil, olive oil, sesame oil or coconut oil or in a mineral oil such as liquid paraffin. The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions of the invention may also be in the form of oil-in-water emulsions. The oily phase may be a vegetable oil, such as olive oil or *arachis* oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 4 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

As stated above the size of the dose required for the therapeutic or prophylactic treatment of a particular disease state will necessarily be varied depending on the host treated, the route of administration and the severity of the illness being treated. A daily dose in the range of 0.1-50 mg/kg may be employed. Accordingly, the optimum dosage may be determined by the practitioner who is treating any particular patient.

The compounds of the invention can be further administered in combination with a therapeutically effective amount of one or more agents to treat a cancer, where examples of the agents include, such as radiation, alkylating agents, angiogenesis inhibitors, antibodies, antimetabolites, antimitotics, antiproliferatives, antivirals, aurora kinase inhibitors, cell death activators (for example, inhibitors of Bcl-2, Bcl-xL, Bcl-w, Bfl-1, or, Mcl-1), activators of death receptor pathway, Bcr-Abl kinase inhibitors, BET (bromodomain) inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs (dual variable domain antibodies), leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase inhibitors, proteosome inhibitors, purine analogs, pyrimidine analogs, receptor tyrosine kinase inhibitors, etinoids/deltoids plant alkaloids, small inhibitory ribonucleic acids (siRNAs), topoisomerase inhibitors, ubiquitin ligase inhibitors, and the like, and in combination with one or more of these agents.

Alkylating agents include altretamine, AMD-473, AP-5280, apaziquone, bendamustine, brostallicin, busulfan, cisplatin, carboplatin, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, nitrosoureas, oxalipiatin, ranimustine, temozolomide, thiotepa, TREANDA® (bendamustine), treosulfan, rofosfamide and the like.

Angiogenesis inhibitors include endothelial-specific receptor, (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGER) inhibitors, ALK inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, pemextred, raltitrexed, Ribavirin, triapine, trimetrexate; S-1, tiazofurin, tegafur, TS-1, vidarabine, UFT and the like.

Bcl-2 protein inhibitors include ABT-199, AT-101 ((---) gossypol), GENASENSE® (G3139 or oblimersen (Bcl-2-targeting anti sense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide (ABT-737), N-(4-(4-((2-(4-chlorophenyl)-5,5-dimethyl-1-cyclohex-1-en-1-yl)methyl)piperazin-1-yl)benzoyl)-4-(1R)-3-(morpholin-4-yl)-1-((phenylsulfanyl)methyl)propyl) amino)-3-((trifluoromethyl)sulfonyl)benzenesulfonamide (ABT-263), GX-070 (obatoclax) and the like.

Bromodomain inhibitors include I-BET 762, OTX-015, CPI-203, LY294002 and the like.

CDK inhibitors include BMI-1040, BMS-032, BMS-387, CVT-2584, flavopyridol, GPC-286199, MCS-5A, PD0332991, PHA-690509, seliciclib (CYC-202; R-roscovitine), ZK-304709 and the like.

EGFR inhibitors include EGFR antibodies, ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib), AZD9291, and the like.

ALK inhibitors include crizotinib, ceritinib, and the like.

ErbB2 receptor inhibitors include CP-724-714, C1-1033 (canertinib), HERCEPTIN® (trastuzumab), TYKERB® (lapatinib), OMINITARG® (2C4, petuzumab), TAK-165, GW-572016 (ionafarnib), GW-282974, EKB-569, P1-166, dHER2 (HER2 vaccine), APC-8024 (HER-2 vaccine), anti-HER/2neu bispecific antibody, B7.her2IgG3, as HER2 bifunctional bispecific antibodies, mAB AR-209, mAB 2B-1 and the like.

Antibody drug conjugates include anti-CD22-MC-MMAF, anti-CD22-MC-MMAE, anti-CD22-MCC-DM1, CR-011-vcMMAE, PSMA-ADC, MEDI-547, SGN-19Am SGN-35, SGN-75 and the like.

Kinesin inhibitors include Eg5 inhibitors such as AZD4877, ARRY-520; CENPE inhibitors such as GSK923295A and the like.

MEK inhibitors include ARMY-142886, ARRY-438162, PD-325901, PD-98059, selumitinib, and the like.

Platinum chemotherapeutics include cisplatin, ELOXATIN® (oxaliplatin) eptapatin, lobaplatin, nedaplatin, PARAPLATIN® (carboplatin), satraplatin, picoplatin and the like.

VEGFR inhibitors include AVASTIN® (bevacizumab), ABT-869, NEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, 1M-862, MACUGEN (pegaptamib), NEXAVAR® (sorafenib, BAY-43-9006), pazopanib (GAN-786034), vatalanib (PTK-787, ZK-222584), SUTENT® (sunitinib, SU-11248), VEGF trap, ZACTDAA™ (vandetanib, ZD-6474), GA101, ofatumumab, ABT-806 (mAb-806), ErbB3 specific antibodies, BSG2 specific antibodies, DLL4 specific antibodies and C-met specific antibodies, and the like.

Antitumor antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirbucin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Inhibitors of DNA repair mechanisms such as CHK kinase; DNA-dependent protein kinase inhibitors; inhibitors of poly (ADP-ribose) polymerase (PARP inhibitors) including ABT-888 (veliparib), olaparib, KU-59436; AZD-2281, AG-014699, BSI-201, BGP-15, INO-1001, ONO-2231 and the like; and Hsp90 inhibitors such as tanespimycin and retaspimycin.

Proteasome inhibitors include VELCADE® (bortezomib), carfilzomib, MG132, NP1-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-n1, combinations thereof and the like. Other agents include ALFAFERONE®. (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lows Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Pyrimidine analogs include cytarabine (ara C or Arabinoside C), cytosine arabinoside, doxifluridine, FLUDARA® (fludarabine), 5-FU (5-fluorouracil), floxuridine. GEMZAR® (gemcitabine), TOMUDEX® (ratitrexed), TROXATYL™ (triacetyluridine troxacitabine) and the like.

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Additionally, compounds having Formula (I) may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MFVACOR® (lovastatin), AMPLIGEN® (poly I:poly $Cl_2U$, a synthetic RNA), APTOSYN® (exisulind), ARENA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexia (tumor necrosis factor), canvaxin (vaccine), CEAVAC® (cancer vaccine), CELEUK® (celmoleukin), CEPLENE® (histamine dihydrochloiide), CERVARIX® (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EP0906 (epithilone B), GARDASH® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (H Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (*Streptomyces staurospores*), talabostat (PT100), TARGRETIN® (bexarotene), TAXOPREXIN® (DHA-paclitaxel), TELCYTA® (canfosfamide, MK286), temilifene, TEMODAR® (temozolomide), tesmilifene, thalidomide, THERATOPE® (Sin-KM), thymitaq (2-amino-3, 4-dihydro-6-methyl-4-oxo-5-(4-pyridylthio)quinazoline dihydrochloride), TNFERADE® (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126 ZINECARD® (dexrazoxane), ZOMETA® (zolendronic acid), zorubicin and the like.

Herein, where the term "combination" is used it is to be understood that this refers to simultaneous, separate or sequential administration. In one embodiment of the invention "combination" refers to simultaneous administration. In another embodiment of the invention "combination" refers to separate administration. In a further embodiment of the invention "combination" refers to sequential administration. Where the administration is sequential or separate, the delay in administering the second component should not be such as to lose the beneficial effect of the combination. Such combination products employ the compounds of this invention, or pharmaceutically acceptable salts thereof, within the dosage range described hereinbefore and the other pharmaceutically-active agent within its approved dosage range. The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

In any of the above-mentioned pharmaceutical composition, process, method, use, medicament, and manufacturing features of the instant invention, any of the alternate embodiments of the compounds of the invention described herein also apply.

In another aspect of the invention compounds of Formula (I) are prepared in accordance with the following general routes.

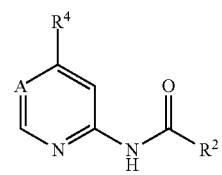

(I)

Route A

Some compounds of Formula (I) may be obtained from another compound of Formula (I); for example, if containing an amino group, by acylation (conditions well known in the art), where A, $R^2$, and $R^4$ are as defined for formula (I).

Note that suitable protecting groups may be used in any routes such as those well known in the art: for instance, for amino: t-butoxycarbonyl or (trimetylsilyl)ethoxymethyl (SEM); for hydroxyl: tert-butyldimethylsilyl or tetrahydropyran-2-yl. Deprotection conditions are well known in the art.

Route B

Other compounds of Formula (I) may be prepared by the reaction of a compound of Formula (II):

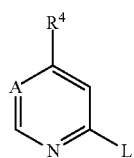

(II)

where L is a halogen atom (for example chloro) or a triflate group with a compound of formula (III):

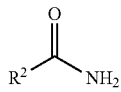
(III)

The reaction may be performed under standard conditions well known to those skilled in the art, for example in the presence of a palladium source (for example tetrakis(triphenylphosphine)palladium(0) or palladium(II) acetate), optionally a phosphine ligand (for example Xantphos), and a suitable base (for example cesium carbonate).

Compound of Formula (II) may be prepared by the reaction of a compound of Formula (IV)

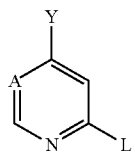
(IV)

and a compound of Formula (V) $R^4$-L

Y is a boronic acid, boronic ester or potassium trifluoroborate group (for example boronic acid, boronic acid pinacol ester, or potassium trifluoroborate) and L is a halogen atom (for example chloro or bromo) or a triflate group. The reaction may be performed under standard conditions well known to those skilled in the art, for example in the presence of a palladium source and a phosphine ligand (for example tetrakis(triphenylphosphine)palladium(0), [1,1'-bis(diphenylphosphino)ferrocene]dichloropalladium(II), also known as $Pd(dppf)Cl_2$, and a suitable base (for example cesium carbonate or potassium phosphate)).

Alternatively, Compound of Formula (II) may be prepared by the reaction of a compound of Formula (XIV)

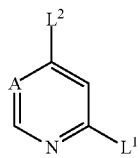
(XIV)

and a compound of Formula (IX): $R^4$—Y

Y is a boronic acid, boronic ester or potassium trifluoroborate group (for example boronic acid, boronic acid pinacol ester, or potassium trifluoroborate), $L^1$ and $L^2$ are a halogen atom or a triflate group, where $L^1$ is less reactive than $L^2$ during the coupling reaction, for example where $L^1$ is chloro and $L^2$ is iodo. The reaction may be performed under standard conditions well known to those skilled in the art, for example in the presence of a palladium source and a phosphine ligand (for example $2^{nd}$ Generation XPhos Precatalyst, and a suitable base, for example potassium phosphate).

Alternatively, Compound of Formula (II) may be prepared by the reaction of a compound of Formula (XIV) and a compound of Formula (XII): $R^4$—H, where $L^1$ and $L^2$ are a halogen atom or a triflate group, where $L^1$ is less reactive than $L^2$ during the coupling reaction, for example where $L^1$ is chloro and $L^2$ is iodo, by a "C—H activation" reaction, for example as described in Example Intermediate 50.

Route C

Some compounds of Formula (I) may for example be prepared by the reaction of a compound of Formula (VI)

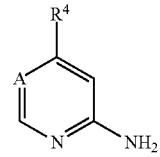
(VI)

with a compound of Formula (VII):

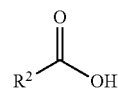
(VII)

Suitable coupling agents for this reaction include for example, 1-chloro-N,N,2-trimethylprop-1-en-1-amine, O-(7-azabenzotriazol-1-yl)-N,N,N',N'-tetramethyluronium hexafluorophosphate also known as HATU, TBTU (2-(1H-benzo[d][1,2,3]triazol-1-yl)-1,1,3,3-tetramethylisouronium tetrafluoroborate), 1-(3-dimethylaminopropyl)-3-ethylcarbodiimide hydrochloride ion or 1-propanephosphonic anhydride ($T_3P$), preferably 1-chloro-N,N,2-trimethylprop-1-en-1-amine or 1-propanephosphonic anhydride ($T_3P$).

The reaction is conveniently carried out in the presence of a suitable base. A suitable base is, for example, an organic amine base such as, for example, pyridine, 2,6-lutidine, collidine, 4-dimethylaminopyridine, triethylamine, N-methylmorpholine, diazabicyclo[5.4.0]undec-7-ene, diisopropylethyl amine, or, for example, an alkali or alkaline earth metal carbonate or hydroxide, for example sodium carbonate, potassium carbonate, calcium carbonate, sodium hydroxide or potassium hydroxide;

Compound of Formula (VI) may be prepared by the reaction of a compound of Formula (VIII)

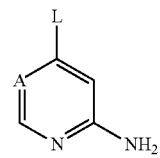
(VIII)

and a compound of Formula (IX): $R^4$—Y

L is a halogen atom (for example iodo or bromo) or a triflate group.

Y is a boronic acid, boronic ester or potassium trifluoroborate group (for example boronic acid, boronic acid pinacol ester, or potassium trifluoroborate)

The reaction may be performed under standard conditions well known to those skilled in the art, for example in the presence of a palladium source and a phosphine ligand, (for example tetrakis (triphenylphosphine)palladium(0), [1,1'-bis(diphenylphosphino)ferrocene]dichloropalladium(II) also known as $Pd(dppf)Cl_2$), and a suitable base (for example cesium carbonate or potassium carbonate).

Compound of Formula (VIII) may be prepared by the reaction of a compound of Formula (X) by reaction with ammonia (as described in Examples 2 and 86)

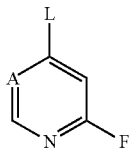

(X)

L is a halogen atom (for example iodo or bromo) or a triflate group.

It is understood that a compound of Formula (VIII) may transformed into another compound of Formulae (VIII), for example as illustrated in Example 39 (preparation of 6-amino-4-chloronicotinonitrile).

Route D

Other compounds of Formula (I) may for example be prepared by the reaction of a compound of Formula (XI) with a compound of Formula (IX) $R^4$—Y:

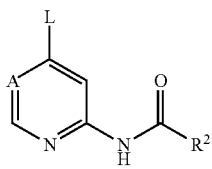

(XI)

L is a halogen atom (for example iodo, bromo or chloro) or a triflate group.

Y is a boronic acid, boronic ester or potassium trifluoroborate group (for example boronic acid, boronic acid pinacol ester, or potassium trifluoroborate)

The reaction may be performed under standard conditions well known to those skilled in the art, for example in the presence of a palladium source and a phosphine ligand (for example: $2^{nd}$ Generation XPhos Precatalyst also known as chloro(2-dicyclohexylphosphino-2',4',6'-triisopropyl-1,1'-biphenyl)[2-(2'-amino-1,1'-biphenyl)]palladium(II), or [1,1'-bis(diphenylphosphino)ferrocene]dichloropalladium (II)), and a suitable base (for example potassium phosphate or cesium carbonate).

Alternatively, Compounds of Formula (I) may for example be prepared by the reaction of a compound of Formula (XI) with a compound of Formula (XII) $R^4$—H, by a "C—H activation" reaction, as described in Example 7 or 22.

Compound of Formula (XI) may be prepared by the reaction of a compound of Formula (VIII)

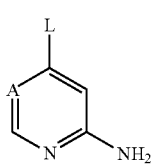

(VIII)

L is a halogen atom (for example iodo, bromo or chloro) or a triflate group.

with a compound of Formula (VII):

(VII)

Suitable coupling agents for this reaction include for example, O-(7-azabenzotriazol-1-yl)-N,N,N',N'-tetramethyluronium hexafluorophosphate, HATU, TBTU (2-(1H-benzo[d][1,2,3]triazol-1-yl)-1,1,3,3-tetramethylisouronium tetrafluoroborate) or 1-(3-dimethylaminopropyl)-3-ethylcarbodiimide hydrochloride ion, preferably 1-chloro-N,N,2-trimethylprop-1-en-1-amine and 1-propanephosphonic anhydride ($T_3P$).

The reaction is conveniently carried out in the presence of a suitable base. A suitable base is, for example, an organic amine base such as, for example, pyridine, 2,6-lutidine, collidine, 4-dimethylaminopyridine, triethylamine, N-methylmorpholine, diazabicyclo[5.4.0]undec-7-ene, diisopropylethyl amine, or, for example, an alkali or alkaline earth metal carbonate or hydroxide, for example sodium carbonate, potassium carbonate, calcium carbonate, sodium hydroxide or potassium hydroxide. It is understood that any compounds of Formulae (XI) can be transformed in another compound of Formulae (XI), for example by acylation of an amino group as in Example 39 or 75.

Route E

Some compounds of Formula (I) may for example be prepared by the reaction of a compound of Formula (XIII) with a compound of Formula (V)

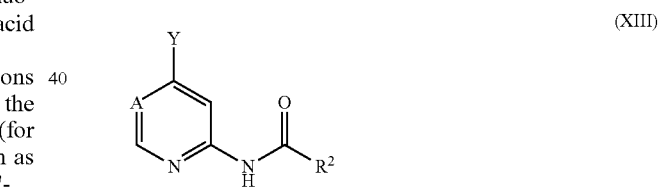

(XIII)

Y is a boronic acid, boronic ester or potassium trifluoroborate group (for example boronic acid, boronic acid pinacol ester, or potassium trifluoroborate)

L is a halogen atom (for example iodo or bromo) or a triflate group.

The reaction may be performed under standard conditions well known to those skilled in the art, for example in the presence of a palladium source and a phosphine ligand (for example tetrakis (triphenylphosphine)palladium(0), [1,1'-bis(diphenylphosphino)ferrocene]dichloropalladium(II) also known as Pd(dppf)$Cl_2$, and a suitable base (for example cesium carbonate or potassium phosphate).

Compounds of Formula (XIII) may for example be prepared by the reaction of a compound of Formula (XI), as described in Example 16.

Route F

Some compounds of Formula (I) may for example be prepared by a "cyclisation" reaction of a compound of Formula (XV):

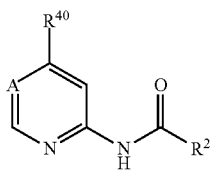

where $R^{40}$ is

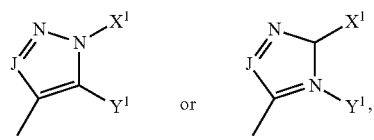

wherein $X^1$ and $Y^1$ are defined such as (XV) is the precursor in the cyclisation reaction, with the proviso that $X^1$ and $Y^1$ together with the atoms to which they are attached do not form a ring. For example, $X^1$ or $Y^1$ can be hydrogen.

The "cyclisation" reaction may be performed under standard conditions well known to those skilled in the art. As an illustration, Examples 78 and 82 describe a particular example of such a "cyclisation" reaction.

Compounds of Formula (XV) may be obtained by analogous routes to routes A to E described for making compounds of Formula (I). As an example, by analogy with route D, compounds of Formula (XV) may be prepared by the reaction of a compound of Formula (XI) with a compound of Formula (XVI): $R^{40}$—Y:

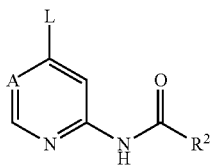

L is a halogen atom (for example iodo, bromo or chloro) or a triflate group.

Y is a boronic acid, boronic ester or potassium trifluoroborate group (for example boronic acid, boronic acid pinacol ester, or potassium trifluoroborate)

Alternatively, Compounds of Formula (XV) may for example be prepared by the reaction of a compound of Formula (XI) with a compound of Formula (XVII) $R^{40}$—H, by a "C—H activation" reaction.

The reaction may be performed under standard conditions well known to those skilled in the art, as described in Route D Compounds of formula (IX) $R_4$—Y, where Y is a boronic acid, boronic ester or potassium trifluoroborate group (for example boronic acid, boronic acid pinacol ester, or potassium trifluoroborate), are key intermediates in some of synthetic routes towards compound of formula (I).

Methods to synthetise a compound of formula (IX) from compound of formula (V) $R_4$-L, where L is a halogen atom (for example iodo, bromo or chloro) or a triflate group, include metallation/borylation reactions, as illustrated by Example 23 and 85, and palladium-catalysed borylations, as illustrated by Example 14.

Compound of formula (V) $R_4$-L are typically accessed from compound of formula (XII) $R_4$—H, by a halogenation reaction.

Compounds of formula (IX) $R_4$—Y, where Y is a boronic acid, boronic ester or potassium trifluoroborate group (for example boronic acid, boronic acid pinacol ester, or potassium trifluoroborate) may also be accessed directly from compounds of formula (XII) $R_4$—H, by a 'C—H activation' reaction, as illustrated in Example 49. Typical conditions use an iridium catalyst (typically methoxy(cyclooctadiene)iridium(I) dimer) and a ligand (typically 4,4'-di-tert-butyl-2,2'-dipyridyl or 3,4,7,8-tetramethyl-1,10-phenanthroline) with a source of boron (typically 4,4,5,5-tetramethyl-1,3,2-dioxaborolane) in an inert solvent (typically THF or dioxane) at around 50° C. to 90° C.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminum trichloride) under Friedel Crafts conditions; the introduction of an alkyl group using an alkyl halide and Lewis acid (such as aluminum trichloride) under Friedel Crafts conditions; and the introduction of a halogen group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or tert-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a tert-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

According to a further aspect of the invention there is provided a pharmaceutical composition which comprises a compound of Formula (I), or a pharmaceutically acceptable salt thereof, as defined herein in association with a pharmaceutically acceptable diluent or carrier.

It is understood that a compound of Formula (I) can be obtained by separation (e.g. chiral separation) from a mixture of compounds of Formula (I); for Examples 9 and 2, 41 and 42, 43 and 14, 59 and 60, 61 and 62, 64 and 65, 68 and 69, 70 and 71, 72 and 73, 79 and 80, 83 and 84.

Some compounds of Formulae (II), (V), (VI), (IX), (XI), (XII), (XIII), (XV), (XVI) and (XVII) are novel.

(1S,3R)-3-(acetamino)cyclohexanecarboxylic acid is a key intermediate in the synthesis of some compounds of Formula (I). The following route (schematic below, described in Example 85), giving access to this key intermediate in an enantiomerically pure form, is novel and useful.

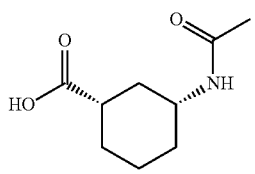

(1S,3R)-3-(acetamino)cyclohexanecarboxylic Acid

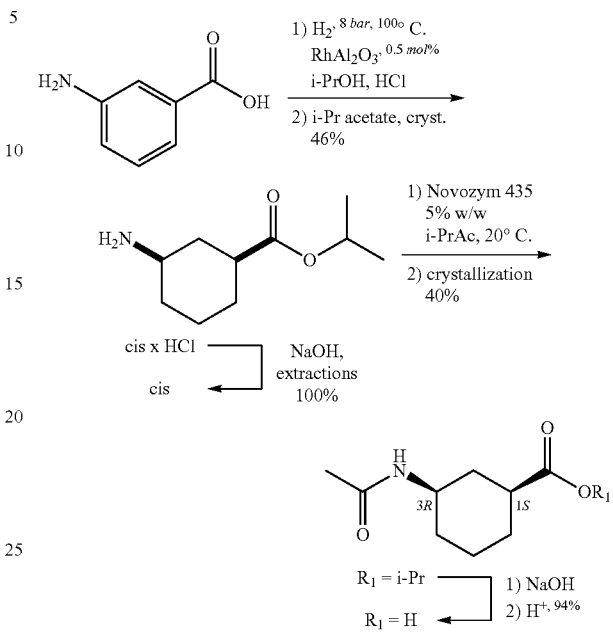

This route is based on the enzymatic enantioselective acylation of isopropyl 3-aminocyclohexylcarboxylate (using Novozym 435) as illustrated below:

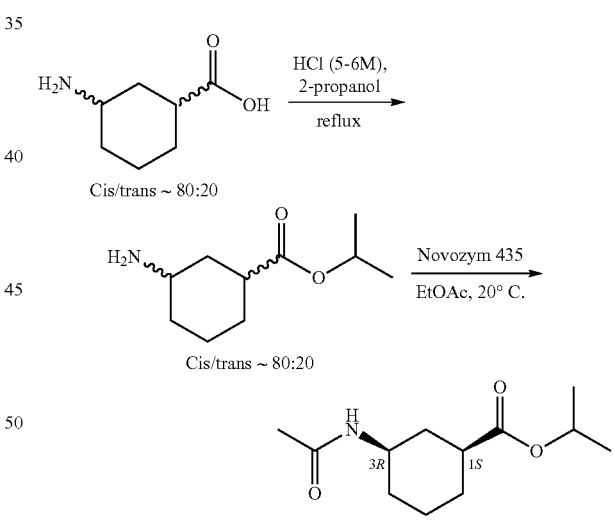

EXAMPLES

Aspects of the present disclosure can be further defined by reference to the following non-limiting examples, which describe in detail preparation of certain compounds and intermediates of the present disclosure and methods for using compounds of the present disclosure. It will be apparent to those skilled in the art that many modifications, both to materials and methods, can be practiced without departing from the scope of the present disclosure.

Unless Stated Otherwise:

(i) operations were carried out at ambient temperature, i.e. in the range 17 to 25° C. and under an atmosphere of an inert gas such as nitrogen unless otherwise stated;

(ii) evaporations were carried out by rotary evaporation or utilising Genevac equipment or a Biotage v10 evaporator in vacuo and work-up procedures were carried out after removal of residual solids by filtration;

(iii) flash chromatography purifications were performed on an automated Teledyne Isco CombiFlash® Rf or Teledyne Isco CombiFlash® Companion® using prepacked RediSep Rf Gold™ Silica Columns (20-40 spherical particles), GraceResolv™ Cartridges (Davisil® silica) or Silicycle cartridges (40-63 μm).

(iv) preparative chromatography was performed on a Gilson prep HPLC instrument with UV collection; alternatively, preparative chromatography was performed on a Waters AutoPurification HPLC-MS instrument with MS- and UV-triggered collection;

(v) chiral preparative chromatography was performed on a Gilson instrument with UV collection (233 injector/fraction collector, 333 & 334 pumps, 155 UV detector) or a Varian Prep Star instrument (2×SD1 pumps, 325 UV detector, 701 fraction collector) pump running with Gilson 305 injection; alternatively, chiral preparative chromatography was performed on a Waters Prep 100 SFC-MS instrument with MS- and UV-triggered collection or a Thar MultiGram III SFC instrument with UV collection.

(vi) yields, where present, are not necessarily the maximum attainable;

(vii) in general, the structures of end-products of the Formula I were confirmed by nuclear magnetic resonance (NMR) spectroscopy; NMR chemical shift values were measured on the delta scale [proton magnetic resonance spectra were determined using a Bruker Avance 500 (500 MHz) or Bruker Avance 400 (400 MHz) instrument]; measurements were taken at ambient temperature unless otherwise specified; the following abbreviations have been used: s, singlet; d, doublet; t, triplet; q, quartet; m, multiplet; dd, doublet of doublets; ddd, doublet of doublet of doublet; dq, double of quartets; dt, doublet of triplets; tt, triplet of triplets; p, pentet; br, broad signal.

(viii) in general, end-products of the Formula I were also characterised by mass spectroscopy following liquid chromatography (LCMS or UPLC); UPLC was carried out using a Waters UPLC fitted with Waters SQ mass spectrometer (Column temp 40, UV=220-300 nm, Mass Spec=ESI with positive/negative switching) at a flow rate of 1 mL/min using a solvent system of 97% A+3% B to 3% A to 97% B over 1.50 min (total runtime with equilibration back to starting conditions etc 1.70 min), where A=0.1% formic acid in water (for acid work) or 0.1% ammonia in water (for base work) B=acetonitrile. For acid analysis the column used was Waters Acquity HSS T3 1.8 μm 2.1×50 mm, for base analysis the column used was Waters Acquity BEH 1.7 μm 2.1×50 mm. Alternatively, UPLC was carried out using a Waters UPLC fitted with a Waters SQ mass spectrometer (Column temp 30, UV=210-400 nm, Mass Spec=ESI with positive/negative switching) at a flow rate of 1 mL/min using a solvent gradient of 2 to 98% B over 1.5 mins (total runtime with equilibration back to starting conditions: 2 min), where A=0.1% formic acid in water and B=0.1% formic acid in acetonitrile (for acid work) or A=0.1% ammonium hydroxide in water and B=acetonitrile (for base work). For acid analysis the column used was a Waters Acquity HSS T3 1.8 μm 2.1×30 mm, for base analysis the column used was a Waters Acquity BEH C18 1.7 μm 2.1×30 mm; LCMS was carried out using a Waters Alliance HT (2795) fitted with a Waters ZQ ESCi mass spectrometer and a Phenomenex Gemini—NX (5 μm×2.1 mm) column at a flow rate of 1.1 mL/min 95% A to 95% B over 4 min with a 0.5 min hold. The modifier was kept at a constant 5% C (50:50 acetonitrile:water 0.1% formic acid) or D (50:50 acetonitrile:water 0.1% ammonium hydroxide depending on whether it was an acidic or basic method. It is understood that, unless specified otherwise, only the most characteristic mass peak is reported, rounded to the lower unit. Typically, when several isotopes of one atom exist, only the lower most common isotope is reported (e.g. $^{35}Cl$, $^{79}Br$, $^{12}C$ . . . )

(ix) ion exchange purification was generally performed using an SCX-2 (Biotage) cartridge.

(x) intermediate purity was assessed by thin layer chromatographic, mass spectral, HPLC (high performance liquid chromatography) and/or NMR analysis;

(xi) Optical rotation is measured in degrees;

(xii) XRPD analysis was performed using a Bruker D4 diffractometer, which is commercially available from Bruker AXS Inc.™ (Madison, Wis.). The XRPD spectra were obtained by mounting a sample (approximately 20 mg) of the material for analysis on a single silicon crystal wafer mount (e.g., a Bruker silicon zero background X-ray diffraction sample holder) and spreading out the sample into a thin layer with the aid of a microscope slide. The sample was spun at 30 revolutions per minute (to improve counting statistics) and irradiated with X-rays generated by a copper long-fine focus tube operated at 40 kV and 40 mA with a wavelength of 1.5406 angstroms (i.e., about 1.54 angstroms). The sample was exposed for 1 second per 0.02 degree 2-theta increment (continuous scan mode) over the range 2 degrees to 40 degrees 2-theta in theta-theta mode. The running time was 31 min, 41 s. The skilled person appreciates that XRPD 2θ values may vary with a reasonable range, e.g., in the range ±0.1° 2θ. The skilled person appreciates that XRPD intensities may vary when measured for essentially the same crystalline form for a variety of reasons including, for example, preferred orientation. Principles of XRPD are described in publications, such as, for example, Giacovazzo, C. et al. (1995), *Fundamentals of Crystallography*, Oxford University Press; Jenkins, R. and Snyder, R. L. (1996), *Introduction to X-Ray Powder Diffractometry*, John Wiley & Sons, New York; and Klug, H. P. & Alexander, L. E. (1974), *X-ray Diffraction Procedures*, John Wiley and Sons, New York. Because the relative intensities are less reliable and instead of numerical values the following definitions are used.

| % Relative Intensity | Definition |
|---|---|
| 25-100 | vs (very strong) |
| 10-25 | s (strong) |
| 3-10 | m (medium) |
| 1-3 | w (weak) |
| <1 | vw (very weak) |

Some additional very weak peaks found in the diffractogram have been omitted.

(xiii) DSC was performed using a TA Instruments model Q1000. A sample (approximately 2 mg) was weighed into an aluminium sample pan and transferred to the DSC. The instrument was purged with nitrogen at 50 mL/min and data collected between 25° C. and 300° C., using a dynamic heating rate of 10° C./min. DSC analysis was performed on samples prepared according to standard methods using a Q SERIES™ Q1000 DSC calorimeter available from TA INSTRUMENTS® (New Castle, Del.). The instrument was purged with nitrogen at 50 mL/min and data collected between 25° C. and 300° C., using a dynamic heating rate of 10° C./minute. Thermal data was analyzed using standard software, e.g., Universal v.4.5A from TA INSTRUMENTS®.

(xiv) Thermogravimetry Analysis (TGA): TGA was performed using a TA Instruments model Q5000. A sample (approximately 5 mg) was placed into an aluminium sample pan and inserted to the TGA furnace. The instrument was purged with nitrogen at 50 mL/min and data collected between 25° C. and 300° C., using a dynamic heating rate of 10° C./min. Thermal data are analyzed using standard software, e.g., Universal v.4.5A from TA INSTRUMENTS®.

(xv) The following abbreviations have been used:
$2^{nd}$ Generation XPhos (or X-Phos) Precatalyst chloro(2-dicyclohexylphosphino-2',4',6'-triisopropyl-1,1'-biphenyl)[2-(2'-amino-1,1'-biphenyl)]palladium(II) $3^{rd}$ Generation RuPhos Precatalyst (2-dicyclohexylphosphino-2',6'-diisopropoxy-1,1'-biphenyl)[2-(2'-amino-1,1'-biphenyl)]palladium(II) methanesulfonate
aq. aqueous
atm atmosphere
BuLi n-butyl lithium
$CDCl_3$ deutero-chloroform
$CD_3OD$ deutero-methanol
CDI carbonyl diimidazole
Conc. concentrated
DCM dichloromethane
DIPEA N,N-diisopropylethylamine
DMA N,N-dimethylacetamide
DMF N,N-dimethylformamide
DMSO dimethyl sulphoxide
DMSO-$d_6$ deutero-dimethyl sulphoxide
dppf 1,1'-bis(diphenylphosphino)ferrocene
DSC differential scanning calorimetry
EtOH ethanol
EtOAc ethyl acetate
HATU 1-[bis(dimethylamino)methylene]-1H-1,2,3-triazolo[4,5-b]pyridinium 3-oxid hexafluorophosphate
h hour(s)
IPA/iPrOH isopropyl alcohol
MeCN acetonitrile
MeOH methanol
MTBE methyl-tert-butyl ether
NBS N-bromosuccinimide
NIS N-iodosuccinimide
NMP N-methylpyrrolidine
$PdCl_2(dppf)$ [1,1'-Bis(diphenylphosphinio)ferrocene]-dichloropalladium(II)
$Pd(P(Cy)_3)_2Cl_2$ Bis(tricyclohexylphosphine)dichloropalladium(II)
r.t. room temperature
SCX/SCX-2 strong cation exchange chromatography
SEM-Cl 2-(trimethylsilyl)ethoxymethyl chloride
SFC supercritical fluid chromatography
$T_3P$® propane phosphonic acid anhydride
TBS/TBDMS tert-butyldimethylsilyl
TBS-Cl tert-butyldimethylsilyl chloride
TEA triethylamine
TFA trifluoroacetic acid
TGA thermogravimetry analysis
THF tetrahydrofuran
TMEDA tetramethylethylenediamine
Xantphos 4,5-bis(diphenylphosphino)-9,9-dimethylxanthene
XRPD X-ray powder diffraction Example 1: (R)—N-(5-chloro-4-(5,6,7,8-tetrahydroimidazo[1,2-a]pyridin-3-yl)pyridin-2-yl)piperidine-3-carboxamide

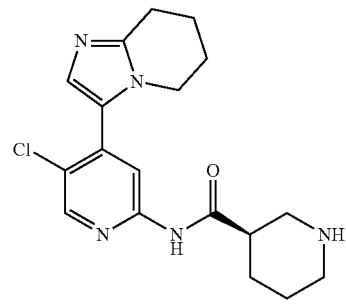 [SMILES: O=C(Nc1cc(-c2cnc3n2CCCC3)c(Cl)cn1)[C@@H]1CCCNC1]

TFA (2 mL, 26.0 mmol) was added dropwise to (R)-tert-butyl 3-((5-chloro-4-(5,6,7,8-tetrahydroimidazo[1,2-a]pyridin-3-yl)pyridin-2-yl)carbamoyl)piperidine-1-carboxylate (0.40 g, 0.52 mmol) in DCM (5 mL). The resulting mixture was stirred at r.t. for 1 h before being concentrated under reduced pressure. The resulting crude product was purified by preparative HPLC (Waters)(Bridge Prep C18 OBD column, 5 μm silica, 30 mm diameter, 100 mm length) using decreasingly polar mixtures of water (containing 0.1% ammonium carbonate) and MeCN as eluents. Fractions containing the desired compound were concentrated to dryness to afford (R)—N-(5-chloro-4-(5,6,7,8-tetrahydroimidazo[1,2-a]pyridin-3-yl)pyridin-2-yl)piperidine-3-carboxamide (22.0 mg, 11.7%) as a white solid. $^1$H NMR (400 MHz, $CD_3OD$, 22° C.) 1.41-1.52 (1H, m), 1.57-1.68 (2H, m), 1.85-1.94 (5H, m), 2.48-2.57 (2H, m), 2.68-2.76 (1H, m), 2.80-2.89 (3H, m), 2.97-3.03 (1H, m), 3.78-3.84 (2H, m), 7.04 (1H, s), 8.10 (1H, s), 8.29 (1H, s), amide and piperidine NH's not observed. m/z: ES+ [M+H]+ 360.

Procedures for preparing the starting material (R)-tert-butyl 3-((5-chloro-4-(5,6,7,8-tetrahydroimidazo[1,2-a]pyridin-3-yl)pyridin-2-yl)carbamoyl)piperidine-1-carboxylate are described below:

Preparation of 3-(2,5-dichloropyridin-4-yl)-5,6,7,8-tetrahydroimidazo[1,2-a]pyridine

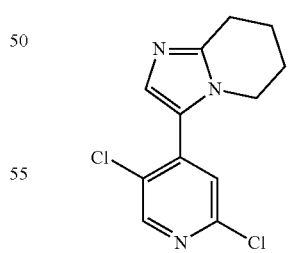

Cesium carbonate (3.24 g, 9.95 mmol) was added to 3-bromo-5,6,7,8-tetrahydroimidazo[1,2-a]pyridine (500 mg, 2.49 mmol), (2,5-dichloropyridin-4-yl)boronic acid (3.34 g, 17.4 mmol) $Pd(dppf)Cl_2 \cdot CH_2Cl_2$ (203 mg, 0.25 mmol), dioxane (10 mL), and water (1 mL) under nitrogen. The resulting mixture was stirred at 90° C. for 2 h. The reaction mixture was concentrated under reduced pressure to dryness and redissolved in EtOAc (50 mL) before being washed sequentially with water (2×20 mL) and saturated aqueous sodium chloride (50 mL). The organic layer was dried over sodium sulfate, filtered, and concentrated under reduced pressure. The resulting crude product was purified by flash silica chromatography, elution gradient 0 to 25% EtOAc in petroleum ether. Pure fractions were concentrated to dryness to afford 3-(2,5-dichloropyridin-4-yl)-5,6,7,8-tetrahydroimidazo[1,2-a]pyridine (500 mg, 75.0%) as a brown solid. m/z: ES+ [M+H]+ 268.

Preparation of (R)-tert-butyl 3-((5-chloro-4-(5,6,7,8-tetrahydroimidazo[1,2-a]pyridin-3-yl)pyridin-2-yl)carbamoyl)piperidine-1-carboxylate

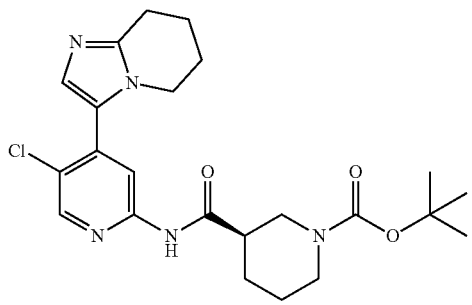 [SMILES: CC(C)(C)OC(=O)N1CCC[C@@H](C(=O)Nc2cc(-c3cnc4n3CCCC4)c(Cl)cn2)C1]

3-(2,5-Dichloropyridin-4-yl)-5,6,7,8-tetrahydroimidazo[1,2-a]pyridine (460 mg, 1.72 mmol) was added to (R)-tert-butyl 3-carbamoylpiperidine-1-carboxylate (470 mg, 2.06 mmol), Pd(PPh$_3$)$_4$ (198 mg, 0.17 mmol), cesium carbonate (1.68 g, 5.15 mmol), Xantphos (199 mg, 0.34 mmol), and dioxane (8 mL) under nitrogen. The resulting mixture was stirred at 120° C. for 2 h. The reaction mixture was then filtered, and the resulting filtrate was purified by flash silica chromatography, elution gradient 0 to 50% EtOAc in petroleum ether. Pure fractions were concentrated under reduced pressure to afford (R)-tert-butyl-3-((5-chloro-4-(5,6,7,8-tetrahydroimidazo[1,2-a]pyridine-3-yl)pyridin-2-yl)carbamoyl)piperidine-1-carboxylate (400 mg, 50.7%) as a yellow oil. m/z: ES+ [M+H]+ 460.

Example 2: (1S,3R)-3-acetamido-N-(5-chloro-4-(4,5,6,7-tetrahydropyrazolo[1,5-a]pyridin-3-yl)pyridin-2-yl)cyclohexanecarboxamide

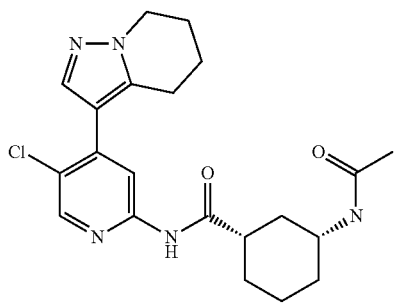 [SMILES: CC(=O)N[C@@H]1CCC[C@H](C(=O)Nc2cc(-c3cnn4c3CCCC4)c(Cl)cn2)C1]

Acetyl chloride (1.0 mL, 14.5 mmol) was added dropwise to a mixture of (1S,3R)-3-amino-N-(5-chloro-4-(4,5,6,7-tetrahydropyrazolo[1,5-a]pyridin-3-yl)pyridin-2-yl)cyclohexanecarboxamide (2.46 g, 6.59 mmol) and pyridine (6.40 mL, 79.1 mmol) in DCM (58.5 mL) at 0° C. After 45 min the mixture was washed with saturated aqueous sodium hydrogencarbonate and saturated aqueous sodium chloride before being dried over sodium sulfate, filtered, and concentrated under reduced pressure. The resulting dark amber oil was purified by flash silica chromatography, elution gradient 0 to 10% methanol in DCM. Product fractions were concentrated under reduced pressure to afford (1S,3R)-3-acetamido-N-(5-chloro-4-(4,5,6,7-tetrahydropyrazolo[1,5-a]pyridin-3-yl)pyridin-2-yl)cyclohexanecarboxamide (2.6 g, 93% yield over three steps) as a light beige foam solid.

Analysis of (1S,3R)-3-acetamido-N-(5-chloro-4-(4,5,6,7-tetrahydropyrazolo[1,5-a]pyridin-3-yl)pyridin-2-yl)cyclohexanecarboxamide by analytical SFC conditions (see below), determined this material to contain 98% (1S,3R)-3-acetamido-N-(5-chloro-4-(4,5,6,7-tetrahydropyrazolo[1,5-a]pyridin-3-yl)pyridin-2-yl)cyclohexanecarboxamide ($R_t$=1.42 min) and 2% (1R, 3S)-3-acetamido-N-(5-chloro-4-(4,5,6,7-tetrahydropyrazolo[1,5-a]pyridin-3-yl)pyridin-2-yl)cyclohexanecarboxamide ($R_t$=2.42 min). This material was purified by preparative SFC conditions (Chiralpak IA column, 5 μm, 30 mm diameter, 250 mm length, 40° C. column temperature, 100 bar outlet pressure, 120 mL/min flow rate), eluting with 40% methanol containing 0.1% dimethylethylamine in CO$_2$, to remove the (1R, 3S) enantiomer. Product fractions for the faster eluting enantiomer were concentrated under reduced pressure to afford 2.3 g of an amber-pink solid. This solid was repurified by flash silica (plug) chromatography, elution gradient 0 to 10% MeOH in ethyl acetate, to afford (1S,3R)-3-acetamido-N-(5-chloro-4-(4,5,6,7-tetrahydropyrazolo[1,5-a]pyridin-3-yl)pyridin-2-yl)cyclohexanecarboxamide (2.25 g) as a white foam solid. The product was treated with 20 mL of acetonitrile and the resulting mixture was warmed to reflux conditions before being allowed to cool to r.t. Additional acetonitrile (~5 mL) was added and the process was repeated until all solid dissolved. The resulting faint yellow solution was cooled to r.t., and a precipitate formed. After 1 h the precipitate was filtered and washed with acetonitrile before being dried under vacuum at 65° C. for 1 h. The solid was cooled to r.t. to afford (1S,3R)-3-acetamido-N-(5-chloro-4-(4,5,6,7-tetrahydropyrazolo[1,5-a]pyridin-3-yl)pyridin-2-yl)cyclohexanecarboxamide (1.76 g). $^1$H NMR (300 MHz, DMSO-d$_6$, 27° C.) 0.97-1.17 (1H, m), 1.20-1.38 (3H, m), 1.68-1.94 (9H, m), 1.96-2.07 (2H, m), 2.54-2.68 (1H, m), 2.80 (2H, t), 3.46-3.65 (1H, m), 4.14 (2H, t), 7.73 (1H, d), 7.76 (1H, s), 8.14 (1H, s), 8.38 (1H, s), 10.57 (1H, s). m/z: ES+ [M+H]+ 416.

Analytical SFC Conditions:
Column: Chiralpak IA column,
Column Dimensions: 5 μm, 4.6 mm diameter, 100 mm length,
Column Temperature: 40° C.
Mobile Phase A: CO$_2$ (100%)
Mobile Phase B: Methanol containing 0.1% dimethylethylamine
Gradient: Isocratic 40% Mobile Phase B
Outlet Pressure: 100 bar
Flow Rate: 5 mL/min over 5 min
Retention Time: 1.42 min
e.e. >98%
Optical Rotation:
Concentration: 0.1 g/dL
Lamp: Sodium
Wavelength: 589 nm
Temperature: 25° C.
Path length: 10 cm Cell volume: 1 mL
Solvent: Methanol
[α]=+70.2

Figure 7:
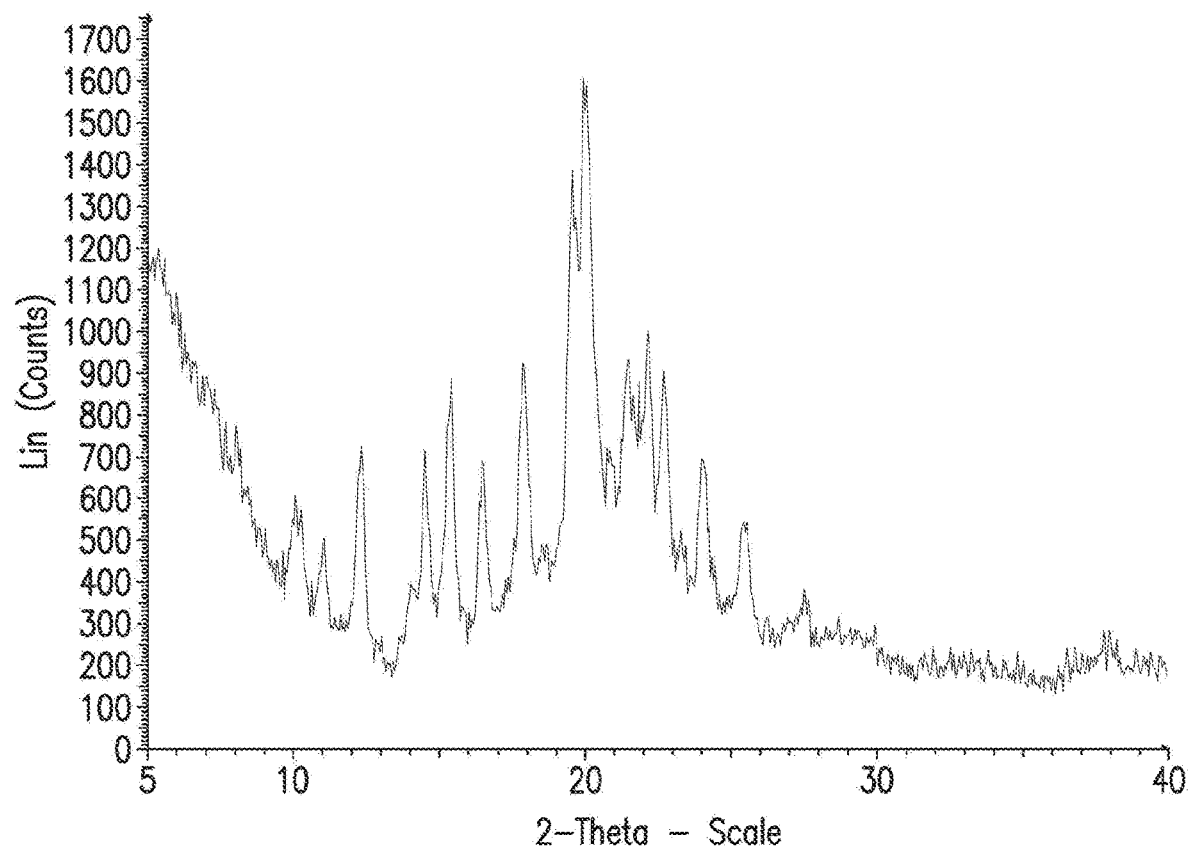
FIG. 7 is a representative X-ray powder diffractogram of Form B of (1S,3R)-3-acetamido-N-(5-chloro-4-(4,5,6,7-tetrahydropyrazolo[1,5-a]pyridin-3-yl)pyridin-2-yl)cyclohexanecarboxamide (Example 2).

The crystals of Example 2 were analyzed by XRPD and the results are tabulated below and are shown in FIG. 7. The XRPD of the solid confirms that the solid contains Example 2 Form B.

Example 2 Form B Main Peaks are Shown in Table 1 Below

| Peak | 2θ | Intensity % |
|---|---|---|
| 1 | 21.2 | 100.0 (vs) |
| 2 | 27.4 | 88.7 (vs) |
| 3 | 20.5 | 76.4 (vs) |
| 4 | 13.6 | 74.4 (vs) |
| 5 | 21.6 | 58.1 (vs) |
| 6 | 5.5 | 45.7 (vs) |
| 7 | 26.7 | 43.8 (vs) |
| 8 | 16.1 | 41.4 (vs) |
| 9 | 6.8 | 37.0 (vs) |
| 10 | 22.8 | 35.3 (vs) |

According to the present invention there is provided a crystalline form, Form B, which has an X-ray powder diffraction pattern with specific peaks at about 2-theta=5.5, 6.8, 13.6, 16.1, 20.5, 21.2, 21.6, 22.8, 26.7, 27.4°.

Figure 8:
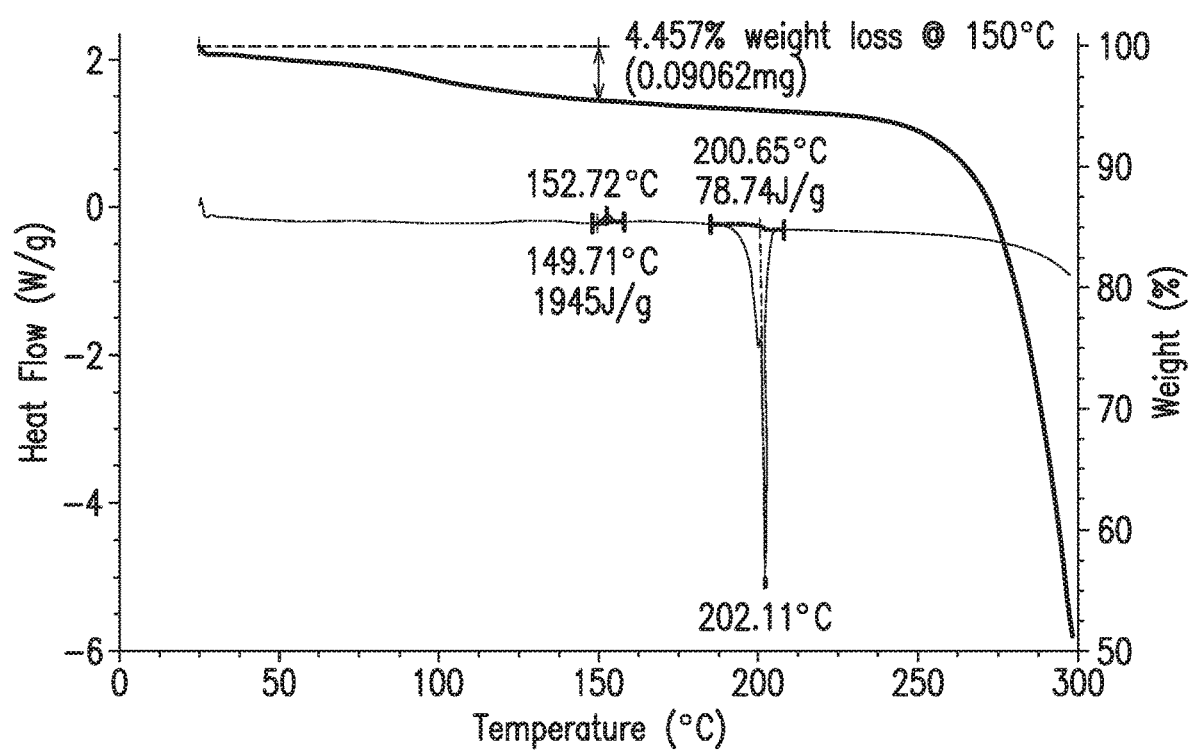
FIG. 8 is a representative DSC/TGA thermogram of Form B of (1S,3R)-3-acetamido-N-(5-chloro-4-(4,5,6,7-tetrahydropyrazolo[1,5-a]pyridin-3-yl)pyridin-2-yl)cyclohexanecarboxamide (Example 2).

The crystals obtained from Example 2 (Form B) were analyzed by thermal techniques. DSC analysis indicated that Form B has several thermal events, including an exotherm event with an onset point at 150° C. and a peak at 153° C., followed by melting with an onset point at 201° C. and a peak at 202° C. TGA indicated that Form B exhibits a mass loss of about 4.5% upon heating from 22° C. to 150° C. A representative DSC/TGA thermogram is shown in FIG. 8.

Procedures for preparing the starting material (1S,3R)-3-amino-N-(5-chloro-4-(4,5,6,7-tetrahydropyrazolo[1,5-a]pyridin-3-yl)pyridin-2-yl)cyclohexanecarboxamide are described below:

Preparation of 5-chloro-4-iodopyridin-2-amine

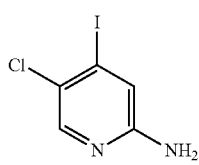

The reaction was split into 4 separate sealed microwave reaction vessels, each containing 750 mg (2.95 mmol) of 5-chloro-2-fluoro-4-iodopyridine, 8.4 mL of concentrated aqueous ammonium hydroxide, and 7.5 mL of NMP. The reaction vessels were each heated at 100° C. for 17 h. The combined batches were then diluted with water (50 mL) and extracted with EtOAc (3×120 mL). The combined organic layers were dried over MgSO$_4$, filtered, and concentrated under reduced pressure to afford a pale yellow oil. The oil was loaded onto a 20 g SCX-2 column and eluted sequentially with DCM, MeOH and 1% NH$_3$ in MeOH. Basic fractions were concentrated to provide the desired product as a colourless solid (2.9 g, 99%). $^1$H NMR (400 MHz, DMSO-d$_6$, 30° C.) 6.21 (2H, s), 7.05 (1H, s), 7.93 (1H, s). m/z: ES+ [M+H]+ 255.

Preparation of 5-chloro-4-(4,5,6,7-tetrahydropyrazolo[1,5-a]pyridin-3-yl)pyridin-2-amine

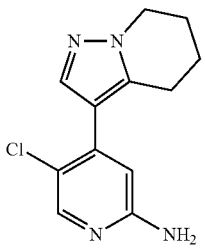 [SMILES: Nc1cc(-c2cnn3c2CCCC3)c(Cl)cn1]

Cesium carbonate (13.4 g, 41.2 mmol) and PdCl$_2$(dppf).CH$_2$Cl$_2$ (0.94 g, 1.2 mmol) were added sequentially to a degassed mixture of 5-chloro-4-iodopyridin-2-amine (4.19 g, 16.5 mmol), 3-(4,4,5,5-tetramethyl-1,3,2-dioxaborolan-2-yl)-4,5,6,7-tetrahydropyrazolo-[1,5-a]pyridine (5.72 g, 23.1 mmol), 1,4-dioxane (141 mL) and water (23.5 mL). The resulting red mixture was warmed to 95° C. and became clear. With vigorous stirring some precipitate formed which gradually mostly redissolved. After 4 h, another 800 mg of boronic ester were added; after another 40 min the reaction was cooled to r.t. and stirred under these conditions for 18 h. The mixture was then diluted with ethyl acetate, and the layers were separated. The organic layer was washed with saturated aqueous sodium chloride, dried over sodium sulfate, filtered, and concentrated under reduced pressure. The resulting oil was purified by flash silica chromatography, elution gradient 0 to 10% methanol in ethyl acetate. Product fractions were combined, concentrated under reduced pressure, and the resulting residue was stirred vigorously in 1:1 DCM:hexane for 20 minutes. The mixture was then diluted with hexane and filtered with a hexane wash. The resulting solid was dried under vacuum to afford 5-chloro-4-(4,5,6,7-tetrahydropyrazolo[1,5-a]pyridin-3-yl)pyridin-2-amine (2.79 g, 68.1%) as light orange-beige needles. $^1$H NMR (300 MHz, DMSO-d$_6$, 27° C.) 1.74-1.88 (2H, m), 1.96-2.06 (2H, m), 2.76 (2H, t), 4.12 (2H, t), 6.03 (2H, br. s), 6.43 (1H, s), 7.63 (1H, s), 7.94 (1H, s). m/z: ES+ [M+H]+ 249.

Preparation of cis-3-(tert-butoxycarbonylamino)cyclohexanecarboxylic Acid

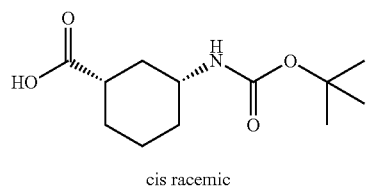 [SMILES: CC(C)(C)OC(=O)N[C@@H]1CCC[C@H](C(=O)O)C1]

cis racemic

A 5 litre fixed vessel was charged with cis-3-aminocyclohexanecarboxylic acid (100 g, 698 mmol; purchased from TCI), water (900 mL), 1,4-dioxane (900 mL) and N-ethyl-N-isopropylpropan-2-amine (487 mL, 2793 mmol). After stirring at r.t. for 5 min, the mixture was cooled to 0°

C. Di-tert-butyl dicarbonate (168 g, 768 mmol) was then added portionwise to the reaction mixture, which was allowed to warm to r.t. after the final portion was added. The reaction mixture was then recooled to 0° C. and 2 M aqueous HCl was added to adjust the pH to 2. A small (<5° C.) exotherm was observed between the addition of each 50 mL portion of 2 M aqueous HCl. The reaction mixture was extracted with EtOAc (2×500 mL), and the combined organic layers were washed with water (400 mL) and dried over sodium sulfate. The mixture was filtered, and the filtrate was concentrated under reduced pressure to afford, upon drying overnight, cis-3-((tert-butoxycarbonyl)amino)cyclohexanecarboxylic acid (170 g, 100%) as a white solid. $^1$H NMR (400 MHz, DMSO-$d_6$, 30° C.) 0.95-1.33 (4H, m), 1.37 (9H, s), 1.64-1.75 (2H, m), 1.79 (1H, d), 1.94 (1H, d), 2.22 (1H, tt), 3.13-3.26 (1H, m), 6.72 (1H, d), 12.01 (1H, s). m/z: ES+ [M+Na]+266.

Preparation of (S)-1-phenylethanaminium (1S,3R)-3-((tert-butoxycarbonyl)amino)cyclohexanecarboxylate

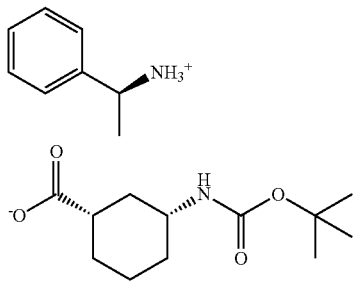

Using a procedure similar to that described in WO2011/1106112, cis-3-((tert-butoxycarbonyl)amino)cyclohexanecarboxylic acid (49.9 g, 166 mmol) was added to a 1 L round bottom flask and dissolved in ethanol (400 mL). The mixture was stirred at r.t. until all starting material dissolved. (S)-1-phenylethanamine (23.6 mL, 183 mmol) was added; the mixture was stirred at r.t. until a white precipitate gradually formed. The reaction mixture was then heated to 80° C. until a clear solution was obtained. The reaction heater was then switched off, and the reaction mixture was allowed to cool to r.t. After stirring at r.t. for another 16 h, the resulting mixture was filtered to give a white solid. This solid was re-dissolved in ethanol (150 mL) and heated to 80° C. until a clear solution was obtained. The reaction heater was then switched off, and the reaction mixture was allowed to cool to r.t. Filtration afforded a white solid (14.6 g), which was again recrystallized from ethanol (100 mL) using the same procedure to afford (S)-1-phenylethanaminium (1S,3R)-3-((tert-butoxycarbonyl)amino)cyclohexanecarboxylate (12.5 g, 20.7%) as a white solid. $^1$H NMR (400 MHz, DMSO-$d_6$, 30° C.) 0.98-1.23 (4H, m), 1.26 (3H, d), 1.38 (9H, s), 1.66-1.84 (3H, m), 1.95 (1H, m), 2.21 (1H, m), 3.21 (1H, m), 4.00 (1H, q), 6.72 (1H, m), 7.16-7.23 (1H, m), 7.30 (2H, m), 7.34-7.4 (2H, m), $NH_3^+$ not observed.

Preparation of (1S,3R)-3-(tert-butoxycarbonylamino)cyclohexanecarboxylic Acid

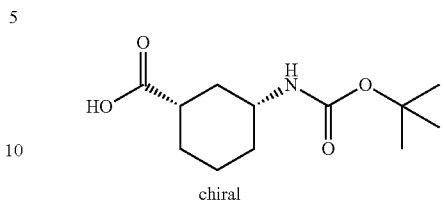

(S)-1-phenylethanaminium (1S,3R)-3-((tert-butoxycarbonyl)amino)cyclohexane-carboxylate (9.85 g, 27.0 mmol) was suspended in 250 mL EtOAc, and the organic layer was washed with 0.5 M HCl (2×125 mL). The organic layer was collected, and the combined aqueous layers were extracted with EtOAc (300 mL). The combined organic layers were washed with water (2×500 mL) and saturated aqueous sodium chloride (500 mL) before being dried over $Na_2SO_4$, filtered, and concentrated under reduced pressure. The resulting solid was then dried under vacuum to afford (1S,3R)-3-((tert-butoxycarbonyl)amino)cyclohexanecarboxylic acid (5.5 g, 84%) as a white solid. $^1$H NMR (400 MHz, DMSO-$d_6$, 30° C.) 0.99-1.35 (4H, m), 1.38 (9H, s), 1.68-1.85 (3H, m), 1.96 (1H, d), 2.23 (1H, tt), 3.15-3.30 (1H, m, partially obscured by water peak), 6.72 (1H, d), 12.01 (1H, s).

Representative Determination of Enantiopurity:

HATU (0.413 g, 1.09 mmol) was added to a solution of (4-methoxyphenyl)methanamine (0.142 mL, 1.09 mmol), (1S,3R)-3-((tert-butoxycarbonyl)amino)cyclohexanecarboxylic acid (0.240 g, 0.99 mmol), DIPEA (0.345 mL, 1.97 mmol), and DMF (1.980 mL). The bright yellow solution became a mixture over 30 min and was then diluted with ethyl acetate and sequentially washed with water, saturated aqueous sodium bicarbonate, and saturated aqueous sodium chloride. The organic layer was then dried over sodium sulfate, filtered, and concentrated under reduced pressure. The resulting residue was purified by flash silica chromatography, eluting with isocratic 5% methanol in DCM, to afford tert-butyl ((1R,3S)-3-((4-methoxybenzyl)carbamoyl)cyclohexyl)carbamate (0.30 g, 84%) as a white solid. $^1$H NMR (300 MHz, DMSO-$d_6$, 27° C.) 0.97-1.14 (1H, m), 1.15-1.32 (3H, m), 1.38 (9H, s), 1.56-1.84 (4H, m), 2.12-2.29 (1H, m), 3.14-3.28 (1H, m), 3.73 (3H, s), 4.17 (2H, br. d), 6.70-6.77 (1H, m), 6.87 (2H, d), 7.14 (2H, d), 8.16 (1H, t). m/z: ES+ [M+H]+ 363.

Samples prepared in this manner were subsequently analyzed by analytical SFC conditions as follows:
Column: Chiralpak OD column,
Column Dimensions: 5 µm, 4.6 mm diameter, 250 mm length,
Column Temperature: 40° C.
Mobile Phase A: $CO_2$ (100%)
Mobile Phase B: Ethanol
Gradient: Isocratic 15% Mobile Phase B
Outlet Pressure: 100 bar
Flow Rate: 2.8 mL/min over 5 min
Retention Time(s):
3.33 min, tert-butyl ((1R,3S)-3-((4-methoxybenzyl)carbamoyl)cyclohexyl)carbamate
5.21 min, tert-butyl ((1S,3R)-3-((4-methoxybenzyl)carbamoyl)cyclohexyl)carbamate Preparation of Tert-butyl ((1R,3S)-34(5-chloro-4-(4,5,6,7-tetrahydropyrazolo[1,5-a]pyridin-3-yl)pyridin-2-yl)carbamoyl)cyclohexyl)carbamate (also Known as Example 31a)

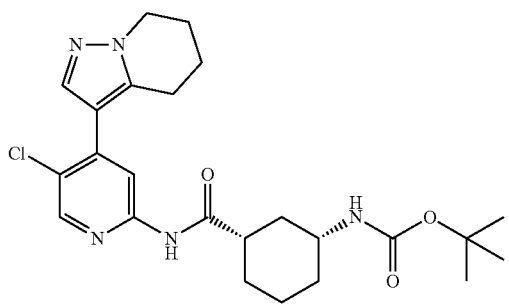 [SMILES: CC(C)(C)OC(=O)N[C@@H]1CCC[C@H](C(=O)Nc2cc(-c3cnn4c3CCCC4)c(Cl)cn2)C1]

1-Chloro-N,N,2-trimethylprop-1-en-1-amine (1.12 mL, 8.44 mmol) was added to a solution of (1S,3R)-3-((tert-butoxycarbonyl)amino)cyclohexanecarboxylic acid (2.01 g, 8.24 mmol) in DCM (50 mL) at 0° C. The reaction was maintained under these conditions for 100 minutes. During this time, 5-chloro-4-(4,5,6,7-tetrahydropyrazolo[1,5-a]pyridin-3-yl)pyridin-2-amine (1.64 g, 6.59 mmol), pyridine (2.1 mL, 26.4 mmol) and DCM (20 mL) were combined in a separate flask. The resulting mixture was warmed gently (~40° C.) until all solids dissolved. The resulting solution was then cooled to 0° C., whereupon a homogeneous light yellow mixture formed. This mixture was added via cannula rapidly to the previously prepared solution of (1S,3R)-3-((tert-butoxycarbonyl)amino)cyclohexanecarboxylic acid and 1-chloro-N,N,2-trimethylprop-1-en-1-amine, resulting in a darker yellow solution. The reaction was allowed to warm to r.t. overnight and was then evaporated to dryness. The gray mixture was then taken on to the next step without further purification. m/z: ES+ [M+H]+ 474.

Preparation of (1S,3R)-3-amino-N-(5-chloro-4-(4,5,6,7-tetrahydropyrazolo[1,5-a]pyridin-3-yl)pyridin-2-yl)cyclohexanecarboxamide Dihydrochloride (also Known as Example 31b)

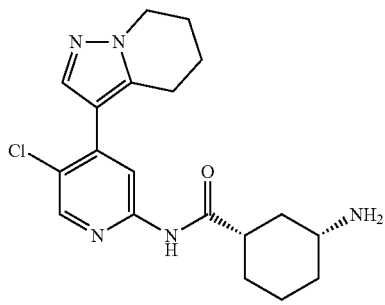 [SMILES: N[C@@H]1CCC[C@H](C(=O)Nc2cc(-c3cnn4c3CCCC4)c(Cl)cn2)C1]

Hydrochloric acid in dioxane (4 M; 10 mL, 40 mmol) was added to a mixture of crude tert-butyl ((1R,3S)-3-((5-chloro-4-(4,5,6,7-tetrahydropyrazolo[1,5-a]pyridin-3-yl)pyridin-2-yl)carbamoyl)cyclohexyl)carbamate (3.12 g, 6.59 mmol) in DCM (5 mL) and methanol (5 mL) at 0° C. The mixture became an amber solution. After 1 h the amber solution was concentrated under reduced pressure, and the resulting residue was dried under vacuum to a beige/gray foam solid. This material was carried on to the next step without further purification. m/z: ES+ [M+H]+ 374.

Example 3: (1S,3R)-3-acetamido-N-(4-(4,5,6,7-tetrahydropyrazolo[1,5-a]pyridin-3-yl)pyridin-2-yl)cyclohexanecarboxamide

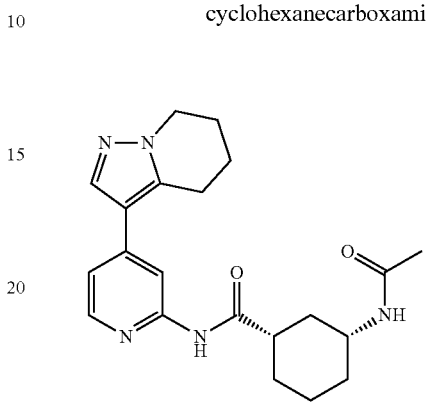

Acetic anhydride (0.016 mL, 0.17 mmol) was added to (1S,3R)-3-amino-N-(4-(4,5,6,7-tetrahydropyrazolo[1,5-a]pyridin-3-yl)pyridin-2-yl)cyclohexanecarboxamide (47 mg, 0.14 mmol) and triethylamine (0.023 mL, 0.17 mmol) in DCM (1 mL) at 21° C. under nitrogen. The resulting solution was stirred under these conditions for 60 h. The reaction mixture was loaded directly onto silica and purified by flash silica chromatography, elution gradient 1 to 10% MeOH in DCM. Pure fractions were evaporated to dryness to afford (1S,3R)-3-acetamido-N-(4-(4,5,6,7-tetrahydropyrazolo[1,5-a]pyridin-3-yl)pyridin-2-yl)cyclohexanecarboxamide (43 mg, 81%) as a white solid. $^1$H NMR (400 MHz, CDCl$_3$, 30° C.) 1.07-1.23 (1H, m), 1.37-1.53 (3H, m), 1.87-2.03 (8H, m), 2.03-2.11 (2H, m), 2.25 (1H, d), 2.39-2.51 (1H, m), 3.06 (2H, t), 3.88 (1H, dtq), 4.20 (2H, t), 5.40 (1H, d), 7.10 (1H, dd), 7.80 (1H, s), 8.17 (1H, dd), 8.32 (1H, s), 8.35 (1H, s). m/z: ES+ [M+H]+ 382.

Procedures for preparing the starting material (1S,3R)-3-amino-N-(4-(4,5,6,7-tetrahydropyrazolo[1,5-a]pyridin-3-yl)pyridin-2-yl)cyclohexanecarboxamide are described below:

Preparation of Tert-butyl ((1R,3S)-3-((4-bromopyridin-2-yl)carbamoyl)cyclohexyl)carbamate

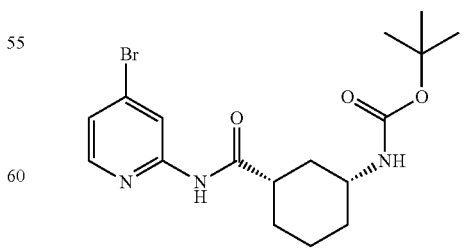

1-Chloro-N,N,2-trimethylprop-1-en-1-amine (0.574 ml, 4.33 mmol) was added to a solution of (1S,3R)-3-((tert-butoxycarbonyl)amino)cyclohexanecarboxylic acid (1.01 g, 4.16 mmol; prepared according to Example 2) in DCM (40 ml) at 0° C. After 1.5 h, a mixture of 4-bromopyridin-2-amine (0.6 g, 3.47 mmol) and pyridine (1.12 ml, 13.9 mmol) in DCM (33.0 ml) was added via cannula. The resulting yellow mixture was allowed to warm to r.t. and was stirred under these conditions for 72 h. The now white mixture was filtered, rinsed with a cold DCM wash, and the white precipitate was dried under vacuum at 70° C. for 30 min to afford tert-butyl ((1R,3S)-3-((4-bromopyridin-2-yl)carbamoyl)cyclohexyl)carbamate (1.38 g, 100%) of 95% purity as a white solid. $^1$H NMR (300 MHz, DMSO-$d_6$, 27° C.) 0.99-1.35 (4H, m) 1.38 (9H, s) 1.68-1.80 (3H, m) 1.88 (1H, d) 2.53-2.64 (1H, m) 3.15-3.35 (1H, m) 6.76 (1H, d) 7.34 (1H, dd) 8.21 (1H, d) 8.33 (1H, d) 10.63 (1H, s). m/z: ES+ [M+H]+ 398.

Preparation of Tert-butyl ((1R,3S)-3-((4-(4,5,6,7-tetrahydropyrazolo[1,5-a]pyridin-3-yl)pyridin-2-yl)carbamoyl)cyclohexyl)carbamate

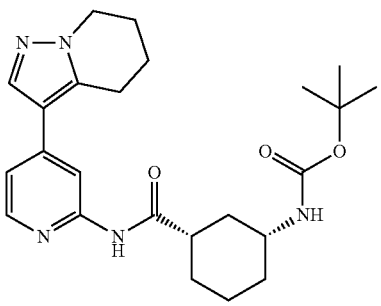 [SMILES: CC(C)(C)OC(=O)N[C@@H]1CCC[C@H](C(=O)Nc2cc(-c3cnn4c3CCCC4)ccn2)C1]

2nd Generation XPhos Precatalyst (9.88 mg, 0.01 mmol) was added in one portion to a degassed mixture of tert-butyl ((1R,3S)-3-((4-bromopyridin-2-yl)carbamoyl)cyclohexyl)carbamate (100 mg, 0.25 mmol), 3-(4,4,5,5-tetramethyl-1,3,2-dioxaborolan-2-yl)-4,5,6,7-tetrahydropyrazolo[1,5-a]pyridine (93 mg, 0.38 mmol), potassium phosphate (160 mg, 0.75 mmol), 1,4-dioxane (2 mL), and water (0.2 mL) at 21° C. under nitrogen. The resulting mixture was stirred at 100° C. for 16 h. The reaction mixture was diluted with EtOAc (10 mL), and washed sequentially with saturated NaHCO$_3$ (10 mL). The aqueous layer was extracted with EtOAc (2×10 mL), and the combined organic layers were dried over Na$_2$SO$_4$, filtered, and concentrated under reduced pressure to afford crude product. The crude product was purified by flash silica chromatography, elution gradient 20 to 80% EtOAc in heptane. Pure fractions were evaporated to dryness to afford tert-butyl ((1R,3S)-3-((4-(4,5,6,7-tetrahydropyrazolo[1,5-a]pyridin-3-yl)pyridin-2-yl)carbamoyl)cyclohexyl)carbamate (70.0 mg, 63.4%) as a white powder. $^1$H NMR (400 MHz, DMSO-$d_6$, 30° C.) 1.12 (1H, d), 1.21-1.33 (3H, m), 1.39 (9H, s), 1.76 (3H, s), 1.82-1.95 (3H, m), 2.00 (2H, d), 2.59 (1H, s), 2.97 (2H, t), 3.89 (1H, s), 4.12 (2H, t), 6.75 (1H, s), 7.19 (1H, dd), 7.85 (1H, s), 8.22 (2H, d), 10.32 (1H, s). m/z: ES+ [M+H]+ 440.

Preparation of (1S,3R)-3-amino-N-(4-(4,5,6,7-tetrahydropyrazolo[1,5-a]pyridin-3-yl)pyridin-2-yl)cyclohexanecarboxamide

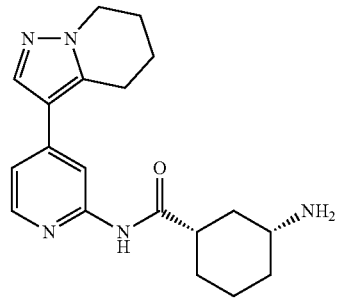 [SMILES: N[C@@H]1CCC[C@H](C(=O)Nc2cc(-c3cnn4c3CCCC4)ccn2)C1]

HCl in dioxane (4 M; 0.199 mL, 0.80 mmol) was added dropwise to tert-butyl ((1R,3S)-3-((4-(4,5,6,7-tetrahydropyrazolo[1,5-a]pyridin-3-yl)pyridin-2-yl)carbamoyl)cyclohexyl)carbamate (70 mg, 0.16 mmol) in DCM (2 mL) at 21° C. under nitrogen. The resulting mixture was stirred at 21° C. for 16 h. MeOH (1 mL) was added, and the mixture was purified directly by ion exchange chromatography, using an SCX-2 column. The desired product was eluted using 1 M NH$_3$ in MeOH, and pure fractions were evaporated to dryness to afford (1S,3R)-3-amino-N-(4-(4,5,6,7-tetrahydropyrazolo[1,5-a]pyridin-3-yl)pyridin-2-yl)cyclohexanecarboxamide (47 mg, 87%) as a white crystalline solid. $^1$H NMR (400 MHz, CD$_3$OD, 30° C.) 0.95-1.08 (1H, m), 1.2-1.4 (3H, m), 1.76-1.91 (5H, m), 1.99 (3H, dtt), 2.44 (1H, ddd), 2.61 (1H, tt), 2.95 (2H, t), 3.25 (1H, s), 4.07 (2H, t), 7.11 (1H, dd), 7.74 (1H, s), 8.07-8.16 (2H, m), NH$_2$ peak not observed. m/z: ES+ [M+H]+ 340.

Example 4: Cis-N-(5-chloro-4-(4,5,6,7-tetrahydropyrazolo[1,5-a]pyridin-3-yl)pyridin-2-yl)-3-hydroxycyclobutanecarboxamide

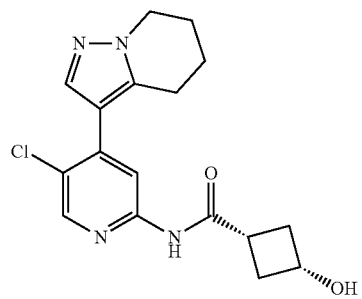 [SMILES: O=C(Nc1cc(-c2cnn3c2CCCC3)c(Cl)cn1)[C@H]1C[C@@H](O)C1]

HCl in dioxane (4 M; 0.388 mL, 1.55 mmol) was added to cis-3-((tert-butyldimethylsilyl)oxy)-N-(5-chloro-4-(4,5,6,7-tetrahydropyrazolo[1,5-a]pyridin-3-yl)pyridin-2-yl)cyclobutanecarboxamide (143 mg, 0.31 mmol) in DCM (3 mL) at 21° C. under nitrogen. The resulting suspension was stirred at 21° C. for 30 minutes. MeOH (1 mL) was added and the mixture stirred at 21° C. for 16 h. The mixture was concentrated and then diluted with EtOAc (25 mL) and saturated aqueous NaHCO$_3$ (25 mL). The layers were separated, and the aqueous layer was extracted with EtOAc (25 mL). The combined organic layers were dried over sodium sulfate and concentrated under reduced pressure. The resulting crude product was purified by flash silica chromatography, elution gradient 50 to 100% EtOAc in heptane. Pure fractions were evaporated to dryness to afford cis-N-(5-chloro-4-(4,5,6,7-tetrahydropyrazolo[1,5-a]pyridin-3-yl)pyridin-2-yl)-3-hydroxycyclobutanecarboxamide (24.0 mg, 22.3%) as a pale yellow solid. $^1$H NMR (400 MHz, CDCl$_3$, 30° C.) 1.88-1.94 (2H, m), 2.05-2.15 (3H, m), 2.2-2.31 (2H, m), 2.62-2.73 (3H, m), 2.93 (2H, t), 4.18-4.31 (3H, m), 7.81 (1H, s), 7.88 (1H, s), 8.23 (1H, s), 8.26 (1H, d). m/z: ES+ [M+H]+ 347.

Procedures for preparing the starting material cis-3-((tert-butyldimethylsilyl)oxy)-N-(5-chloro-4-(4,5,6,7-tetrahydropyrazolo[1,5-a]pyridin-3-yl)pyridin-2-yl)cyclobutanecarboxamide are described below:

Preparation of cis-tert-butyldimethylsilyl 3-((tert-butyldimethylsilyl)oxy)cyclobutanecarboxylate

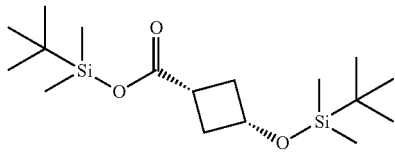 [SMILES: CC(C)(C)[Si](C)(C)OC(=O)[C@H]1C[C@@H](O[Si](C)(C)C(C)(C)C)C1]

Cis-3-hydroxycyclobutanecarboxylic acid (300 mg, 2.58 mmol) was dissolved in DCM (17.2 mL). Tert-butylchlorodimethylsilane (818 mg, 5.43 mmol) and 1H-imidazole (369 mg, 5.43 mmol) were added sequentially, and the solution was placed under nitrogen. The reaction was allowed to stir for 16 h at r.t. The mixture was diluted with ethyl acetate (100 mL) and washed with 1N aqueous HCl (30 mL), water (30 mL), and saturated aqueous sodium chloride (40 mL) before being dried over magnesium sulfate, filtered, and concentrated under reduced pressure to afford cis-tert-butyldimethylsilyl 3-((tert-butyldimethylsilyl)oxy)cyclobutanecarboxylate (802 mg, 90%) as a white solid. $^1$H NMR (400 MHz, CDCl$_3$, 30° C.) 0.03 (6H, s), 0.26 (6H, s), 0.88 (9H, s), 0.94 (9H, d), 2.11-2.21 (2H, m), 2.43-2.63 (3H, m), 4.07-4.17 (1H, m).

Preparation of cis-3-((tert-butyldimethylsilyl)oxy)cyclobutanecarboxylic Acid

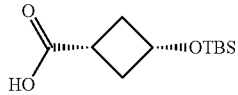

Potassium carbonate (644 mg, 4.66 mmol) was added to a solution of cis-tert-butyldimethylsilyl 3-((tert-butyldimethylsilyl)oxy)cyclobutanecarboxylate (803 mg, 2.33 mmol) in THF (15 mL) and water (3 mL). The resulting mixture was stirred at r.t. for 20 h. The reaction mixture was diluted with water and washed with EtOAc. The aqueous layer was acidified with 0.1N aqueous HCl and extracted with EtOAc (×2). The combined organic layers were dried over sodium sulfate, filtered, and concentrated to give crude product which was used without purification in the next step. $^1$H NMR (400 MHz, CDCl$_3$, 30° C.) 0.00 (6H, s), 0.84 (9H, s), 2.09-2.29 (2H, m), 2.36-2.66 (3H, m), 3.97-4.23 (1H, m), CO$_2$H not observed.

Preparation of 3-(5-chloro-2-fluoropyridin-4-yl)-4,5,6,7-tetrahydropyrazolo[1,5-a]pyridine

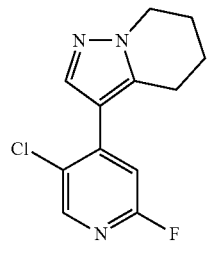 [SMILES: Fc1cc(-c2cnn3c2CCCC3)c(Cl)cn1]

3-(4,4,5,5-Tetramethyl-1,3,2-dioxaborolan-2-yl)-4,5,6,7-tetrahydropyrazolo[1,5-a]pyridine (500 mg, 2.02 mmol), 5-chloro-2-fluoro-4-iodopyridine (432 mg, 1.68 mmol), 2nd Generation XPhos Pre-catalyst (132 mg, 0.17 mmol) and potassium phosphate (1069 mg, 5.03 mmol) were suspended in dioxane (5 mL) and water (0.50 mL). The reaction was degassed by bubbling nitrogen through the reaction mixture for 5 minutes before being heated to 90° C. The reaction was maintained under these conditions for 20 h and then diluted with water (20 mL) and EtOAc (20 mL). The layers were separated and the aqueous layer was extracted with EtOAc (3×20 mL). The combined organic layers were washed with saturated aqueous sodium chloride (20 mL), dried over MgSO$_4$, filtered, and concentrated under reduced pressure. The resulting crude product was purified by flash silica chromatography, elution gradient 20 to 80% EtOAc in heptane. Pure fractions were evaporated to dryness to afford 3-(5-chloro-2-fluoropyridin-4-yl)-4,5,6,7-tetrahydropyrazolo[1,5-a]pyridine (440 mg, 104%) as a cream-colored crystalline solid. This material was taken on to the next step without further purification.

$^1$H NMR (400 MHz, CDCl$_3$, 30° C.) 1.87-1.96 (2H, m), 2.08-2.16 (2H, m), 2.83 (2H, t), 4.23 (2H, t), 6.82 (1H, d), 7.80 (1H, s), 8.23 (1H, s). m/z: ES$^+$[M+H]$^+$ 252.

Preparation of 5-chloro-4-(4,5,6,7-tetrahydropyrazolo[1,5-a]pyridin-3-yl)pyridin-2-amine

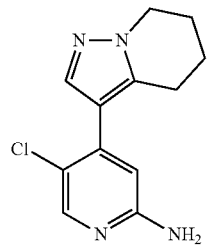 [SMILES: Nc1cc(-c2cnn3c2CCCC3)c(Cl)cn1]

3-(5-Chloro-2-fluoropyridin-4-yl)-4,5,6,7-tetrahydropyrazolo[1,5-a]pyridine (440 mg, 1.49 mmol) and ammonium hydroxide (2.0 mL, 51 mmol) were combined and sealed into a microwave tube. The reaction was heated to 150° C. for 2 h in a microwave reactor and cooled to r.t. The reaction mixture was diluted with EtOAc (25 mL) and water (25 mL). The layers were separated, and the aqueous layer was extracted with EtOAc (3×25 mL). The organic layers were combined and washed with saturated aqueous sodium chloride (25 mL), dried over Na$_2$SO$_4$, filtered and concentrated under reduced pressure. The resulting crude product was purified by flash silica chromatography, eluting with 50% EtOAc in heptane and then 10% MeOH in DCM. Pure fractions were evaporated to dryness to afford 5-chloro-4-(4,5,6,7-tetrahydropyrazolo[1,5-a]pyridin-3-yl)pyridin-2-amine (80 mg, 22%) as a white solid, already characterised (See Example 3, Intermediates)

Preparation of cis-3-((tert-butyldimethylsilyl)oxy)-N-(5-chloro-4-(4,5,6,7-tetrahydropyrazolo pyridin-3-yl)pyridin-2-yl)cyclobutanecarboxamide

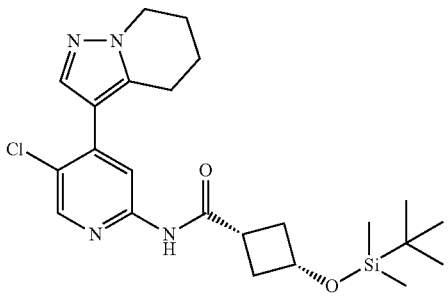 [SMILES: CC(C)(C)[Si](C)(C)O[C@H]1C[C@@H](C(=O)Nc2cc(-c3cnn4c3CCCC4)c(Cl)cn2)C1]

N-Ethyl-N-isopropylpropan-2-amine (0.167 mL, 0.94 mmol) was added to cis-3-((tert-butyldimethylsilyl)oxy)cyclobutanecarboxylic acid (79 mg, 0.34 mmol) and 2-(3H-[1,2,3]triazolo[4,5-b]pyridin-3-yl)-1,1,3,3-tetramethylisouronium hexafluorophosphate(V) (179 mg, 0.47 mmol) in DMF (1 mL) at 21° C. under nitrogen. The resulting solution was stirred at 21° C. for 10 minutes. A solution of 5-chloro-4-(4,5,6,7-tetrahydropyrazolo[1,5-a]pyridin-3-yl)pyridin-2-amine (78 mg, 0.31 mmol) in DMF (1 mL) was added and the resulting mixture was stirred at 21° C. for 16 h. Stirring continued for 72 h and additional cis-3-((tert-butyldimethylsilyl)oxy)cyclobutanecarboxylic acid (79 mg, 0.34 mmol), 2-(3H-[1,2,3]triazolo[4,5-b]pyridin-3-yl)-1,1,3,3-tetramethylisouronium hexafluorophosphate(V) (179 mg, 0.47 mmol) and N-ethyl-N-isopropylpropan-2-amine (0.167 mL, 0.94 mmol) were added. The mixture was stirred for a further 24 h before EtOAc (20 mL) and saturated aqueous sodium hydrogencarbonate (20 mL) were added. The layers were separated, and the organic layer was washed with water (20 mL) and saturated aqueous sodium chloride (20 mL), dried over $Na_2SO_4$, filtered, and concentrated under reduced pressure. The crude residue was taken immediately onto the next step and recovery was assumed to be quantitative. m/z: ES+ [M+H]+ 461.

Example 5: (R)—N-(5-chloro-4-(4,5,6,7-tetrahydropyrazolo[1,5-a]pyridin-3-yl)pyridin-2-yl)piperidine-3-carboxamide

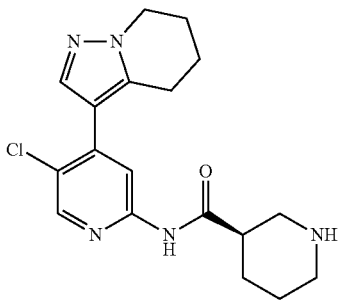 [SMILES: O=C(Nc1cc(-c2cnn3c2CCCC3)c(Cl)cn1)[C@@H]1CCCNC1]

TFA (1 mL, 13 mmol) was added to (R)-tert-butyl 3-((5-chloro-4-(4,5,6,7-tetrahydropyrazolo[1,5-a]pyridin-3-yl)pyridin-2-yl)carbamoyl)piperidine-1-carboxylate (90 mg, 0.20 mmol) in DCM (2 mL) at 20° C. The resulting mixture was stirred at r.t. for 1 h and then concentrated under reduced pressure. The resulting crude product was purified by preparative HPLC (XBridge Prep C18 OBD column, 5 μm silica, 19 mm diameter, 150 mm length), using decreasingly polar mixtures of water (containing 0.05% $NH_3$) and MeCN as eluents. Fractions containing the desired compound were evaporated to dryness to afford (R)—N-(5-chloro-4-(4,5,6,7-tetrahydropyrazolo[1,5-a]pyridin-3-yl)pyridin-2-yl)piperidine-3-carboxamide (18.0 mg, 25.6%) as a white solid. $^1$H NMR (400 MHz, DMSO-$d_6$, 23° C.) 1.30-1.47 (1H, m), 1.52-1.62 (2H, m), 1.76-1.90 (3H, m), 1.97-2.07 (2H, m), 2.52-2.62 (2H, m), 2.69 (1H, t), 2.75-2.87 (3H, m), 2.91-3.01 (1H, m), 4.14 (2H, t), 7.77 (1H, s), 8.15 (1H, s), 8.37 (1H, s), 10.84 (1H, s), piperidine NH not observed. m/z: ES+ [M+H]+ 360.

Procedures for preparing the starting material (R)-tert-butyl 3-((5-chloro-4-(4,5,6,7-tetrahydropyrazolo[1,5-a]pyridin-3-yl)pyridin-2-yl)carbamoyl)piperidine-1-carboxylate are described below:

Preparation of Tert-butyl 3-((5-chloro-4-(4,5,6,7-tetrahydropyrazolo[1,5-a]pyridin-3-yl) pyridin-2-yl)carbamoyl)piperidine-1-carboxylate

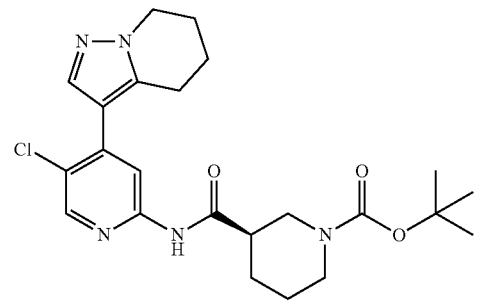 [SMILES: CC(C)(C)OC(=O)N1CCC[C@@H](C(=O)Nc2cc(-c3cnn4c3CCCC4)c(Cl)cn2)C1]

Pyridine (0.10 mL, 1.3 mmol) was added to 1-(tert-butoxycarbonyl)piperidine-3-carboxylic acid (74 mg, 0.32 mmol) and 1-chloro-N,N,2-trimethylprop-1-en-1-amine (0.050 mL, 0.64 mmol) in DCM (2 mL) at 20° C. The resulting mixture was stirred at r.t. for 20 minutes. Then 5-chloro-4-(4,5,6,7-tetrahydropyrazolo[1,5-a]pyridin-3-yl)pyridin-2-amine (80 mg, 0.32 mmol; prepared according to Example 4) was added to the mixture. The resulting mixture was stirred at r.t. for 1 h. The reaction mixture was concentrated under reduced pressure and diluted with DCM (100 mL) before being washed sequentially with 0.1 M HCl (2×25 mL), saturated aqueous sodium bicarbonate (25 mL), and saturated aqueous sodium chloride (2×25 mL). The organic layer was dried over sodium sulfate, filtered and concentrated under reduced pressure. The resulting residue was purified by preparative TLC (petroleum ether:EtOAc=10:1) to afford tert-butyl 3-((5-chloro-4-(4,5,6,7-tetrahydropyrazolo[1,5-a]pyridin-3-yl) pyridin-2-yl)carbamoyl)piperidine-1-carboxylate (100 mg, 67.6%) as a yellow solid. m/z: ES+ [M+H]+ 460.

Example 6: cis-3-hydroxy-N-(4-(4,5,6,7-tetrahydropyrazolo[1,5-a]pyridin-3-yl)pyridin-2-yl)cyclobutanecarboxamide

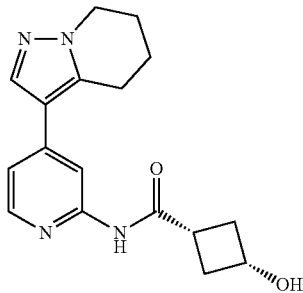 [SMILES: O=C(Nc1cc(-c2cnn3c2CCCC3)ccn1)[C@H]1C[C@@H](O)C1]

HCl in dioxane (4 M; 0.388 mL, 1.55 mmol) was added to cis-3-((tert-butyldimethylsilyl)oxy)-N-(4-(4,5,6,7-tetrahydropyrazolo[1,5-a]pyridin-3-yl)pyridin-2-yl)cyclobutanecarboxamide (132 mg, 0.31 mmol) in DCM (3 mL) and MeOH (1 mL) at 21° C. under nitrogen. The resulting suspension was stirred at 21° C. for 3 h before the mixture was concentrated under reduced pressure. The resulting residue was diluted with EtOAc (25 mL) and saturated aqueous sodium hydrogencarbonate (25 mL). The layers were then separated, and the aqueous layer was extracted with EtOAc (25 mL). The combined organic layers were dried over MgSO$_4$ and concentrated under reduced pressure. The resulting crude solid was triturated with Et$_2$O and dried under vacuum to afford cis-3-hydroxy-N-(4-(4,5,6,7-tetrahydropyrazolo[1,5-a]pyridin-3-yl)pyridin-2-yl)cyclobutanecarboxamide (35.0 mg, 36.1%) as a white solid. $^1$H NMR (400 MHz, CDCl$_3$, 30° C.) 1.89-2.01 (2H, m), 2.08 (3H, ddd), 2.28 (2H, ddd), 2.67 (3H, tq), 3.08 (2H, t), 4.23 (3H, dt), 7.10 (1H, dd), 7.81 (1H, s), 7.83 (1H, s), 8.19 (1H, dd), 8.33 (1H, s). m/z: ES+ [M+H]+ 313.

Procedures for preparing the starting material cis-3-((tert-butyldimethylsilyl)oxy)-N-(4-(4,5,6,7-tetrahydropyrazolo[1,5-a]pyridin-3-yl)pyridin-2-yl)cyclobutanecarboxamide are described below:

Preparation of cis-N-(4-bromopyridin-2-yl)-3-((tert-butyldimethylsilyl)oxy)cyclobutanecarboxamide

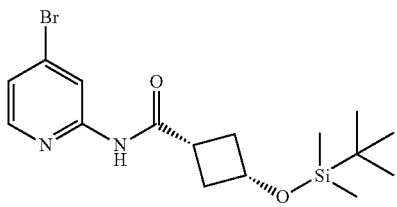 [SMILES: CC(C)(C)[Si](C)(C)O[C@H]1C[C@@H](C(=O)Nc2cc(Br)ccn2)C1]

N-Ethyl-N-isopropylpropan-2-amine (0.461 mL, 2.60 mmol) was added to cis-3-((tert-butyldimethylsilyl)oxy)cyclobutanecarboxylic acid (220 mg, 0.95 mmol; prepared as in Example 4) and 2-(3H-[1,2,3]triazolo[4,5-b]pyridin-3-yl)-1,1,3,3-tetramethylisouronium hexafluorophosphate(V) (494 mg, 1.30 mmol) in DMF (3 mL) at 21° C. under nitrogen. The resulting solution was stirred at 21° C. for 10 minutes before 4-bromopyridin-2-amine (150 mg, 0.87 mmol) was added, and the resulting mixture was stirred at 21° C. for 16 h. Stirring continued for 72 h, and additional cis-3-((tert-butyldimethylsilyl)oxy)cyclobutanecarboxylic acid (79 mg, 0.34 mmol), 2-(3H-[1,2,3]triazolo[4,5-b]pyridin-3-yl)-1,1,3,3-tetramethylisouronium hexafluorophosphate(V) (179 mg, 0.47 mmol) and N-ethyl-N-isopropylpropan-2-amine (0.167 mL, 0.94 mmol) were added. The mixture was stirred for a further 24 h, and then EtOAc (25 mL) and saturated aqueous sodium hydrogencarbonate solution (25 mL) were added. The layers were separated, and the organic layer was washed with water (2×25 mL) and saturated aqueous sodium chloride (2×25 mL), dried over Na$_2$SO$_4$, filtered, and concentrated under reduced pressure. The resulting crude product was purified by flash silica chromatography, elution gradient 0 to 100% EtOAc in heptane. Pure fractions were evaporated to dryness to afford cis-N-(4-bromopyridin-2-yl)-3-((tert-butyldimethylsilyl)oxy)cyclobutanecarboxamide (96 mg, 29%) as a colourless oil. $^1$H NMR (400 MHz, CDCl$_3$, 30° C.) 0.06 (6H, s), 0.89 (9H, s), 1.11-1.18 (1H, m), 2.23-2.31 (2H, m), 2.54-2.58 (2H, m), 4.15-4.26 (1H, m), 7.18 (1H, dd), 7.82 (1H, s), 8.06 (1H, dd), 8.49 (1H, d). m/z: ES+ [M+H]+ 385 ($^{79}$Br isotope), 387 ($^{81}$Br isotope).

Preparation of cis-3-((tert-butyldimethylsilyl)oxy)-N-(4-(4,5,6,7-tetrahydropyrazolo[1,5-a]pyridin-3-yl)pyridin-2-yl)cyclobutanecarboxamide

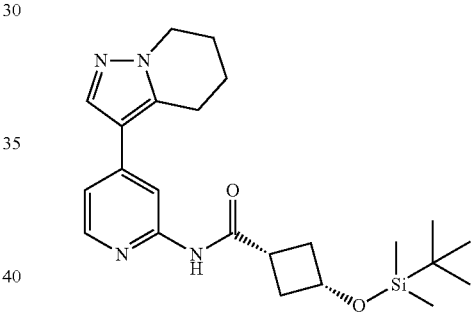

2nd Generation XPhos Precatalyst (19.40 mg, 0.02 mmol) was added to a degassed mixture of cis-N-(4-bromopyridin-2-yl)-3-((tert-butyldimethylsilyl)oxy)cyclobutanecarboxamide (95 mg, 0.25 mmol), 3-(4,4,5,5-tetramethyl-1,3,2-dioxaborolan-2-yl)-4,5,6,7-tetrahydropyrazolo[1,5-a]pyridine (73.4 mg, 0.30 mmol) and potassium phosphate (157 mg, 0.74 mmol) in dioxane (2 mL) and water (0.2 mL) at 21° C. under nitrogen. The resulting mixture was stirred at 100° C. for 16 h. The reaction mixture was diluted with EtOAc (25 mL) and washed sequentially with saturated aqueous sodium hydrogencarbonate (10 mL), water (10 mL), and saturated aqueous sodium chloride (10 mL). The organic layer was dried over Na$_2$SO$_4$, filtered and concentrated under reduced pressure. The resulting crude product was purified by flash silica chromatography, elution gradient 30 to 70% EtOAc in heptane. Pure fractions were evaporated to dryness to afford cis-3-((tert-butyldimethylsilyl)oxy)-N-(4-(4,5,6,7-tetrahydropyrazolo[1,5-a]pyridin-3-yl)pyridin-2-yl)cyclobutanecarboxamide (60.0 mg, 57.1%) as a white solid. $^1$H NMR (400 MHz, CDCl$_3$, 30° C.) 0.05 (6H, s), 0.89 (9H, s), 1.9-2.01 (2H, m), 2.02-2.12 (2H, m), 2.25-2.33 (2H, m), 2.5-2.62 (3H, m), 3.08 (2H, t), 4.21 (3H, t), 7.09 (1H, dd), 7.76 (1H, s), 7.80 (1H, s), 8.18 (1H, dd), 8.33 (1H, s). m/z: ES+ [M+H]+ 427.

Example 7: (1S,3R)-3-acetamido-N-(5-chloro-4-(5,6,7,8-tetrahydroimidazo[1,2-a]pyridin-3-yl)pyridin-2-yl)cyclohexanecarboxamide

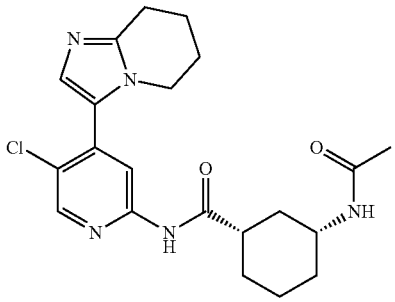 [SMILES: CC(=O)N[C@@H]1CCC[C@H](C(=O)Nc2cc(-c3cnc4n3CCCC4)c(Cl)cn2)C1]

(1S,3R)-3-Acetamido-N-(4-bromo-5-chloropyridin-2-yl)cyclohexanecarboxamide (0.20 g, 0.53 mmol), 5,6,7,8-tetrahydroimidazo[1,2-a]pyridine (47 mg, 0.38 mmol), cesium carbonate (0.14 g, 0.42 mmol), triethylamine (0.11 mL, 0.76 mmol), triphenylphosphine (0.02 g, 0.06 mmol) and diacetoxypalladium (6.85 mg, 0.0300 mmol) were suspended in 1,4-dioxane (5 mL) and sealed in a microwave tube. The reaction was heated to 100° C. for 16 h in a microwave reactor and then cooled to r.t. The reaction was concentrated under reduced pressure and the crude product was purified by ion exchange chromatography using an SCX-2 column. The desired product was eluted from the column using 1 M NH$_3$ in MeOH, and pure fractions were evaporated to dryness. The resulting crude product was purified by preparative HPLC (Waters)(Bridge Prep C18 OBD column, 5μ silica, 50 mm diameter, 100 mm length), using decreasingly polar mixtures of water (containing 1% NH$_3$) and MeCN as eluents. Fractions containing the desired compound were concentrated under reduced pressure to afford (1S,3R)-3-acetamido-N-(5-chloro-4-(5,6,7,8-tetrahydroimidazo[1,2-a]pyridin-3-yl)pyridin-2-yl)cyclohexanecarboxamide (0.069 g, 44%) as a yellow gum. $^1$H NMR (500 MHz, DMSO-d$_6$, 30° C.) 0.95-1.16 (1H, m), 1.19-1.39 (3H, m), 1.78 (3H, s), 1.83-1.97 (2H, m), 2.55-2.68 (1H, m), 2.84 (2H, s), 3.18 (2H, dd), 3.31 (3H, s), 3.57 (1H, dt), 3.83 (2H, s), 4.08 (1H, q), 7.13 (1H, s), 7.75 (1H, d), 8.16 (1H, s), 8.47 (1H, s), 10.70 (1H, s). m/z: ES+ [M+H]+ 417 ($^{13}$C, $^{35}$Cl isotope secondary peak).

Procedures for preparing the starting material (1S,3R)-3-acetamido-N-(4-bromo-5-chloropyridin-2-yl)cyclohexanecarboxamide are described below:

Preparation of 4-bromo-3-chloropyridin-2-amine

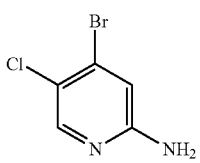

N-Chloro-succinimide (3.70 g, 27.7 mmol) dissolved in DMF (20 mL) was added dropwise to 4-bromopyridin-2-amine (4.40 g, 25.4 mmol) in DMF (50 mL) at −78° C. over a period of 30 minutes under nitrogen. The resulting suspension was then allowed to warm to r.t. After stirring under these conditions for 24 h, the reaction mixture was diluted with Et$_2$O (50 mL) and washed sequentially with 1 M aqueous NaOH (2×50 mL), water (50 mL), and saturated aqueous sodium chloride (25 mL). The organic layer was dried over MgSO$_4$, filtered and concentrated under reduced pressure. The resulting crude product was purified by flash silica chromatography, elution gradient 0 to 25% EtOAc in DCM. Pure fractions were evaporated to dryness to afford 4-bromo-5-chloropyridin-2-amine (2.30 g, 43.7%) as a cream solid. $^1$H NMR (400 MHz, DMSO-d$_6$, 30° C.) 6.35 (2H, s), 6.82 (1H, s), 8.01 (1H, s). m/z: ES+ [M+H]+ 209 ($^{35}$Cl $^{81}$Br and $^{37}$Cl $^{79}$Br isotopes).

Preparation of Tert-butyl (1R,3S)-3-((4-bromo-5-chloropyridin-2-yl)carbamoyl)cyclohexyl)carbamate

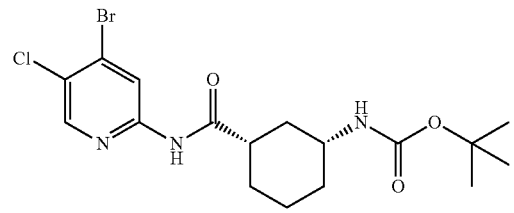 [SMILES: CC(C)(C)OC(=O)N[C@@H]1CCC[C@H](C(=O)Nc2cc(Br)c(Cl)cn2)C1]

A solution of (1S,3R)-3-((tert-butoxycarbonyl)amino)cyclohexanecarboxylic acid (1.50 g, 6.15 mmol; prepared according to Example 2) dissolved in DCM (20 mL) at 0° C. was treated with 1-chloro-N,N,2-trimethylprop-1-en-1-amine (0.976 mL, 7.38 mmol). The mixture was stirred at r.t. for 1.5 h before 4-bromo-5-chloropyridin-2-amine (1.02 g, 4.92 mmol) and pyridine (0.594 mL, 7.38 mmol) were added sequentially. The resulting solution was stirred at r.t. for 16 h. The reaction mixture was diluted with DCM (25 mL), and washed sequentially with water (2×25 mL) and saturated aqueous sodium chloride (25 mL). The organic layer was dried over MgSO$_4$, filtered, and concentrated under reduced pressure. The resulting crude product was purified by ion exchange chromatography, using an SCX-2 column. The desired product was eluted from the column using methanol to afford tert-butyl ((1R,3S)-3-((4-bromo-5-chloropyridin-2-yl)carbamoyl)cyclohexyl)carbamate (2.34 g, 110%) as a white solid. $^1$H NMR (400 MHz, DMSO-d$_6$, 30° C.) 1.12 (1H, dd), 1.22-1.32 (3H, m), 1.38 (9H, s), 1.72 (3H, dd), 1.83-1.94 (2H, m), 2.11 (1H, dt), 8.48 (1H, s), 8.50 (1H, s), 10.77 (1H, s), one proton not observed. m/z: ES− [M−H]− 430.

Preparation of (1S,3R)-3-amino-N-(4-bromo-5-chloropyridin-2-yl)cyclohexanecarboxamide Dihydrochloride

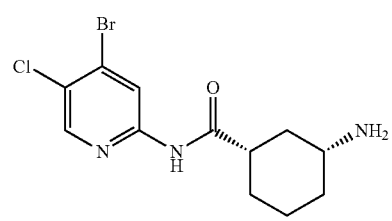 [SMILES: N[C@@H]1CCC[C@H](C(=O)Nc2cc(Br)c(Cl)cn2)C1]

HCl in dioxane (4 M; 5.89 mL, 23.6 mmol) was added to tert-butyl ((1R,3S)-3-((4-bromo-5-chloropyridin-2-yl)carbamoyl)cyclohexyl)carbamate (1.20 g, 2.77 mmol) in MeOH (7.01 mL) under air. The resulting solution was stirred at ambient temperature for 16 h. The reaction mixture was evaporated to afford (1S,3R)-3-amino-N-(4-bromo-5-chloropyridin-2-yl)cyclohexanecarboxamide dihydrochloride as a white solid. This was used in the next step without further purification. m/z: ES+ [M+H]+ 332 ($^{35}$Cl $^{79}$Br isotope), 334 ($^{35}$Cl $^{81}$Br and $^{37}$Cl $^{79}$Br isotopes).

Preparation of (1S,3R)-3-acetamido-N-(4-bromo-5-chloropyridin-2-yl)cyclohexanecarboxamide

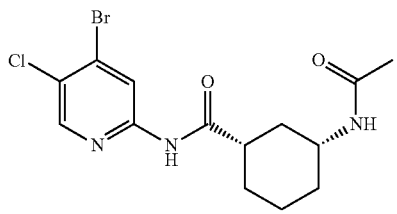

Acetic anhydride (0.259 mL, 2.74 mmol) was added dropwise to (1S,3R)-3-amino-N-(4-bromo-5-chloropyridin-2-yl)cyclohexanecarboxamide (0.760 g, 2.28 mmol), 4-dimethylaminopyridine (0.014 g, 0.11 mmol) and triethylamine (0.987 mL, 7.08 mmol) in DCM (8.44 mL) at r.t. under nitrogen. The resulting solution was stirred at r.t. overnight before being quenched with saturated aqueous NH$_4$Cl (50 mL) and extracted with DCM (2×50 mL). The combined organic layers were dried over MgSO$_4$, filtered, and concentrated under reduced pressure to afford (1S,3R)-3-acetamido-N-(4-bromo-5-chloropyridin-2-yl)cyclohexanecarboxamide (0.96 g, 95%) as a white solid. The product was used in the next step without further purification. $^1$H NMR (400 MHz, DMSO-d$_6$, 30° C.) 1.23-1.41 (4H, m), 1.67-1.85 (4H, m), 2.39 (3H, tt), 2.75-2.92 (1H, m), 3.53 (1H, dtd), 7.59-7.83 (1H, m), 8.50 (2H, dd), 10.80 (1H, d). m/z: ES+ [M+H]+ 374 ($^{35}$Cl $^{79}$Br isotope), 376 ($^{35}$Cl $^{81}$Br and $^{37}$Cl $^{79}$Br isotopes).

Example 8: (1S,3R)-3-acetamido-N-(5-chloro-4-(6,7-dihydro-5H-pyrazolo[5,1-b][1,3]oxazin-3-yl)pyridin-2-yl)cyclohexanecarboxamide

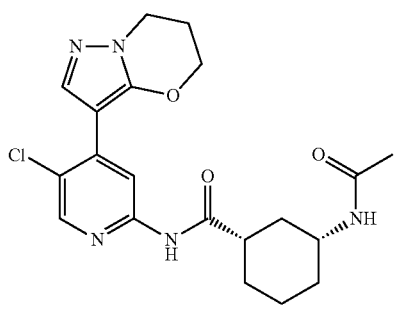 [SMILES: CC(=O)N[C@@H]1CCC[C@H](C(=O)Nc2cc(-c3cnn4c3OCCC4)c(Cl)cn2)C1]

(1S,3R)-3-Acetamido-N-(4-bromo-5-chloropyridin-2-yl)cyclohexanecarboxamide (0.100 g, 0.27 mmol; prepared as in Example 7) was added in one portion to a degassed mixture of 3-(4,4,5,5-tetramethyl-1,3,2-dioxaborolan-2-yl)-6,7-dihydro-5H-pyrazolo[5,1-b][1,3]oxazine (0.067 g, 0.27 mmol), 2nd Generation X-Phos Precatalyst (0.021 g, 0.03 mmol), potassium phosphate (0.170 g, 0.80 mmol), 1,4-dioxane (2.270 mL) and water (0.454 mL) at r.t. The resulting mixture was stirred at r.t. for 16 h and then evaporated to dryness before being purified by ion exchange chromatography using an SCX-2 cartridge. The desired product was eluted from the column using 1 M NH$_3$ in MeOH, and pure fractions were evaporated to dryness to afford crude (1S,3R)-3-acetamido-N-(5-chloro-4-(6,7-dihydro-5H-pyrazolo[5,1-b][1,3]oxazin-3-yl)pyridin-2-yl)cyclohexanecarboxamide as a yellow gum. The semipure product was purified by preparative HPLC (Waters)(Bridge Prep C18 OBD column, 5µ silica, 30 mm diameter, 100 mm length) using decreasingly polar mixtures of water (containing 1% NH$_3$) and MeCN as eluents. Fractions containing the desired compound were evaporated to dryness to afford (1S,3R)-3-acetamido-N-(5-chloro-4-(6,7-dihydro-5H-pyrazolo[5,1-b][1,3]oxazin-3-yl)pyridin-2-yl)cyclohexanecarboxamide (0.017 g, 16%) as a white gum. $^1$H NMR (500 MHz, DMSO-d$_6$, 30° C.) 1.21-1.32 (1H, m), 1.4-1.53 (3H, m), 1.95 (1H, s), 1.96 (3H, s), 2.06 (1H, d), 2.39-2.48 (2H, m), 2.7-2.85 (3H, m), 3.74 (1H, dt), 4.34 (2H, t), 4.53-4.68 (2H, m), 7.93 (1H, d), 8.05 (1H, s), 8.48 (1H, d), 8.58 (1H, s), 10.62 (1H, s). m/z: ES+ [M+H]+ 418 ($^{12}$C, $^{35}$Cl isotope), 419 ($^{13}$C, $^{35}$Cl isotope secondary peak).

Procedures for preparing the starting material 3-(4,4,5,5-tetramethyl-1,3,2-dioxaborolan-2-yl)-6,7-dihydro-5H-pyrazolo[5,1-b][1,3]oxazine are described below:

Preparation of 1,2-dihydropyrazol-3-one

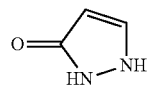

To a solution of methyl prop-2-ynoate (150 g, 1785.7 mmol) in MeOH (1500 mL) was added hydrazine hydrate (89.2 g, 1784.0 mmol) dropwise at 0° C. The reaction was stirred at r.t. for 30 min. Saturated aqueous sodium chloride (400 mL) was added, and then methanol was removed under vacuum. The aqueous layer was extracted with EtOAc (3×500 mL), and the combined organic layers were dried over Na$_2$SO$_4$ and concentrated under reduced pressure to afford 1,2-dihydropyrazol-3-one (99.5 g, 66%) as a white solid. m/z: ES+ [M+H]+ 85.

Preparation of 6,7-dihydro-5H-pyrazolo[5,1-b][1,3]oxazine

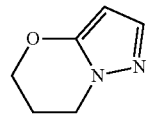

To a solution of 1,2-dihydropyrazol-3-one (99.5 g, 1184 mmol) in DMF (4000 mL) was added K$_2$CO$_3$ (560.0 g, 4057 mmol), and the mixture was heated at 130° C. for 1 h. Then 1,3-dibromopropane (143.4 mL, 1421 mmol) was added, and the mixture was stirred at 130° C. for 2 h and then concentrated. The resulting residue was partitioned between DCM (2000 mL) and water (2000 mL). The organic layer was separated and the aqueous layer was extracted with DCM (3×1000 mL). The combined organic extracts were dried over Na$_2$SO$_4$ and concentrated to give 6,7-dihydro-5H-pyrazolo[5,1-b][1,3]oxazine (83.0 g, 56.8%) as a yellow oil. $^1$H NMR (300 MHz, CDCl$_3$, 30° C.) 2.18-2.11 (2H, m), 4.13-4.05 (2H, m), 4.19-4.16 (2H, m), 5.37-5.37 (1H, m), 7.21-7.20 (1H, m).

Preparation of 3-iodo-6,7-dihydro-5H-pyrazolo[5,1-b][1,3]oxazine

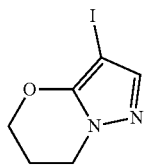

To a solution of 6,7-dihydro-5H-pyrazolo[5,1-b][1,3]oxazine (83.0 g, 669.3 mmol) in CH$_3$CN (1500 mL) was added N-iodosuccinimide (155.0 g, 688.8 mmol). The mixture was stirred at r.t. for 1 h before being slowly poured into vigorously stirred water (1000 mL). Saturated aqueous sodium thiosulphate (500 mL) was added, and the resulting mixture was extracted with ethyl acetate (2×800 mL). The combined organic layers were washed with water, dried over Na$_2$SO$_4$, and concentrated under reduced pressure. The resulting residue was purified by column chromatography on silica gel (petroleum ether:EtOAc=1:1) to give 3-iodo-6,7-dihydro-5H-pyrazolo[5,1-b][1,3]oxazine (105.0 g, 62.2%) as a yellow solid. $^1$H NMR (300 MHz, DMSO-d$_6$, 30° C.) 2.19-2.12 (2H, m), 4.10-3.98 (2H, m), 4.34-4.31 (2H, m), 7.28 (1H, m). m/z: ES+ [M+H]+ 251.

Preparation of 3-(4,4,5,5-tetramethyl-1,3,2-dioxaborolan-2-yl)-6,7-dihydro-5H-pyrazolo[5,1-b][1,3]oxazine

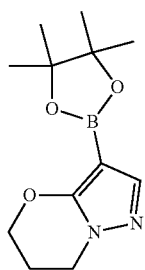 [SMILES: CC1(C)OB(c2cnn3c2OCCC3)OC1(C)C]

To a solution of 3-iodo-6,7-dihydro-5H-pyrazolo[5,1-b][1,3]oxazine (105 g, 420 mmol) in THF (1000 mL) was added 2-isopropoxy-4,4,5,5-tetramethyl-1,3,2-dioxaborolane (126 mL, 630 mmol). The mixture was cooled to 5° C. Then isopropyl magnesium lithium chloride (410 mL, 420 mmol) was added, and the mixture was stirred at 5° C. for 3 h. The reaction was quenched by addition of MeOH (500 mL) and then concentrated. The resulting residue was purified by flash silica chromatography, eluting with isocratic 50% ethyl acetate in petroleum ether, to afford a pale yellow oil. Crystallisation from heptane (100 mL) yielded 3-(4,4,5,5-tetramethyl-1,3,2-dioxaborolan-2-yl)-6,7-dihydro-5H-pyrazolo[5,1-b][1,3]oxazine (38.6 g, 36.7%) as a white solid. $^1$H NMR (400 MHz, DMSO-d$_6$, 30° C.) 1.21 (12H, s), 2.15-2.12 (2H, m), 4.06-4.03 (2H, m), 4.31-4.29 (2H, m), 7.32 (1H, m). m/z: ES+ [M+H]+ 251.

Example 9: (1R,3S)-3-acetamido-N-(5-chloro-4-(4,5,6,7-tetrahydropyrazolo[1,5-a]pyridin-3-yl)pyridin-2-yl)cyclohexanecarboxamide and (1S,3R)-3-acetamido-N-(5-chloro-4-(4,5,6,7-tetrahydropyrazolo[1,5-a]pyridin-3-yl)pyridin-2-yl)cyclohexanecarboxamide (Example 2)

Example 2

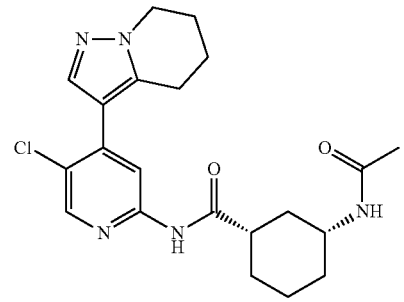

Example 9

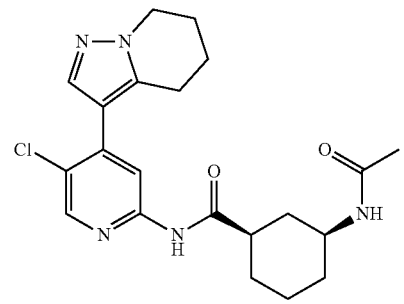

Acetyl chloride (0.280 mL, 3.93 mmol) was added to a solution of cis-3-amino-N-(5-chloro-4-(4,5,6,7-tetrahydropyrazolo[1,5-a]pyridin-3-yl)pyridin-2-yl)cyclohexanecarboxamide (0.639 g, 1.71 mmol; ratio of enantiomers unknown, prepared as in Example 2 from 5-chloro-4-(4,5,6,7-tetrahydropyrazolo[1,5-a]pyridin-3-yl)pyridin-2-amine and cis-3-(tert-butoxycarbonylamino)cyclohexanecarboxylic acid, ratio of enantiomers unknown) in DCM (14.1 mL) and pyridine (2.77 mL, 34.2 mmol) at 0° C. After 30 min the light yellow reaction was poured into DCM and saturated aqueous sodium bicarbonate. The layers were separated, and the organic layer was washed with saturated aqueous sodium chloride and dried over sodium sulfate, filtered, and concentrated under reduced pressure. The resulting residue was purified by flash silica chromatography, elution gradient 0 to 20% methanol in EtOAc. Product fractions were concentrated under reduced pressure to afford semipure product as a white solid. This material was further purified by preparative HPLC (Waters)(Bridge Prep C18 column, 5 µm, 30 mm diameter, 100 mm length), eluting with 60 to 80% methanol in water (containing 0.2% ammonium hydroxide at pH 10) as eluent. Product fractions were concentrated to dryness under reduced pressure to afford cis-3-amino-N-(5-chloro-4-(4,5,6,7-tetrahydropyrazolo[1,5-a]pyridin-3-yl)pyridin-2-yl)cyclohexanecarboxamide, ratio of enantiomers unknown, as a white solid (403 mg).

This material was transferred to a round-bottom flask using DCM and concentrated under reduced pressure to a white solid. The solid was taken up in approximately 10 mL of MeCN and warmed to reflux conditions. The solution was cooled, and a precipitate rapidly started to form. After 10 min the mixture was put in the freezer. After 2 h, the mixture was warmed to r.t. and stirred vigorously overnight. The white mixture was then filtered, washed with MeCN first and then hexane. The resulting precipitate was dried under vacuum at 60° C. for 30 min to afford 159 mg of a crystalline solid (flakes).

Analysis of this solid by analytical SFC conditions (see conditions in Example 2), determined it to be 60.5% e.e. (major component=Example 2). A portion of this material (112 mg) was purified by preparative SFC conditions (Chiralpak IA column, 5 μm, 21.2 mm diameter, 250 mm length, 40° C. column temperature, 100 bar outlet pressure, 75 mL/min flow rate), eluting with 40% methanol containing 0.1% dimethylethylamine in $CO_2$, to afford (1S,3R)-3-acetamido-N-(5-chloro-4-(4,5,6,7-tetrahydropyrazolo[1,5-a]pyridin-3-yl)pyridin-2-yl)cyclohexanecarboxamide (70 mg, 67%, Example 2) as a white foam solid and (1R,3S)-3-acetamido-N-(5-chloro-4-(4,5,6,7-tetrahydropyrazolo[1,5-a]pyridin-3-yl)pyridin-2-yl)cyclohexanecarboxamide (13.2 mg, 11.8%, Example 9) as a white foam solid.

(1R,3S)-3-acetamido-N-(5-chloro-4-(4,5,6,7-tetrahydropyrazolo[1,5-a]pyridin-3-yl)pyridin-2-yl)cyclohexanecarboxamide $^1$H NMR (300 MHz, DMSO-$d_6$, 27° C.) 0.99-1.17 (1H, m), 1.19-1.37 (3H, m), 1.70-1.90 (9H, m), 1.96-2.08 (2H, m), 2.54-2.68 (1H, m), 2.80 (2H, t), 3.46-3.68 (1H, m), 4.14 (2H, t), 7.73 (1H, d), 7.76 (1H, s), 8.14 (1H, s), 8.38 (1H, s), 10.57 (1H, s). m/z: ES+ [M+H]+ 416.

Analytical SFC Conditions:

Column: Chiralpak IA column,

Column Dimensions: 5 μm, 4.6 mm diameter, 100 mm length,

Column Temperature: 40° C.

Mobile Phase A: $CO_2$ (100%)

Mobile Phase B: Methanol containing 0.1% dimethylethylamine

Gradient: Isocratic 40% Mobile Phase B

Outlet Pressure: 100 bar

Flow Rate: 5 mL/min over 5 min

Retention Time: 2.42 min e.e. >98%

Optical Rotation:

Concentration: 0.1 g/dL

Lamp: Sodium

Wavelength: 589 nm

Temperature: 25° C.

Path length: 10 cm

Cell volume: 1 mL

Solvent: DCM

[α]=−57.1

Example 10: (1S,3R)-3-acetamido-N-(5-chloro-4-(5,6-dihydro-4H-pyrrolo[1,2-b]pyrazol-3-yl)pyridin-2-yl)cyclohexanecarboxamide

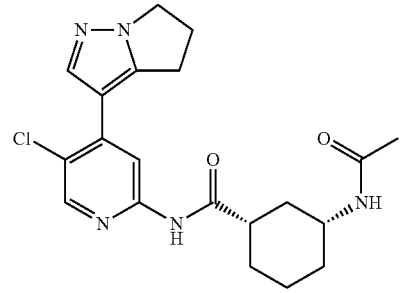 [SMILES: CC(=O)N[C@@H]1CCC[C@H](C(=O)Nc2cc(-c3cnn4c3CCC4)c(Cl)cn2)C1]

(1S,3R)-3-Amino-N-(5-chloro-4-(5,6-dihydro-4H-pyrrolo[1,2-b]pyrazol-3-yl)pyridin-2-yl)cyclohexanecarboxamide (0.093 g, 0.26 mmol) in DCM (2 mL) was treated with triethylamine (0.079 mL, 0.57 mmol) followed by acetic anhydride (0.029 mL, 0.31 mmol). The reaction mixture was stirred at r.t. for 0.5 h and then washed with water. The organic layer was purified by flash silica chromatography, elution gradient 0 to 10% MeOH in DCM. Pure fractions were evaporated to dryness to afford (1S,3R)-3-acetamido-N-(5-chloro-4-(5,6-dihydro-4H-pyrrolo[1,2-b]pyrazol-3-yl)pyridin-2-yl)cyclohexanecarboxamide (0.075 g, 72%) as a white solid. $^1$H NMR (400 MHz, CDCl$_3$, 30° C.) 1.09-1.22 (1H, m), 1.38-1.58 (2H, m), 1.88-2.03 (6H, m), 2.26 (1H, d), 2.43-2.56 (1H, m), 2.69 (2H, p), 3.14-3.21 (2H, m), 3.49 (1H, s), 3.87 (1H, dtt), 4.21 (2H, t), 5.59 (1H, d), 8.14 (1H, s), 8.22 (1H, s), 8.33 (1H, s), 8.43 (1H, s). m/z: ES+ [M+H]+ 402.

Procedures for preparing the starting material (1S,3R)-3-amino-N-(5-chloro-4-(5,6-dihydro-4H-pyrrolo[1,2-b]pyrazol-3-yl)pyridin-2-yl)cyclohexanecarboxamide are described below:

Preparation of 3-iodo-5,6-dihydro-4H-pyrrolo[1,2-b]pyrazole

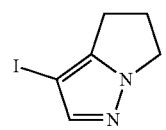

5,6-Dihydro-4H-pyrrolo[1,2-b]pyrazole-3-carboxylic acid (0.75 g, 4.93 mmol) dissolved in DMF (4 mL) was treated with N-iodosuccinimide (1.331 g, 5.92 mmol) and sodium bicarbonate (0.497 g, 5.92 mmol) at r.t. The mixture was stirred at r.t. for 15 h. The reaction was stirred at 60° C. for a further 16 h and then concentrated under reduced pressure. The resulting residue was dissolved in EtOAc (50 mL) and washed with water (2×50 mL). The organic layer was concentrated under reduced pressure, and the crude product was purified by flash silica chromatography, elution gradient 0 to 70% EtOAc in heptane. Pure fractions were evaporated to dryness to afford 3-iodo-5,6-dihydro-4H-pyrrolo[1,2-b]pyrazole (0.88 g, 76%) as a beige solid. $^1$H NMR (400 MHz, DMSO-$d_6$, 30° C.) 2.53-2.6 (2H, m), 2.69-2.79 (2H, m), 4.04-4.19 (2H, m), 7.46 (1H, s). m/z: ES+ [M+H]+ 235.

Preparation of 3-(4,4,5,5-tetramethyl-1,3,2-dioxaborolan-2-yl)-5,6-dihydro-4H-pyrrolo[1,2-b]pyrazole

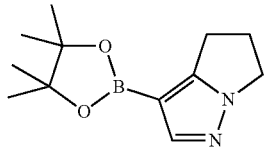 [SMILES: CC1(C)OB(c2cnn3c2CCC3)OC1(C)C]

3-Iodo-5,6-dihydro-4H-pyrrolo[1,2-b]pyrazole (0.800 g, 3.42 mmol) and 2-isopropoxy-4,4,5,5-tetramethyl-1,3,2-dioxaborolane (0.954 g, 5.13 mmol) were dissolved in THF (8 mL) at 4° C. and then treated dropwise with isopropylmagnesium chloride lithium chloride complex in THF (1.3 M; 2.63 mL, 3.42 mmol). The mixture was stirred at 4° C. for 2 h and then concentrated under reduced pressure. The resulting crude product was purified by flash silica chromatography, elution gradient 0 to 70% EtOAc in heptane. Pure fractions were evaporated to dryness to afford 3-(4,4,5,5-tetramethyl-1,3,2-dioxaborolan-2-yl)-5,6-dihydro-4H-pyrrolo[1,2-b]pyrazole (0.67 g, 84%) as a white solid. $^1$H NMR (400 MHz, CDCl$_3$, 30° C.) 1.29 (12H, s), 2.60 (2H, p), 2.91-3.02 (2H, m), 4.05-4.19 (2H, m), 7.77 (1H, s). m/z: ES+ [M+H]+ 235.

Preparation of Tert-butyl ((1R,3S)-3-((5-chloro-4-iodopyridin-2-yl)carbamoyl)cyclohexyl)carbamate

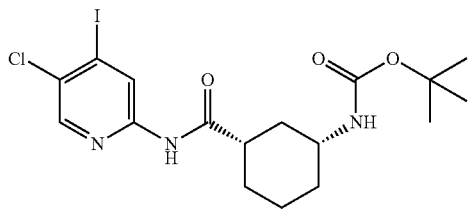 [SMILES: CC(C)(C)OC(=O)N[C@@H]1CCC[C@H](C(=O)Nc2cc(I)c(Cl)cn2)C1]

1-Chloro-N,N,2-trimethylpropenylamine (1.149 mL, 8.68 mmol) was added to a stirred solution of (1S,3R)-3-((tert-butoxycarbonyl)amino)cyclohexanecarboxylic acid (1.41 g, 5.79 mmol; prepared according to Example 2) in DCM (25 mL) cooled in an ice bath under a nitrogen atmosphere. The resulting mixture was stirred at ambient temperature for 1 h. 5-Chloro-4-iodopyridin-2-amine (1.47 g, 5.79 mmol; prepared according to Example 2) and pyridine (0.702 mL, 8.68 mmol) were added, and the resulting mixture was stirred at ambient temperature for 16 h. The reaction was quenched by the addition of saturated aqueous NH$_4$Cl (50 mL). The resulting mixture was extracted with DCM (3×75 mL), and the combined organic layers were dried over MgSO$_4$, filtered, and concentrated under reduced pressure. The resulting pale yellow solid was slurried with Et$_2$O (10 mL) and filtered to yield tert-butyl ((1R,3S)-3-((5-chloro-4-iodopyridin-2-yl)carbamoyl)cyclohexyl)carbamate (1.79 g, 3.73 mmol, 64.4%) as a cream-colored solid. $^1$H NMR (400 MHz, CDCl$_3$, 30° C.) 1.04-1.18 (1H, m), 1.24-1.41 (2H, m), 1.44 (9H, s), 1.92 (2H, dq), 2.00 (1H, d), 2.28 (1H, d), 2.31-2.41 (1H, m), 3.27-3.62 (2H, m), 4.44 (1H, s), 7.80 (1H, s), 8.19 (1H, s), 8.81 (1H, s). m/z: ES− [M−H]− 478.

Preparation of Tert-butyl ((1R,3S)-3-((5-chloro-4-(5,6-dihydro-4H-pyrrolo[1,2-b]pyrazol-3-yl)pyridin-2-yl)carbamoyl)cyclohexyl)carbamate

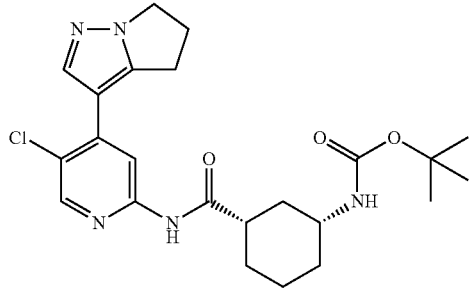 [SMILES: CC(C)(C)OC(=O)N[C@@H]1CCC[C@H](C(=O)Nc2cc(-c3cnn4c3CCC4)c(Cl)cn2)C1]

3-(4,4,5,5-Tetramethyl-1,3,2-dioxaborolan-2-yl)-5,6-dihydro-4H-pyrrolo[1,2-b]pyrazole (0.14 g, 0.58 mmol), tert-butyl ((1R,3S)-3-((5-chloro-4-iodopyridin-2-yl)carbamoyl)cyclohexyl)carbamate (0.18 g, 0.38 mmol), 2nd Generation X-Phos Precatalyst (0.03 g, 0.04 mmol) and potassium phosphate, dibasic (0.200 g, 1.15 mmol) were dissolved in 1,4-dioxane (4 mL) and water (0.8 mL) at 21° C. The mixture was stirred at 21° C. for 18 h. The mixture was then heated at 40° C. for 17 h then at 50° C. for 2 h. The mixture was diluted with EtOAc (30 mL) and then washed with water (10 mL). The organic layer was concentrated under reduced pressure, and the resulting crude product was purified by flash silica chromatography, elution gradient 0 to 70% EtOAc in heptane. Pure fractions were evaporated to dryness to afford tert-butyl ((1R,3S)-3-((5-chloro-4-(5,6-dihydro-4H-pyrrolo[1,2-b]pyrazol-3-yl)pyridin-2-yl)carbamoyl)cyclohexyl)carbamate (0.119 g, 67.5%) as a white solid. $^1$H NMR (400 MHz, CDCl$_3$, 30° C.) 1.04-1.17 (1H, m), 1.34-1.41 (2H, m), 1.44 (9H, s), 1.89-2.03 (4H, m), 2.29 (1H, d), 2.33-2.44 (1H, m), 2.69 (2H, p), 3.14-3.21 (2H, m), 3.45-3.59 (1H, m), 4.17-4.24 (2H, m), 4.44 (1H, s), 7.93 (1H, s), 8.15 (1H, s), 8.23 (1H, s), 8.33 (1H, s). m/z: ES+ [M+H]+ 460.

Preparation of (1S,3R)-3-amino-N-(5-chloro-4-(5,6-dihydro-4H-pyrrolo[1,2-b]pyrazol-3-yl)pyridin-2-yl)cyclohexanecarboxamide Dihydrochloride

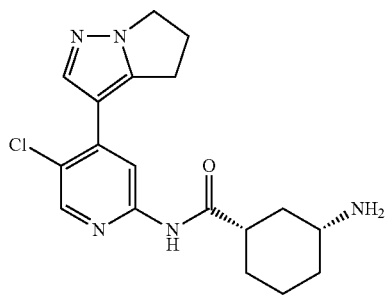 [SMILES: N[C@@H]1CCC[C@H](C(=O)Nc2cc(-c3cnn4c3CCC4)c(Cl)cn2)C1]

To a solution of tert-butyl ((1R,3S)-3-((5-chloro-4-(5,6-dihydro-4H-pyrrolo[1,2-b]pyrazol-3-yl)pyridin-2-yl)carbamoyl)cyclohexyl)carbamate (0.12 g, 0.26 mmol) dissolved in DCM (3 mL) was added HCl (4 M in dioxane; 1.294 mL, 5.17 mmol). The mixture was stirred at r.t. for 30 minutes before being concentrated under reduced pressure. The resulting crude product was used directly in the next step. m/z: ES+ [M+H]+ 360.

Example 11: (1S,3R)-3-acetamido-N-(5-chloro-4-(6,7-dihydro-4H-pyrazolo[5,1-c][1,4]oxazin-3-yl)pyridin-2-yl)cyclohexanecarboxamide

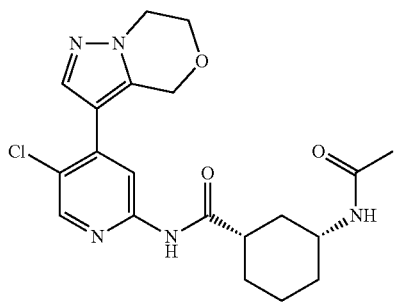

To a mixture of tert-butyl ((1R,3S)-3-((5-chloro-4-(6,7-dihydro-4H-pyrazolo[5,1-c][1,4]oxazin-3-yl)pyridin-2-yl)carbamoyl)cyclohexyl)carbamate (0.072 g, 0.15 mmol) suspended in DCM (3 mL) at r.t. was added HCl (4 M in dioxane; 0.756 mL, 3.03 mmol). The mixture became a solution which was stirred at r.t. for 30 minutes. The reaction was concentrated under reduced pressure to yield crude (1S,3R)-3-amino-N-(5-chloro-4-(6,7-dihydro-4H-pyrazolo[5,1-c][1,4]oxazin-3-yl)pyridin-2-yl)cyclohexanecarboxamide dihydrochloride as a solid. The crude product was dissolved in DCM (2 mL), and the resulting solution was treated sequentially with triethylamine (0.047 mL, 0.33 mmol) and acetic anhydride (0.017 mL, 0.18 mmol) at r.t. The reaction mixture was stirred at r.t. for 30 minutes and then concentrated under reduced pressure. The resulting residue was purified by flash silica chromatography, elution gradient 50 to 100% EtOAc in heptane, then 0 to 10% MeOH in DCM. Pure fractions were evaporated to dryness to afford (1S,3R)-3-acetamido-N-(5-chloro-4-(6,7-dihydro-4H-pyrazolo[5,1-c][1,4]oxazin-3-yl)pyridin-2-yl)cyclohexanecarboxamide (0.056 g, 88%) as a white solid. $^1$H NMR (400 MHz, DMSO-$d_6$, 30° C.) 1.08 (1H, d), 1.29 (4H, q), 1.78 (1H, s), 1.91 (3H, s), 2.61 (2H, s), 3.57 (1H, dt), 4.08-4.27 (4H, m), 4.89 (2H, s), 7.74 (1H, d), 7.88 (1H, s), 8.01 (1H, s), 8.39 (1H, s), 10.59 (1H, s), 11.90 (1H, s). m/z: ES+ [M+H]+ 418.

Procedures for preparing the starting material tert-butyl ((1R,3S)-3-((5-chloro-4-(6,7-dihydro-4H-pyrazolo[5,1-c][1,4]oxazin-3-yl)pyridin-2-yl)carbamoyl)cyclohexyl)carbamate are described below:

Preparation of 3-iodo-6,7-dihydro-4H-pyrazolo[5,1-c][1,4]oxazine

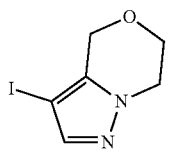

6,7-Dihydro-4H-pyrazolo[5,1-c][1,4]oxazine-3-carboxylic acid (0.750 g, 4.46 mmol) dissolved in DMF (4 mL) was treated with N-iodosuccinimide (1.204 g, 5.35 mmol) and sodium bicarbonate (0.450 g, 5.35 mmol) at r.t. The mixture was stirred at 70° C. for 4 h and then cooled to r.t. After 60 h the mixture was concentrated under reduced pressure, and the resulting residue was dissolved in EtOAc (70 mL) and washed with water (2×70 mL). The organic layer was concentrated under reduced pressure, and the resulting crude product was purified by flash silica chromatography, elution gradient 0 to 70% EtOAc in heptane. Pure fractions were evaporated to dryness to afford 3-iodo-6,7-dihydro-4H-pyrazolo[5,1-c][1,4]oxazine (0.90 g, 81%). $^1$H NMR (400 MHz, DMSO-$d_6$, 30° C.) 3.98-4.06 (2H, m), 4.07-4.15 (2H, m), 4.65 (2H, s), 7.53 (1H, s). m/z: ES+ [M+H]+ 251.

Preparation of 3-(4,4,5,5-tetramethyl-1,3,2-dioxaborolan-2-yl)-6,7-dihydro-4H-pyrazolo[5,1-c][1,4]oxazine

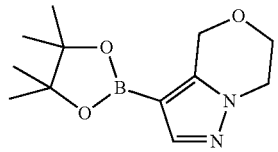 [SMILES: CC1(C)OB(c2cnn3c2COCC3)OC1(C)C]

3-Iodo-6,7-dihydro-4H-pyrazolo[5,1-c][1,4]oxazine (0.850 g, 3.40 mmol) and 2-isopropoxy-4,4,5,5-tetramethyl-1,3,2-dioxaborolane (0.949 g, 5.10 mmol) were dissolved in THF (8 mL) at 4° C. The resulting solution was treated dropwise with isopropylmagnesium chloride lithium chloride complex in THF (1.3 M; 2.61 mL, 3.40 mmol). The reaction mixture was stirred at 4° C. for 5 h before being concentrated under reduced pressure. The resulting crude product was purified by flash silica chromatography, elution gradient 0 to 70% EtOAc in heptane. Pure fractions were evaporated to dryness to afford 3-(4,4,5,5-tetramethyl-1,3,2-dioxaborolan-2-yl)-6,7-dihydro-4H-pyrazolo[5,1-c][1,4]oxazine (0.80 g, 95%) as a colourless gum. $^1$H NMR (400 MHz, CDCl$_3$, 30° C.) 1.29 (12H, s), 4.08 (2H, dd), 4.17-4.23 (2H, m), 4.96 (2H, s), 7.74 (1H, s). m/z: ES+ [M+H]+ 251.

Preparation of Tert-butyl ((1R,3S)-3-((5-chloro-4-(6,7-dihydro-4H-pyrazolo[5,1-c][1,4]oxazin-3-yl)pyridin-2-yl)carbamoyl)cyclohexyl)carbamate

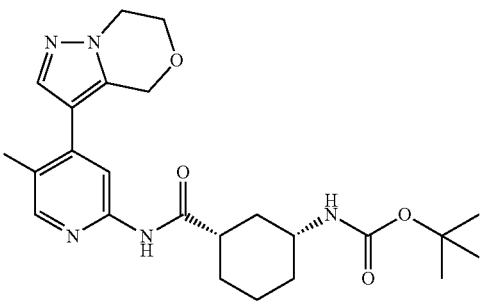

3-(4,4,5,5-Tetramethyl-1,3,2-dioxaborolan-2-yl)-6,7-dihydro-4H-pyrazolo[5,1-c][1,4]oxazine (0.094 g, 0.38 mmol), tert-butyl ((1R,3S)-3-((5-chloro-4-iodopyridin-2-yl)

carbamoyl)cyclohexyl)carbamate (0.120 g, 0.25 mmol; as prepared in Example 10), 2nd Generation X-Phos Precatalyst (0.020 g, 0.03 mmol) and potassium phosphate dibasic (0.131 g, 0.75 mmol) were dissolved in 1,4-dioxane (4 mL) and water (0.800 mL) at 50° C. The mixture was stirred at 50° C. for 1 h and then diluted with EtOAc (30 mL). The resulting mixture was washed with water (10 mL), and the organic layer was concentrated under reduced pressure. The resulting crude product was purified by flash silica chromatography, elution gradient 0 to 70% EtOAc in heptane. Pure fractions were evaporated to dryness to afford tert-butyl ((1R,3S)-3-((5-chloro-4-(6,7-dihydro-4H-pyrazolo[5,1-c][1,4]oxazin-3-yl)pyridin-2-yl)carbamoyl)cyclohexyl)carbamate (0.081 g, 68%). $^1$H NMR (400 MHz, DMSO-$d_6$, 30° C.) 1.22-1.35 (4H, m), 1.38 (9H, s), 1.75 (3H, s), 1.90 (1H, d), 2.54-2.63 (1H, m), 4.12-4.26 (4H, m), 4.90 (2H, s), 5.75 (1H, s), 6.76 (1H, d), 7.89 (1H, s), 8.01 (1H, s), 8.39 (1H, s), 10.58 (1H, s). m/z: ES+ [M+H]+ 476.

Example 12: (1S,3R)-3-acetamido-N-(5-chloro-4-(6,7-dihydro-5H-pyrrolo[1,2-a]imidazol-3-yl)pyridin-2-yl)cyclohexanecarboxamide

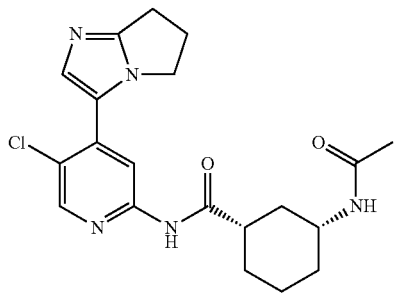 [SMILES: CC(=O)N[C@@H]1CCC[C@H](C(=O)Nc2cc(-c3cnc4n3CCC4)c(Cl)cn2)C1]

(1S,3R)-3-Acetamido-N-(5-chloro-4-iodopyridin-2-yl)cyclohexanecarboxamide (130 mg, 0.31 mmol), (6,7-dihydro-5H-pyrrolo[1,2-a]imidazol-3-yl)boronic acid hydrochloride (145 mg, 0.77 mmol), barium hydroxide (211 mg, 1.23 mmol) and PdCl$_2$(dppf) (22 mg, 0.030 mmol) were suspended in dioxane (2 mL) and water (0.4 mL) and sealed into a microwave tube. The reaction was heated to 75° C. in a microwave reactor and maintained under these conditions for 2 h before being cooled to r.t. The reaction mixture was filtered with a methanol wash, and the filtrate was then concentrated under reduced pressure. The resulting crude product was purified by preparative HPLC (Waters)(Bridge Prep C18 OBD column, 5 µm silica, 19 mm diameter, 100 mm length), using decreasingly polar mixtures of water (containing 1% NH$_3$) and MeCN as eluents. Fractions containing the desired compound were evaporated to dryness to afford (1S,3R)-3-acetamido-N-(5-chloro-4-(6,7-dihydro-5H-pyrrolo[1,2-a]imidazol-3-yl)pyridin-2-yl)cyclohexanecarboxamide (21.3 mg, 17.2%) as a solid. $^1$H NMR (500 MHz, DMSO-$d_6$, 30° C.) 1.09 (1H, d), 1.30 (3H, q), 1.78 (5H, s), 1.91 (1H, d), 2.57-2.73 (4H, m), 2.85 (2H, t), 3.58 (1H, dd), 4.16 (2H, t), 7.55 (1H, s), 7.75 (1H, d), 8.35 (1H, s), 8.42 (1H, s), 10.67 (1H, s). m/z: ES+ [M+H]+ 402.

Procedures for preparing the starting materials (1S,3R)-3-Acetamido-N-(5-chloro-4-iodopyridin-2-yl)cyclohexanecarboxamide and (6,7-dihydro-5H-pyrrolo[1,2-a]imidazol-3-yl)boronic acid hydrochloride are described below:

Preparation of 5-methoxy-3,4-dihydro-2H-pyrrole

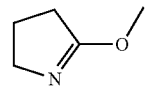

Pyrrolidin-2-one (85 g, 1000 mmol) and Me$_2$SO$_4$ (126 g, 1000 mmol) were stirred at r.t. for 30 minutes, and then the mixture was stirred at 60° C. for 6 h. The mixture was slowly poured into a solution of triethylamine (140 mL) in DCM at 0° C. and stirred under these conditions for 15 min. Water was added, and the layers were separated. The organic layer was dried over MgSO$_4$ and concentrated under reduced pressure at r.t. to yield 5-methoxy-3,4-dihydro-2H-pyrrole, which was used directly in the next step without further purification. $^1$H NMR (400 MHz, CDCl$_3$, 30° C.) 2.03-1.95 (2H, m), 2.43-2.39 (2H, m), 3.64-3.60 (2H, m), 3.76 (3H, s).

Preparation of 6,7-dihydro-5H-pyrrolo[1,2-a]imidazole

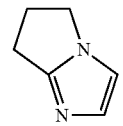

To a solution of 5-methoxy-3,4-dihydro-2H-pyrrole (crude) in DCM (200 mL) was added MeOH (800 mL) and aminoacetaldehyde dimethyl acetal (105 g, 1000 mmol). The mixture was stirred at 60° C. for 6 h before being concentrated under reduced pressure to afford N-(2,2-dimethoxyethyl)-3,4-dihydro-2H-pyrrol-5-amine (82 g, 48%). The crude product was dissolved in formic acid (400 mL) and stirred at reflux for 17 h before being concentrated under reduced pressure to afford 6,7-dihydro-5H-pyrrolo[1,2-a]imidazole (46 g, 90%). $^1$H NMR (400 MHz, DMSO-$d_6$, 30° C.) 2.51-2.44 (2H, m), 2.69-2.65 (2H, m), 3.91-3.88 (2H, m), 6.84 (1H, s), 7.02 (1H, s).

Preparation of (6,7-dihydro-5H-pyrrolo[1,2-a]imidazol-3-yl)boronic Acid Hydrochloride

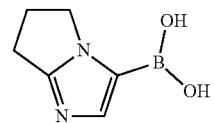 [SMILES: OB(O)c1cnc2n1CCC2]

To a stirred solution of 6,7-dihydro-5H-pyrrolo[1,2-a]imidazole (60 g, 560 mmol) in anhydrous THF (700 mL) at −78° C. was added n-BuLi (250 mL, 625 mmol), and the mixture was stirred for 1 h at this temperature. Triisopropyl borate (115 g, 610 mmol) was added at −78° C., and then the mixture was allowed to warm to r.t. overnight. The reaction was cooled to 0° C., and aqueous HCl (1M; 1000 mL) was added. The reaction was concentrated under reduced pressure to remove tetrahydrofuran. The pH of the remaining aqueous layer was adjusted to 2 by careful addition of concentrated HCl, and the precipitate was collected and dried to afford (6,7-dihydro-5H-pyrrolo[1,2-a]imidazol-3-yl)boronic acid hydrochloride (42 g, 40%). ¹H NMR (400 MHz, DMSO-d₆, 30° C.) 2.64-2.49 (2H, m), 3.08 (2H, t), 4.19 (2H, t), 7.92 (1H, s), 8.84 (2H, s), 14.34 (1H, s). m/z: ES+ [M+H]+ 153.

Preparation of 3-amino-N-(5-chloro-4-iodopyridin-2-yl)cyclohexanecarboxamide

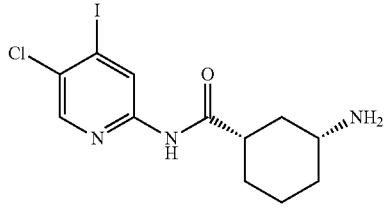 [SMILES: N[C@@H]1CCC[C@H](C(=O)Nc2cc(I)c(Cl)cn2)C1]

Tert-butyl (3-((5-chloro-4-iodopyridin-2-yl)carbamoyl)cyclohexyl)carbamate (1 g, 2.08 mmol; as prepared in Example 10) was suspended in DCM (15 mL) at ambient temperature. HCl (4M) in dioxane (2.61 mL, 10.42 mmol) was added and the resulting mixture stirred for 16 h. The reaction mixture was then loaded onto a 50 g SCX column and eluted sequentially with DCM, MeOH, and 1% NH₃ in MeOH. Basic fractions were concentrated under reduced pressure to afford 3-amino-N-(5-chloro-4-iodopyridin-2-yl)cyclohexanecarboxamide as a colourless amorphous solid (782 mg, 99%). m/z: ES+ [M+H]+ 380.

Preparation of (1S,3R)-3-acetamido-N-(5-chloro-4-iodopyridin-2-yl)cyclohexanecarboxamide

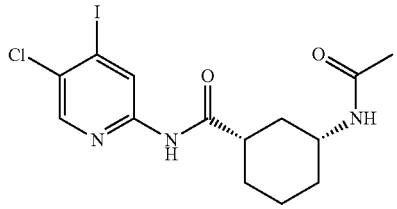 [SMILES: CC(=O)N[C@@H]1CCC[C@H](C(=O)Nc2cc(I)c(Cl)cn2)C1]

Acetic anhydride (0.214 mL, 2.27 mmol) was added to a stirred solution of (1S,3R)-3-amino-N-(5-chloro-4-iodopyridin-2-yl)cyclohexanecarboxamide (782 mg, 2.06 mmol) and triethylamine (0.632 mL, 4.53 mmol) in DCM (10 mL) at ambient temperature. The reaction mixture was stirred for 5 days before being filtered and washed with DCM to provide (1S,3R)-3-acetamido-N-(5-chloro-4-iodopyridin-2-yl)cyclohexanecarboxamide (480 mg, 55%) as a colourless solid. The liquors were concentrated and purified by flash silica chromatography, elution gradient 20 to 60% EtOAc in heptane. Pure fractions were evaporated to dryness to afford more (1S,3R)-3-acetamido-N-(5-chloro-4-iodopyridin-2-yl)cyclohexanecarboxamide (193 mg, 22%) as a colourless crystalline solid (combined yield: 77%). ¹H NMR (400 MHz, DMSO-d₆, 30° C.) 1.01-1.17 (1H, m), 1.18-1.39 (3H, m), 1.68-1.84 (2H, m), 1.78 (3H, s), 1.89 (1H, m), 2.51 (2H, m), 3.48-3.65 (1H, m), 7.74 (1H, d), 8.38 (1H, s), 8.71 (1H, s), 10.66 (1H, s). m/z: ES+ [M+H]+ 422.

Example 13: (1S,3R)-3-acetamido-N-(5-chloro-4-(5-methyl-4,5,6,7-tetrahydropyrazolo[1,5-a]pyrazin-3-yl)pyridin-2-yl)cyclohexanecarboxamide

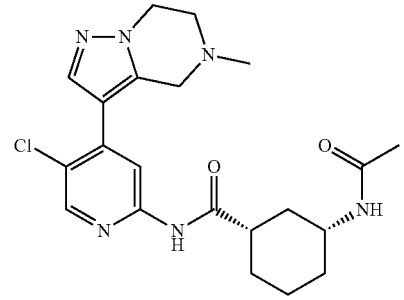 [SMILES: CC(=O)N[C@@H]1CCC[C@H](C(=O)Nc2cc(-c3cnn4c3CN(C)CC4)c(Cl)cn2)C1]

To a solution of tert-butyl ((1R,3S)-3-((5-chloro-4-(5-methyl-4,5,6,7-tetrahydropyrazolo[1,5-a]pyrazin-3-yl)pyridin-2-yl)carbamoyl)cyclohexyl)carbamate (0.042 g, 0.090 mmol) dissolved in DCM (2 mL) was added HCl (4 M in dioxane; 0.429 mL, 1.72 mmol). The mixture was stirred at r.t. for 2 h before being concentrated under reduced pressure to afford a crude solid (33 mg). This solid was dissolved in DCM (2 mL) and triethylamine (0.026 mL, 0.19 mmol). Then acetic anhydride (9.6 µL, 0.10 mmol) was added. The mixture was stirred at r.t. for 30 min and then concentrated under reduced pressure. The resulting crude product was purified by flash silica chromatography, elution gradient 0 to 100% EtOAc in (10% MeOH in DCM). Pure fractions were evaporated to dryness to afford (1S,3R)-3-acetamido-N-(5-chloro-4-(5-methyl-4,5,6,7-tetrahydropyrazolo[1,5-a]pyrazin-3-yl)pyridin-2-yl)cyclohexanecarboxamide (0.027 g, 74%) as a colourless dry film. ¹H NMR (400 MHz, CDCl₃, 30° C.) 1.09-1.24 (1H, m), 1.41-1.56 (3H, m), 1.87-2.04 (6H, m), 2.25 (1H, d), 2.51 (4H, s), 2.9-2.98 (2H, m), 3.73 (2H, s), 3.87 (1H, dtd), 4.26 (2H, t), 5.60 (1H, d), 7.84 (1H, s), 8.11 (1H, s), 8.25 (1H, d), 8.30 (1H, s). m/z: ES+ [M+H]+ 431.

Procedures for preparing the starting material tert-butyl ((1R,3S)-3-((5-chloro-4-(5-methyl-4,5,6,7-tetrahydropyrazolo[1,5-a]pyrazin-3-yl)pyridin-2-yl)carbamoyl)cyclohexyl)carbamate are described below:

Preparation of 3-bromo-5-methyl-4,5,6,7-tetrahydropyrazolo[1,5-a]pyrazine

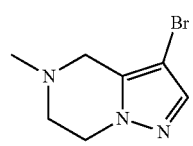

HCl (4 M in dioxane; 3.31 mL, 13.24 mmol) was added in one portion to tert-butyl 3-bromo-6,7-dihydropyrazolo[1,5-a]pyrazine-5(4H)-carboxylate (0.400 g, 1.32 mmol) in DCM (6 mL) at 20° C. The resulting mixture was stirred at 20° C. for 60 minutes. A white solid formed. The mixture was concentrated under reduced pressure, and the resulting residue was redissolved in formic acid (12.7 mL, 331 mmol) and treated with formaldehyde (0.64 mL, 8.6 mmol). This new mixture was heated at 100° C. for 8 h before being concentrated under reduced pressure. The resulting residue was dissolved in EtOAc (25 mL) and then washed with saturated aqueous sodium hydrogencarbonate (2×25 mL); the combined aqueous layers were then extracted with EtOAc (2×25 mL). The combined organic layers were concentrated under reduced pressure, and the resulting crude residue was purified by flash silica chromatography, elution gradient 0 to 100% EtOAc in heptane. Pure fractions were evaporated to dryness to afford 3-bromo-5-methyl-4,5,6,7-tetrahydropyrazolo[1,5-a]pyrazine (0.185 g, 64.7%) as a colourless oil. $^1$H NMR (400 MHz, CDCl$_3$, 30° C.) 2.45 (3H, s), 2.75-2.85 (2H, m), 3.48 (2H, s), 4.05-4.15 (2H, m), 7.35 (1H, s). m/z: ES+ [M+H]+ 218 ($^{81}$Br isotope).

Preparation of 5-methyl-3-(4,4,5,5-tetramethyl-1,3,2-dioxaborolan-2-yl)-4,5,6,7-tetrahydropyrazolo[1,5-a]pyrazine

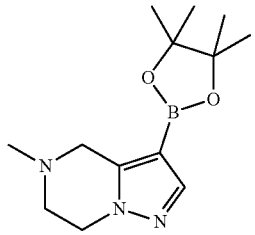

3-Bromo-5-methyl-4,5,6,7-tetrahydropyrazolo[1,5-a]pyrazine (0.185 g, 0.860 mmol), 4,4,4',4',5,5,5',5'-octamethyl-2,2'-bi(1,3,2-dioxaborolane) (0.435 g, 1.71 mmol), potassium acetate (0.294 g, 3.00 mmol) and Pd(P(Cy)$_3$)$_2$Cl$_2$ (0.063 g, 0.090 mmol) were suspended in DMA (3 mL). The reaction was heated to 80° C. for 5 h then 90° C. for 16 h. The reaction mixture was cooled to r.t. and then diluted with water (20 mL) and extracted with EtOAc (20 mL). The combined organics were concentrated under reduced pressure. The resulting crude product was purified by flash silica chromatography, elution gradient 0 to 100% DCM in heptane followed by 0 to 10% MeOH in DCM. Pure fractions were evaporated to dryness to afford 5-methyl-3-(4,4,5,5-tetramethyl-1,3,2-dioxaborolan-2-yl)-4,5,6,7-tetrahydropyrazolo[1,5-a]pyrazine (0.20 g, 89%) as a colourless oil. $^1$H NMR (400 MHz, CDCl$_3$, 30° C.) 1.29 (12H, s), 2.52 (3H, s), 2.88-2.92 (2H, m), 3.80 (2H, s), 4.22 (2H, t), 7.72 (1H, s). m/z: ES+ [M+H]+ 264.

Preparation of Tert-butyl ((1R,3S)-3-((5-chloro-4-(5-methyl-4,5,6,7-tetrahydropyrazolo[1,5-a]pyrazin-3-yl)pyridin-2-yl)carbamoyl)cyclohexyl)carbamate

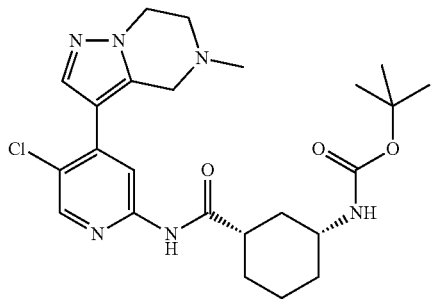 [SMILES: CN1CCn2ncc(-c3cc(NC(=O)[C@H]4CCC[C@@H](NC(=O)OC(C)(C)C)C4)ncc3Cl)c2C1]

Tert-butyl ((1R,3S)-3-((5-chloro-4-iodopyridin-2-yl)carbamoyl)cyclohexyl)carbamate (0.200 g, 0.42 mmol; as prepared in Example 10), 5-methyl-3-(4,4,5,5-tetramethyl-1,3,2-dioxaborolan-2-yl)-4,5,6,7-tetrahydropyrazolo[1,5-a]pyrazine (0.197 g, 0.750 mmol), 2nd Generation X-Phos Precatalyst (0.033 g, 0.040 mmol) and potassium phosphate dibasic (0.218 g, 1.25 mmol) were dissolved in 1,4-dioxane (4 mL) and water (0.800 mL) at 45° C. The mixture was stirred at 45° C. for 18 h. More 2nd Generation X-Phos Precatalyst (0.033 g, 0.04 mmol) was added, and the temperature was raised to 60° C. for 1 h. The reaction mixture was cooled and passed through an SCX-2 column. The desired product was eluted from the column using 1 M NH$_3$ in MeOH, and pure fractions were concentrated under reduced pressure. The resulting crude product was purified by flash silica chromatography, elution gradient 0 to 100% EtOAc in heptane, then 0 to 10% MeOH in DCM. Pure fractions were evaporated to dryness to afford tert-butyl ((1R,3S)-3-((5-chloro-4-(5-methyl-4,5,6,7-tetrahydropyrazolo[1,5-a]pyrazin-3-yl)pyridin-2-yl)carbamoyl)cyclohexyl)carbamate (0.054 g, 27%). $^1$H NMR (400 MHz, CDCl$_3$, 30° C.) 1.04-1.19 (1H, m), 1.44 (12H, s), 1.87-2.02 (3H, m), 2.29 (1H, d), 2.33-2.46 (1H, m), 2.53 (3H, s), 2.95-3 (2H, m), 3.50 (1H, s), 3.76 (2H, s), 4.28 (2H, t), 4.52 (1H, s), 7.85 (1H, s), 8.12 (2H, s), 8.26 (1H, s). m/z: ES+ [M+H]+ 489.

Example 14: (1S,3R)-3-acetamido-N-(5-chloro-4-(5,5-dimethyl-5,6-dihydro-4H-pyrrolo[1,2-b]pyrazol-3-yl)pyridin-2-yl)cyclohexanecarboxamide

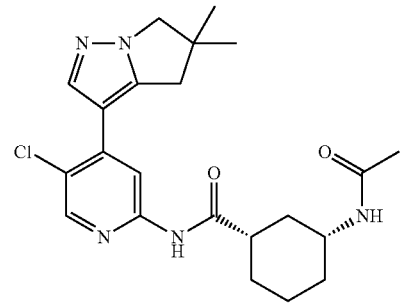 [SMILES: CC(=O)N[C@@H]1CCC[C@H](C(=O)Nc2cc(-c3cnn4c3CC(C)(C)C4)c(Cl)cn2)C1]

To a stirred solution of (1S,3R)-3-amino-N-(5-chloro-4-(5,5-dimethyl-5,6-dihydro-4H-pyrrolo[1,2-b]pyrazol-3-yl)pyridin-2-yl)cyclohexanecarboxamide (111 mg, 0.290 mmol), triethylamine (0.084 mL, 0.60 mmol) and N,N-dimethylpyridin-4-amine (1.748 mg, 0.01 mmol) in DCM (10 mL) was added acetic anhydride (0.032 mL, 0.34 mmol). The reaction mixture was stirred at r.t. for 4 h and then purified by ion exchange chromatography using an SCX-2 column. The desired product was eluted from the column using 1 M NH$_3$ in MeOH, and product-containing fractions were concentrated under reduced pressure. The resulting crude product was purified by flash silica chromatography, elution gradient 0 to 100% EtOAc in heptane. Pure fractions were evaporated to dryness to afford (1S,3R)-3-acetamido-N-(5-chloro-4-(5,5-dimethyl-5,6-dihydro-4H-pyrrolo[1,2-b]pyrazol-3-yl)pyridin-2-yl)cyclohexanecarboxamide (86 mg, 70%) as a white solid (Form A). $^1$H NMR (400 MHz, DMSO-d$_6$, 30° C.) 1.09 (1H, d), 1.28 (9H, s), 1.78 (6H, s), 1.90 (1H, d), 2.62 (1H, s), 2.89 (2H, s), 3.57 (1H, dt), 3.95 (2H, s), 7.73 (1H, d), 7.99 (1H, s), 8.25 (1H, s), 8.33-8.36 (1H, m), 10.53 (1H, s). m/z: ES+ [M+H]+ 430.

Optical Rotation
Concentration: 0.1 g/dL
Lamp: Sodium
Wavelength: 589 nm
Temperature: 20° C.
Path length: 10 cm
Cell volume: 1 mL
Solvent: DMSO
[α]=+66.4

Method 1: The title material (10 mg) was dissolved in 1 mL of acetonitrile and the clear solution was slowly evaporated at r.t. over 3 days. The resulting solid was found to be the Example 14 in crystalline Form A.

Method 2: The title material (10 mg) was added to 0.1 mL acetonitrile and the resulting suspension was stirred at ambient temperature for 18 h and then air dried over 3 days. The resulting solid was found to be Example 14 in crystalline Form A.

Crystals of Form A were analyzed by XRPD and results are tabulated below and are shown in FIG. 1. The XRPD of the solid confirms that the solid contains exclusively Form A which has an X-ray powder diffraction pattern with specific peaks at about 2-theta=5.9, 7.0, 9.4, 10.5, 11.5, 11.7, 17.6, 18.0, 20.2 and 21.0°.

Example 14 Form a Main Peaks

| Peak | 2θ | Intensity % |
|---|---|---|
| 1 | 5.9 | 83.1 (vs) |
| 2 | 7.0 | 100.0 (vs) |
| 3 | 9.4 | 69.8 (vs) |
| 4 | 10.5 | 71.7 (vs) |
| 5 | 11.5 | 59.6 (vs) |
| 6 | 11.7 | 59.4 (vs) |
| 7 | 17.6 | 53.7 (vs) |
| 8 | 18.0 | 61.0 (vs) |
| 9 | 20.2 | 77.3 (vs) |
| 10 | 21.0 | 88.7 (vs) |

Figure 2:
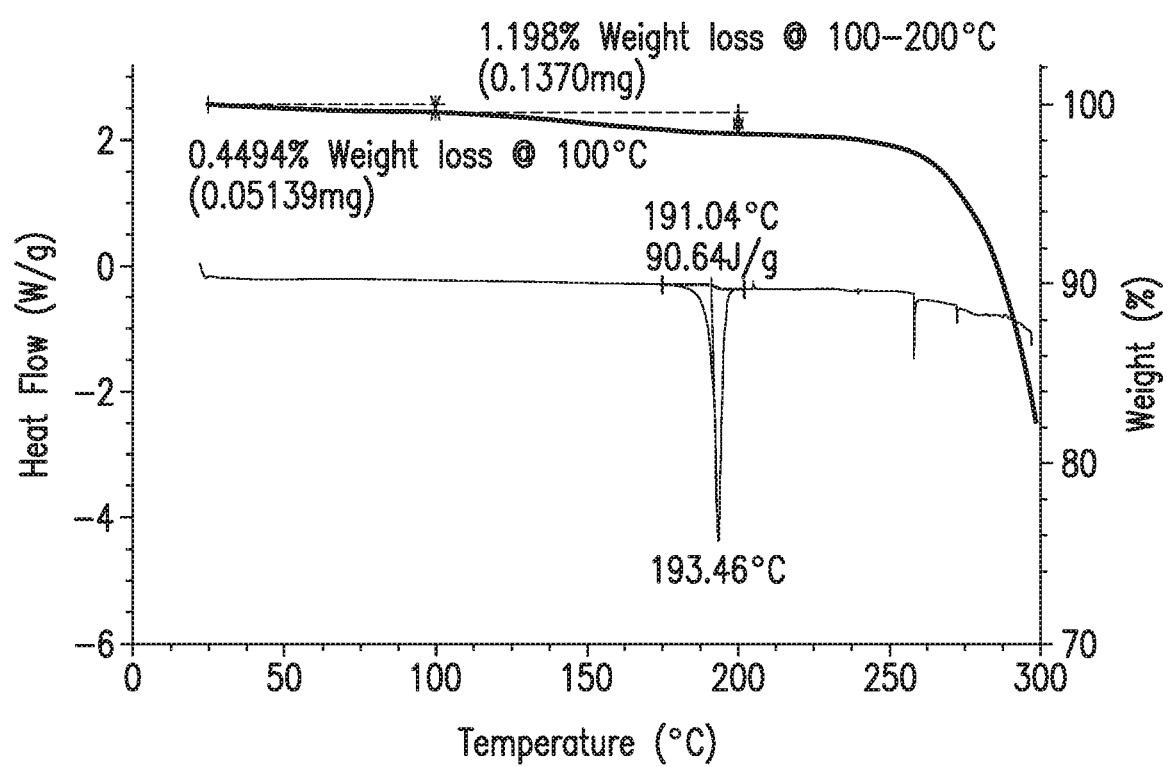
FIG. 2 is a representative DSC/TGA thermograph of Form A of (1S,3R)-3-acetamido-N-(5-chloro-4-(5,5-dimethyl-5,6-dihydro-4H-pyrrolo[1,2-b]pyrazol-3-yl)pyridin-2-yl)cyclohexanecarboxamide (Example 14).

Crystals (Form A) obtained according to the Example 14 were analyzed by thermal techniques. DSC analysis indicated that Form A melts with an onset point at 191° and a peak at 193°. TGA indicated that Form A exhibits a mass loss of about 1.6% upon heating from 22 to 200° C. A representative DSC/TGA thermogram is shown in FIG. 2.

An alternative procedure for making Example 14 is described in Example 85.

Procedures for preparing the starting material (1S,3R)-3-amino-N-(5-chloro-4-(5,5-dimethyl-5,6-dihydro-4H-pyrrolo[1,2-b]pyrazol-3-yl)pyridin-2-yl)cyclohexanecarboxamide are described below:

Preparation of Ethyl
2,2-dimethyl-3-(1H-pyrazol-1-yl)propanoate

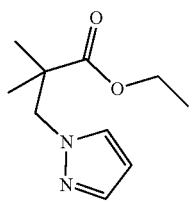

1H-Pyrazole (20 g, 293.78 mmol), ethyl 3-bromo-2,2-dimethylpropanoate (61.4 g, 293.78 mmol) and cesium carbonate (144 g, 440.68 mmol) in DMA (200 mL) were stirred at 80° C. for 16 h. The mixture was then poured into water (400 mL) and extracted with ethyl acetate (150 mL). The organic layer was concentrated under reduced pressure to give a colourless oil. This oil was purified by flash silica chromatography, elution gradient 10 to 40% ethyl acetate in heptane). Product fractions were concentrated under reduced pressure to afford ethyl 2,2-dimethyl-3-(1H-pyrazol-1-yl)propanoate (46.0 g, 80.0%), as a colourless oil. $^1$H NMR (400 MHz, CDCl$_3$, 30° C.) 0.97 (6H, s), 1.02 (3H, t), 3.93 (2H, q), 4.10 (2H, s), 6.00 (1H, t), 7.16 (1H, d), 7.26 (1H, d). m/z: (ES+) [M+H]+=197.

Preparation of
2,2-dimethyl-3-(1H-pyrazol-1-yl)propanoic Acid

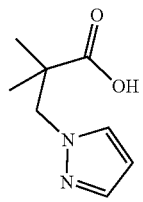

Aqueous sodium hydroxide (5 M; 94 mL, 46 mmol) was added portionwise to a stirred solution of ethyl 2,2-dimethyl-3-(1H-pyrazol-1-yl)propanoate (46 g, 234 mmol) dissolved in methanol (250 mL) at r.t. The mixture was allowed to exotherm to 37° C. during addition. The resulting solution was stirred under these conditions for 30 minutes and then cooled to r.t. before being concentrated under reduced pressure to 1/3 volume. This new solution was acidified to ~pH 3 with concentrated HCl. A colourless oil separated from the mixture. The flask was swirled in an ice bath and a colourless solid crystallised. The mixture was allowed to stand overnight at r.t., and the solid was isolated by filtration and dried under reduced pressure to afford 2,2-dimethyl-3-(1H-pyrazol-1-yl)propanoic acid (30.0 g, 76%) as a colourless crystalline solid. $^1$H NMR (400 MHz, DMSO-d$_6$, 30° C.) 1.05 (6H, s), 4.23 (2H, s), 6.21 (1H, t), 7.35-7.44 (1H, m), 7.54-7.67 (1H, m), 12.41 (1H, br s). m/z: (ES+) [M+H]+=169.

Preparation of 5,5-dimethyl-5,6-dihydro-4H-pyrrolo[1,2-b]pyrazol-4-one

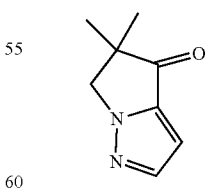

n-BuLi in hexane (9.03 mL, 24.38 mmol) was added dropwise to 2,2-dimethyl-3-(1H-pyrazol-1-yl)propanoic acid (2 g, 11.89 mmol) in 2-methyl tetrahydrofuran (40 mL) at −78° C. over a period of 20 minutes under nitrogen. The resulting suspension was stirred at −78° C. for 15 minutes, and then the reaction was stirred at approximately −45° C.

for 1 h then allowed to warm to 15° C. before the reaction was quenched slowly onto ice cold saturated ammonium chloride (100 ml). The reaction mixture was diluted with EtOAc (100 mL) and the ammonium chloride layer was separated and extracted one more time with EtOAc (50 ml). The combined organics layers were washed with saturated aqueous sodium chloride (50 mL). The organic layer was dried over MgSO4, filtered and evaporated to afford 5,5-dimethyl-5,6-dihydro-4H-pyrrolo[1,2-b]pyrazol-4-one (0.970 g, 54.3%) as a pale yellow oil which crystallised on standing. ¹H NMR (400 MHz, DMSO-d6, 30° C.) 1.29 (6H, s), 4.36 (2H, s), 6.77 (1H, d), 7.89 (1H, d). m/z: ES+ [M+H]+ 151.

Preparation of 5,5-dimethyl-5,6-dihydro-4H-pyrrolo[1,2-b]pyrazole

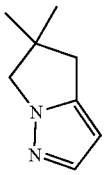

Hydrazine hydrate (4.13 mL, 85.23 mmol) was added to a stirred solution of 5,5-dimethyl-5,6-dihydro-4H-pyrrolo[1,2-b]pyrazol-4-one (2.56 g, 17.1 mmol) dissolved in 2,2'-oxydiethanol (48.5 mL, 511 mmol). The resulting solution was stirred at 180° C. for 1 h. Potassium hydroxide (3.35 mL, 59.7 mmol) was carefully added to the mixture and the resulting suspension was stirred at 150° C. for 2 h. After cooling to r.t., the reaction mixture was diluted with water (50 mL), and the pH was adjusted to 4.5 with dilute aqueous HCl (2N). Following extraction with Et2O (5×50 mL), the combined organic layers were washed with water (2×20 mL) and then saturated aqueous sodium chloride (20 mL). The organic layers were dried over MgSO4, filtered and concentrated under reduced pressure to give 5,5-dimethyl-5,6-dihydro-4H-pyrrolo[1,2-b]pyrazole (0.922 g, 39.7%) as a clear yellow oil. ¹H NMR (400 MHz, CDCl3, 30° C.) 1.21 (6H, s), 2.61 (2H, s), 3.80 (2H, s), 5.82-5.93 (1H, m), 7.41 (1H, d).

Preparation of 3-bromo-5,5-dimethyl-5,6-dihydro-4H-pyrrolo[1,2-b]pyrazole

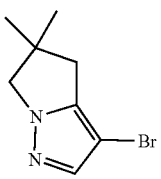

N-Bromosuccinimide (1166 mg, 6.55 mmol) was added to a stirred solution of 5,5-dimethyl-5,6-dihydro-4H-pyrrolo[1,2-b]pyrazole (892 mg, 6.55 mmol) dissolved in DCM (10 mL) at 23° C. The resulting mixture was stirred at 23° C. for 16 h before being diluted with DCM (20 mL) and washed sequentially with water (2×20 mL) and saturated aqueous sodium chloride (20 mL). The organic layer was dried over MgSO4, filtered, and concentrated under reduced pressure to afford 3-bromo-5,5-dimethyl-5,6-dihydro-4H-pyrrolo[1,2-b]pyrazole (1394 mg, 99%) as a yellow oil. ¹H NMR (400 MHz, CDCl3, 30° C.) 1.23 (6H, s), 2.58 (2H, s), 3.83 (2H, s), 7.35 (1H, s).

Preparation of 5,5-dimethyl-3-(4,4,5,5-tetramethyl-1,3,2-dioxaborolan-2-yl)-5,6-dihydro-4H-pyrrolo[1,2-b]pyrazole

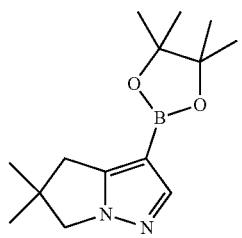

Pd(P(Cy)3)2Cl2 (0.247 g, 0.33 mmol) was added to 4,4,4',4',5,5,5',5'-octamethyl-2,2'-bi(1,3,2-dioxaborolane) (1.70 g, 6.69 mmol), 3-bromo-5,5-dimethyl-5,6-dihydro-4H-pyrrolo[1,2-b]pyrazole (0.720 g, 3.35 mmol) and potassium acetate (1.150 g, 11.72 mmol) in DMA (7 mL). The resulting suspension was degassed and stirred at 85° C. for 5 h. Dichloro[1,1'-bis(diphenylphosphino)ferrocene]palladium DCM adduct (0.273 g, 0.33 mmol) was then added to the reaction mixture, and stirring was continued under these conditions for 18 h before the reaction mixture was cooled to r.t. The reaction mixture was diluted with EtOAc (20 mL) and washed sequentially with water (2×15 mL), and saturated aqueous sodium chloride (15 mL). The organic layer was dried over MgSO4, filtered, and concentrated under reduced pressure. The resulting crude product was purified by flash silica chromatography, elution gradient 0 to 50% EtOAc in heptane. Pure fractions were evaporated to dryness to afford 5,5-dimethyl-3-(4,4,5,5-tetramethyl-1,3,2-dioxaborolan-2-yl)-5,6-dihydro-4H-pyrrolo[1,2-b]pyrazole (0.458 g, 52.2%) as a cream solid. ¹H NMR (400 MHz, CDCl3, 30° C.) 1.24 (6H, s), 1.27 (12H, s), 2.79 (2H, s), 3.87 (2H, s), 7.76 (1H, s).

Preparation of Tert-butyl ((1R,3S)-3-((5-chloro-4-(5,5-dimethyl-5,6-dihydro-4H-pyrrolo[1,2-b]pyrazol-3-yl)pyridin-2-yl)carbamoyl)cyclohexyl)carbamate

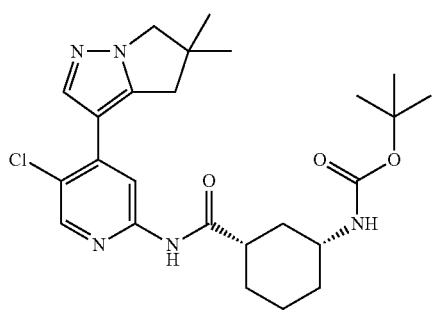 [SMILES: CC1(C)Cc2c(-c3cc(NC(=O)[C@H]4CCC[C@@H](NC(=O)OC(C)(C)C)C4)ncc3Cl)cnn2C1]

5,5-Dimethyl-3-(4,4,5,5-tetramethyl-1,3,2-dioxaborolan-2-yl)-5,6-dihydro-4H-pyrrolo[1,2-b]pyrazole (433 mg, 0.83 mmol), tert-butyl ((1R,3S)-3-((5-chloro-4-iodopyridin-2-yl)

carbamoyl)cyclohexyl)carbamate (360 mg, 0.75 mmol; as prepared in Example 10), 2nd Generation X-Phos Precatalyst (59.0 mg, 0.08 mmol) and potassium phosphate dibasic (392 mg, 2.25 mmol) were dissolved in 1,4-dioxane (4 mL) and water (0.8 mL) and stirred at 50° C. for 5 h. The reaction mixture was cooled to r.t. and then purified by ion exchange chromatography using an SCX-2 column. The desired product was eluted from the column using 1 M NH$_3$ in MeOH, and pure fractions were concentrated under reduced pressure. The resulting crude product was purified by flash silica chromatography, elution gradient 0 to 100% EtOAc in heptane. Pure fractions were evaporated to dryness to afford tert-butyl ((1R,3S)-3-((5-chloro-4-(5,5-dimethyl-5,6-dihydro-4H-pyrrolo[1,2-b]pyrazol-3-yl)pyridin-2-yl)carbamoyl)cyclohexyl)carbamate (188 mg, 51.3%) as a white solid. $^1$H NMR (400 MHz, DMSO-d$_6$, 23° C.) 1.25 (12H, d), 1.37 (7H, s), 1.74 (3H, s), 1.87 (1H, d), 2.52-2.62 (1H, m), 2.88 (2H, s), 3.18-3.29 (1H, m), 3.93 (2H, s), 6.80 (1H, d), 7.99 (1H, s), 8.24 (1H, s), 8.32-8.35 (1H, m), 10.56 (1H, s). m/z: ES+ [M+H]+ 488.

Preparation of (1S,3R)-3-amino-N-(5-chloro-4-(5,5-dimethyl-5,6-dihydro-4H-pyrrolo[1,2-b]pyrazol-3-yl)pyridin-2-yl)cyclohexanecarboxamide

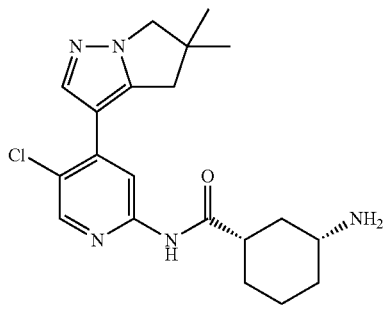 [SMILES: CC1(C)Cc2c(-c3cc(NC(=O)[C@H]4CCC[C@@H](N)C4)ncc3Cl)cnn2C1]

Tert-butyl ((1R,3S)-3-((5-chloro-4-(5,5-dimethyl-5,6-dihydro-4H-pyrrolo[1,2-b]pyrazol-3-yl)pyridin-2-yl)carbamoyl)cyclohexyl)carbamate (186 mg, 0.380 mmol) was dissolved in HCl in dioxane (4 M; 0.810 mL, 3.24 mmol) and MeOH (5 mL) and stirred at r.t. for 18 h. The reaction mixture was purified by ion exchange chromatography using an SCX-2 column. The desired product was eluted from the column using 1 M NH$_3$ in MeOH, and pure fractions were evaporated to dryness to afford (1S,3R)-3-amino-N-(5-chloro-4-(5,5-dimethyl-5,6-dihydro-4H-pyrrolo[1,2-b]pyrazol-3-yl)pyridin-2-yl)cyclohexanecarboxamide (114 mg, 77%) as a white solid which was used directly in the next step. m/z: ES+ [M+H]+ 388.

Example 15: (1S,3R)-3-acetamido-N-(5-chloro-4-(4,5,6,7-tetrahydropyrazolo[1,5-a]pyrimidin-3-yl)pyridin-2-yl)cyclohexanecarboxamide

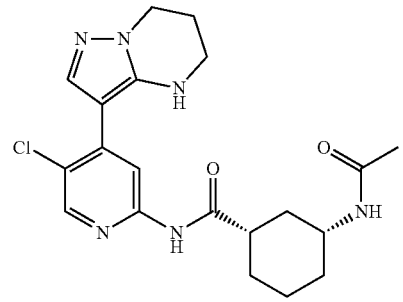 [SMILES: CC(=O)N[C@@H]1CCC[C@H](C(=O)Nc2cc(-c3cnn4c3NCCC4)c(Cl)cn2)C1]

Acetic anhydride (0.021 mL, 0.22 mmol) was added dropwise to (1S,3R)-3-amino-N-(5-chloro-4-(4,5,6,7-tetrahydropyrazolo[1,5-a]pyrimidin-3-yl)pyridin-2-yl)cyclohexanecarboxamide (0.066 g, 0.18 mmol), 4-dimethylaminopyridine (1.141 mg, 9.34 µmol) and triethylamine (0.081 mL, 0.58 mmol) in DCM (1 mL) at r.t. under nitrogen. The resulting solution was stirred at r.t. for 2 h before being quenched with saturated aqueous NH$_4$Cl (10 mL). The resulting mixture was extracted with DCM (2×10 mL). The combined organic layers were dried over MgSO$_4$, filtered, and concentrated under reduced pressure. The resulting white solid was purified by flash silica chromatography, elution gradient 0 to 100% EtOAc in heptane. Fractions were evaporated to dryness to afford semipure product which was further purified by preparative HPLC (Waters) (Bridge Prep C18 OBD column, 5 µm silica, 30 mm diameter, 100 mm length) using decreasingly polar mixtures of water (containing 1% NH$_3$) and MeCN as eluents. Fractions containing the desired compound were evaporated to dryness to afford (1S,3R)-3-acetamido-N-(5-chloro-4-(4,5,6,7-tetrahydropyrazolo[1,5-a]pyrimidin-3-yl)pyridin-2-yl)cyclohexanecarboxamide (9.80 mg, 12.6%). $^1$H NMR (400 MHz, CDCl$_3$, 30° C.) 1.13 (1H, dd), 1.31-1.52 (4H, m), 1.87-1.95 (2H, m), 1.96 (4H, s), 2.20 (3H, dd), 2.39-2.5 (1H, m), 3.39-3.45 (2H, m), 4.16 (2H, t), 4.81 (1H, s), 5.49 (1H, d), 7.79 (1H, s), 8.14 (1H, s), 8.19 (1H, s), 8.30 (1H, s). m/z: ES+ [M+H]+ 417.

Procedures for preparing the starting material (1S,3R)-3-amino-N-(5-chloro-4-(4,5,6,7-tetrahydropyrazolo[1,5-a]pyrimidin-3-yl)pyridin-2-yl)cyclohexanecarboxamide are described below:

Preparation of 3-iodo-4,5,6,7-tetrahydropyrazolo[1,5-a]pyrimidine

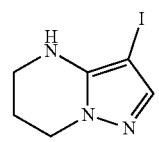

N-Iodosuccinimide (0.581 g, 2.58 mmol) was added to 4,5,6,7-tetrahydropyrazolo[1,5-a]pyrimidine (0.265 g, 2.15 mmol) in acetonitrile (5 mL) at r.t. under nitrogen. The resulting solution was stirred at r.t. for 1 h before water (20 mL) was added. Stirring was continued for 1.5 h, and then the reaction mixture was extracted with MTBE (3×20 mL). The combined organic layers were washed sequentially with 2 M aqueous NaOH (20 mL), Na$_2$S$_2$O$_3$ solution (20 mL, 10% w/v), and saturated aqueous sodium chloride (20 mL) before being dried over MgSO$_4$, filtered, and concentrated under reduced pressure. The resulting crude product was purified by flash silica chromatography, elution gradient 0 to 100% EtOAc in heptane. Pure fractions were evaporated to dryness to afford 3-iodo-4,5,6,7-tetrahydropyrazolo[1,5-a]pyrimidine (0.155 g, 28.9%) as a white crystalline solid. $^1$H NMR (400 MHz, CDCl$_3$, 30° C.) 2.16 (2H, q), 3.32-3.44 (2H, m), 3.98 (1H, s), 4.12 (2H, t), 7.24 (1H, s). m/z: ES+ [M+H]+ 250.

Preparation of Tert-butyl ((1R,3S)-3-((5-chloro-4-(4,5,6,7-tetrahydropyrazolo[1,5-a]pyrimidin-3-yl)pyridin-2-yl)carbamoyl)cyclohexyl)carbamate

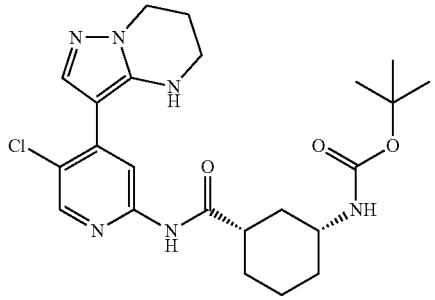 [SMILES: CC(C)(C)OC(=O)N[C@@H]1CCC[C@H](C(=O)Nc2cc(-c3cnn4c3NCCC4)c(Cl)cn2)C1]

3-Iodo-4,5,6,7-tetrahydropyrazolo[1,5-a]pyrimidine (0.150 g, 0.600 mmol) and 2-isopropoxy-4,4,5,5-tetramethyl-1,3,2-dioxaborolane (0.184 mL, 0.9 mmol) were dissolved in THF (4 mL) at 4° C. Then isopropylmagnesium chloride lithium chloride complex in THF (1.3 M; 2.78 mL, 3.61 mmol) was added dropwise. The resulting mixture was stirred at 4° C. for 16 h, then further isopropylmagnesium chloride lithium chloride complex in THF (1.3 M; 2.78 mL, 3.61 mmol) and 2-isopropoxy-4,4,5,5-tetramethyl-1,3,2-dioxaborolane (0.184 mL, 0.90 mmol) were added. The reaction was stirred under these conditions for 1 h and then concentrated under reduced pressure. The resulting residue was redissolved in EtOAc (20 mL) and washed sequentially with saturated aqueous NH$_4$Cl (25 mL), water (20 mL), and saturated saturated sodium chloride (20 mL). The combined aqueous layers were washed with DCM (2×20 mL). The combined organic layers were dried over Na$_2$SO$_4$, filtered, and concentrated under reduced pressure to afford crude 3-(4,4,5,5-tetramethyl-1,3,2-dioxaborolan-2-yl)-4,5,6,7-tetrahydropyrazolo[1,5-a]pyrimidine which was added to tert-butyl ((1R,3S)-3-((5-chloro-4-iodopyridin-2-yl)carbamoyl)cyclohexyl)carbamate (0.160 g, 0.33 mmol; as prepared in Example 10), 2nd Generation X-Phos Precatalyst (0.026 g, 0.03 mmol) and potassium phosphate tribasic (0.175 g, 1.00 mmol) dissolved in 1,4-dioxane (4 mL) and water (0.8 mL) at 50° C. The resulting mixture was stirred at 50° C. for 2 h and then at 80° C. for 16 h. The reaction mixture was concentrated under reduced pressure and the resulting residue was redissolved in DCM (20 mL) and washed with water (20 mL). The organic layer was dried over MgSO$_4$, filtered and concentrated under reduced pressure to afford crude product which was purified by flash silica chromatography, elution gradient 0 to 30% EtOAc in heptane. Pure fractions were evaporated to dryness to afford tert-butyl ((1R,3S)-3-((5-chloro-4-(4,5,6,7-tetrahydropyrazolo[1,5-a]pyrimidin-3-yl)pyridin-2-yl)carbamoyl)cyclohexyl)carbamate (0.082 g, 52%) as a yellow gum. $^1$H NMR (400 MHz, CDCl$_3$, 30° C.) 1.44 (12H, s), 1.82-2.46 (8H, m), 3.27-3.36 (3H, m), 4.12 (3H, t), 5.33 (1H, d), 7.80 (1H, s), 8.13 (1H, s), 8.19 (1H, s), 8.20 (1H, s). m/z: ES+ [M+H]+ 475.

Preparation of (1S,3R)-3-amino-N-(5-chloro-4-(4,5,6,7-tetrahydropyrazolo[1,5-a]pyrimidin-3-yl)pyridin-2-yl)cyclohexanecarboxamide Trihydrochloride

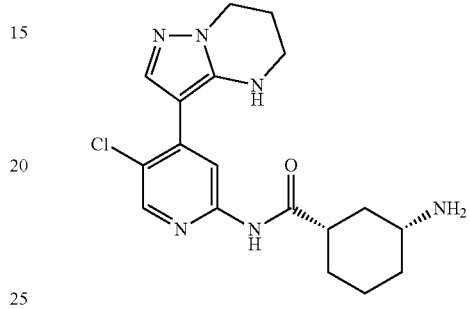

Tert-butyl ((1R,3S)-3-((5-chloro-4-(4,5,6,7-tetrahydropyrazolo[1,5-a]pyrimidin-3-yl)pyridin-2-yl)carbamoyl)cyclohexyl)carbamate (0.086 g, 0.18 mmol) and HCl in dioxane (4 M; 0.362 mL, 1.45 mmol) were dissolved in methanol (2 mL) at r.t. under air. The resulting solution was stirred at r.t. for 3 h before being concentrated under reduced pressure. The resulting material (66 mg) was used directly in the next step without further purification. m/z: ES+ [M+H]+ 375.

Example 16: (1S,3R)-3-acetamido-N-(4-(5,5-dimethyl-5,6-dihydro-4H-pyrrolo[1,2-b]pyrazol-3-yl)pyridin-2-yl)cyclohexanecarboxamide

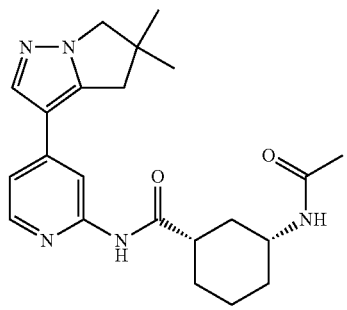 [SMILES: CC(=O)N[C@@H]1CCC[C@H](C(=O)Nc2cc(-c3cnn4c3CC(C)(C)C4)ccn2)C1]

To a stirred solution of (1S,3R)-3-amino-N-(4-(5,5-dimethyl-5,6-dihydro-4H-pyrrolo[1,2-b]pyrazol-3-yl)pyridin-2-yl)cyclohexanecarboxamide (65 mg, 0.18 mmol), triethylamine (0.054 mL, 0.39 mmol) and N,N-dimethylpyridin-4-amine (1.123 mg, 9.19 µmol) in DCM (5 mL) was added acetic anhydride (0.021 mL, 0.22 mmol). The reaction mixture was stirred at r.t. for 1 h. The crude product was purified by ion exchange chromatography using an SCX-2 column. The desired product was eluted from the column using 1 M NH$_3$ in MeOH, and fractions were evaporated to afford (1S,3R)-3-acetamido-N-(4-(5,5-dimethyl-5,6-dihydro-4H-pyrrolo[1,2-b]pyrazol-3-yl)pyridin-2-yl)cyclohexanecarboxamide (60.0 mg, 82.0%) as a colourless oil which was crystallised from an ether/heptane mix to afford a white solid. $^1$H NMR (400 MHz, DMSO-d$_6$, 30° C.) 1.10 (1H, t), 1.29 (9H, s), 1.79 (6H, s), 1.85-1.94 (1H, m), 2.57-2.66 (1H, m), 2.93 (2H, s), 3.58 (1H, dt), 3.90 (2H, s), 7.21 (1H, dd), 7.74 (1H, d), 7.96 (1H, s), 8.18-8.24 (2H, m), 10.32 (1H, s). m/z: ES+ [M+H]+ 396.

Procedures for preparing the starting material (1S,3R)-3-amino-N-(4-(5,5-dimethyl-5,6-dihydro-4H-pyrrolo[1,2-b]pyrazol-3-yl)pyridin-2-yl)cyclohexanecarboxamide are described below:

Preparation of Tert-butyl ((1R,3S)-3-((4-(4,4,5,5-tetramethyl-1,3,2-dioxaborolan-2-yl)pyridin-2-yl)carbamoyl)cyclohexyl)carbamate

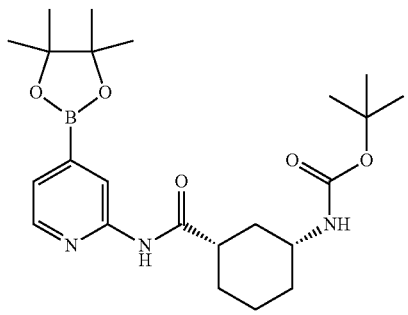 [SMILES: CC(C)(C)OC(=O)N[C@@H]1CCC[C@H](C(=O)Nc2cc(B3OC(C)(C)C(C)(C)O3)ccn2)C1]

Tert-butyl ((1R,3S)-3-((4-bromopyridin-2-yl)carbamoyl)cyclohexyl)carbamate (1.50 g, 3.77 mmol; as prepared in Example 3), potassium acetate (1.11 g, 11.3 mmol), 4,4,4',4',5,5,5',5'-octamethyl-2,2'-bi(1,3,2-dioxaborolane) (1.44 g, 5.65 mmol), and PdCl$_2$(dppf) (0.276 g, 0.380 mmol) were charged to a flask. 1,4-Dioxane (30 mL) was added, and the mixture heated at 90° C. under nitrogen for 3 h. The mixture was allowed to cool, and the solids were removed by filtration. Ethyl acetate (100 mL) and water (50 mL) were added, and the layers were separated. The aqueous layer was extracted with EtOAc (2×50 mL), and the combined organic layers were dried over Na$_2$SO$_4$ and concentrated under reduced pressure to afford the crude product, tert-butyl ((1R,3S)-3-((4-(4,4,5,5-tetramethyl-1,3,2-dioxaborolan-2-yl)pyridin-2-yl)carbamoyl)cyclohexyl)carbamate (2.76 g), as a dark brown oil. This oil was used directly in the next step without further purification. m/z: ES+ [M+H]+ 446.

Preparation of Tert-butyl ((1R,3S)-3-((4-(5,5-dimethyl-5,6-dihydro-4H-pyrrolo[1,2-b]pyrazol-3-yl)pyridin-2-yl)carbamoyl)cyclohexyl)carbamate

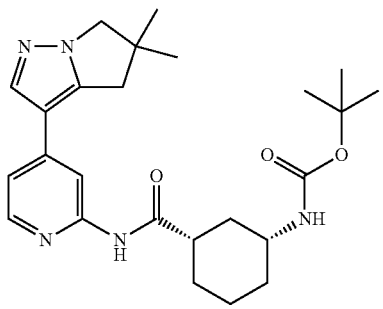 [SMILES: CC1(C)Cc2c(-c3ccnc(NC(=O)[C@H]4CCC[C@@H](NC(=O)OC(C)(C)C)C4)c3)cnn2C1]

Dichloro[1,1'-bis(di-t-butylphosphino)ferrocene]palladium(II) (45.5 mg, 0.07 mmol) was added to a degassed solution of tert-butyl ((1R,3S)-3-((4-(4,4,5,5-tetramethyl-1,3,2-dioxaborolan-2-yl)pyridin-2-yl)carbamoyl)cyclohexyl)carbamate (518 mg, 0.70 mmol), 3-bromo-5,5-dimethyl-5,6-dihydro-4H-pyrrolo[1,2-b]pyrazole (150 mg, 0.70 mmol; as prepared in Example 14) and potassium phosphate tribasic (444 mg, 2.09 mmol) in 1,4-dioxane (5 mL) and water (0.5 mL). The resulting mixture was stirred at 90° C. for 18 h and then purified by ion exchange chromatography using an SCX-2 column. The desired product was eluted from the column using 1 M NH$_3$ in MeOH, and pure fractions were concentrated under reduced pressure to afford crude product as a brown oil. This oil was purified by flash silica chromatography, elution gradient 0 to 100% EtOAc in heptane. Pure fractions were evaporated to dryness to afford tert-butyl ((1R,3S)-3-((4-(5,5-dimethyl-5,6-dihydro-4H-pyrrolo[1,2-b]pyrazol-3-yl)pyridin-2-yl)carbamoyl)cyclohexyl)carbamate (100 mg, 31.6%) as a white solid. m/z: ES+ [M+H]+ 454.

Preparation of (1S,3R)-3-amino-N-(4-(5,5-dimethyl-5,6-dihydro-4H-pyrrolo[1,2-b]pyrazol-3-yl)pyridin-2-yl)cyclohexanecarboxamide

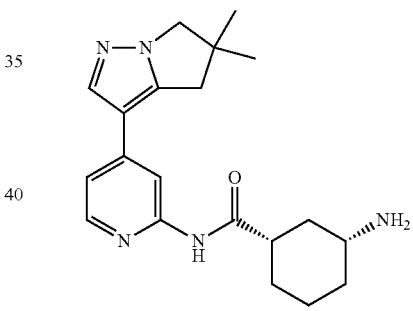

Tert-butyl ((1R,3S)-3-((4-(5,5-dimethyl-5,6-dihydro-4H-pyrrolo[1,2-b]pyrazol-3-yl)pyridin-2-yl)carbamoyl)cyclohexyl)carbamate (93 mg, 0.21 mmol) was dissolved in HCl in dioxane (4 M; 0.436 mL, 1.74 mmol) and MeOH (5 mL), and the reaction mixture was stirred at r.t. for 18 h. The reaction mixture was then purified by ion exchange chromatography using an SCX-2 column. The desired product was eluted from the column using 1 M NH$_3$ in MeOH, and fractions were concentrated under reduced pressure. The resulting crude product was further purified by flash silica chromatography, elution gradient 0 to 10% (7N ammonia in methanol) in DCM. Pure fractions were evaporated to dryness to afford (1S,3R)-3-amino-N-(4-(5,5-dimethyl-5,6-dihydro-4H-pyrrolo[1,2-b]pyrazol-3-yl)pyridin-2-yl)cyclohexanecarboxamide (68.0 mg, 94%) as a white solid. m/z: ES+ [M+H]+ 354.

Example 17: (1S,3R)—N-(4-(5,5-dimethyl-5,6-di-hydro-4H-pyrrolo[1,2-b]pyrazol-3-yl)pyridin-2-yl)-3-(1-hydroxycyclopropanecarboxamido)cyclohexan-ecarboxamide

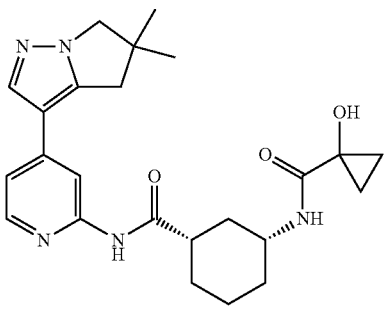 [SMILES: CC1(C)Cc2c(-c3ccnc(NC(=O)[C@H]4CCC[C@@H](NC(=O)C5(O)CC5)C4)c3)cnn2C1]

HATU (108 mg, 0.28 mmol) was added to a solution of 1-hydroxycyclopropanecarboxylic acid (35 mg, 0.34 mmol), (1S,3R)-3-amino-N-(4-(5,5-dimethyl-5,6-dihydro-4H-pyrrolo[1,2-b]pyrazol-3-yl)pyridin-2-yl)cyclohexanecarboxamide (100 mg, 0.28 mmol; prepared according to Example 16), and triethylamine (0.12 mL, 0.85 mmol) in DMF (1 mL). The reaction mixture was heated at 50° C. for 4 h and then cooled to r.t. The reaction mixture was purified directly by preparative HPLC (Waters)(Bridge Prep C18 OBD column, 5μ silica, 19 mm diameter, 100 mm length), using decreasingly polar mixtures of water (containing 1% NH$_3$) and MeCN as eluents. Fractions containing the desired compound were concentrated under reduced pressure to afford (1S,3R)—N-(4-(5,5-dimethyl-5,6-dihydro-4H-pyrrolo[1,2-b]pyrazol-3-yl)pyridin-2-yl)-3-(1-hydroxycyclo-propanecarboxamido)cyclohexanecarboxamide (92 mg, 74%) as a solid. $^1$H NMR (500 MHz, DMSO-d$_6$, 30° C.) 0.74 (2H, m), 0.85-1.01 (2H, m), 1.15-1.27 (9H, m), 1.44 (1H, q), 1.61-1.77 (3H, m), 1.79-1.87 (1H, br. d), 2.52-2.59 (1H, m), 2.86 (2H, s), 3.54-3.63 (1H, m), 3.83 (2H, s), 6.10 (1H, s), 7.12-7.16 (1H, m), 7.57 (1H, d), 7.90 (1H, s), 8.13-8.16 (2H, m), 10.27 (1H, s). m/z: ES+ [M+H]+ 438.

Example 18: N-((1R,3S)-3-((4-(5,5-dimethyl-5,6-dihydro-4H-pyrrolo[1,2-b]pyrazol-3-yl)pyridin-2-yl)carbamoyl)cyclohexyl)oxetane-3-carboxamide

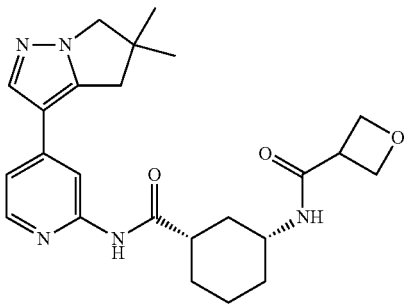 [SMILES: CC1(C)Cc2c(-c3ccnc(NC(=O)[C@H]4CCC[C@@H](NC(=O)C5COC5)C4)c3)cnn2C1]

HATU (77 mg, 0.20 mmol) was added to a solution of oxetane-3-carboxylic acid (25 mg, 0.24 mmol), (1S,3R)-3-amino-N-(4-(5,5-dimethyl-5,6-dihydro-4H-pyrrolo[1,2-b]pyrazol-3-yl)pyridin-2-yl)cyclohexanecarboxamide (72 mg, 0.20 mmol; prepared according to Example 16), and triethylamine (0.085 mL, 0.61 mmol) in DMF (1 mL). The mixture was stirred at r.t. for 4 hh and then purified directly by preparative HPLC (Waters)(Bridge Prep C18 OBD column, 5μ silica, 19 mm diameter, 100 mm length), using decreasingly polar mixtures of water (containing 1% NH$_3$) and MeCN as eluents. Fractions containing the desired compound were concentrated under reduced pressure to afford N-((1R,3S)-3-((4-(5,5-dimethyl-5,6-dihydro-4H-pyrrolo[1,2-b]pyrazol-3-yl)pyridin-2-yl)carbamoyl)cyclohexyl)oxetane-3-carboxamide (17 mg, 19%) as a solid. $^1$H NMR (400 MHz, DMSO-d$_6$, 30° C.) 1.06-1.17 (1H, m), 1.26-1.39 (9H, m), 1.77-1.86 (3H, m), 1.91-1.94 (1H, br d), 2.57-2.7 (1H, m), 2.93 (2H, s), 3.54-3.76 (2H, m), 3.90 (2H, s), 4.4-4.71 (4H, m), 7.21 (1H, dd), 7.82 (1H, d), 7.96 (1H, s), 8.21-8.24 (2H, m), 10.33 (1H, s). m/z: ES+ [M+H]+ 438.

Example 19: N-((1R,3S)-3-((5-chloro-4-(5,5-dimethyl-5,6-dihydro-4H-pyrrolo[1,2-b]pyrazol-3-yl)pyridin-2-yl)carbamoyl)cyclohexyl)oxetane-3-carboxamide

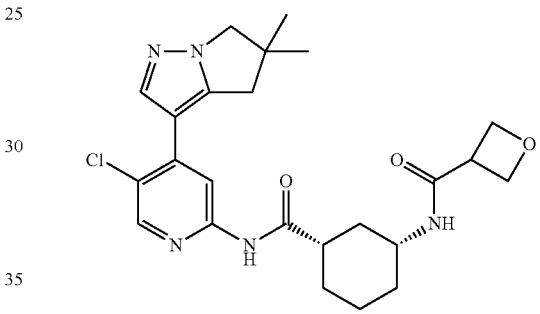

HATU (118 mg, 0.31 mmol) was added to a solution of oxetane-3-carboxylic acid (32 mg, 0.31 mmol), (1S,3R)-3-amino-N-(5-chloro-4-(5,5-dimethyl-5,6-dihydro-4H-pyrrolo[1,2-b]pyrazol-3-yl)pyridin-2-yl)cyclohexanecarboxamide (100 mg, 0.26 mmol; prepared according to Example 14), and triethylamine (0.11 mL, 0.77 mmol) in DMA (2 mL). The mixture was stirred at r.t. for 16 h before being quenched with water (20 mL). The mixture was then extracted with DCM (50 mL), and the organic layer was washed with saturated aqueous sodium chloride (50 mL) before being passed through a phase separation cartridge. The combined organics were dried over MgSO$_4$, filtered, and concentrated under reduced pressure. The resulting residue was purified by preparative HPLC (Waters)(Bridge Prep C18 OBD column, 5μ silica, 30 mm diameter, 100 mm length), using decreasingly polar mixtures of water (containing 1% NH$_3$) and MeCN as eluents. Fractions containing the desired compound were concentrated under reduced pressure to afford N-((1R,3S)-3-((5-chloro-4-(5,5-dimethyl-5,6-dihydro-4H-pyrrolo[1,2-b]pyrazol-3-yl)pyridin-2-yl)carbamoyl)cyclohexyl)oxetane-3-carboxamide (39 mg, 32%) as a solid. $^1$H NMR (500 MHz, DMSO-d$_6$, 30° C.) 1.06-1.14 (1H, m), 1.62-1.75 (9H, m), 1.72-1.81 (3H, m), 1.92 (1H, br. d), 2.59-2.7 (1H, m), 2.90 (2H, s), 3.56-3.73 (2H, m), 3.95 (2H, s), 4.53-4.66 (4H, m), 7.80 (1H, d), 8.00 (1H, m), 8.25 (1H, s), 8.35 (1H, s), 10.56 (1H, s). m/z: ES+ [M+H]+ 472.

Example 20: (1S,3R)—N-(5-chloro-4-(5,5-dimethyl-5,6-dihydro-4H-pyrrolo[1,2-b]pyrazol-3-yl)pyridin-2-yl)-3-((S)-2-hydroxypropanamido)cyclohexanecarboxamide

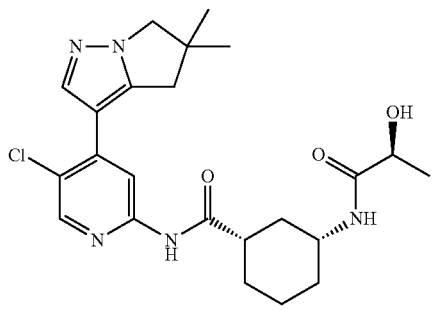 [SMILES: C[C@H](O)C(=O)N[C@@H]1CCC[C@H](C(=O)Nc2cc(-c3cnn4c3CC(C)(C)C4)c(Cl)cn2)C1]

HATU (78 mg, 0.21 mmol) was added to a solution of (S)-2-hydroxypropanoic acid (19 mg, 0.21 mmol), (1S,3R)-3-amino-N-(5-chloro-4-(5,5-dimethyl-5,6-dihydro-4H-pyrrolo[1,2-b]pyrazol-3-yl)pyridin-2-yl)cyclohexanecarboxamide (80 mg, 0.21 mmol; prepared according to Example 14), and triethylamine (0.086 mL, 0.62 mmol) in DMF (1 mL). The mixture was stirred at r.t. for 1 h and then purified directly by preparative HPLC (Waters)(Bridge Prep C18 OBD column, 5μ silica, 19 mm diameter, 100 mm length), using decreasingly polar mixtures of water (containing 1% NH$_3$) and MeCN as eluents. Fractions containing the desired compound were concentrated under reduced pressure to afford (1S,3R)—N-(5-chloro-4-(5,5-dimethyl-5,6-dihydro-4H-pyrrolo[1,2-b]pyrazol-3-yl)pyridin-2-yl)-3-((S)-2-hydroxypropanamido)cyclohexanecarboxamide (56 mg, 59%) as a solid. $^1$H NMR (300 MHz, DMSO-d$_6$, 27° C.) 1.14-1.21 (3H, m), 1.23-1.54 (10H, m), 1.66-1.91 (4H, m), 2.56-2.70 (1H, m), 2.90 (2H, s), 3.53-3.72 (1H, m), 3.87-3.97 (3H, m), 5.37 (1H, d), 7.49 (1H, d), 8.00 (1H, s), 8.25 (1H, s), 8.35 (1H, s), 10.55 (1H, s). m/z: ES+ [M+H]+ 460.

Example 21: (1S,3R)—N-(5-chloro-4-(5,5-dimethyl-5,6-dihydro-4H-pyrrolo[1,2-b]pyrazol-3-yl)pyridin-2-yl)-3-(1-hydroxycyclopropanecarboxamido)cyclohexanecarboxamide

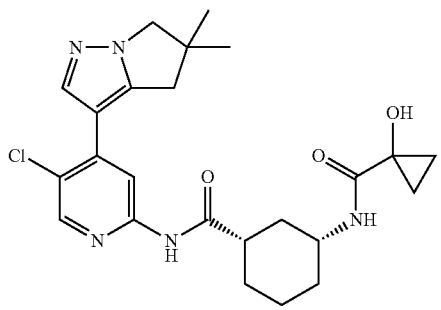 [SMILES: CC1(C)Cc2c(-c3cc(NC(=O)[C@H]4CCC[C@@H](NC(=O)C5(O)CC5)C4)ncc3Cl)cnn2C1]

HATU (78 mg, 0.21 mmol) was added to a solution of 1-hydroxycyclopropanecarboxylic acid (25 mg, 0.25 mmol), (1S,3R)-3-amino-N-(5-chloro-4-(5,5-dimethyl-5,6-dihydro-4H-pyrrolo[1,2-b]pyrazol-3-yl)pyridin-2-yl)cyclohexanecarboxamide (80 mg, 0.21 mmol; prepared according to Example 14), and triethylamine (0.086 mL, 0.62 mmol) in DMF (1 mL). The mixture was heated at 50° C. for 3 h then cooled to r.t. The reaction mixture was purified directly by preparative HPLC (Waters)(Bridge Prep C18 OBD column, 5μ silica, 30 mm diameter, 100 mm length), using decreasingly polar mixtures of water (containing 1% NH$_3$) and MeCN as eluents. Fractions containing the desired compound were concentrated under reduced pressure to afford (1S,3R)—N-(5-chloro-4-(5,5-dimethyl-5,6-dihydro-4H-pyrrolo[1,2-b]pyrazol-3-yl)pyridin-2-yl)-3-(1-hydroxycyclopropanecarboxamido)cyclohexanecarboxamide (25 mg, 26%) as a solid. $^1$H NMR (500 MHz, DMSO-d$_6$, 30° C.) 0.72-0.85 (2H, m), 0.94-1.08 (2H, m), 1.23-1.49 (9H, m), 1.47-1.58 (1H, m), 1.67-1.84 (3H, m), 1.87 (1H, br. d), 2.57-2.66 (1H, m), 2.90 (2H, s), 3.60-3.71 (1H, m), 3.95 (2H, s), 6.16 (1H, s), 7.62 (1H, d), 8.01 (1H, s), 8.26 (1H, s), 8.35 (1H, s), 10.55 (1H, s). m/z: ES+ [M+H]+ 472.

Example 22: (1S,3R)-3-acetamido-N-(5-chloro-4-(6,6-dimethyl-6,7-dihydro-5H-pyrrolo[1,2-a]imidazol-3-yl)pyridin-2-yl)cyclohexanecarboxamide

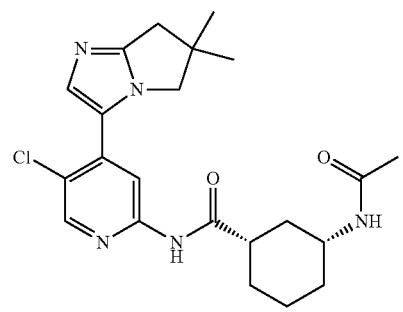 [SMILES: CC(=O)N[C@@H]1CCC[C@H](C(=O)Nc2cc(-c3cnc4n3CC(C)(C)C4)c(Cl)cn2)C1]

(1S,3R)-3-Acetamido-N-(5-chloro-4-iodopyridin-2-yl)cyclohexanecarboxamide (800 mg, 1.90 mmol; prepared according to Example 12), 6,6-dimethyl-6,7-dihydro-5H-pyrrolo[1,2-a]imidazole (825 mg, 5.69 mmol), palladium acetate (171 mg, 0.76 mmol) and potassium acetate (372 mg, 3.79 mmol) were suspended in DMA (15 mL) and sealed into a microwave tube. The tube was degassed and purged with nitrogen (3×). The reaction was then subjected to microwave conditions (150° C., 16 h) and cooled to r.t. The reaction mixture was purified by preparative HPLC (Waters) (Bridge Prep C18 OBD column, 5μ silica, 30 mm diameter, 100 mm length), using decreasingly polar mixtures of water (containing 1% NH$_3$) and MeCN as eluents. Fractions containing the desired compound were concentrated under reduced pressure. The resulting light brown solid was recrystallised using EtOAc/heptane and dried under vacuum to give (1S,3R)-3-acetamido-N-(5-chloro-4-(6,6-dimethyl-6,7-dihydro-5H-pyrrolo[1,2-a]imidazol-3-yl)pyridin-2-yl)cyclohexanecarboxamide (180 mg, 22%) as a white solid. The filtrate was concentrated under reduced pressure to provide a second batch of (1S,3R)-3-acetamido-N-(5-chloro-4-(6,6-dimethyl-6,7-dihydro-5H-pyrrolo[1,2-a]imidazol-3-yl)pyridin-2-yl)cyclohexanecarboxamide (118 mg, 14%). $^1$H NMR (500 MHz, DMSO-d$_6$, 30° C.) 1.03-1.16 (1H, m), 1.19-1.41 (9H, m), 1.72-1.81 (6H, m), 1.91 (1H, br. d), 2.57-2.68 (1H, m), 2.71 (2H, s), 3.50-3.62 (1H, m), 3.91 (2H, s), 7.51 (1H, s), 7.75 (1H, d), 8.28 (1H, s), 8.42 (1H, s), 10.66 (1H, s). m/z: ES+ [M+H]+ 430.

Preparation of 4,4-dimethylpyrrolidine-2-thione

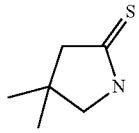

Lawesson's Reagent (9.83 g, 24.30 mmol) was added to a stirred solution of 4,4-dimethylpyrrolidin-2-one (5.0 g, 44.19 mmol) in toluene (100 mL). The resulting mixture was heated under reflux conditions under nitrogen for 4.5 h. The mixture was then cooled to r.t. and maintained under these conditions for 18 h before being concentrated under reduced pressure to provide a yellow solid. The solid was dissolved in DCM, silica was added, and the mixture was filtered. The filtrate was concentrated under reduced pressure to provide a yellow oil. This oil was purified by flash silica chromatography, eluting with DCM, to afford 4,4-dimethylpyrrolidine-2-thione (2.8 g, 48%) as a colourless crystalline solid. Impure fractions were concentrated under reduced pressure to provide a second batch of 4,4-dimethylpyrrolidine-2-thione as cream/pale yellow crystals (3.1 g, 55%). Despite a slightly lower purity, this second batch of material was also suitable for use in subsequent steps. $^1$H NMR (400 MHz, CDCl$_3$, 30° C.) 1.19 (6H, s), 2.70 (2H, s), 3.36 (2H, s), 7.75 (1H, br. s).

Preparation of 3,3-dimethyl-5-(methylthio)-3,4-dihydro-2H-pyrrole Hydroiodide

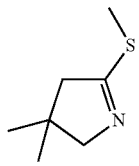

Iodomethane in MTBE (2 M; 42.7 mL, 85.4 mmol) was added to a stirred solution of 4,4-dimethylpyrrolidine-2-thione (2.76 g, 21.3 mmol) in iPrOH (45 mL) at r.t. A white precipitate formed over time. The reaction was stirred at r.t. for 18 h and then filtered. The collected solid was washed with Et$_2$O and then dried to provide 3,3-dimethyl-5-(methylthio)-3,4-dihydro-2H-pyrrole as the hydroiodide salt (4.3 g, 75%). This material was carried into the next stage without further purification. $^1$H NMR (500 MHz, DMSO-d$_6$, 27° C.) 1.17 (6H, s), 2.74 (3H, s), 3.10 (2H, s), 3.72 (2H, s), 12.3 (1H, br. s).

Preparation of N-(2,2-dimethoxyethyl)-3,3-dimethyl-3,4-dihydro-2H-pyrrol-5-amine Hydroiodide

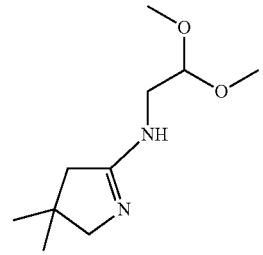

2,2-Dimethoxyethanamine (1.82 mL, 16.7 mmol) was added to a stirred suspension of 3,3-dimethyl-5-(methylthio)-3,4-dihydro-2H-pyrrole hydroiodide (4.32 g, 15.9 mmol) in ethanol (40 mL) at r.t. The hydroiodide salt dissolved upon addition of the amine. The resulting mixture was heated under reflux conditions (using a bleach scrubber) for 4.5 h and then removed from heat. After another 18 h the reaction mixture was concentrated under reduced pressure to provide crude N-(2,2-dimethoxyethyl)-3,3-dimethyl-3,4-dihydro-2H-pyrrol-5-amine hydroiodide (5.35 g, 102%) as a colourless crystalline solid. $^1$H NMR (400 MHz, DMSO-d$_6$, 30° C.) 1.12 (6H, s), 2.58-2.7 (2H, m), 3.34 (8H, s), 3.37 (2H, d), 4.51 (1H, m), 9.35 (2H, br. s).

Preparation of 6,6-dimethyl-6,7-dihydro-5H-pyrrolo[1,2-a]imidazole

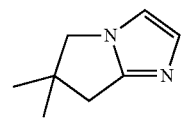

Hydrochloric acid (4 M; 5 mL, 20 mmol) was added to a stirred solution of N-(2,2-dimethoxyethyl)-3,3-dimethyl-3,4-dihydro-2H-pyrrol-5-amine hydroiodide (5.35 g, 16.3 mmol) in 1,4-dioxane (50 mL) at r.t. The resulting mixture was heated at 90° C. for 3 h. The mixture was then cooled to r.t. and stirred under these conditions for 2.5 days before being concentrated under reduced pressure to provide a dark brown tar. This mixture was dissolved in DCM and diluted with Et$_2$O. Aqueous ammonia (28-30%; 2.8 mL) was added to the stirring mixture. The layers were separated, and the organic layer was dried over MgSO$_4$, filtered, and concentrated under reduced pressure to provide 6,6-dimethyl-6,7-dihydro-5H-pyrrolo[1,2-a]imidazole (2.32 g, 100%) as a brown oil. $^1$H NMR (400 MHz, CDCl$_3$, 21° C.) 1.28 (6H, s), 2.70 (2H, s), 3.69 (2H, s), 6.84 (1H, d), 7.03 (1H, d).

Example 23: (R)—N-((1R,3S)-3-((5-chloro-4-(5,5-dimethyl-5,6-dihydro-4H-pyrrolo[1,2-b]pyrazol-3-yl)pyridin-2-yl)carbamoyl)cyclohexyl)tetrahydrofuran-3-carboxamide

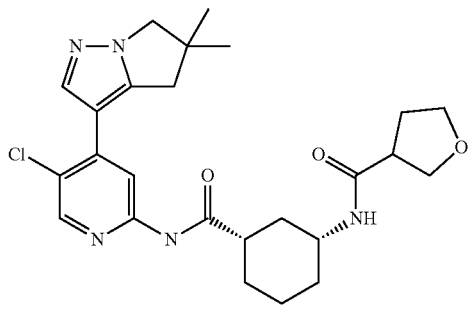 [SMILES: CC1(C)Cc2c(-c3cc(NC(=O)[C@H]4CCC[C@@H](NC(=O)C5CCOC5)C4)ncc3Cl)cnn2C1]

(R)-Tetrahydrofuran-3-carboxylic acid (0.036 g, 0.31 mmol), HATU (0.118 g, 0.31 mmol) and triethylamine (0.11 mL, 0.77 mmol) were stirred together in DMF (2 mL) under nitrogen for 20 minutes. Then (1S,3R)-3-amino-N-(5-chloro-4-(5,5-dimethyl-5,6-dihydro-4H-pyrrolo[1,2-b]pyrazol-3-yl)pyridin-2-yl)cyclohexanecarboxamide (0.100 g, 0.26 mmol; prepared according to Example 14 using 5,5-dimethyl-3-(4,4,5,5-tetramethyl-1,3,2-dioxaborolan-2-yl)-5,6-dihydro-4H-pyrrolo[1,2-b]pyrazole prepared as described below) in DMF (1 mL) was added, and the mixture was stirred for another 30 minutes. The reaction was concentrated under reduced pressure, and the mixture was purified by flash C18 chromatography, elution gradient 20 to 60% MeCN in water containing 1% aqueous NH$_4$OH. Pure fractions were concentrated under reduced pressure to afford (R)—N-((1R,3S)-3-((5-chloro-4-(5,5-dimethyl-5,6-dihydro-4H-pyrrolo[1,2-b]pyrazol-3-yl)pyridin-2-yl)carbamoyl)cyclohexyl)tetrahydrofuran-3-carboxamide (0.113 g, 90%) as a white solid. $^1$H NMR (400 MHz, DMSO-d$_6$, 30° C.) 1.05-1.2 (1H, m), 1.20-1.38 (9H, sm), 1.79 (3H, br. d), 1.86-2.03 (3H, m), 2.56-2.63 (1H, m), 2.81-2.91 (3H, m), 3.52-3.78 (4H, m), 3.83 (1H, t), 3.95 (2H, s), 7.83 (1H, d), 7.99 (1H, s), 8.25 (1H, s), 8.34 (1H, s), 10.53 (1H, s). m/z: ES+ [M+H]+ 486.

An alternative procedure used to prepare 5,5-dimethyl-3-(4,4,5,5-tetramethyl-1,3,2-dioxaborolan-2-yl)-5,6-dihydro-4H-pyrrolo[1,2-b]pyrazole (already described in Example 14, Intermediates) is described below:

Preparation of 3-iodo-5,5-dimethyl-5,6-dihydro-4H-pyrrolo[1,2-b]pyrazole

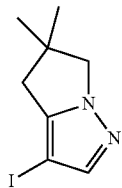

NIS (1.646 g, 7.32 mmol) was added portionwise to 5,5-dimethyl-5,6-dihydro-4H-pyrrolo[1,2-b]pyrazole (0.906 g, 6.65 mmol; prepared according to Example 14) in acetonitrile (40 mL) at r.t. under nitrogen. The resulting mixture was stirred at 23° C. for 18 h. The reaction mixture was diluted with EtOAc (50 mL) and washed sequentially with water (40 mL), aqueous sodium thiosulfate (10 g in 30 mL), and saturated aqueous sodium chloride (20 mL). The organic layer was dried over MgSO$_4$, filtered, and concentrated under reduced pressure to afford crude product (1.59 g, 91%) as an orange oil. This oil was purified by distillation under reduced pressure (0.12 mbar), with collection at a head temperature of 140° C. Distillate collected in this manner afforded 3-iodo-5,5-dimethyl-5,6-dihydro-4H-pyrrolo[1,2-b]pyrazole (1.38 g, 79%) as a colourless liquid. Alternatively, the iodide was carried on to the next step without distillation. $^1$H NMR (400 MHz, CDCl$_3$, 30° C.) 1.30 (6H, s), 2.63 (2H, s), 3.94 (2H, s), 7.47 (1H, s).

Preparation of 5,5-dimethyl-3-(4,4,5,5-tetramethyl-1,3,2-dioxaborolan-2-yl)-5,6-dihydro-4H-pyrrolo[1,2-b]pyrazole

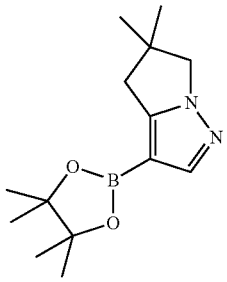 [SMILES: CC1(C)Cc2c(B3OC(C)(C)C(C)(C)O3)cnn2C1]

Isopropylmagnesium chloride lithium chloride complex in THF (1.3 M; 1.69 mL, 2.20 mmol) was added dropwise over 10 minutes to 3-iodo-5,5-dimethyl-5,6-dihydro-4H-pyrrolo[1,2-b]pyrazole (0.444 g, 1.69 mmol) in THF (5 mL) at −78° C. under nitrogen. The resulting mixture was stirred at −78° C. for 45 minutes. Then 2-isopropoxy-4,4,5,5-tetramethyl-1,3,2-dioxaborolane (0.473 g, 2.54 mmol) was added dropwise to the reaction mixture, keeping the internal temperature at −78° C. Once addition was complete, the reaction mixture was allowed to warm up to r.t. over 18 h. The reaction mixture was then concentrated under reduced pressure and diluted with EtOAc (40 mL). The resulting mixture was washed sequentially with saturated aqueous ammonium chloride (20 mL), water (20 mL), and saturated aqueous sodium chloride (20 mL). The organic layer was dried over MgSO$_4$, filtered, and concentrated under reduced pressure to afford 5,5-dimethyl-3-(4,4,5,5-tetramethyl-1,3,2-dioxaborolan-2-yl)-5,6-dihydro-4H-pyrrolo[1,2-b]pyrazole (0.41 g, 93%) contaminated with ~13 mol % of des-iodo starting material based on NMR analysis as a waxy solid. Trituration with heptane afforded pure 5,5-dimethyl-3-(4,4,5,5-tetramethyl-1,3,2-dioxaborolan-2-yl)-5,6-dihydro-4H-pyrrolo[1,2-b]pyrazole (0.24 g, 55%) as a white solid.

Example 24: (S)—N-((1R,3S)-3-((5-chloro-4-(5,5-dimethyl-5,6-dihydro-4H-pyrrolo[1,2-b]pyrazol-3-yl)pyridin-2-yl)carbamoyl)cyclohexyl)tetrahydrofuran-3-carboxamide

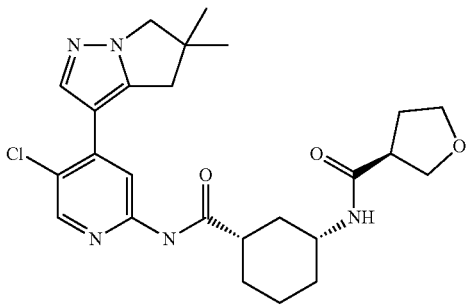 [SMILES: CC1(C)Cc2c(-c3cc(NC(=O)[C@H]4CCC[C@@H](NC(=O)[C@H]5CCOC5)C4)ncc3Cl)cnn2C1]

A solution of (S)-tetrahydrofuran-3-carboxylic acid (0.036 g, 0.31 mmol), HATU (0.12 g, 0.31 mmol) and triethylamine (0.11 mL, 0.77 mmol) in DMF (2 mL) was stirred under nitrogen for 20 minutes. Then (1S,3R)-3-amino-N-(5-chloro-4-(5,5-dimethyl-5,6-dihydro-4H-pyrrolo[1,2-b]pyrazol-3-yl)pyridin-2-yl)cyclohexanecarboxamide (0.10 g, 0.26 mmol; prepared according to Example 14 using 5,5-dimethyl-3-(4,4,5,5-tetramethyl-1,3,2-dioxaborolan-2-yl)-5,6-dihydro-4H-pyrrolo[1,2-b]pyrazole prepared as described in Example 23) in DMF (1 mL) was added, and the resulting mixture was stirred under these conditions for 30 minutes. The mixture was concentrated under reduced pressure, and the resulting residue was purified by flash C18 chromatography, elution gradient 20 to 60% MeCN in water containing 1% NH$_4$OH. Pure fractions were concentrated under reduced pressure to afford (S)—N-((1R,3S)-3-((5-chloro-4-(5,5-dimethyl-5,6-dihydro-4H-pyrrolo[1,2-b]pyrazol-3-yl)pyridin-2-yl)carbamoyl)cyclohexyl)tetrahydrofuran-3-carboxamide (0.10 g, 81%) as a white solid. $^1$H NMR (400 MHz, DMSO-d$_6$, 30° C.) 1.05-1.16 (1H, m), 1.21-1.41 (9H, m), 1.72-1.83 (3H, m), 1.87-2.04 (3H, m), 2.57-2.66 (1H, m), 2.82-2.91 (3H, m), 3.54-3.77 (4H, m), 3.83 (1H, t), 3.95 (2H, s), 7.83 (1H, d), 7.99 (1H, s), 8.25 (1H, s), 8.35 (1H, s), 10.54 (1H, s). m/z: ES+ [M+H+] 486.

Example 25: (1S,3R)-3-acetamido-N-(4-(5,5-dimethyl-5,6-dihydro-4H-pyrrolo[1,2-b]pyrazol-3-yl)-5-fluoropyridin-2-yl)cyclohexanecarboxamide

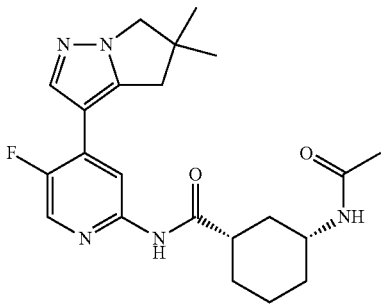 [SMILES: CC(=O)N[C@@H]1CCC[C@H](C(=O)Nc2cc(-c3cnn4c3CC(C)(C)C4)c(F)cn2)C1]

Tetrakis(triphenylphosphine)palladium(0) (0.13 g, 0.12 mmol) and Xantphos (0.13 g, 0.23 mmol) were added together in one portion to a degassed mixture of tert-butyl ((1R,3S)-3-carbamoylcyclohexyl)carbamate (0.670 g, 2.76 mmol), 3-(2-chloro-5-fluoropyridin-4-yl)-5,5-dimethyl-5,6-dihydro-4H-pyrrolo[1,2-b]pyrazole (0.61 g, 2.3 mmol), cesium carbonate (1.88 g, 5.76 mmol), and 1,4-dioxane (26 mL). The resulting bright yellow mixture was maintained under reflux conditions by immersion in an oil bath that had been preheated to 120° C. After 20 h the reaction was cooled, diluted with 50% saturated aqueous sodium chloride, and extracted with ethyl acetate (2×). The combined organic layers were dried over sodium sulfate, filtered, and concentrated under reduced pressure to afford crude tert-butyl ((1R,3S)-3-((4-(5,5-dimethyl-5,6-dihydro-4H-pyrrolo[1,2-b]pyrazol-3-yl)-5-fluoropyridin-2-yl)carbamoyl)cyclohexyl)carbamate as a light yellow solid. Hydrochloric acid in dioxane (4 M; 10 mL, 40 mmol) and DCM (5 mL) were added, resulting in a clear orange solution that rapidly became cloudy and yellow. Methanol (~3 mL) was titrated into the reaction until the mixture became mostly clear. After 15 min the orange mixture was concentrated under reduced pressure to afford an orange solid. Pyridine (3.7 ml, 46 mmol) was added to this solid along with DCM (19 mL). A slight exotherm was noted, and the reaction was immersed in a water bath. Then acetic anhydride (0.43 mL, 4.6 mmol) was added dropwise. After another 10 min, another 200 µL of acetic anhydride were added. After another 30 min, another 600 µL of anhydride and 6 mL of pyridine were added. The reaction was maintained under these conditions for another 45 min and was then poured into saturated aqueous sodium bicarbonate and ethyl acetate. The layers were separated, and the aqueous layer was extracted with ethyl acetate. The combined organic layers were dried over sodium sulfate, filtered, and concentrated under reduced pressure. The resulting orange residue was purified by flash silica chromatography, elution gradient 50 to 100% EtOAc in hexane followed by 0 to 20% methanol in ethyl acetate, and pure fractions were concentrated under reduced pressure to afford (1S,3R)-3-acetamido-N-(4-(5,5-dimethyl-5,6-dihydro-4H-pyrrolo[1,2-b]pyrazol-3-yl)-5-fluoropyridin-2-yl)cyclohexanecarboxamide (0.89 g, 94%) as a faint yellow foam solid. $^1$H NMR (DMSO-d$_6$, 27° C.): 1.00-1.16 (1H, m), 1.22-1.40 (9H, m), 1.74-1.81 (6H, m), 1.83-1.94 (1H, m), 2.55-2.68 (1H, m), 2.93 (2H, s), 3.49-3.65 (1H, m), 3.94 (s, 2H), 7.75 (1H, d), 7.88 (1H, d), 8.28 (1H, d), 8.30 (1H, d), 10.46 (1H, s). m/z: ES+ [M+H]+ 414.

Method 1: A slurry of Example 25 (381 mg) in EtOAc was stirred at r.t. for 18 h, then filtered and washed with cold EtOAc to afford (1S,3R)-3-acetamido-N-(4-(5,5-dimethyl-5,6-dihydro-4H-pyrrolo[1,2-b]pyrazol-3-yl)-5-fluoropyridin-2-yl)cyclohexanecarboxamide (149 mg) as a crystalline white solid known as Example 25 Form A.

Method 2: Approximately 5 g of Example 25 were taken up in 1:1:1 hexanes:DCM:acetone (~20 mL) and then concentrated under reduced pressure to give a slightly translucent gel. This gel was then treated with a small amount of the same solvent (~5 mL) and stirred vigorously for 10 min until a homogeneous white mixture formed and no gel was visible. This mixture was filtered with a 30% acetone in hexane wash, and the precipitate was dried under vacuum at 50° C. to afford Example 25 Form A as a white solid.

Figure 3:
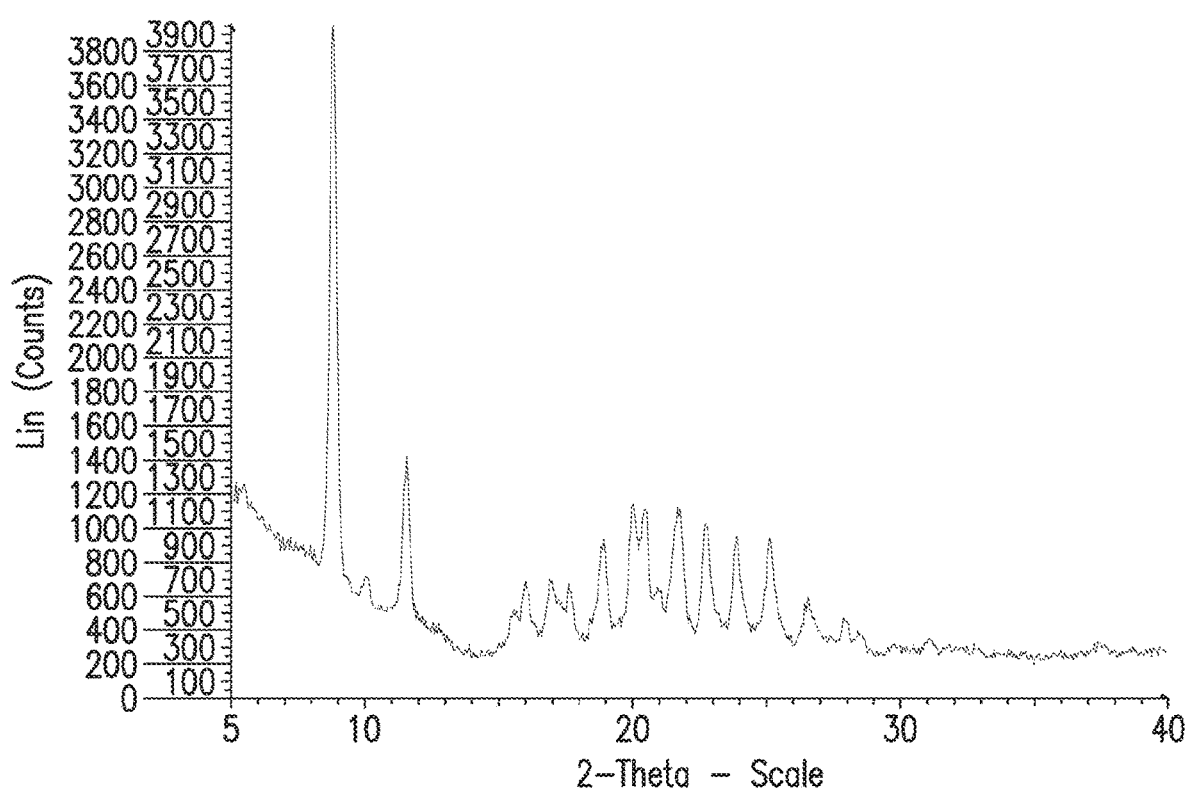
FIG. 3 is a representative X-ray powder diffractogram of Form A of (1S,3R)-3-acetamido-N-(4-(5,5-dimethyl-5,6-dihydro-4H-pyrrolo[1,2-b]pyrazol-3-yl)-5-fluoropyridin-2-yl)cyclohexanecarboxamide (Example 25).

Crystals of Example 25 (Form A) were analyzed by XRPD and the results are tabulated below and are shown in FIG. 3. The XRPD of the solid confirms that the solid contains Form A.

Example 25 Form a Main Peaks are Shown in Table 2 Below

| Peak | 2θ | Intensity % |
|---|---|---|
| 1 | 8.8 | 100.0 (vs) |
| 2 | 10.1 | 18.0 (s) |
| 3 | 11.5 | 35.8 (vs) |
| 4 | 18.9 | 23.5 (s) |
| 5 | 20.0 | 28.7 (vs) |
| 6 | 20.5 | 28.1 (vs) |
| 7 | 21.8 | 28.3 (vs) |
| 8 | 22.8 | 25.8 (vs) |
| 9 | 23.9 | 23.9 (s) |
| 10 | 25.2 | 23.9 (s) |

According to the present invention there is provided a crystalline form, Form A, which has an X-ray powder diffraction pattern with specific peaks at about 2-theta=8.8, 10.1, 11.5, 18.9, 20.0, 20.5, 21.8, 22.8, 23.9 and 25.2°.

Figure 4:
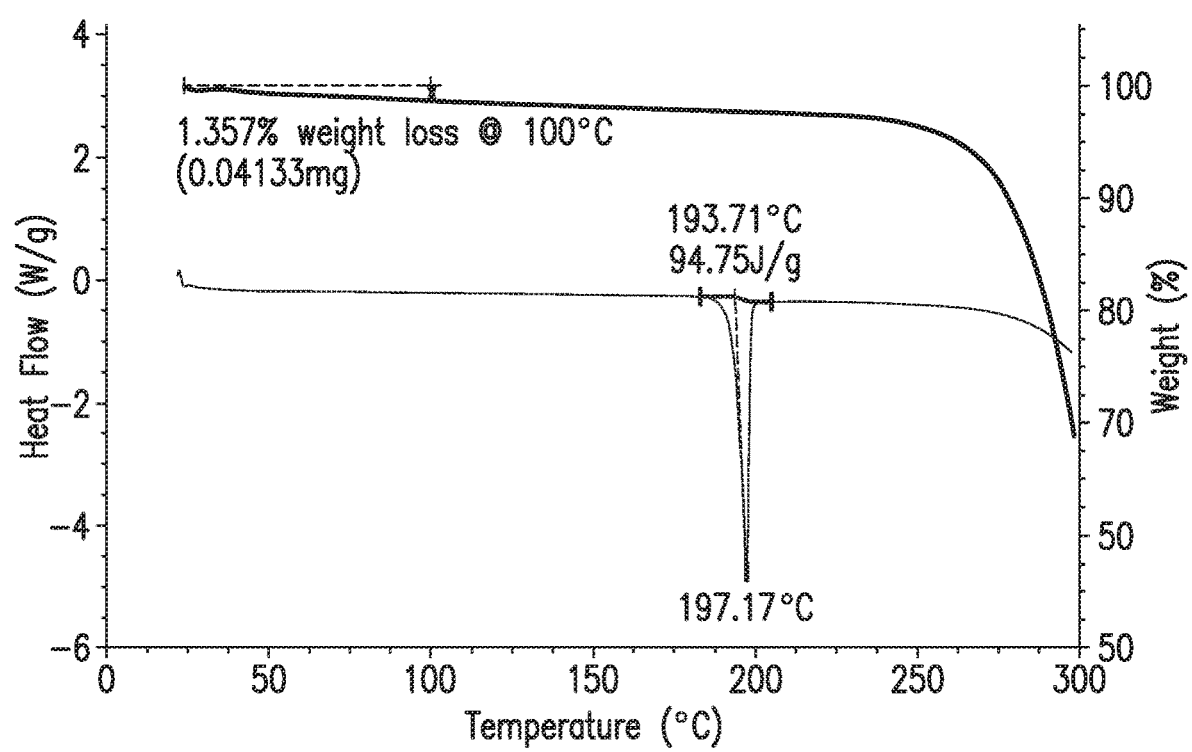
FIG. 4 is a representative DSC/TGA thermograph of Form A of (1S,3R)-3-acetamido-N-(4-(5,5-dimethyl-5,6-dihydro-4H-pyrrolo[1,2-b]pyrazol-3-yl)-5-fluoropyridin-2-yl)cyclohexanecarboxamide (Example 25).

Crystals obtained according to Methods 1 and 2 (Form A) were analyzed by thermal techniques. DSC analysis indicated that Form A melts with an onset point at 194° and a peak at 197°. TGA indicated that Form A exhibits a mass loss of about 1.4% upon heating from 22 to 100° C. A representative DSC/TGA thermogram is shown in FIG. 4.

An alternative procedure for making (1S,3R)-3-acetamido-N-(4-(5,5-dimethyl-5,6-dihydro-4H-pyrrolo[1,2-b]pyrazol-3-yl)-5-fluoropyridin-2-yl)cyclohexanecarboxamide is described in Example 86

Procedures used to prepare the starting materials tert-butyl ((1R,3S)-3-carbamoylcyclohexyl)carbamate and 3-(2-chloro-5-fluoropyridin-4-yl)-5,5-dimethyl-5,6-dihydro-4H-pyrrolo[1,2-b]pyrazole are described below:

Preparation of 3-(2-chloro-5-fluoropyridin-4-yl)-5,5-dimethyl-5,6-dihydro-4H-pyrrolo[1,2-b]pyrazole

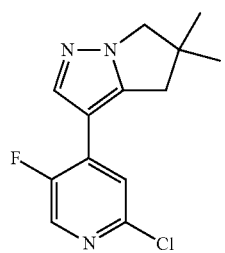 [SMILES: CC1(C)Cc2c(-c3cc(Cl)ncc3F)cnn2C1]

2-Chloro-5-fluoro-4-iodopyridine (1.00 g, 3.88 mmol), 5,5-dimethyl-3-(4,4,5,5-tetramethyl-1,3,2-dioxaborolan-2-yl)-5,6-dihydro-4H-pyrrolo[1,2-b]pyrazole (1.53 g, 5.83 mmol; prepared according to Example 23), 2nd Generation XPhos Precatalyst (0.31 g, 0.39 mmol) and dibasic potassium phosphate (2.03 g, 11.65 mmol) were dissolved in degassed dioxane (10 mL) and water (2 mL) at 21° C. The reaction mixture was stirred at 80° C. for 3 h, and then the mixture was cooled, diluted with EtOAc (30 mL), and washed with water (10 mL). The organic layer was concentrated under reduced pressure. The resulting residue was purified by flash silica chromatography, elution gradient 0 to 50% EtOAc in heptane. Pure fractions were concentrated under reduced pressure to afford 3-(2-chloro-5-fluoropyridin-4-yl)-5,5-dimethyl-5,6-dihydro-4H-pyrrolo[1,2-b]pyrazole (1.00 g, 97%) as a white solid. $^1$H NMR (500 MHz, CDCl$_3$, 27° C.) 1.36 (6H, s), 2.95 (2H, d), 3.97 (2H, s), 7.31 (1H, d), 7.94 (1H, d), 8.20 (1H, d). m/z: ES+ [M+H]+ 266.

Preparation of (cis)-benzyl 3-((tert-butoxycarbonyl)amino)cyclohexanecarboxylate

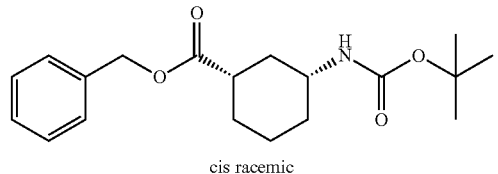 [SMILES: CC(C)(C)OC(=O)N[C@@H]1CCC[C@H](C(=O)OCc2ccccc2)C1]

cis racemic

Benzyl bromide (12.4 mL, 104 mmol) was added dropwise as a solution in DMF (10 mL) to a degassed mixture of cis-3-((tert-butoxycarbonyl)amino)cyclohexanecarboxylic acid (19.5 g, 80.0 mmol, prepared according to Example 2 Intermediates), cesium carbonate (33.9 g, 104 mmol), and DMF (80 mL) at 0° C. The ice bath was removed, and the reaction was stirred under these conditions for 18 h. The mixture was then diluted with an equal volume of ethyl acetate and filtered with an ethyl acetate wash. The organic layer was washed with 50% saturated aqueous sodium chloride (3×) and then saturated aqueous sodium chloride. The organic layer was then dried over sodium sulfate, filtered, and concentrated under reduced pressure. The resulting light yellow oil was purified by flash silica chromatography, elution gradient 0 to 30% ethyl acetate in hexanes, to afford cis-benzyl 3-((tert-butoxycarbonyl)amino)cyclohexanecarboxylate (25.4 g, 95%) as a clear colorless oil that solidified to a white solid on standing. $^1$H NMR (DMSO-d$_6$, 27° C.) 0.98-1.34 (4H, m), 1.38 (9H, s), 1.67-1.78 (2H, m), 1.84 (1H, d), 1.99 (1H, d), 2.35-2.49 (1H, m), 3.17-3.31 (1H, s), 5.09 (2H, s), 6.76 (1H, d), 7.30-7.42 (5H, m). m/z: ES+ [M+Na]+356.

Preparation of (1S,3R)-benzyl 3-((tert-butoxycarbonyl)amino)cyclohexanecarboxylate and (1R,3S)-benzyl 3-((tert-butoxycarbonyl)amino)cyclohexanecarboxylate

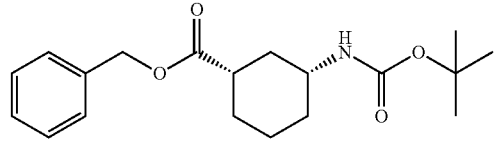

(1S,3R)

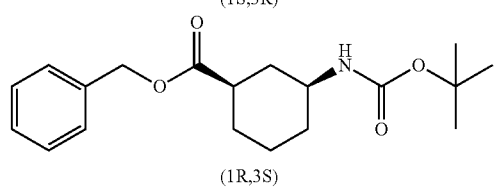

(1R,3S)

Cis-benzyl 3-((tert-butoxycarbonyl)amino)cyclohexanecarboxylate (25.4 g, 76.2 mmol) was resolved by preparative SFC conditions (Column: Lux Amylose-2, 5 μm, 21.2 mm diameter, 250 mm length, 40° C. column temperature, 80 mL/min flow rate), eluting with 10% isopropanol in CO$_2$, to afford (1S,3R)-benzyl 3-((tert-butoxycarbonyl)amino)cyclohexanecarboxylate (11.5 g, 45%) as a white solid and (1R,3S)-benzyl 3-((tert-butoxycarbonyl)amino)cyclohexanecarboxylate (11.5 g, 45%) as a white solid.

(1S,3R)-benzyl 3-((tert-butoxycarbonyl)amino)cyclohexanecarboxylate $^1$H NMR (DMSO-$d_6$, 27° C.) 0.96-1.34 (4H, m), 1.37 (9H, s), 1.68-1.88 (3H, m), 1.98 (1H, d), 2.37-2.48 (1H, m), 3.16-3.32 (1H, m), 5.09 (2H, s), 6.59-6.84 (1H, m), 7.26-7.50 (5H, m). m/z: ES+ [M+Na]+356.
Optical Rotation:
Concentration: 0.1 g/dL
Lamp: Sodium
Wavelength: 589 nm
Temperature: 25° C.
Path length: 10 cm
Cell volume: 1 mL
Solvent: DCM
[α]=+21.9

(1R,3S)-benzyl 3-((tert-butoxycarbonyl)amino)cyclohexanecarboxylate $^1$H NMR (DMSO-$d_6$, 27° C.) 0.95-1.34 (4H, m), 1.37 (9H, s), 1.68-1.78 (2H, m), 1.84 (1H, d), 1.98 (1H, d), 2.36-2.48 (1H, m), 3.17-3.34 (1H, m), 5.09 (2H, s), 6.76 (1H, d), 7.30-7.41 (5H, m). m/z: ES+ [M+Na]+356.
Optical Rotation:
Concentration: 0.1 g/dL
Lamp: Sodium
Wavelength: 589 nm
Temperature: 25° C.
Path length: 10 cm
Cell volume: 1 mL
Solvent: DCM
[α]=−28.3
Analytical SFC Conditions:
Column: Lux Amylose-2
Column Dimensions: 5 μm, 4.6 mm diameter, 50 mm length,
Column Temperature: 40° C.
Mobile Phase A: $CO_2$ (100%)
Mobile Phase B: Isopropanol
Gradient: Isocratic 10% Mobile Phase B
Flow Rate: 1 mL/min over 5 min
Retention Time:
0.66 min, (1S,3R)-benzyl 3-((tert-butoxycarbonyl)amino) cyclohexanecarboxylate
0.96 min, (1R,3S)-benzyl 3-((tert-butoxycarbonyl)amino) cyclohexanecarboxylate
e. e.
>98%, (1S,3R)-benzyl 3-((tert-butoxycarbonyl)amino) cyclohexanecarboxylate
97.5%, (1R,3S)-benzyl 3-((tert-butoxy carbonyl)amino) cyclohexanecarboxylate
An alternative procedure for the preparation of (1S,3R)-3-((tert-butoxycarbonyl)amino)cyclohexanecarboxylic acid (already described in Example 2, Intermediates) is described below:

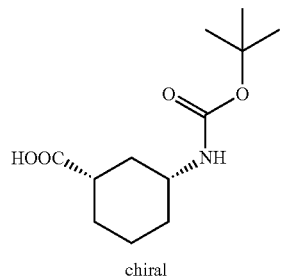 [SMILES: CC(C)(C)OC(=O)N[C@@H]1CCC[C@H](C(=O)O)C1]

chiral

A degassed mixture of (1S,3R)-benzyl 3-((tert-butoxycarbonyl)amino)cyclohexanecarboxylate (11.5 g, 34.6 mmol), palladium on carbon (10 wt %; 3.68 g, 34.5 mmol), and methanol (86 mL) was subjected to a hydrogen atmosphere (1 atm, balloon). After 18 h, the mixture was filtered with a methanol wash. The filtrate was concentrated to a slightly turbid faint gray oil. This oil was taken up in ethyl acetate, dried over sodium sulfate, filtered, and concentrated under reduced pressure. The resulting white oily solid was heated under vacuum until all bubbling from solvent evaporation stopped. Cooling to r.t. afforded (1S,3R)-3-((tert-butoxycarbonyl)amino)cyclohexanecarboxylic acid (8.4 g, 99%) as a white solid (See Example 2, Intermediates, for characterization).
Optical Rotation:
Concentration: 0.1 g/dL
Lamp: Sodium
Wavelength: 589 nm
Temperature: 25° C.
Path length: 10 cm
Cell volume: 1 mL
Solvent: DMSO
[α]=+44.6

Preparation of Tert-butyl ((1R,3S)-3-carbamoylcyclohexyl)carbamate

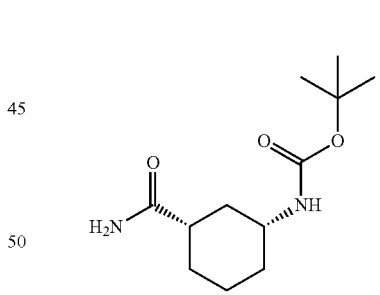

Carbonyl diimidazole (6.44 g, 39.74 mmol) was added to a solution of (1S,3R)-3-((tert-butoxycarbonyl)amino)cyclohexanecarboxylic acid (3.22 g, 13.3 mmol) in DMF (30 mL) at 40° C. The resulting mixture was stirred at 40° C. for 4 h. The reaction mixture was then cooled to 0° C., and ammonium acetate (7.15 g, 92.7 mmol) was added in one portion with vigorous stirring. This was followed by gas evolution and generation of a foam. A small amount (~2 mL) of DCM was added along the sides of the flask to break apart the foam and prevent it from reaching the flask opening. Gradually this foam was reabsorbed by the reaction mixture, which was allowed to warm to r.t. overnight. After a total of 18 h under these conditions, the reaction mixture was poured into ice water, and the resulting mixture was stirred under these conditions for 5 min before being filtered with a water wash. The resulting precipitate was dried under vacuum at 80° C. for 2 h before being cooled to r.t. Vacuum drying was then continued for 18 h to afford tert-butyl ((1R,3S)-3-carbamoylcyclohexyl)carbamate (2.76 g, 86%) as a white fluffy solid. ¹H NMR (DMSO-d₆, 27° C.) 0.99-1.31 (4H, m), 1.38 (9H, s), 1.58-1.85 (4H, m), 2.06-2.19 (1H, m), 3.14-3.26 (1H, m), 6.63 (1H, br s), 6.73 (1H, d), 7.17 (1H, br s). m/z: ES+ [M+Na]+265.

Optical Rotation:

Concentration: 0.1 g/dL

Lamp: Sodium

Wavelength: 589 nm

Temperature: 25° C.

Path length: 10 cm

Cell volume: 1 mL

Solvent: Methanol

[α]=+51.3

Example 26: cis-N-(4-(5,5-dimethyl-5,6-dihydro-4H-pyrrolo[1,2-b]pyrazol-3-yl)pyridin-2-yl)-3-hydroxycyclobutanecarboxamide

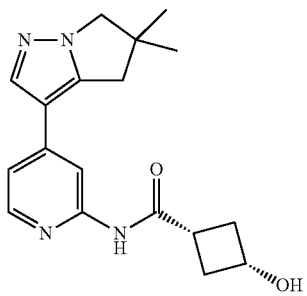 [SMILES: CC1(C)Cc2c(-c3ccnc(NC(=O)[C@H]4C[C@@H](O)C4)c3)cnn2C1]

Tetrabutylammonium fluoride in THF (1 M; 0.154 mL, 0.15 mmol) was added to a stirred solution of cis-3-((tert-butyldimethylsilyl)oxy)-N-(4-(5,5-dimethyl-5,6-dihydro-4H-pyrrolo[1,2-b]pyrazol-3-yl)pyridin-2-yl)cyclobutanecarboxamide (68 mg, 0.15 mmol) in THF (3 mL) at r.t. under a nitrogen atmosphere. The reaction mixture was stirred under these conditions for 2 h and then purified using an SCX column, eluting sequentially with DCM, MeOH, and 1% NH₃ in MeOH. Product fractions were concentrated under reduced pressure. The resulting residue was purified by preparative HPLC (Waters)(Bridge Prep C18 OBD column, 5μ silica, 30 mm diameter, 100 mm length), using decreasingly polar mixtures of water (containing 1% NH₃) and MeCN as eluents to afford cis-N-(4-(5,5-dimethyl-5,6-dihydro-4H-pyrrolo[1,2-b]pyrazol-3-yl)pyridin-2-yl)-3-hydroxycyclobutanecarboxamide (43 mg, 85%). ¹H NMR (500 MHz, DMSO-d₆, 30° C.) 1.30 (6H, s), 2.05 (2H, qd), 2.28-2.43 (2H, m), 2.71-2.85 (1H, m), 2.95 (2H, s), 3.91 (2H, s), 3.98 (1H, q), 5.13 (1H, d), 7.17-7.26 (1H, m), 7.98 (1H, s), 8.21 (1H, dd), 8.25 (1H, s), 10.30 (1H, s). m/z: ES+ [M+H]+ 327.

Procedures used to prepare the starting material cis-3-((tert-butyldimethylsilyl)oxy)-N-(4-(5,5-dimethyl-5,6-dihydro-4H-pyrrolo[1,2-b]pyrazol-3-yl)pyridin-2-yl)cyclobutanecarboxamide are described below:

Preparation of cis-3-((tert-butyldimethylsilyl)oxy)-N-(4-(5,5-dimethyl-5,6-dihydro-4H-pyrrolo[1,2-b]pyrazol-3-yl)pyridin-2-yl)cyclobutanecarboxamide Cis-N-(4-bromopyridin-2-yl)-3-((tert-butyldimethylsilyl)oxy)cyclobutanecarboxamide (365 mg, 0.800 mmol; prepared according to Example 6), 5,5-dimethyl-3-(4,4,5,5-tetramethyl-1,3-dioxolan-2-yl)-5,6-dihydro-4H-pyrrolo[1,2-b]pyrazole (185 mg, 0.700 mmol; prepared according to Example 23), potassium phosphate (446 mg, 2.10 mmol) and 2nd Generation XPhos Precatalyst (55 mg, 0.070 mmol) were suspended in 1,4-dioxane (4 mL) and water (0.80 mL) at r.t. The resulting mixture was degassed, purged with nitrogen, and then heated at 85° C. for 18 h. The reaction mixture was cooled to r.t. and partitioned between EtOAc (50 mL) and water (25 mL). The layers were separated, and the aqueous layer was extracted with EtOAc (2×50 mL) and DCM (50 mL). The combined organic layers were dried over MgSO₄, filtered, and concentrated under reduced pressure. The resulting orange gum was purified by flash silica chromatography, eluting with 0 to 40% EtOAc in heptane. Product fractions were concentrated under reduced pressure to afford cis-3-((tert-butyldimethylsilyl)oxy)-N-(4-(5,5-dimethyl-5,6-dihydro-4H-pyrrolo[1,2-b]pyrazol-3-yl)pyridin-2-yl)cyclobutanecarboxamide (68 mg, 22%) as a colourless crystalline solid. ¹H NMR (400 MHz, CDCl₃, 22° C.) 0.06 (6H, s), 0.89 (9H, s), 1.36 (6H, s), 2.22-2.38 (2H, m), 2.49-2.67 (3H, m), 3.02 (2H, s), 3.93 (2H, s), 4.15-4.35 (1H, m), 7.11 (1H, dd), 7.82 (1H, s), 7.92 (1H, s), 8.17 (1H, d), 8.30 (1H, s). m/z: ES+ [M+H]+ 441.

Example 27: cis-N-(5-chloro-4-(5,5-dimethyl-5,6-dihydro-4H-pyrrolo[1,2-b]pyrazolo-3-yl)pyridin-2-yl)-3-hydroxycyclobutanecarboxamide Tetrabutylammonium fluoride in THF (1 M; 0.21 mL, 0.21 mmol) was added to a stirred solution of cis-3-((tert-butyldimethylsilyl)oxy)-N-(5-chloro-4-(5,5-dimethyl-5,6- dihydro-4H-pyrrolo[1,2-b]pyrazol-3-yl)pyridin-2-yl)cyclobutanecarboxamide (101 mg, 0.210 mmol) in THF (3 mL) at r.t. under a nitrogen atmosphere. The resulting solution was stirred under these conditions for 18 h. The reaction mixture purified using an SCX column, eluting sequentially with DCM, MeOH, and 1% $NH_3$ in MeOH. Product fractions were concentrated under reduced pressure. The resulting residue was purified by preparative HPLC (Waters)(Bridge Prep C18 OBD column, 5μ silica, 30 mm diameter, 100 mm length), using decreasingly polar mixtures of water (containing 1% $NH_3$) and MeCN as eluents. Product fractions were concentrated under reduced pressure, and the resulting residue was further purified by preparative HPLC (Waters SunFire column, 5μ silica, 30 mm diameter, 100 mm length), using decreasingly polar mixtures of water (containing 0.1% formic acid) and MeCN as eluents. Fractions containing the desired compound were concentrated under reduced pressure to afford cis-N-(5-chloro-4-(5,5-dimethyl-5,6-dihydro-4H-pyrrolo[1,2-b]pyrazol-3-yl)pyridin-2-yl)-3-hydroxycyclobutane carboxamide (35 mg, 45%). $^1$H NMR (500 MHz, DMSO-$d_6$, 30° C.) 1.29 (6H, s), 2.04 (2H, qd), 2.37 (2H, qd), 2.77 (1H, ddd), 2.92 (2H, s), 3.96 (2H, s), 3.96-4.02 (1H, m), 5.14 (1H, d), 8.02 (1H, s), 8.29 (1H, s), 8.34 (1H, d), 10.51 (1H, s). m/z: ES+ [M+H]+ 361.

Procedures for preparing the starting material cis-3-((tert-butyldimethylsilyl)oxy)-N-(5-chloro-4-(5,5-dimethyl-5,6-dihydro-4H-pyrrolo[1,2-b]pyrazol-3-yl)pyridin-2-yl)cyclobutanecarboxamide are described below.

Preparation of cis-3-((tert-butyldimethylsilyl)oxy)-N-(5-chloro-4-iodopyridin-2-yl)cyclobutanecarboxamide

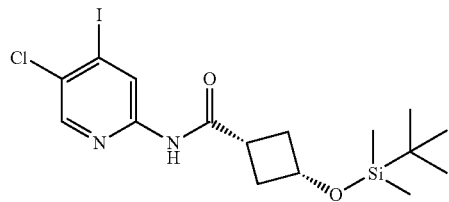 [SMILES: CC(C)(C)[Si](C)(C)O[C@H]1C[C@@H](C(=O)Nc2cc(I)c(Cl)cn2)C1]

$T_3P$ in ethyl acetate (50 wt %; 2.85 mL, 4.79 mmol) was added to a stirred solution of 5-chloro-4-iodopyridin-2-amine (610 mg, 2.40 mmol; prepared according to Example 2), cis-3-((tert-butyldimethylsilyl)oxy)cyclobutanecarboxylic acid (552 mg, 2.40 mmol; prepared according to Example 4) and pyridine (0.78 mL, 9.6 mmol) in EtOAc (10 mL) at r.t. The resulting solution was stirred at r.t. for 18 h. The reaction was quenched by the addition of saturated aqueous ammonium chloride (30 mL). The layers were separated and the aqueous layer was extracted with EtOAc (3×50 mL). The combined organic layers were dried over $MgSO_4$, filtered, and concentrated under reduced pressure to afford cis-3-((tert-butyldimethylsilyl)oxy)-N-(5-chloro-4-iodopyridin-2-yl)cyclobutane carboxamide (1.07 g, 96%) as a cream-colored crystalline solid. $^1$H NMR (400 MHz, CDCl$_3$, 21° C.) 0.06 (6H, s), 0.89 (9H, s), 2.23-2.35 (2H, m), 2.47-2.64 (3H, m), 4.17-4.32 (1H, m), 7.95 (1H, bs), 8.18 (1H, s), 8.86 (1H, s). m/z: ES+ [M+H]+ 467.

Preparation of cis-3-((tert-butyldimethylsilyl)oxy)-N-(5-chloro-4-(5,5-dimethyl-5,6-dihydro-4H-pyrrolo[1,2-b]pyrazol-3-yl)pyridin-2-yl)cyclobutanecarboxamide

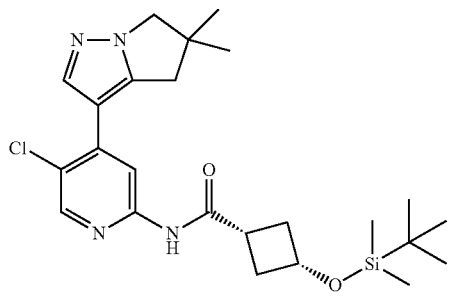 [SMILES: CC1(C)Cc2c(-c3cc(NC(=O)[C@H]4C[C@@H](O[Si](C)(C)C(C)(C)C)C4)ncc3Cl)cnn2C1]

Cis-3-((tert-butyldimethylsilyl)oxy)-N-(5-chloro-4-iodopyridin-2-yl)cyclobutanecarboxamide (461 mg, 0.840 mmol), 5,5-dimethyl-3-(4,4,5,5-tetramethyl-1,3,2-dioxaborolan-2-yl)-5,6-dihydro-4H-pyrrolo[1,2-b]pyrazole (200 mg, 0.76 mmol; prepared according to Example 23), potassium phosphate (486 mg, 2.29 mmol) and 2nd Generation XPhos Precatalyst (60.0 mg, 0.08 mmol) were suspended in 1,4-dioxane and water at r.t. The resulting mixture was degassed, purged with nitrogen, and heated at 85° C. overnight. The reaction was cooled to r.t. and partitioned between EtOAc (50 mL) and water (25 mL). The layers were separated, and the aqueous layer was extracted with EtOAc (3×50 mL). The combined organic layers were dried over $MgSO_4$, filtered, and concentrated under reduced pressure. The resulting orange gum was purified by flash silica chromatography, eluting with 0 to 40% EtOAc in heptane. Product fractions were evaporated to dryness to afford cis-3-((tert-butyldimethylsilyl)oxy)-N-(5-chloro-4-(5,5-dimethyl-5,6-dihydro-4H-pyrrolo[1,2-b]pyrazol-3-yl)pyridin-2-yl)cyclobutanecarboxamide (101 mg, 28%) as a colourless crystalline solid. $^1$H NMR (400 MHz, CDCl$_3$, 21° C.) 0.06 (6H, s), 0.89 (9H, s), 1.35 (6H, s), 2.24-2.45 (2H, m), 2.5-2.74 (3H, m), 2.98 (2H, s), 3.96 (2H, s), 4.18-4.24 (1H, m), 7.77 (1H, s), 8.14 (1H, s), 8.23 (1H, s), 8.29 (1H, s). m/z: ES+ [M+H]+ 475.

Example 28: (1S,3R)-3-acetamido-N-(6-(4,5,6,7-tetrahydropyrazolo[1,5-a]pyridin-3-yl)pyrimidin-4-yl)cyclohexanecarboxamide

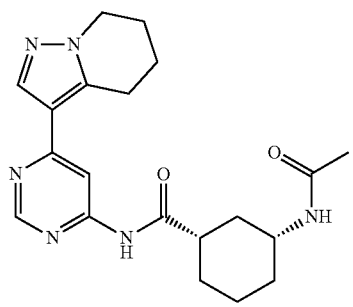 [SMILES: CC(=O)N[C@@H]1CCC[C@H](C(=O)Nc2cc(-c3cnn4c3CCCC4)ncn2)C1]

A flask charged with (1S,3R)-3-acetamido-N-(6-chloropyrimidin-4-yl)cyclohexanecarboxamide (100 mg, 0.34 mmol), 3-(4,4,5,5-tetramethyl-1,3,2-dioxaborolan-2-yl)-4,5, 6,7-tetrahydropyrazolo[1,5-a]pyridine (84 mg, 0.34 mmol), dichloro[1,1'-bis(di-tertbutylphosphino)ferrocene]palladium(II) (11 mg, 0.020 mmol) and potassium phosphate (215 mg, 1.01 mmol) was evacuated and back filled with nitrogen (3×). Degassed 1,4-dioxane (1 mL) followed by water (0.2 mL) were added, and the mixture was heated to 90° C. and maintained under these conditions for 18 h. The reaction was then concentrated under reduced pressure, and the resulting residue was partitioned between saturated aqueous sodium bicarbonate (20 mL) and ethyl acetate (20 mL). The layers were separated, and the aqueous layer was extracted with ethyl acetate (2×20 mL). The combined organic layers were washed with saturated aqueous sodium chloride (20 mL), dried over sodium sulfate, filtered and concentrated under reduced pressure. The resulting residue was purified by column chromatography on basic alumina, elution gradient 0 to 100% (10% MeOH in EtOAc) in heptane to afford (1S,3R)-3-acetamido-N-(6-(4,5,6,7-tetrahydropyrazolo[1,5-a]pyridin-3-yl)pyrimidin-4-yl)cyclohexanecarboxamide (55 mg, 43%) as a tan solid. $^1$H NMR (400 MHz, DMSO-$d_6$, 30° C.) 1.01-1.38 (4H, m), 1.76-2.02 (11H, m), 2.62-2.69 (1H, m), 3.10 (2H, t), 3.52-3.61 (1H, m), 4.13 (2H, t), 7.74 (1H, d), 7.96 (1H, s), 8.21 (1H, d), 8.75 (1H, d), 10.72 (1H, s). m/z: ES+ [M+H]+ 383.

Procedures used to prepare the starting material (1S,3R)-3-acetamido-N-(6-chloropyrimidin-4-yl)cyclohexanecarboxamide are described below:

Preparation of Tert-butyl ((1R,3S)-3-((6-chloropyrimidin-4-yl)carbamoyl)cyclohexyl)carbamate

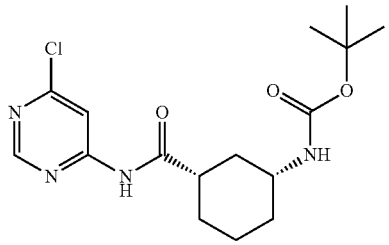 [SMILES: CC(C)(C)OC(=O)N[C@@H]1CCC[C@H](C(=O)Nc2cc(Cl)ncn2)C1]

1-Chloro-N,N,2-trimethylpropenylamine (3.26 mL, 24.7 mmol) was added to a solution of (1S,3R)-3-((tert-butoxycarbonyl)amino)cyclohexanecarboxylic acid (5.00 g, 20.6 mmol; prepared as in Example 2) in DCM (50 mL) and the resulting mixture stirred for 90 min at r.t. Then 6-chloropyrimidin-4-amine (2.66 g, 20.6 mmol) and pyridine (2.0 mL, 25 mmol) were added, and the resulting mixture was stirred under these conditions for 18 h. The reaction was quenched with saturated aqueous sodium bicarbonate (50 mL), and the layers were separated. The aqueous layer was extracted with DCM (2×50 mL), and the combined organic layers were washed with saturated aqueous sodium chloride and dried over sodium sulfate, filtered, and concentrated under reduced pressure. The resulting residue was purified by flash silica chromatography, eluting with 0 to 100% (10% methanol in ethyl acetate) in heptane. Product fractions were combined and concentrated under reduced pressure to give tert-butyl ((1R,3S)-3-((6-chloropyrimidin-4-yl)carbamoyl)cyclohexyl)carbamate (1.0 g, 14%) as a white solid. m/z: ES− [M−H]− 353.

Preparation of (1S,3R)-3-amino-N-(6-chloropyrimidin-4-yl)cyclohexanecarboxamide Dihydrochloride

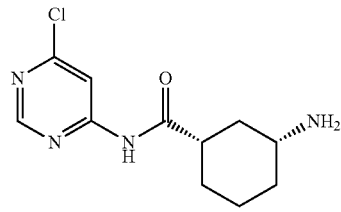 [SMILES: N[C@@H]1CCC[C@H](C(=O)Nc2cc(Cl)ncn2)C1]

Hydrochloric acid in dioxane (4 M; 0.655 mL, 21.6 mmol) was added to a solution of tert-butyl ((1R,3S)-3-((6-chloropyrimidin-4-yl)carbamoyl)cyclohexyl)carbamate (900 mg, 2.54 mmol) in methanol (5 mL), and the resulting mixture was stirred overnight at r.t. The mixture was then diluted with toluene (10 mL) and concentrated under reduced pressure to give (1S,3R)-3-amino-N-(6-chloropyrimidin-4-yl)cyclohexanecarboxamide dihydrochloride (880 mg, 106%) as a white solid which was used directly in the next stage without further purification.

Preparation of (1S,3R)-3-acetamido-N-(6-chloropyrimidin-4-yl)cyclohexanecarboxamide

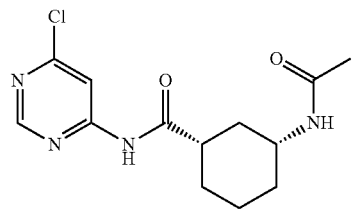 [SMILES: CC(=O)N[C@@H]1CCC[C@H](C(=O)Nc2cc(Cl)ncn2)C1]

Acetyl chloride (0.11 mL, 1.5 mmol) was added to a mixture of (1S,3R)-3-amino-N-(6-chloropyrimidin-4-yl)cyclohexanecarboxamide (0.217 g, 0.85 mmol), pyridine (0.69 mL, 8.5 mmol), and DCM (7.7 mL) at 0° C. After 30 min, another 200 μL of acetyl chloride were added. This was again repeated after another 30 min a final time. The reaction was then quenched with saturated aqueous sodium bicarbonate and extracted with ethyl acetate (2×). The combined organic layers were dried over sodium sulfate, filtered, and concentrated under reduced pressure. The resulting residue was purified by flash silica chromatography, elution gradient 10 to 100% ethyl acetate in hexane then 0 to 15% methanol in ethyl acetate) to afford (1S,3R)-3-acetamido-N-(6-chloropyrimidin-4-yl)cyclohexanecarboxamide (0.22 g, 87%) as an off-white solid. $^1$H NMR (300 MHz, DMSO-$d_6$) 0.99-1.16 (1H, m), 1.18-1.38 (3H, m), 1.72-1.84 (6H, m), 1.85-1.97 (m, 1H), 2.58-2.73 (1H, m) 3.50-3.64 (1H, m) 7.76 (1H, d) 8.12 (1H, d) 8.74 (1H, d) 11.18 (1H, s). m/z: ES+ [M+H]+ 297.

Example 29: trans-3-hydroxy-N-(6-(4,5,6,7-tetrahydropyrazolo[1,5-a]pyridin-3-yl)pyrimidin-4-yl)cyclobutanecarboxamide

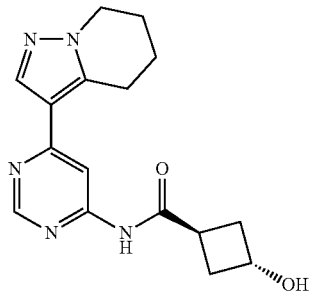 [SMILES: O=C(Nc1cc(-c2cnn3c2CCCC3)ncn1)[C@H]1C[C@H](O)C1]

Hydrochloric acid in dioxane (4 M; 0.085 mL, 0.34 mmol) was added to a solution of trans-3-((tert-butyldimethylsilyl)oxy)-N-(6-(4,5,6,7-tetrahydropyrazolo[1,5-a]pyridin-3-yl)pyrimidin-4-yl)cyclobutanecarboxamide (29 mg, 0.070 mmol) in MeOH (1 mL), and the resulting mixture was stirred at r.t. for 2 h. The mixture was concentrated under reduced pressure, and the resulting residue was purified by preparative HPLC (Waters)(Bridge Prep C18 OBD column, 5μ silica, 50 mm diameter, 100 mm length), using decreasingly polar mixtures of water (containing 1% $NH_3$) and MeCN as eluents. Fractions containing the desired compound were concentrated under reduced pressure to afford trans-3-hydroxy-N-(6-(4,5,6,7-tetrahydropyrazolo[1,5-a]pyridin-3-yl)pyrimidin-4-yl)cyclobutanecarboxamide (10 mg, 47%) as a white solid. $^1$H NMR (400 MHz, $CD_3OD$, 30° C.) 1.93-2.05 (2H, m), 2.07-2.18 (2H, m), 2.26 (2H, m), 2.60 (2H, m), 3.17-3.28 (3H, m), 4.21 (2H, t), 4.49 (1H, p), 8.06 (1H, s), 8.33 (1H, d), 8.71 (1H, d). m/z: ES+ [M+H]+ 314.

Procedures for preparing the starting material trans-3-((tert-butyldimethylsilyl)oxy)-N-(6-(4,5,6,7-tetrahydropyrazolo[1,5-a]pyridin-3-yl)pyrimidin-4-yl)cyclobutanecarboxamide are described below:

Preparation of trans-3-((tert-butyldimethylsilyl)oxy)-N-(6-chloropyrimidin-4-yl)cyclobutanecarboxamide

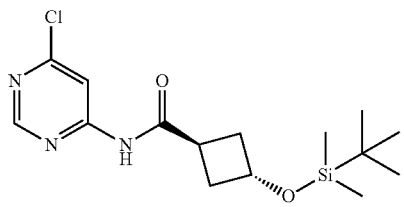 [SMILES: CC(C)(C)[Si](C)(C)O[C@H]1C[C@H](C(=O)Nc2cc(Cl)ncn2)C1]

1-Chloro-N,N,2-trimethylpropenylamine (0.383 mL, 2.89 mmol) was added to a solution of trans-3-((tert-butyldimethylsilyl)oxy)cyclobutanecarboxylic acid (0.667 g, 2.89 mmol; prepared according to Example 4, substituting trans-3-hydroxycyclobutanecarboxylic acid for cis-3-hydroxycyclobutanecarboxylic acid) in DCM (10 mL) and the resulting mixture stirred at r.t. for 1.5 h. 6-Chloropyrimidin-4-amine (0.25 g, 1.93 mmol) and pyridine (0.23 mL, 2.9 mmol) were then added and the mixture was stirred at r.t. overnight. The reaction was quenched with saturated aqueous sodium bicarbonate (50 mL), and the layers separated. The aqueous layer was extracted with DCM (2×50 mL). The combined organic layers were washed with saturated aqueous sodium chloride, dried over sodium sulfate, filtered, and concentrated under reduced pressure. The resulting residue was purified by flash silica chromatography, elution gradient 0 to 100% ethyl acetate in heptane. The fractions containing product were combined, concentrated under reduced pressure to give trans-3-((tert-butyldimethylsilyl)oxy)-N-(6-chloropyrimidin-4-yl)cyclobutanecarboxamide (0.230 g, 35%) as a white solid. $^1$H NMR (400 MHz, DMSO-$d_6$, 30° C.) 0.00 (6H, s), 0.84 (9H, s), 2.10 (2H, m), 2.38-2.45 (2H, m), 3.21 (1H, t), 4.44 (1H, p), 8.14 (1H, s), 8.71 (1H, s), 11.13 (1H, s br). m/z: ES+ [M+H]+ 342.

Preparation of trans-3-((tert-butyldimethylsilyl)oxy)-N-(6-(4,5,6,7-tetrahydropyrazolo[1,5-a]pyridin-3-yl)pyrimidin-4-yl)cyclobutanecarboxamide

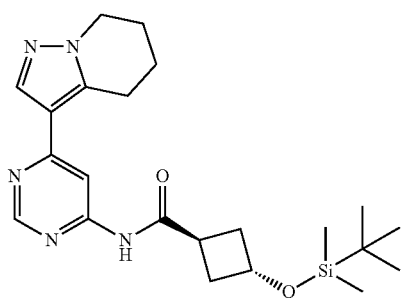 [SMILES: CC(C)(C)[Si](C)(C)O[C@H]1C[C@H](C(=O)Nc2cc(-c3cnn4c3CCCC4)ncn2)C1]

Trans-3-((tert-butyldimethylsilyl)oxy)-N-(6-chloropyrimidin-4-yl)cyclobutanecarboxamide (100 mg, 0.29 mmol), 3-(4,4,5,5-tetramethyl-1,3,2-dioxaborolan-2-yl)-4,5,6,7-tetrahydropyrazolo[1,5-a]pyridine (73 mg, 0.29 mmol), dichloro-[1,1'-bis(di-tertbutylphosphino)ferrocene]palladium(II) (9.5 mg, 0.01 mmol) and potassium phosphate (186 mg, 0.88 mmol) were charged to a flask, and the flask was evacuated and back filled with nitrogen (3×). Degassed 1,4-dioxane (1 mL) was then added, and the mixture was heated to 90° C. and maintained under these conditions for 2 h. The reaction was concentrated under reduced pressure, and the resulting residue was partitioned between saturated aqueous sodium bicarbonate (20 mL) and ethyl acetate (20 mL). The layers were separated, and the aqueous layer was extracted with ethyl acetate (2×20 mL). The combined organic layers were washed with saturated aqueous sodium chloride (20 mL), dried over sodium sulfate, filtered, and concentrated under reduced pressure. The resulting residue was purified by flash silica chromatography, elution gradient 0 to 100% EtOAc in heptane to give trans-3-((tert-butyldimethylsilyl)oxy)-N-(6-(4,5,6,7-tetrahydropyrazolo[1,5-a]pyridin-3-yl)pyrimidin-4-yl)cyclobutanecarboxamide (29 mg, 23%) as a white solid. $^1$H NMR (400 MHz, $CDCl_3$, 30° C.) 0.00 (6H, s), 0.89 (9H, s), 1.91-1.99 (2H, m), 2.08 (2H, m), 2.29 (2H, m), 2.63 (2H, m), 3.01-3.10 (1H, m), 3.23 (2H, t), 4.21 (2H, t), 4.52-4.63 (1H, m), 8.08 (1H, s), 8.31 (1H, d), 8.43 (1H, s br), 8.73 (1H, d). m/z: ES+ [M+H]+ 428.

Example 30: (1S,3R)-3-acetamido-N-(6-(5,5-dimethyl-5,6-dihydro-4H-pyrrolo[1,2-b]pyrazol-3-yl)pyrimidin-4-yl)cyclohexanecarboxamide

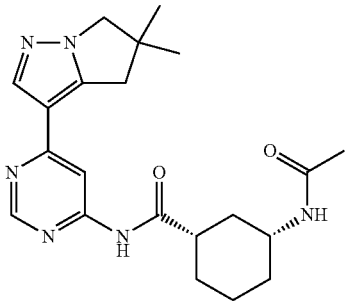 [SMILES: CC(=O)N[C@@H]1CCC[C@H](C(=O)Nc2cc(-c3cnn4c3CC(C)(C)C4)ncn2)C1]

Acetic anhydride (0.038 mL, 0.41 mmol) was added dropwise to crude (1S,3R)-3-amino-N-(6-(5,5-dimethyl-5,6-dihydro-4H-pyrrolo[1,2-b]pyrazol-3-yl)pyrimidin-4-yl)cyclohexanecarboxamide hydrochloride (0.120 g, 0.308 mmol), 4-dimethylaminopyridine (2.07 mg, 0.02 mmol), and triethylamine (0.15 mL, 1.1 mmol) in DCM (2 mL) at r.t. under nitrogen. The resulting solution was stirred at r.t. for 4 h. The reaction mixture was then quenched with saturated aqueous NH$_4$Cl (10 mL), extracted with DCM (2×10 mL), and the combined organic layers were dried over MgSO$_4$, filtered, and concentrated under reduced pressure. The resulting residue was purified by preparative HPLC (Waters)(Bridge Prep C18 OBD column, 5μ silica, 30 mm diameter, 100 mm length), using decreasingly polar mixtures of water (containing 1% NH$_3$) and MeCN as eluents. Fractions containing the desired compound were concentrated under reduced pressure to afford (1S,3R)-3-acetamido-N-(6-(5,5-dimethyl-5,6-dihydro-4H-pyrrolo[1,2-b]pyrazol-3-yl)pyrimidin-4-yl)cyclohexanecarboxamide (0.066 g, 55%) as a white solid. $^1$H NMR (500 MHz, DMSO-d$_6$, 30° C.) 1.02-1.12 (1H, m), 1.25-1.37 (9H, m), 1.76-1.88 (6H, m), 1.90-1.96 (1H, m), 2.61-2.67 (1H, m), 2.95 (2H, s), 3.54-3.61 (1H, m), 3.92 (2H, s), 7.76 (1H, br d), 8.03 (1H, d), 8.15 (1H, d), 8.73 (1H, dd), 10.75 (1H, s br). m/z: ES+ [M+H]+ 397.

Procedures for preparing the starting material (1S,3R)-3-amino-N-(6-(5,5-dimethyl-5,6-dihydro-4H-pyrrolo[1,2-b]pyrazol-3-yl)pyrimidin-4-yl)cyclohexanecarboxamide hydrochloride are described below:

Preparation of Tert-butyl ((1R,3S)-3-((6-bromopyrimidin-4-yl)carbamoyl)cyclohexyl) Carbamate

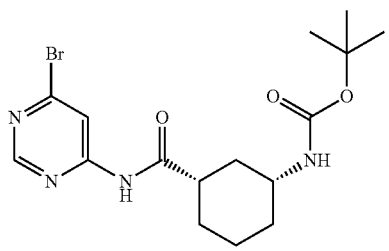 [SMILES: CC(C)(C)OC(=O)N[C@@H]1CCC[C@H](C(=O)Nc2cc(Br)ncn2)C1]

1-Chloro-N,N,2-trimethylpropenylamine (0.46 mL, 3.5 mmol) was added dropwise to a solution of (1S,3R)-3-((tert-butoxycarbonyl)amino)cyclohexanecarboxylic acid (699 mg, 2.87 mmol; prepared according to Example 2) in DCM (10 mL) at 0° C. under nitrogen. The resulting solution was stirred at 0° C. for 1.5 h. 6-Bromopyrimidin-4-amine (400 mg, 2.30 mmol) and pyridine (0.28 mL, 3.5 mmol) were then added, and the reaction mixture was stirred at r.t. overnight. The crude reaction mixture was concentrated under reduced pressure. To the resulting solid, DCM was then added. The resulting mixture was then filtered, and the resulting precipitate was purified by flash silica chromatography, elution gradient 0 to 2% MeOH in DCM. Pure fractions were concentrated under reduced pressure to afford tert-butyl ((1R,3S)-3-((6-bromopyrimidin-4-yl)carbamoyl)cyclohexyl)carbamate (605 mg, 66%) as a white solid. m/z: ES+ [M+H]+ 399

Preparation of Tert-butyl ((1R,3S)-3-((6-(5,5-dimethyl-5,6-dihydro-4H-pyrrolo[1,2-b]pyrazol-3-yl)pyrimidin-4-yl)carbamoyl)cyclohexyl)carbamate

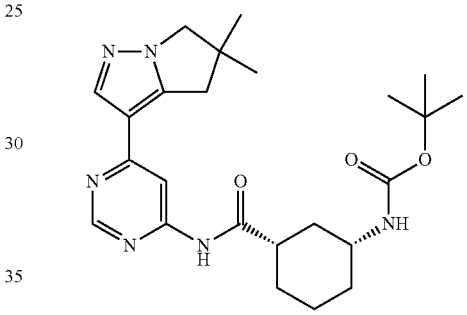

2nd Generation XPhos Precatalyst (0.039 g, 0.050 mmol) was added to a degassed mixture of 5,5-dimethyl-3-(4,4,5,5-tetramethyl-1,3,2-dioxaborolan-2-yl)-5,6-dihydro-4H-pyrrolo[1,2-b]pyrazole (0.18 g, 0.60 mmol; prepared according to Example 23), tert-butyl ((1R,3S)-3-(6-bromopyrimidin-4-yl)carbamoyl)cyclohexyl)carbamate (0.20 g, 0.50 mmol) and potassium phosphate, tribasic, (0.262 g, 1.50 mmol) in 1,4-dioxane (10 mL) and, water (2 mL). The mixture was degassed and was stirred at 90° C. for 2 h under nitrogen. The reaction mixture was then concentrated under reduced pressure, and the resulting residue was taken up in water (20 mL). The resulting mixture was extracted sequentially with EtOAc (2×20 mL) and DCM (20 mL). The combined organic layers were dried over MgSO$_4$, filtered, and concentrated under reduced pressure. The resulting residue was purified by flash silica chromatography, elution gradient 0 to 100% EtOAc in heptane. Pure fractions were concentrated under reduced pressure to afford tert-butyl ((1R,3S)-3-((6-(5,5-dimethyl-5,6-dihydro-4H-pyrrolo[1,2-b]pyrazol-3-yl)pyrimidin-4-yl)carbamoyl)cyclohexyl)carbamate (0.18 g, 79%) as a cream-colored solid. $^1$H NMR (400 MHz, CDCl$_3$, 30° C.) 1.06-1.13 (1H, m), 1.35 (6H, s), 1.41-1.50 (12H, m), 1.87-1.96 (3H, m), 2.26-2.37 (1H, d), 2.38-2.44 (1H, m), 3.04 (2H, s), 3.44-3.58 (1H, m) 3.93 (2H, s), 4.44-4.52 (1H, m), 8.00 (1H, br s), 8.13 (1H, s), 8.18 (1H, d), 8.72 (1H, d m/z: ES+ [M+H]+ 455.

Preparation of (1S,3R)-3-amino-N-(6-(5,5-dimethyl-5,6-dihydro-4H-pyrrolo[1,2-b]pyrazol-3-yl)pyrimidin-4-yl)cyclohexanecarboxamide Hydrochloride

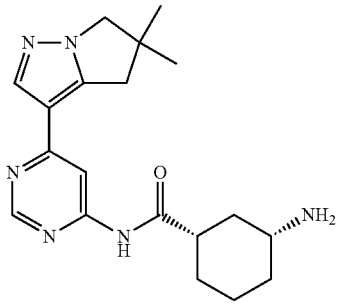 [SMILES: CC1(C)Cc2c(-c3cc(NC(=O)[C@H]4CCC[C@@H](N)C4)ncn3)cnn2C1]

Tert-butyl ((1R,3S)-3-((6-(5,5-dimethyl-5,6-dihydro-4H-pyrrolo[1,2-b]pyrazol-3-yl)pyrimidin-4-yl)carbamoyl)cyclohexyl)carbamate (0.160 g, 0.35 mmol) and hydrochloric acid in dioxane (4 M; 0.71 mL, 2.8 mmol) were dissolved in methanol (2 mL) at r.t. under air. The resulting solution was stirred at r.t. for 16 h. The reaction mixture was concentrated under reduced pressure, and the resulting crude (1S,3R)-3-amino-N-(6-(5,5-dimethyl-5,6-dihydro-4H-pyrrolo[1,2-b]pyrazol-3-yl)pyrimidin-4-yl)cyclohexanecarboxamide hydrochloride (0.120 g, 88%) was carried on to the next step without further purification. m/z: ES+ [M+H]+ 355.

Example 31: (1S,3R)—N-(5-chloro-4-(4,5,6,7-tetrahydropyrazolo[1,5-a]pyridin-3-yl)pyridin-2-yl)-3-(2-cyanoacetamido)cyclohexanecarboxamide

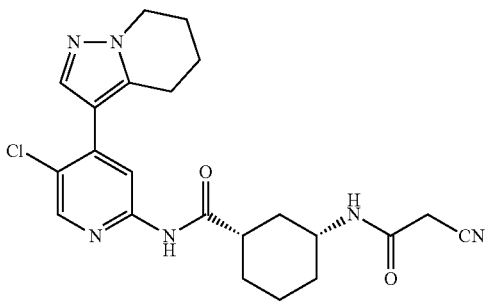 [SMILES: N#CCC(=O)N[C@@H]1CCC[C@H](C(=O)Nc2cc(-c3cnn4c3CCCC4)c(Cl)cn2)C1]

HATU (140 mg, 0.37 mmol) was added to a solution of (1S,3R)-3-amino-N-(5-chloro-4-(4,5,6,7-tetrahydropyrazolo[1,5-a]pyridin-3-yl)pyridin-2-yl)cyclohexanecarboxamide dihydrochloride (150 mg, 0.34 mmol; prepared according to Example 2), 2-cyanoacetic acid (31.4 mg, 0.37 mmol), DIPEA (0.18 mL, 1.0 mmol) and DMF (1.2 mL). The reaction was stirred at r.t. for 3 h. The reaction was diluted with EtOAc and washed with saturated NaHCO₃ and saturated aqueous sodium chloride. The organic layer was dried over sodium sulfate, filtered and concentrated under reduced pressure. The resulting residue was purified by flash silica chromatography, eluting with 80 to 100% EtOAc in hexane, to afford (1S,3R)—N-(5-chloro-4-(4,5,6,7-tetrahydropyrazolo[1,5-a]pyridin-3-yl)pyridin-2-yl)-3-(2-cyanoacetamido)cyclohexanecarboxamide (51 mg, 35%) as a white solid. ¹H NMR (300 MHz, DMSO-d₆, 27° C.) 1.04-1.19 (1H, m), 1.21-1.39 (3H, m), 1.73-1.88 (5H, m), 1.93 (1H, br d), 1.99-2.10 (2H, m), 2.56-2.68 (1H, m), 2.80 (2H, t), 3.52-3.64 (3H, m), 4.14 (2H, t), 7.76 (1H, s), 8.14 (1H, s), 8.19 (1H, d), 8.38 (1H, s), 10.59 (1H, s). m/z: ES+ [M+H]+ 441.

Optical Rotation:
Concentration: 0.1 g/dL
Lamp: Sodium
Wavelength: 589 nm
Temperature: 20° C.
Path length: 10 cm
Cell volume: 1 mL
Solvent: DMSO
[α]=+76.3

Example 31a: Tert-butyl ((1R,3S)-34(5-chloro-4-(4,5,6,7-tetrahydropyrazolo[1,5-a]pyridin-3-yl)pyridin-2-yl)carbamoyl)cyclohexyl)carbamate

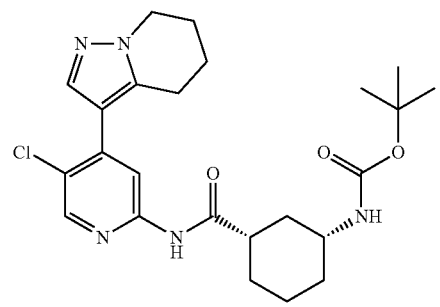 [SMILES: CC(C)(C)OC(=O)N[C@@H]1CCC[C@H](C(=O)Nc2cc(-c3cnn4c3CCCC4)c(Cl)cn2)C1]

1-Chloro-N,N,2-trimethylprop-1-en-1-amine (0.344 g, 2.57 mmol) was added dropwise to a stirred solution of (1S,3R)-3-((tert-butoxycarbonyl)amino)cyclohexanecarboxylic acid (0.611 g, 2.51 mmol; prepared according to Example 2) in DCM (12 mL) at 0° C. The resulting mixture was stirred at 0° C. for 1.5 h. Then a solution of 5-chloro-4-(4,5,6,7-tetrahydropyrazolo[1,5-a]pyridin-3-yl)pyridin-2-amine (0.50 g, 2.0 mmol; prepared according to Example 2) and pyridine (0.65 mL, 8.0 mmol) in DCM (18 mL) was added dropwise. The colorless reaction mixture became yellow. The ice bath was removed, and the reaction was maintained under these conditions for 18 h. This same reaction was then repeated as follows: 1-Chloro-N,N,2-trimethylprop-1-en-1-amine (1.032 g, 7.72 mmol) was added dropwise to a stirred solution of (1S,3R)-3-((tert-butoxycarbonyl)amino)cyclohexanecarboxylic acid (1.8 g, 7.5 mmol) in DCM (30 mL) at 0° C. The resulting mixture was stirred at 0° C. for 1.5 h. Then a solution of 5-chloro-4-(4,5,6,7-tetrahydropyrazolo[1,5-a]pyridin-3-yl)pyridin-2-amine (1.5 g, 6.0 mmol) and pyridine (2.0 mL, 24 mmol) in DCM (50 mL) was added dropwise. The colorless reaction mixture became yellow. The ice bath was removed, and the reaction was maintained under these conditions for 18 h. Both reactions were then combined and diluted with MeOH (10 mL) to dissolve precipitates. The resulting solution was washed with saturated aqueous sodium chloride, and the organic layer dried over Na₂SO₄, filtered, and concentrated under reduced pressure to minimum volume. The resulting solution flash silica chromatography, elution gradient 50 to 80% ethyl acetate in hexanes, to afford tert-butyl ((1R,3S)-3-((5-chloro-4-(4,5,6,7-tetrahydropyrazolo[1,5-a]pyridin-3-yl)pyridin-2-yl)carbamoyl)cyclohexyl)carbamate (2.6 g, 68%) as a solid. ¹H NMR (300 MHz, CDCl₃, 27° C.) 1.04-1.21 (1H, m), 1.38-1.52 (12H, m), 1.87-2.19 (7H, m), 2.31 (1H, br d), 2.36-2.49 (m, 1H), 2.95 (2H, t), 3.45-3.61 (m, 1H), 4.24 (2H, t), 4.34-4.52 (1H, m), 7.92 (s, 1H). m/z (ES+), [M+H]+=474.

Example 31b: (1S,3R)-3-amino-N-(5-chloro-4-(4,5,6,7-tetrahydropyrazolo[1,5-a]pyridin-3-yl)pyridin-2-yl)cyclohexanecarboxamide

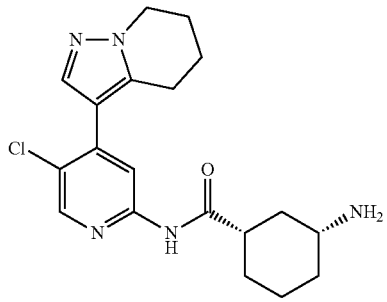 [SMILES: N[C@@H]1CCC[C@H](C(=O)Nc2cc(-c3cnn4c3CCCC4)c(Cl)cn2)C1]

Hydrochloric acid in dioxane (4 M; 3.2 mL, 13 mmol) was added to a stirred suspension of tert-butyl ((1R,3S)-3-((5-chloro-4-(4,5,6,7-tetrahydropyrazolo[1,5-a]pyridin-3-yl)pyridin-2-yl)carbamoyl)cyclohexyl)carbamate (1 g, 2.11 mmol) in MeOH (4 mL) and DCM (4 mL). The reaction suspension turned into a clear solution. The reaction was stirred at r.t. for 2 h and then concentrated under reduced pressure to 1S,3R)-3-amino-N-(5-chloro-4-(4,5,6,7-tetrahydropyrazolo[1,5-a]pyridin-3-yl)pyridin-2-yl)cyclohexanecarboxamide isolated as the dihydrochloride salt (0.91 g, 97%) as a white solid. $^1$H NMR (300 MHz, DMSO-$d_6$, 27° C.) 1.12-1.39 (3H, m), 1.50 (1H, q), 1.77-1.90 (4H, m), 1.90-2.10 (4H, m), 2.57-2.69 (1H, m), 2.81 (2H, t), 2.95-3.09 (1H, m), 4.14 (2H, t), 7.77 (1H, s), 7.99-8.21 (4H, m), 8.39 (1H, s), 10.67 (1H, s). Additional HCl protons under a broad singlet at 5.61 ppm. m/z (ES+), [M+H]+=374.

Example 32: (1S,3R)—N-(5-chloro-4-(4,5,6,7-tetrahydropyrazolo[1,5-a]pyridin-3-yl)pyridin-2-yl)-3-(1-hydroxycyclopropanecarboxamido)cyclohexanecarboxamide

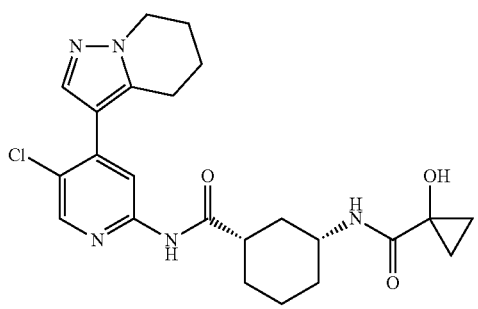 [SMILES: O=C(Nc1cc(-c2cnn3c2CCCC3)c(Cl)cn1)[C@H]1CCC[C@@H](NC(=O)C2(O)CC2)C1]

HATU (140 mg, 0.37 mmol) was added to a solution of (1S,3R)-3-amino-N-(5-chloro-4-(4,5,6,7-tetrahydropyrazolo[1,5-a]pyridin-3-yl)pyridin-2-yl)cyclohexanecarboxamide dihydrochloride (150 mg, 0.34 mmol; prepared according to Example 31b), 1-hydroxycyclopropanecarboxylic acid (34 mg, 0.34 mmol), DIPEA (0.18 mL, 1.0 mmol) and DMF (1.2 mL). The reaction was stirred at r.t. for 3 h. The reaction was diluted with EtOAc and washed with saturated aqueous NaHCO$_3$ and saturated aqueous sodium chloride. The organic layer was dried over sodium sulfate, filtered and concentrated under reduced pressure. The resulting residue was purified by flash silica chromatography elution gradient 80 to 100% EtOAc in hexane, to afford (1S,3R)—N-(5-chloro-4-(4,5,6,7-tetrahydropyrazolo[1,5-a]pyridin-3-yl)pyridin-2-yl)-3-(1-hydroxycyclopropanecarboxamido)cyclohexanecarboxamide (61 mg, 40%) as a white solid. $^1$H NMR (300 MHz, CDCl$_3$, 27° C.) 1.00-1.09 (m, 2H), 1.19-1.31 (1H, m), 1.34-1.40 (2H, m), 1.42-1.59 (3H, m), 1.88-2.17 (7H, m), 2.30 (1H, br d), 2.44-2.58 (1H, m), 2.83 (1H, s), 2.90-2.99 (2H, m), 3.83-3.95 (1H, m), 4.24 (2H, t), 6.83 (1H, d), 7.94 (1H, s), 8.19 (1H, s), 8.27 (1H, s), 8.46 (1H, br s). m/z: ES+ [M+H]+ 458.

Optical Rotation:
Concentration: 0.1 g/dL
Lamp: Sodium
Wavelength: 589 nm
Temperature: 20° C.
Path length: 10 cm
Cell volume: 1 mL
Solvent: DMSO
[α]=+105.4

Example 33: (R)—N-((1R,3S)-3-((5-chloro-4-(4,5,6,7-tetrahydropyrazolo[1,5-a]pyridin-3-yl)pyridin-2-yl)carbamoyl)cyclohexyl)tetrahydrofuran-3-carboxamide

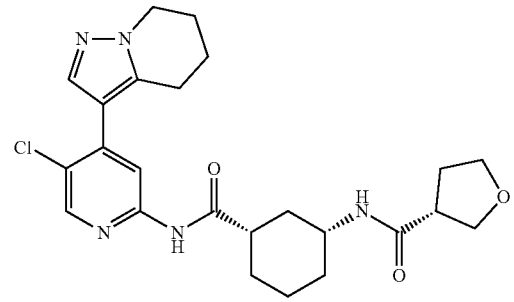 [SMILES: O=C(Nc1cc(-c2cnn3c2CCCC3)c(Cl)cn1)[C@H]1CCC[C@@H](NC(=O)[C@@H]2CCOC2)C1]

HATU (140 mg, 0.37 mmol) was added to a solution of (1S,3R)-3-amino-N-(5-chloro-4-(4,5,6,7-tetrahydropyrazolo[1,5-a]pyridin-3-yl)pyridin-2-yl)cyclohexanecarboxamide dihydrochloride (150 mg, 0.34 mmol; prepared according to Example 31b), (R)-tetrahydrofuran-3-carboxylic acid (43 mg, 0.37 mmol), DIPEA (0.18 mL, 1.0 mmol) and DMF (1.2 mL). The reaction was stirred at r.t. for 3 h. The reaction was diluted with EtOAc and washed with saturated aqueous sodium hydrogencarbonate and saturated aqueous sodium chloride. The organic layer was dried over sodium sulfate, filtered, and concentrated under reduced pressure. The resulting residue was purified by flash silica chromatography, elution gradient 80 to 100% EtOAc in hexane, to afford (R)—N-((1R,3S)-3-((5-chloro-4-(4,5,6,7-tetrahydropyrazolo[1,5-a]pyridin-3-yl)pyridin-2-yl)carbamoyl)cyclohexyl)tetrahydrofuran-3-carboxamide (77 mg, 49%) as a white solid. $^1$H NMR (300 MHz, CDCl$_3$, 27° C.) 1.10-1.29 (1H, m), 1.36-1.58 (3H, m), 1.84-2.04 (5H, m), 1.85-2.05 (5H, m), 2.06-2.21 (4H, m), 2.25 (1H, br d), 2.41-2.55 (1H, m), 2.82-2.97 (4H, m), 3.76-3.99 (4H, m), 4.23 (2H, t), 5.66 (1H, d), 7.92 (1H, s), 8.13 (1H, s), 8.21-8.33 (2H, m). m/z: ES+ [M+H]+ 472.

Optical Rotation:
Concentration: 0.1 g/dL
Lamp: Sodium
Wavelength: 589 nm
Temperature: 20° C.
Path length: 10 cm
Cell volume: 1 mL
Solvent: DMSO
[α]=+79.7

Example 34: N-((1R,3S)-3-((5-chloro-4-(4,5,6,7-tetrahydropyrazolo[1,5-a]pyridin-3-yl)pyridin-2-yl)carbamoyl)cyclohexyl)-3-methyloxetane-3-carboxamide

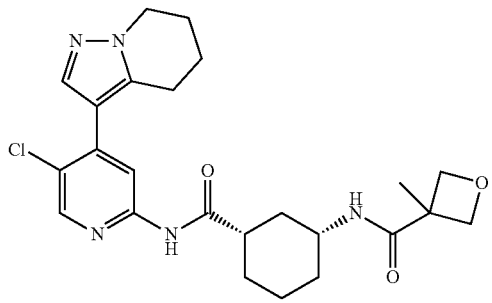 [SMILES: CC1(C(=O)N[C@@H]2CCC[C@H](C(=O)Nc3cc(-c4cnn5c4CCCC5)c(Cl)cn3)C2)COC1]

Example 35: (S)—N-((1R,3S)-34(5-chloro-4-(4,5,6,7-tetrahydropyrazolo[1,5-a]pyridin-3-yl)pyridin-2-yl)carbamoyl)cyclohexyl)tetrahydrofuran-2-carboxamide

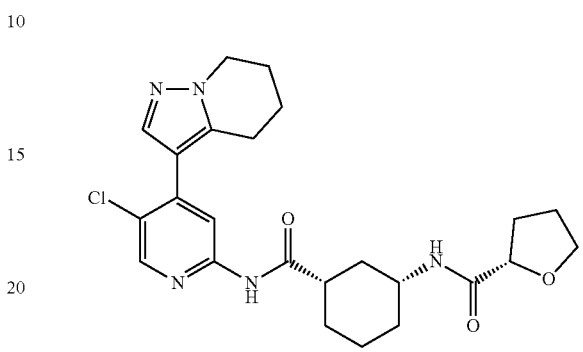

HATU (140 mg, 0.37 mmol) was added to a solution of (1S,3R)-3-amino-N-(5-chloro-4-(4,5,6,7-tetrahydropyrazolo[1,5-a]pyridin-3-yl)pyridin-2-yl)cyclohexanecarboxamide dihydrochloride (150 mg, 0.34 mmol; prepared according to Example 31b), 3-methyloxetane-3-carboxylic acid (43 mg, 0.37 mmol), DIPEA (0.18 mL, 1.0 mmol) and DMF (1.2 mL). The reaction was stirred at r.t. for 3 h. The reaction was diluted with EtOAc and washed with saturated aqueous sodium hydrogencarbonate and saturated aqueous sodium chloride. The organic layer was dried over sodium sulfate, filtered, and concentrated under reduced pressure. The resulting residue was purified by flash silica chromatography, eluting gradient 80 to 100% EtOAc in hexane, to afford N-((1R,3S)-3-((5-chloro-4-(4,5,6,7-tetrahydropyrazolo[1,5-a]pyridin-3-yl)pyridin-2-yl)carbamoyl)cyclohexyl)-3-methyloxetane-3-carboxamide (71 mg, 45%) as a white solid. $^1$H NMR (300 MHz, CDCl$_3$, 27° C.) 1.17-1.33 (1H, m), 1.42-1.62 (6H, m), 1.86-2.16 (7H, m), 2.21-2.34 (1H, m), 2.44-2.57 (1H, m), 2.90-2.99 (1H, m), 3.89-4.02 (1H, m), 4.24 (2H, t), 4.46 (2H, d), 4.84-4.89 (2H, m), 5.86 (1H, d), 7.91 (1H, s), 8.09 (1H, br s), 8.19 (1H, s), 8.28 (1H, s). m/z: ES+ [M+H]+ 472.

Optical Rotation:
Concentration: 0.1 g/dL
Lamp: Sodium
Wavelength: 589 nm
Temperature: 20° C.
Path length: 10 cm
Cell volume: 1 mL
Solvent: DMSO
[α]=+64.2

HATU (140 mg, 0.37 mmol) was added to a solution of (1S,3R)-3-amino-N-(5-chloro-4-(4,5,6,7-tetrahydropyrazolo[1,5-a]pyridin-3-yl)pyridin-2-yl)cyclohexanecarboxamide dihydrochloride (150 mg, 0.34 mmol; prepared according to Example 31b), (S)-tetrahydrofuran-2-carboxylic acid (43 mg, 0.37 mmol), DIPEA (0.18 mL, 1.0 mmol) and DMF (1.2 mL). The reaction was stirred at r.t. for 3 h. The reaction was diluted with EtOAc and washed with saturated NaHCO$_3$ and saturated aqueous sodium chloride. The organic layer was dried over sodium sulfate, filtered and concentrated under reduced pressure. The resulting residue was purified by flash silica chromatography, elution gradient 80 to 100% EtOAc in hexane, to afford (S)—N-((1R,3S)-3-((5-chloro-4-(4,5,6,7-tetrahydropyrazolo[1,5-a]pyridin-3-yl)pyridin-2-yl)carbamoyl)cyclohexyl)tetrahydrofuran-2-carboxamide (41 mg, 26%) as a white solid. $^1$H NMR (300 MHz, CDCl$_3$, 27° C.) 1.12-1.26 (1H, m), 1.35-1.57 (3H, m), 1.79-2.15 (10H, m), 2.20-2.35 (2H, m), 2.41-2.53 (1H, m), 2.94 (2H, t), 3.81-3.96 (3H, m), 4.23 (2H, t), 4.33 (1H, dd), 6.60 (1H, d), 7.92 (1H, s), 8.26 (2H, s), 8.36 (1H, br s). m/z: ES+ [M+H]+ 472.

Optical Rotation:
Concentration: 0.1 g/dL
Lamp: Sodium
Wavelength: 589 nm
Temperature: 20° C.
Path length: 10 cm
Cell volume: 1 mL
Solvent: DMSO
[α]=+54.1

Example 36: (R)—N-((1R,3S)-3-((5-chloro-4-(4,5,6,7-tetrahydropyrazolo[1,5-a]pyridin-3-yl)pyridin-2-yl)carbamoyl)cyclohexyl)tetrahydrofuran-2-carboxamide

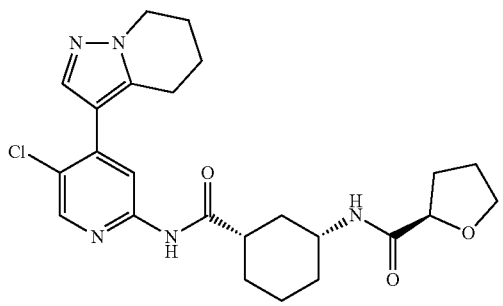 [SMILES: O=C(Nc1cc(-c2cnn3c2CCCC3)c(Cl)cn1)[C@H]1CCC[C@@H](NC(=O)[C@H]2CCCO2)C1]

HATU (140 mg, 0.37 mmol) was added to a solution of (1S,3R)-3-amino-N-(5-chloro-4-(4,5,6,7-tetrahydropyrazolo[1,5-a]pyridin-3-yl)pyridin-2-yl)cyclohexanecarboxamide dihydrochloride (150 mg, 0.34 mmol; prepared according to Example 31b), (R)-tetrahydrofuran-2-carboxylic acid (43 mg, 0.37 mmol), DIPEA (0.18 mL, 1.0 mmol) and DMF (1.2 mL). The reaction was stirred at r.t. for 3 h. The reaction was diluted with EtOAc and washed with saturated aqueous sodium hydrogencarbonate and saturated aqueous sodium chloride. The organic layer was dried over sodium sulfate, filtered, and concentrated under reduced pressure. The resulting residue was purified by flash silica chromatography, elution gradient 80 to 100% EtOAc in hexane, to afford (R)—N-((1R,3S)-3-((5-chloro-4-(4,5,6,7-tetrahydropyrazolo[1,5-a]pyridin-3-yl)pyridin-2-yl)carbamoyl)cyclohexyl)tetrahydrofuran-2-carboxamide (55 mg, 35%) as a white solid. $^1$H NMR (300 MHz, CDCl$_3$, 27° C.) 1.13-1.37 (1H, m), 1.37-1.58 (3H, m), 1.82-2.17 (11H, m), 2.20-2.36 (2H, m), 2.51 (1H, br s), 2.90-3.00 (1H, m), 3.81-3.98 (3H, m), 4.25 (2H, t), 4.33 (1H, dd), 6.62 (1H, d), 7.96 (1H, s), 8.26 (1H, s), 8.27-8.31 (1H, s), 8.78 (1H, br s). m/z: ES+ [M+H]+ 472.

Optical Rotation:
Concentration: 0.1 g/dL
Lamp: Sodium
Wavelength: 589 nm
Temperature: 20° C.
Path length: 10 cm
Cell volume: 1 mL
Solvent: DMSO
[α]=+46.5

Example 37: (1S,3R)—N-(5-chloro-4-(4,5,6,7-tetrahydropyrazolo[1,5-a]pyridin-3-yl)pyridin-2-yl)-3-((S)-2-hydroxypropanamido)cyclohexanecarboxamide

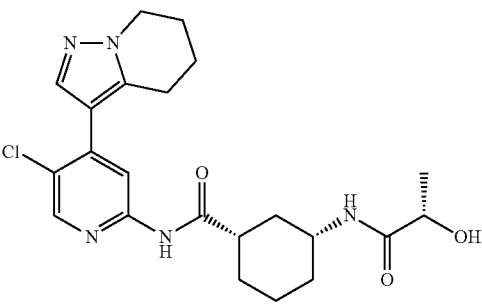 [SMILES: C[C@H](O)C(=O)N[C@@H]1CCC[C@H](C(=O)Nc2cc(-c3cnn4c3CCCC4)c(Cl)cn2)C1]

HATU (140 mg, 0.37 mmol) was added to a solution of (1S,3R)-3-amino-N-(5-chloro-4-(4,5,6,7-tetrahydropyrazolo[1,5-a]pyridin-3-yl)pyridin-2-yl)cyclohexanecarboxamide dihydrochloride (150 mg, 0.34 mmol; prepared according to Example 31b), (S)-2-hydroxypropanoic acid (0.033 g, 0.37 mmol), DIPEA (0.18 mL, 1.0 mmol) and DMF (1.2 mL). The reaction was stirred at r.t. for 3 h. The reaction was diluted with EtOAc and washed with saturated aqueous sodium hydrogencarbonate and saturated aqueous sodium chloride. The organic layer was dried over sodium sulfate, filtered and concentrated under reduced pressure. The resulting residue was purified by preparative HPLC (Waters)(Bridge Prep C18 column, 5μ silica, 19 mm diameter, 150 mm length) using decreasingly polar mixtures of water (containing 0.2% ammonium hydroxide, pH 10) and MeCN as eluents. Fractions containing product were concentrated under reduced pressure to afford (1S,3R)—N-(5-chloro-4-(4,5,6,7-tetrahydropyrazolo[1,5-a]pyridin-3-yl)pyridin-2-yl)-3-((S)-2-hydroxypropanamido)cyclohexanecarboxamide (0.066 g, 44%) as a white solid. $^1$H NMR (300 MHz, CDCl$_3$, 27° C.) 1.15-1.31 (1H, m), 1.39-1.59 (6H, m), 1.87-2.17 (8H, m), 2.28 (1H, br d), 2.48-2.61 (1H, m), 2.96 (2H, t), 3.84-3.98 (1H, m), 4.20-4.28 (3H, m), 6.43 (1H, d), 7.95 (1H, s), 8.25 (1H, s), 8.33 (1H, s), 8.96 (1H, br s). m/z: ES+ [M+H]+ 446.

Optical Rotation:
Concentration: 0.1 g/dL
Lamp: Sodium
Wavelength: 589 nm
Temperature: 20° C.
Path length: 10 cm
Cell volume: 1 mL
Solvent: DMSO
[α]=+56.6

Example 38: (S)—N-((1R,3S)-3-((5-chloro-4-(4,5,6,7-tetrahydropyrazolo[1,5-a]pyridin-3-yl)pyridin-2-yl)carbamoyl)cyclohexyl)tetrahydrofuran-3-carboxamide

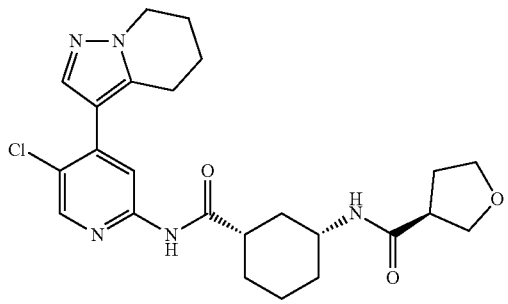 [SMILES: O=C(Nc1cc(-c2cnn3c2CCCC3)c(Cl)cn1)[C@H]1CCC[C@@H](NC(=O)[C@H]2CCOC2)C1]

HATU (140 mg, 0.37 mmol) was added to a solution of (1S,3R)-3-amino-N-(5-chloro-4-(4,5,6,7-tetrahydropyrazolo[1,5-a]pyridin-3-yl)pyridin-2-yl)cyclohexanecarboxamide dihydrochloride (150 mg, 0.34 mmol; prepared according to Example 31b), (S)-tetrahydrofuran-3-carboxylic acid (43 mg, 0.37 mmol) DIPEA (0.18 mL, 1.0 mmol) and DMF (1.2 mL). The reaction was stirred at r.t. for 3 h. The reaction was diluted with EtOAc and washed with saturated aqueous sodium hydrogencarbonate and saturated aqueous sodium chloride. The organic layer was dried over sodium sulfate, filtered and concentrated under reduced pressure. The resulting residue was purified by flash silica chromatography, elution gradient 80 to 100% EtOAc in hexane, to afford (S)—N-((1R,3S)-3-((5-chloro-4-(4,5,6,7-tetrahydropyrazolo[1,5-a]pyridin-3-yl)pyridin-2-yl)carbamoyl)cyclohexyl)tetrahydrofuran-3-carboxamide (70 mg, 44%). $^1$H NMR (300 MHz, CDCl$_3$, 27° C.) 1.09-1.26 (m, 1H), 1.38-1.59 (m, 3H), 1.87-2.05 (m, 5H), 2.07-2.21 (m, 4H), 2.29 (1H, d), 2.38-2.58 (1H, m), 2.82-2.99 (4H, m), 3.78-4.00 (4H, m), 4.24 (2H, t), 5.63 (1H, d), 7.92 (1H, s), 8.25 (1H, s), 8.27 (1H, s), 8.40 (1H, br s). m/z: ES+ [M+H]+ 472.

Optical Rotation:
Concentration: 0.1 g/dL
Lamp: Sodium
Wavelength: 589 nm
Temperature: 20° C.
Path length: 10 cm
Cell volume: 1 mL
Solvent: DMSO
[α]=+60.4

Example 39: (1S,3R)-3-acetamido-N-(5-cyano-4-(5,5-dimethyl-5,6-dihydro-4H-pyrrolo[1,2-b]pyrazol-3-yl)pyridin-2-yl)cyclohexanecarboxamide

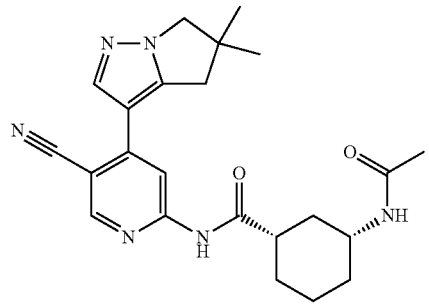 [SMILES: CC(=O)N[C@@H]1CCC[C@H](C(=O)Nc2cc(-c3cnn4c3CC(C)(C)C4)c(C#N)cn2)C1]

5,5-Dimethyl-3-(4,4,5,5-tetramethyl-1,3,2-dioxaborolan-2-yl)-5,6-dihydro-4H-pyrrolo[1,2-b]pyrazole (195 mg, 0.57 mmol; prepared according to Example 14), (1S,3R)-3-acetamido-N-(4-chloro-5-cyanopyridin-2-yl)cyclohexanecarboxamide (184 mg, 0.57 mmol), cesium carbonate (561 mg, 1.72 mmol), dioxane (4.3 mL) and water (1.4 mL) were combined in a 100-mL round bottom flask to give a colorless solution. The solution was purged with nitrogen for 15 min, and 2nd Generation X-Phos Precatalyst (33 mg, 0.04 mmol) was added. The reaction was heated at 95° C. under nitrogen for 1 hour, then cooled and diluted with DCM (50 mL). The organic layer was washed with water (2×25 mL) before being concentrated under reduced pressure. The resulting residue was adsorbed onto silica gel and purified by flash column chromatography, elution gradient 0 to 10% methanol in DCM. Product fractions were concentrated under reduced pressure, and the resulting residue was repurified by reverse phase HPLC (15 g RediSep Rf Gold(R) reversed-phase HP C18 column by Teledyne Isco, 10-40µ silica), elution gradient 0 to 80% acetonitrile in water. Product fractions were concentrated under reduced pressure to afford (1S,3R)-3-acetamido-N-(5-cyano-4-(5,5-dimethyl-5,6-dihydro-4H-pyrrolo[1,2-b]pyrazol-3-yl)pyridin-2-yl)cyclohexanecarboxamide (59 mg, 24%) as a white solid. $^1$H NMR (300 MHz, DMSO-d$_6$, 27° C.) 0.99-1.19 (1H, m), 1.21-1.40 (9H. m), 1.73-1.84 (6H, m), 1.90 (1H, br s), 2.60-2.73 (1H, m), 2.95 (2H, s), 3.49-3.67 (1H, m), 3.97 (2H, s), 7.74 (1H, d), 8.12 (1H, s), 8.31 (1H, s), 8.72 (1H, s), 10.90 (1H, s). m/z: ES+ [M+H]+ 421.

Procedures to prepare the starting material (1S,3R)-3-acetamido-N-(4-chloro-5-cyanopyridin-2-yl)cyclohexanecarboxamide are described below:

Preparation of 6-amino-4-chloronicotinonitrile

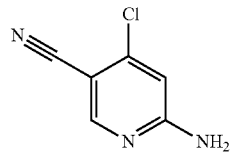

A degassed mixture of dicyanozinc (0.57 g, 4.8 mmol), 5-bromo-4-chloropyridin-2-amine (1.00 g, 4.82 mmol), tetrakis(triphenylphosphine)palladium(0) (0.28 g, 0.24 mmol), and DMF (12 mL) was subjected to microwave conditions (170° C., 2 min). The reaction was cooled and purified directly by flash silica chromatography, elution gradient 0 to 70% ethyl acetate in hexanes. Product fractions were combined and concentrated under reduced pressure. The resulting yellow oil was repurified using the same conditions just described to afford 6-amino-4-chloronicotinonitrile (0.47 g, 64%) as an off-white solid. $^1$H NMR (300 MHz, DMSO-$d_6$, 27° C.) 6.63 (1H, s), 7.34 (2H, br s), 8.38 (1H, s). $^{13}$C NMR (75 MHz, DMSO-$d_6$, 27° C.) 95.59 (1C, s) 107.12 (1C, s) 116.17 (1C, s) 143.41 (1C, s) 154.87 (1C, s) 162.32 (1C, s). m/z: ES+ [M+H]+ 154.

Preparation of Tert-butyl ((1R,3S)-3-((4-chloro-5-cyanopyridin-2-yl)carbamoyl)cyclohexyl)carbamate

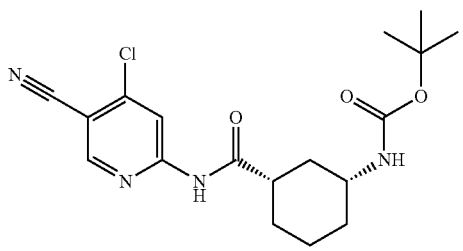 [SMILES: CC(C)(C)OC(=O)N[C@@H]1CCC[C@H](C(=O)Nc2cc(Cl)c(C#N)cn2)C1]

1-Chloro-N,N,2-trimethylprop-1-en-1-amine (0.23 mL, 1.7 mmol) was added to a solution of (1S,3R)-3-((tert-butoxycarbonyl)amino)cyclohexanecarboxylic acid (310 mg, 1.27 mmol; prepared according to Example 2) in DCM (5.5 mL) at r.t., resulting in a colorless solution. The reaction was maintained under these conditions for 2 h, and this reaction was added directly to a solution of 6-amino-4-chloronicotinonitrile (178 mg, 1.16 mmol) and pyridine (0.37 ml, 4.6 mmol) in DCM (11 mL) at 0° C. The reaction was allowed to warm to r.t. and was maintained under these conditions for 18 h. The reaction was then diluted with DCM and washed with water and saturated aqueous sodium chloride, dried over magnesium sulfate, filtered, and concentrated under reduced pressure. The resulting residue was adsorbed onto silica gel and purified flash silica chromatography, elution gradient 0 to 10% methanol in DCM. The resulting material was repurified by flash silica chromatography, elution gradient 0 to 100% ethyl acetate in hexanes, to afford tert-butyl ((1R,3S)-3-((4-chloro-5-cyanopyridin-2-yl)carbamoyl)cyclohexyl)carbamate (330 mg, 75%) as a white solid. m/z: ES+ [M+Na$^+$]+ 401.

Preparation of (1S,3R)-3-acetamido-N-(4-chloro-5-cyanopyridin-2-yl)cyclohexanecarboxamide

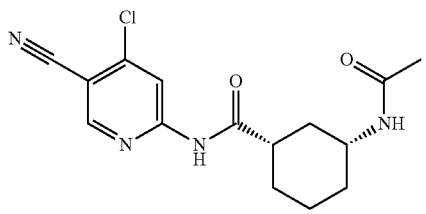 [SMILES: CC(=O)N[C@@H]1CCC[C@H](C(=O)Nc2cc(Cl)c(C#N)cn2)C1]

Hydrochloric acid in dioxane (4 M; 1.5 mL, 44 mmol) was added to a solution of tert-butyl ((1R,3S)-3-((4-chloro-5-cyanopyridin-2-yl)carbamoyl)cyclohexyl)carbamate (330 mg, 0.87 mmol) in MeOH (2.9 mL) under nitrogen to give a colorless solution. After 2 h, the reaction was concentrated under reduced pressure to afford a white solid (302 mg). This solid was dissolved in DCM (4.8 mL) and triethylamine (0.61 mL, 4.4 mmol) and acetic anhydride (123 µL, 1.31 mmol) were added. The reaction was stirred at r.t. for 2 h and then diluted with DCM. The reaction mixture was washed with water (30 mL), and saturated aqueous sodium chloride (30 mL), dried over sodium sulfate, filtered, and concentrated under reduced pressure. The resulting residue was adsorbed onto silica gel and purified by flash silica chromatography, elution gradient 0 to 10% methanol in DCM then isocratic 10% methanol in ethyl acetate, to afford (1S,3R)-3-acetamido-N-(4-chloro-5-cyanopyridin-2-yl)cyclohexanecarboxamide (184 mg, 66%) as a white solid. m/z: ES+ [M+H]+ 321.

Example 40: (1S,3R)-3-acetamido-N-(5-chloro-4-(5-methyl-5,6-dihydro-4H-pyrrolo[1,2-b]pyrazol-3-yl)pyridin-2-yl)cyclohexanecarboxamide

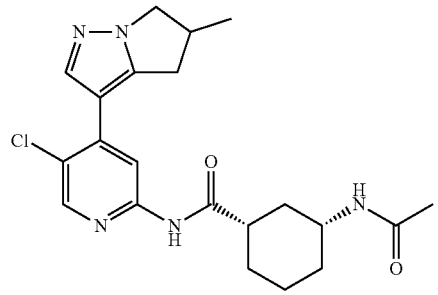 [SMILES: CC(=O)N[C@@H]1CCC[C@H](C(=O)Nc2cc(-c3cnn4c3CC(C)C4)c(Cl)cn2)C1]

Mixture of Examples 41 and 42, Unknown Ratio

Acetic anhydride (0.20 mL, 2.2 mmol) was added to a stirred solution of (1S,3R)-3-amino-N-(5-chloro-4-(5-methyl-5,6-dihydro-4H-pyrrolo[1,2-b]pyrazol-3-yl)pyridin-2-yl)cyclohexanecarboxamide (670 mg, 1.79 mmol), triethylamine (0.52 mL, 3.8 mmol) and N,N-dimethylpyridin-4-amine (11 mg, 0.09 mmol) in DCM (10 mL). The reaction mixture was stirred at r.t. for 18 h. The mixture was purified by ion exchange chromatography using an SCX column, and the desired product was eluted from the column using 1 M NH$_3$ in MeOH. Product fractions were concentrated under reduced pressure. The resulting crude product was purified by flash silica chromatography, using an elution gradient of 0 to 100% EtOAc in heptane followed by isocratic 10% MeOH in EtOAc. Pure fractions were concentrated under reduced pressure to afford (1S,3R)-3-acetamido-N-(5-chloro-4-(5-methyl-5,6-dihydro-4H-pyrrolo[1,2-b]pyrazol-3-yl)pyridin-2-yl)cyclohexanecarboxamide (693 mg, 93%) as a white solid. $^1$H NMR (400 MHz, DMSO-$d_6$, 30° C.) 1.05-1.11 (1H, m), 1.23 (3H, d), 1.27-1.38 (3H, m), 1.72-1.81 (6H, m), 1.89 (1H, br d), 2.52-2.63 (1H, m), 2.67 (1H, dd), 3.13-3.19 (1H, m), 3.20-3.28 (1H, m), 3.50-3.63 (1H, m), 3.76 (1H, dd), 4.27-4.37 (1H, m), 7.75 (1H, d), 8.00 (1H, s), 8.27 (1H, s), 8.35 (1H, s), 10.55 (1H, s). m/z: ES+ [M+H]+ 416.

Procedures used to prepare the starting material (1S,3R)-3-amino-N-(5-chloro-4-(5-methyl-5,6-dihydro-4H-pyrrolo[1,2-b]pyrazol-3-yl)pyridin-2-yl)cyclohexanecarboxamide are described below:

Preparation of 5-methyl-5,6-dihydro-4H-pyrrolo[1,2-b]pyrazol-4-one

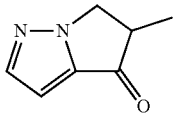

n-Butyl lithium in hexane (1.6 M; 49.9 mL, 79.8 mmol) was added dropwise to 2-methyl-3-(1H-pyrazol-1-yl)propanoic acid (4.92 g, 31.9 mmol) in THF (150 mL) at −78° C. over a period of 20 minutes under nitrogen. The resulting suspension was stirred at −78° C. for 15 minutes. The reaction mixture was then warmed to −45° C. and maintained under these conditions for 30 mins before being allowed to warm to 15° C. The reaction was then poured slowly into ice cold saturated aqueous NH$_4$Cl (100 mL). The mixture was diluted with Et$_2$O (100 mL), the phases separated, and the aqueous layer was extracted with Et$_2$O (50 mL). The combined organic layers were washed with saturated aqueous sodium chloride (50 mL), dried with MgSO$_4$, filtered, and concentrated under reduced pressure. The resulting oil was purified by flash silica chromatography, elution gradient 0 to 50% EtOAc in heptane. Pure fractions were evaporated to dryness to afford 5-methyl-5,6-dihydro-4H-pyrrolo[1,2-b]pyrazol-4-one (1.3 g, 30%) as a colourless oil. $^1$H NMR (400 MHz, CDCl$_3$, 21° C.) 1.45 (3H, d), 3.27-3.38 (1H, m), 4.09 (1H, dd), 4.74 (1H, dd), 6.65 (1H, d), 7.79 (1H, d).

Preparation of 5-methyl-5,6-dihydro-4H-pyrrolo[1,2-b]pyrazole

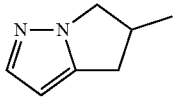

Hydrazine hydrate (2.28 mL, 47.0 mmol) was added to a stirred solution of 5-methyl-5,6-dihydro-4H-pyrrolo[1,2-b]pyrazol-4-one (1.28 g, 9.40 mmol) in diethylene glycol (26.8 mL, 282 mmol). The resulting solution was stirred at 180° C. for 1 hour. The reaction mixture was then allowed to cool slightly. Potassium hydroxide (1.85 g, 32.9 mmol) was carefully added to the mixture, and the resulting suspension was stirred at 150° C. for 2 h. The mixture was then allowed to cool before being diluted with water, acidified with dilute 2 M HCl to pH 4.5, and extracted with Et$_2$O (5×30 mL). The combined organic layers were washed with water (3×20 mL) and saturated aqueous sodium chloride (20 mL), dried over MgSO$_4$, filtered, and concentrated under reduced pressure to give 5-methyl-5,6-dihydro-4H-pyrrolo[1,2-b]pyrazole (0.98 g, 86%) as a clear colorless oil. $^1$H NMR (500 MHz, CDCl$_3$, 30° C.) 1.28 (3H, d), 2.39-2.54 (1H, m), 2.99-3.16 (2H, m), 3.66-3.76 (1H, m), 4.23-4.33 (1H, m), 5.92 (1H, d), 7.48 (1H, d).

Preparation of 3-iodo-5-methyl-5,6-dihydro-4H-pyrrolo[1,2-b]pyrazole

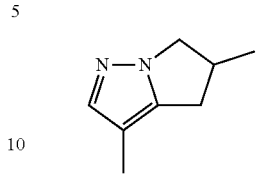

NIS (1.81 g, 8.04 mmol) was added portionwise to 5-methyl-5,6-dihydro-4H-pyrrolo[1,2-b]pyrazole (0.89 g, 7.31 mmol) in acetonitrile (15 mL) at r.t. under nitrogen. The reaction mixture was stirred at 23° C. for 18 h. The reaction mixture was diluted with EtOAc (20 mL) and washed sequentially with water (20 mL) and saturated aqueous sodium chloride (10 mL). The organic layer was dried over MgSO$_4$, filtered and concentrated under reduced pressure to afford 3-iodo-5-methyl-5,6-dihydro-4H-pyrrolo[1,2-b]pyrazole (1.8 g, 99%) as an orange oil. $^1$H NMR (500 MHz, CDCl$_3$, 30° C.) 1.28 (3H, d), 2.43 (1H, dd), 3.00 (1H, dd), 3.06-3.14 (1H, m), 3.79 (1H, dd), 4.36 (1H, dd), 7.46 (1H, s). m/z: ES+ [M+H]+ 249.

Preparation of 5-methyl-3-(4,4,5,5-tetramethyl-1,3,2-dioxaborolan-2-yl)-5,6-dihydro-4H-pyrrolo[1,2-b]pyrazole

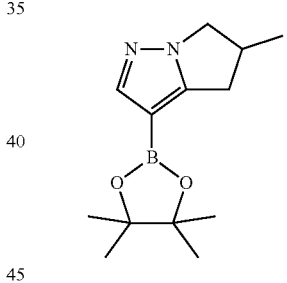

Isopropylmagnesium chloride lithium chloride complex in THF (1.3 M; 6.85 mL, 8.91 mmol) was added dropwise to 3-iodo-5-methyl-5,6-dihydro-4H-pyrrolo[1,2-b]pyrazole (1.7 g, 6.9 mmol) in THF (20 mL) at 0° C. over a period of 5 minutes under nitrogen. The resulting mixture was stirred at 0° C. for 30 minutes. 2-Isopropoxy-4,4,5,5-tetramethyl-1,3,2-dioxaborolane (2.10 mL, 10.3 mmol) was then added dropwise to the mixture keeping the internal temperature at 0° C. The reaction mixture was then allowed to warm to r.t. overnight before being diluted with EtOAc (50 mL) and washed sequentially with saturated aqueous NH$_4$Cl (50 mL), water (50 mL), and saturated aqueous sodium chloride (50 mL). The organic layer was dried over MgSO$_4$, filtered and evaporated to afford 5-methyl-3-(4,4,5,5-tetramethyl-1,3,2-dioxaborolan-2-yl)-5,6-dihydro-4H-pyrrolo[1,2-b]pyrazole (1.5 g, 87%) as a pale brown oil that crystallised. $^1$H NMR (400 MHz, CDCl$_3$, 22° C.) 1.26 (3H, d), 1.29 (12H, s), 2.57 (1H, dd), 3.01-3.22 (2H, m), 3.64-3.75 (1H, m), 4.27 (1H, ddd), 7.76 (1H, s).

Preparation of Tert-butyl ((1R,3S)-3-((5-chloro-4-(5-methyl-5,6-dihydro-4H-pyrrolo[1,2-b]pyrazol-3-yl)pyridin-2-yl)carbamoyl)cyclohexyl)carbamate

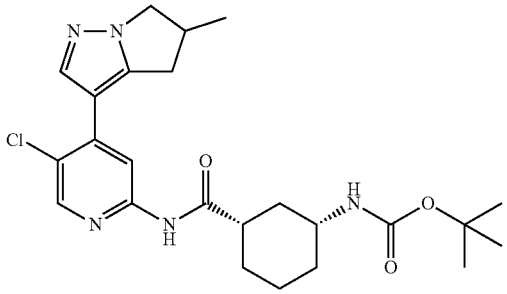 [SMILES: CC1Cc2c(-c3cc(NC(=O)[C@H]4CCC[C@@H](NC(=O)OC(C)(C)C)C4)ncc3Cl)cnn2C1]

2nd Generation XPhos Precatalyst (0.25 g, 0.31 mmol) was added to a degassed mixture of 5-methyl-3-(4,4,5,5-tetramethyl-1,3,2-dioxaborolan-2-yl)-5,6-dihydro-4H-pyrrolo[1,2-b]pyrazole (1.03 g, 3.75 mmol), tert-butyl ((1R,3S)-3-((5-chloro-4-iodopyridin-2-yl)carbamoyl)cyclohexyl)carbamate (1.5 g, 3.13 mmol; prepared according to Example 10) and dibasic potassium phosphate (1.63 g, 9.38 mmol) in 1,4-dioxane (15 mL) and water (3 mL). The resulting mixture was degassed and stirred at 90° C. for 18 h under nitrogen. The reaction mixture was then allowed to cool to r.t., diluted with EtOAc (100 mL) and washed sequentially with water (100 mL) and saturated aqueous sodium chloride (50 mL). The organic extract was dried over MgSO$_4$, filtered, and concentrated under reduced pressure. The resulting residue was purified by flash silica chromatography, elution gradient 0 to 70% EtOAc in heptane. Pure fractions were concentrated under reduced pressure to afford tert-butyl ((1R,3S)-3-((5-chloro-4-(5-methyl-5,6-dihydro-4H-pyrrolo[1,2-b]pyrazol-3-yl)pyridin-2-yl)carbamoyl)cyclohexyl)carbamate (1.0 g, 69%) as a yellow foam. $^1$H NMR (400 MHz, DMSO, 30° C.) 1.07-1.12 (1H, m), 1.70-1.82 (3H, m), 1.85-1.93 (1H, m), 2.53-2.62 (1H, m), 2.66 (1H, dd), 3.11-3.18 (1H, m), 3.19-3.29 (1H, m), 3.76 (1H, dd), 4.32 (1H, dd), 6.76 (1H, d), 8.00 (1H, s), 8.27 (1H, s), 8.34 (1H, s), 10.52 (1H, s). m/z: ES+ [M+H]+ 474.

Preparation of (1S,3R)-3-amino-N-(5-chloro-4-(5-methyl-5,6-dihydro-4H-pyrrolo[1,2-b]pyrazol-3-yl)pyridin-2-yl)cyclohexanecarboxamide

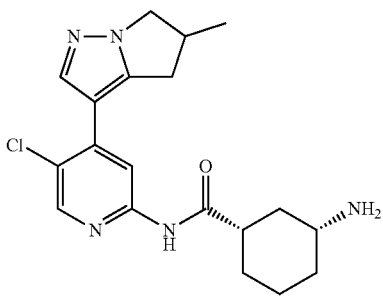 [SMILES: CC1Cc2c(-c3cc(NC(=O)[C@H]4CCC[C@@H](N)C4)ncc3Cl)cnn2C1]

Tert-butyl ((1R,3S)-3(5-chloro-4-(5-methyl-5,6-dihydro-4H-pyrrolo[1,2-b]pyrazol-3-yl)pyridin-2-yl)carbamoyl)cyclohexyl)carbamate (1.11 g, 2.34 mmol) was dissolved in DCM (20 mL). Trifluoroacetic acid (1.8 mL, 23 mmol) was added and the reaction mixture was stirred at r.t. for 18 h. The reaction was purified by ion exchange chromatography using an SCX column. The desired product was eluted from the column using 1 M NH$_3$ in MeOH, and pure fractions were evaporated to dryness to afford (1S,3R)-3-amino-N-(5-chloro-4-(5-methyl-5,6-dihydro-4H-pyrrolo[1,2-b]pyrazol-3-yl)pyridin-2-yl)cyclohexanecarboxamide (0.68 g, 77%) as a white solid. m/z: ES+ [M+H]+ 374.

Examples 41 and 42: Isomer 1 and isomer 2 of (1S,3R)-3-acetamido-N-(5-chloro-4-(5-methyl-5,6-dihydro-4H-pyrrolo[1,2-b]pyrazol-3-yl)pyridin-2-yl)cyclohexanecarboxamide

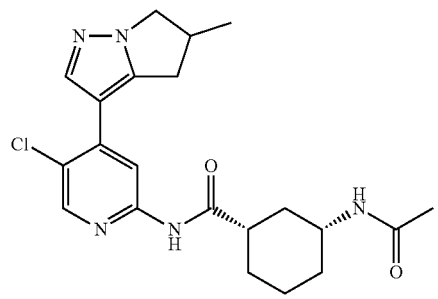

Example 41, Isomer 1

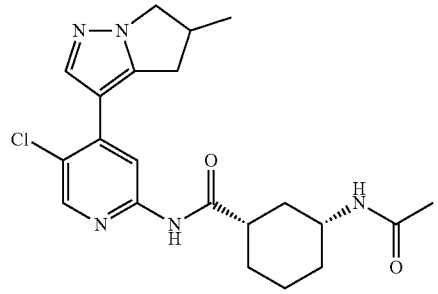

Example 42, Isomer 2

Pure enantiomers. The configuration of the methyl is unknown for Example 41 and 42, but is opposite in Example 41 vs. Example 42

(1S,3R)-3-acetamido-N-(5-chloro-4-(5-methyl-5,6-dihydro-4H-pyrrolo[1,2-b]pyrazol-3-yl)pyridin-2-yl)cyclohexanecarboxamide (670 mg, 1.79 mmol; Example 40) was resolved by preparative HPLC (Chiral Technologies IA column, 20 μm silica, 100 mm diameter, 250 mm length), using a 70/15/15 mixture of heptane/EtOH/MeOH as eluents and a flow rate of 450 mL/min, fractions containing the desired compounds were concentrated under reduced pressure to give the faster eluting isomer 1 of (1S,3R)-3-acetamido-N-(5-chloro-4-(5-methyl-5,6-dihydro-4H-pyrrolo[1,2-b]pyrazol-3-yl)pyridin-2-yl)cyclohexanecarboxamide (356 mg, 48%) and the slower eluting isomer 2 of (1S,3R)-3-acetamido-N-(5-chloro-4-(5-methyl-5,6-dihydro-4H-pyrrolo[1,2-b]pyrazol-3-yl)pyridin-2-yl)cyclohexanecarboxamide (348 mg, 47%).

Example 41: Isomer 1 of (1S,3R)-3-acetamido-N-(5-chloro-4-(5-methyl-5,6-dihydro-4H-pyrrolo[1,2-b]pyrazol-3-yl)pyridin-2-yl)cyclohexanecarboxamide $^1$H NMR (400 MHz, DMSO-d$_6$, 30° C.) 1.05-1.15 (1H, m), 1.25 (3H, d), 1.26-1.39 (3H, m), 1.72-1.83 (6H, m), 1.90

(1H, br d), 2.55-2.62 (1H, m), 2.67 (1H, dd), 3.11-3.19 (1H, m), 3.21-3.28 (1H, m), 3.51-3.62 (1H, m), 3.76 (1H, dd), 4.27-4.37 (1H, m), 7.75 (1H, d br), 8.00 (1H, s), 8.27 (1H, s), 8.35 (1H, s), 10.55 (1H, s). m/z: ES+ [M+H]+ 416.

Example 42: Isomer 2 of (1S,3R)-3-acetamido-N-(5-chloro-4-(5-methyl-5,6-dihydro-4H-pyrrolo[1,2-b]pyrazol-3-yl)pyridin-2-yl)cyclohexanecarboxamide $^1$H NMR (400 MHz, DMSO-d$_6$, 30° C.) 1.08-1.13 (1H, m), 1.24 (3H, d), 1.25-1.36 (3H, m), 1.62-1.85 (6H, m), 1.91 (1H, br d), 2.52-2.61 (1H, m), 2.67 (1H, dd), 3.13-3.19 (1H, m), 3.21-3.29 (1H, m), 3.51-3.60 (1H, m), 3.76 (1H, dd), 4.32 (1H, dd), 7.74 (1H, d), 7.98 (1H, s), 8.28 (1H, s), 8.34 (1H, s), 10.54 (1H, s).

Analytical Reverse Phase Chiral Conditions:
Column: Chiral Technologies IA column,
Column Dimensions: 5 μm, 4.6 mm diameter, 250 mm length,
Mobile Phase A: Heptane
Mobile Phase B: 1:1 EtOH:MeOH
Gradient: Isocratic 30% Mobile Phase B
Flow Rate: 2 mL/min over 15 min
Retention Time: 7.9 min, Isomer 1
9.3 min, Isomer 2
e.e. 99.4%, Isomer 1
97.6%, Isomer 2

Example 43: (1R,3S)-3-acetamido-N-(5-chloro-4-(5,5-dimethyl-5,6-dihydro-4H-pyrrolo[1,2-b]pyrazol-3-yl)pyridin-2-yl)cyclohexanecarboxamide and (1S,3R)-3-acetamido-N-(5-chloro-4-(5,5-dimethyl-5,6-dihydro-4H-pyrrolo[1,2-b]pyrazol-3-yl)pyridin-2-yl)cyclohexanecarboxamide (Example 14)

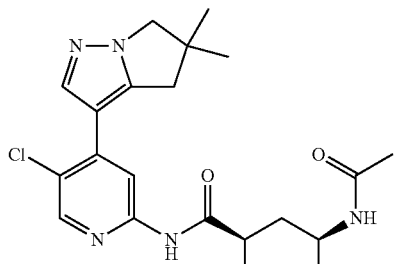

Example 43

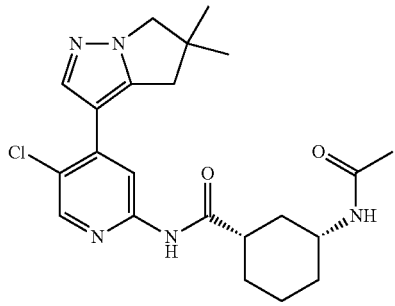

Example 14

2nd Generation XPhos Precatalyst (0.019 g, 0.02 mmol) and cesium carbonate (0.464 g, 1.42 mmol) were added to a degassed solution of 5,5-dimethyl-3-(4,4,5,5-tetramethyl-1,3,2-dioxaborolan-2-yl)-5,6-dihydro-4H-pyrrolo[1,2-b]pyrazole (1.6 mL, 0.50 mmol, as a 0.106 g/mL solution in dioxane; prepared according to Example 14), cis-3-acetamido-N-(5-chloro-4-iodopyridin-2-yl)cyclohexanecarboxamide (0.20 g, 0.47 mmol; prepared according to Examples 10 and 12, substituting cis-3-((tert-butoxycarbonyl)amino)cyclohexanecarboxylic acid (prepared in Example 2, Intermediates) for (1S,3R)-3-((tert-butoxycarbonyl)amino)cyclohexanecarboxylic acid and acetyl chloride for acetic anhydride), 1,4-dioxane (2.6 mL), and water (0.52 mL). The resulting mixture was immersed in a preheated oil bath set at 85° C. After 3 h, another 300 μL of 5,5-dimethyl-3-(4,4,5,5-tetramethyl-1,3,2-dioxaborolan-2-yl)-5,6-dihydro-4H-pyrrolo[1,2-b]pyrazole stock solution (0.106 g/mL in dioxane) were added to the now light orange reaction. The reaction was maintained at this temperature for another 45 min and then cooled to r.t. The reaction was diluted with saturated aqueous sodium chloride and extracted with ethyl acetate (×2). The combined organic layers were dried over sodium sulfate, filtered, and concentrated under reduced pressure. The resulting yellow residue was purified by flash silica chromatography, elution gradient 10 to 100% ethyl acetate in hexanes then 0 to 20% methanol in ethyl acetate, to afford cis-3-acetamido-N-(5-chloro-4-(5,5-dimethyl-5,6-dihydro-4H-pyrrolo[1,2-b]pyrazol-3-yl)pyridin-2-yl)cyclohexanecarboxamide (0.147 g, 72%) contaminated with a small amount of pinacol diol as an off-white solid.

This material was resolved into its enantiomers using SFC conditions (Column: (S,S) Whelk-01, 5 μm, 21.2 mm diameter, 250 mm length, 40° C. column temperature, 100 bar outlet pressure, 75 mL/min flow rate), eluting with 30% isopropanol in CO$_2$, to afford Example 14, (1S,3R)-3-acetamido-N-(5-chloro-4-(5,5-dimethyl-5,6-dihydro-4H-pyrrolo[1,2-b]pyrazol-3-yl)pyridin-2-yl)cyclohexanecarboxamide (0.053 g, 26%), as a white foam solid and Example 43, (1R,3S)-3-acetamido-N-(5-chloro-4-(5,5-dimethyl-5,6-dihydro-4H-pyrrolo[1,2-b]pyrazol-3-yl)pyridin-2-yl)cyclohexanecarboxamide (0.061 g, 30%), as a white foam solid.

(1R,3S)-3-acetamido-N-(5-chloro-4-(5,5-dimethyl-5,6-dihydro-4H-pyrrolo[1,2-b]pyrazol-3-yl)pyridin-2-yl)cyclohexanecarboxamide (Example 43)

$^1$H NMR (300 MHz, DMSO-d$_6$, 27° C.) 1.05 (1H, d), 1.22-1.40 (9H, m), 1.78 (6H, s), 1.90 (1H, d), 2.56-2.69 (1H, m), 2.89 (2H, s), 3.47-3.65 (1H, m), 3.95 (2H, s), 7.74 (1H, br d), 7.99 (1H, s), 8.25 (1H, s), 8.35 (1H, s), 10.54 (1H, s). m/z: ES+ [M+H]+ 430.

Analytical SFC Conditions:
Column: (S,S) Whelk-O1
Column Dimensions: 5 μm, 4.6 mm diameter, 100 mm length,
Column Temperature: 40° C.
Mobile Phase A: CO$_2$ (100%)
Mobile Phase B: Isopropanol
Gradient: Isocratic 30% Mobile Phase B
Flow Rate: 5 mL/min over 5 min
Retention Time: 2.92 min, Example 14
3.54 min, Example 43
e.e. >98%, Example 14
95.5%, Example 43

Optical Rotation for (1R,3S)-3-acetamido-N-(5-chloro-4-(5,5-dimethyl-5,6-dihydro-4H-pyrrolo[1,2-b]pyrazol-3-yl)pyridin-2-yl)cyclohexanecarboxamide (Example 43)

Concentration: 0.1 g/dL
Lamp: Sodium
Wavelength: 589 nm
Temperature: 20° C.
Path length: 10 cm
Cell volume: 1 mL
Solvent: DMSO
[α]=−60.6

Example 44: (1S,3R)-3-acetamido-N-(4-(5,5-dimethyl-4,5,6,7-tetrahydropyrazolo[1,5-a]pyridin-3-yl)pyridin-2-yl)cyclohexanecarboxamide

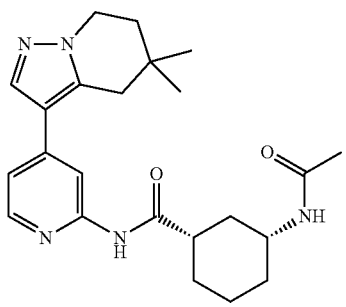 [SMILES: CC(=O)N[C@@H]1CCC[C@H](C(=O)Nc2cc(-c3cnn4c3CC(C)(C)CC4)ccn2)C1]

Acetic anhydride (0.022 mL, 0.23 mmol) was added to a stirred solution of (1S,3R)-3-amino-N-(4-(5,5-dimethyl-4,5,6,7-tetrahydropyrazolo[1,5-a]pyridin-3-yl)pyridin-2-yl)cyclohexanecarboxamide (70 mg, 0.19 mmol), triethylamine (0.056 mL, 0.40 mmol), and N,N-dimethylpyridin-4-amine (1.2 mg, 9.5 μmol) in DCM (10 mL). The reaction mixture was stirred at r.t. for 4 h, and the crude reaction was purified by ion exchange chromatography using an SCX column. The desired product was eluted from the column using 1 M $NH_3$ in MeOH and product-containing fractions were concentrated under reduced pressure. The resulting residue was further purified by preparative HPLC (Waters)(Bridge Prep C18 OBD column, 5μ silica, 30 mm diameter, 100 mm length), using decreasingly polar mixtures of water (containing 1% $NH_3$) and MeCN as eluents. Fractions containing the desired compound were concentrated under reduced pressure to afford (1S,3R)-3-acetamido-N-(4-(5,5-dimethyl-4,5,6,7-tetrahydropyrazolo[1,5-a]pyridin-3-yl)pyridin-2-yl)cyclohexanecarboxamide (44 mg, 56%) as a solid. $^1$H NMR (500 MHz, DMSO-$d_6$, 30° C.) 1.04 (6H, s), 1.06-1.15 (1H, m), 1.32-1.38 (3H, m), 1.66-1.82 (6H, m), 1.83-1.94 (3H, m), 2.58-2.64 (1H, m), 2.78 (2H, s), 3.54-3.62 (1H, m), 4.14 (2H, t), 7.16 (1H, dd), 7.76 (1H, d), 7.84 (1H, s), 8.18 (1H, s), 8.24 (1H, d), 10.34 (1H, s). m/z: ES+ [M+H]+ 410.

Procedures for preparing the starting material (1S,3R)-3-amino-N-(4-(5,5-dimethyl-4,5,6,7-tetrahydropyrazolo[1,5-a]pyridin-3-yl)pyridin-2-yl)cyclohexanecarboxamide are described below:

Preparation of Ethyl 1-(4-ethoxy-4-oxobutyl)-1H-pyrazole-5-carboxylate

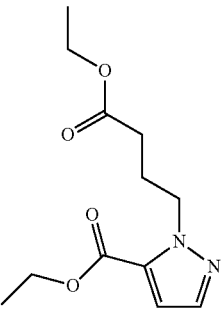 [SMILES: CCOC(=O)CCCn1nccc1C(=O)OCC]

Ethyl 4-bromobutanoate (10 mL, 71 mmol) was added to a stirred mixture of ethyl 1H-pyrazole-5-carboxylate (9.9 g, 71 mmol) and potassium carbonate (11.7 g, 84.8 mmol) in DMF (70 mL). The mixture was stirred at r.t. for 24 h. Water was added and the mixture was extracted with ethyl acetate (3×). The combined organic layers were washed with water (2×), dried over $MgSO_4$, and concentrated under reduced pressure. The resulting residue was purified by flash silica chromatography, eluting with 20% ethyl acetate in pentane to afford desired ethyl 1-(4-ethoxy-4-oxobutyl)-1H-pyrazole-5-carboxylate (9.0 g, 50%) as a solid. $^1$H NMR (400 MHz, $CDCl_3$, 30° C.) 1.24 (3H, t), 1.38 (3H, t), 2.11-2.25 (2H, m), 2.25-2.38 (2H, m), 4.12 (2H, q), 4.34 (2H, q), 4.63 (2H, t), 6.83 (1H, d), 7.47 (1H, d). m/z: ES+ [M+H]+ 255. Also isolated was ethyl 1-(4-ethoxy-4-oxobutyl)-1H-pyrazole-3-carboxylate (8 g, 44.5%).

Preparation of Ethyl 4-oxo-4,5,6,7-tetrahydropyrazolo[1,5-a]pyridine-5-carboxylate

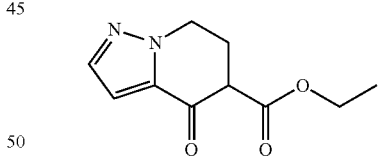

Potassium tert-butoxide (1.39 g, 12.4 mmol) was added to a stirring solution of ethyl 1-(4-ethoxy-4-oxobutyl)-1H-pyrazole-5-carboxylate (2.1 g, 8.3 mmol) in toluene (20 mL). The mixture was stirred at r.t. for 10 minutes and was then warmed to 110° C., resulting in formation of a thick precipitate. The mixture was heated under these conditions for 30 minutes and then cooled to r.t. before being acidified with dilute HCl and extracted with ethyl acetate (3×). The combined organic layers were dried over $MgSO_4$, filtered, and concentrated under reduced pressure to afford ethyl 4-oxo-4,5,6,7-tetrahydropyrazolo[1,5-a]pyridine-5-carboxylate (1.7 g, 99%) as a solid. m/z: ES+ [M+H]+ 209.

Preparation of 6,7-dihydropyrazolo[1,5-a]pyridin-4(5H)-one

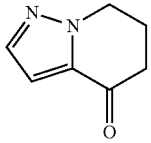

Lithium chloride (0.458 g, 10.8 mmol) was added to a stirred solution of ethyl 4-oxo-4,5,6,7-tetrahydropyrazolo[1,5-a]pyridine-5-carboxylate (1.5 g, 7.2 mmol) in DMSO (15 mL). The mixture was heated at 120° C. for 24 h then cooled to r.t. Water was added, and the mixture was extracted with ethyl acetate (3×). The combined organic layers were combined and concentrated under reduced pressure. The resulting residue was purified by flash silica chromatography, eluting with 50% ethyl acetate in heptane to give 6,7-dihydropyrazolo[1,5-a]pyridin-4(5H)-one (0.90 g, 92%) as a solid. $^1$H NMR (400 MHz, CDCl$_3$, 30° C.) 2.26-2.45 (2H, m), 2.65-2.75 (2H, m), 4.35-4.45 (2H, m), 6.87 (1H, d), 7.55 (1H, d).

Preparation of 5,5-dimethyl-6,7-dihydropyrazolo[1,5-a]pyridin-4(5H)-one

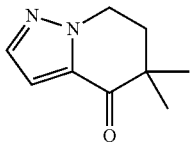

Sodium hydride (60 wt % in mineral oil; 705 mg, 17.6 mmol) was added to a solution of 6,7-dihydropyrazolo[1,5-a]pyridin-4(5H)-one (800 mg, 5.88 mmol) in DMF (5.0 mL) at 0° C. The mixture was stirred for 10 minutes under these conditions and then iodomethane (1.10 mL, 17.6 mmol) was added. The ice bath was removed, and the reaction was maintained under these conditions for 18 h. Water was added, and the mixture was acidified with dilute aqueous hydrochloric acid to pH 7. The reaction was then extracted with ether (3×), and the combined organic layers were dried over sodium sulfate, filtered, and concentrated under reduced pressure. The resulting residue was purified by flash silica chromatography, eluting with 30% ethyl acetate in heptane to afford 5,5-dimethyl-6,7-dihydropyrazolo[1,5-a]pyridin-4(5H)-one (800 mg, 83%) as a white solid. $^1$H NMR (400 MHz, CDCl$_3$, 30° C.) 1.27 (6H, s), 2.06-2.26 (2H, m), 4.32-4.5 (2H, m), 6.86 (1H, d), 7.54 (1H, d). m/z: ES+ [M+H]+ 165.

Preparation of 5,5-dimethyl-4,5,6,7-tetrahydropyrazolo[1,5-a]pyridine

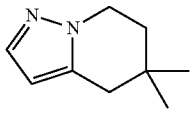

Hydrazine hydrate (1.18 mL, 24.4 mmol) was added to a stirred solution of 5,5-dimethyl-6,7-dihydropyrazolo[1,5-a]pyridin-4(5H)-one (800 mg, 4.87 mmol) dissolved in diethylene glycol (10 mL, 105 mmol). The resulting solution was stirred at 180° C. for 1 hour. The reaction was then removed from heat, and potassium hydroxide (957 mg, 17.1 mmol) was carefully added to the mixture. The resulting suspension was stirred at 170° C. for 2 h. After cooling, the reaction mixture was diluted with water, acidified to pH 5 with dilute aqueous hydrochloric acid (2N), and extracted with Et$_2$O (5×50 mL). The combined organic layers were washed with water (2×20 mL) and then dried over MgSO$_4$, filtered, and concentrated under reduced pressure to give 5,5-dimethyl-4,5,6,7-tetrahydropyrazolo[1,5-a]pyridine (650 mg, 89%) as a solid. $^1$H NMR (400 MHz, CDCl$_3$, 30° C.) 1.05 (6H, s), 1.66-1.97 (2H, m), 2.57 (2H, s), 4.15 (2H, t), 5.92-5.94 (1H, m), 7.44 (1H, d).

Preparation of 3-iodo-5,5-dimethyl-4,5,6,7-tetrahydropyrazolo[1,5-a]pyridine

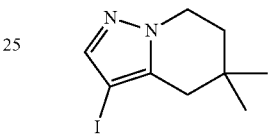

NIS (1.07 g mg, 4.76 mmol) was added to a stirred solution of 5,5-dimethyl-4,5,6,7-tetrahydropyrazolo[1,5-a]pyridine (650 mg, 4.33 mmol) dissolved in acetonitrile (10 mL) at 23° C. The resulting mixture was stirred at 23° C. for 16 h. The reaction mixture was then diluted with EtOAc (20 mL) and washed sequentially with water (2×20 mL) and saturated aqueous sodium chloride (20 mL). The organic layer was dried over MgSO$_4$, filtered, and concentrated under reduced pressure to afford crude 3-iodo-5,5-dimethyl-4,5,6,7-tetrahydropyrazolo[1,5-a]pyridine (1.1 g, 92%) as a solid. $^1$H NMR (400 MHz, CDCl$_3$, 30° C.) 1.07 (6H, s), 1.80 (2H, t), 2.43 (2H, s), 4.24 (2H, t), 7.48 (1H, s).

Preparation of Tert-butyl ((1R,3S)-3-((4-(5,5-dimethyl-4,5,6,7-tetrahydropyrazolo[1,5-a]pyridin-3-yl)pyridin-2-yl)carbamoyl)cyclohexyl)carbamate

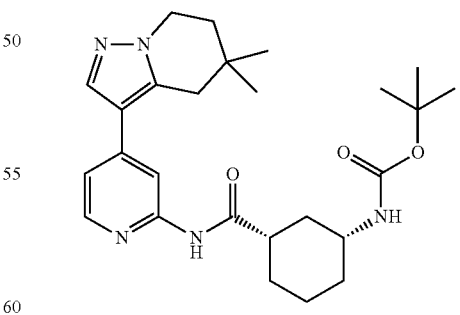

Dichloro[1,1'-bis(di-t-butylphosphino)ferrocene]palladium(II) (44 mg, 0.070 mmol) was added to a degassed solution of tert-butyl ((1R,3S)-3-((4-(4,4,5,5-tetramethyl-1,3,2-dioxaborolan-2-yl)pyridin-2-yl)carbamoyl)cyclohexyl)carbamate (300 mg, 0.67 mmol; prepared according to Example 16), 3-iodo-5,5-dimethyl-4,5,6,7-tetrahydropyrazolo[1,5-a]pyridine (242 mg, 0.88 mmol), and potassium phosphate, tribasic (429 mg, 2.02 mmol), in 1,4-dioxane (10 mL) and water (1 mL). The resulting mixture was stirred at 90° C. for 18 h. The crude reaction was cooled and purified by ion exchange chromatography using an SCX column. The desired product was eluted from the column using 1 M NH₃ in MeOH, and product-containing fractions were concentrated under reduced pressure to afford crude product as a brown oil. The crude product was purified by flash silica chromatography, elution gradient 0 to 100% EtOAc in heptane. Pure fractions were concentrated under reduced pressure to afford tert-butyl ((1R,3S)-3-((4-(5,5-dimethyl-4,5,6,7-tetrahydropyrazolo[1,5-a]pyridin-3-yl)pyridin-2-yl)carbamoyl)cyclohexyl)carbamate (170 mg, 54%) as a solid. ¹H NMR (400 MHz, DMSO-d₆, 30° C.) 1.03 (6H, s), 1.04-1.15 (1H, m), 1.21-1.41 (12H, m), 1.72-1.81 (3H, m), 1.83-1.92 (3H, m), 2.53-2.62 (1H, m), 2.65-2.69 (2H, m), 4.16 (2H, t), 6.76 (1H, br d), 7.76 (1H, d), 8.19 (1H, d), 8.29 (1H, d), 10.43 (1H, s). Broad (1H) multiplet underneath base of HOD peak at 3.3 ppm. m/z: ES+ [M+H]+ 468.

Preparation of (1S,3R)-3-amino-N-(4-(5,5-dimethyl-4,5,6,7-tetrahydropyrazolo[1,5-a]pyridin-3-yl)pyridin-2-yl)cyclohexanecarboxamide

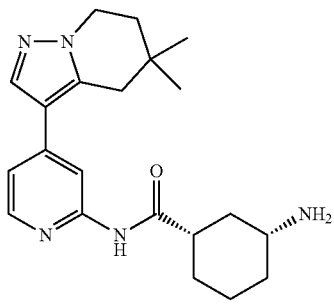 [SMILES: CC1(C)CCn2ncc(-c3ccnc(NC(=O)[C@H]4CCC[C@@H](N)C4)c3)c2C1]

Trifluoroacetic acid (1 mL) was added to tert-butyl ((1R,3S)-3-((4-(5,5-dimethyl-4,5,6,7-tetrahydropyrazolo[1,5-a]pyridin-3-yl)pyridin-2-yl)carbamoyl)cyclohexyl)carbamate (170 mg, 0.36 mmol) in DCM (10 mL). The resulting mixture was stirred at r.t. for 6 h. The reaction was then concentrated under reduced pressure, and the resulting residue was subjected to ion exchange chromatography using an SCX column. The desired product was eluted from the column using 2 M NH₃ in MeOH. Product fractions were concentrated under reduced pressure, and the resulting residue was purified by flash silica chromatography, eluting with 7% (1% ammonia in methanol) in DCM to afford (1S,3R)-3-amino-N-(4-(5,5-dimethyl-4,5,6,7-tetrahydropyrazolo[1,5-a]pyridin-3-yl)pyridin-2-yl)cyclohexanecarboxamide (70 mg, 52%) as a solid. m/z: ES+ [M+H]+ 368.

Example 45: (S)—N-((1R,3S)-3-((5-chloro-4-(5,5-dimethyl-5,6-dihydro-4H-pyrrolo[1,2-b]pyrazol-3-yl)pyridin-2-yl)carbamoyl)cyclohexyl)tetrahydrofuran-2-carboxamide

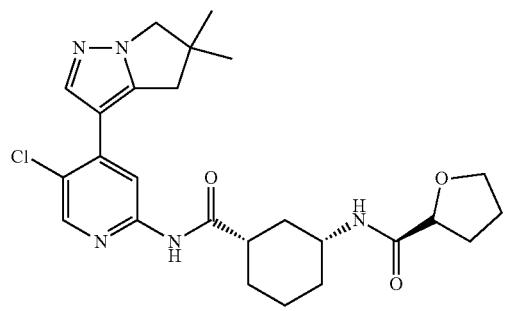

HATU (118 mg, 0.31 mmol) was added to a solution of (S)-tetrahydrofuran-2-carboxylic acid (0.03 mL, 0.31 mmol), (1S,3R)-3-amino-N-(5-chloro-4-(5,5-dimethyl-5,6-dihydro-4H-pyrrolo[1,2-b]pyrazol-3-yl)pyridin-2-yl)cyclohexanecarboxamide (100 mg, 0.26 mmol; prepared according to Example 14) and triethylamine (0.11 mL, 0.77 mmol) in DMA (2 mL). The reaction mixture was stirred at r.t. for 16 h and then quenched with water (20 mL). The mixture was extracted with DCM (50 mL), and the organic layer was washed with brine (50 mL). The organic layer was dried over MgSO₄, filtered, and concentrated under reduced pressure. The resulting residue was purified by preparative HPLC (Waters)(Bridge Prep C18 OBD column, 5µ silica, 30 mm diameter, 100 mm length) using decreasingly polar mixtures of water (containing 1% NH₃) and MeCN as eluents. Fractions containing the desired compound were concentrated under pressure to afford (S)—N-((1R,3S)-3-((5-chloro-4-(5,5-dimethyl-5,6-dihydro-4H-pyrrolo[1,2-b]pyrazol-3-yl)pyridin-2-yl)carbamoyl)cyclohexyl)tetrahydrofuran-2-carboxamide (59 mg, 47%) as a white solid. ¹H NMR (500 MHz, DMSO-d₆, 30° C.) 1.19-1.36 (9H, s), 1.49 (1H, q), 1.70 (1H, d), 1.74-1.89 (6H, m), 2.02-2.16 (1H, m), 2.58-2.68 (1H, m), 2.90 (2H, s), 3.63 (1H, dd), 3.75 (1H, q), 3.89 (1H, q), 3.95 (2H, s), 4.17 (1H, dd), 7.60 (1H, d), 8.00 (1H, s), 8.26 (1H, s), 8.31-8.38 (1H, m), 10.55 (1H, s). m/z: ES+ [M+H]+ 486.

Example 46: (R)—N-((1R,3S)-3-((5-chloro-4-(5,5-dimethyl-5,6-dihydro-4H-pyrrolo[1,2-b]pyrazol-3-yl)pyridin-2-yl)carbamoyl)cyclohexyl)tetrahydrofuran-2-carboxamide

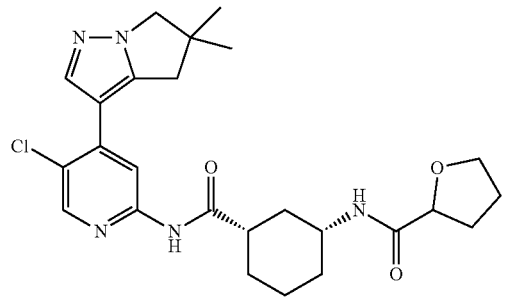 [SMILES: CC1(C)Cc2c(-c3cc(NC(=O)[C@H]4CCC[C@@H](NC(=O)C5CCCO5)C4)ncc3Cl)cnn2C1]

HATU (118 mg, 0.31 mmol) was added to a solution of (R)-tetrahydrofuran-2-carboxylic acid (0.03 mL, 0.31 mmol), (1S,3R)-3-amino-N-(5-chloro-4-(5,5-dimethyl-5,6-dihydro-4H-pyrrolo[1,2-b]pyrazol-3-yl)pyridin-2-yl)cyclohexanecarboxamide (100 mg, 0.26 mmol; prepared according to Example 14) and triethylamine (0.11 mL, 0.77 mmol) in DMA (2 mL). The reaction mixture was stirred at r.t. for 16 h and then quenched with water (20 mL). The mixture was extracted with DCM (50 mL), and the organic layer was washed with saturated aqueous sodium chloride (50 mL), dried over MgSO$_4$, filtered, and concentrated under reduced pressure. The resulting residue was purified by preparative HPLC (Waters)(Bridge Prep C18 OBD column, 5μ silica, 30 mm diameter, 100 mm length) using decreasingly polar mixtures of water (containing 1% NH$_3$) and MeCN as eluents. Fractions containing the desired compound were evaporated to dryness to afford (R)—N-((1R,3S)-3-((5-chloro-4-(5,5-dimethyl-5,6-dihydro-4H-pyrrolo[1,2-b]pyrazol-3-yl)pyridin-2-yl)carbamoyl)cyclohexyl)tetrahydrofuran-2-carboxamide (61 mg, 49%) as a white solid. $^1$H NMR (500 MHz, DMSO-d$_6$, 30° C.) 1.20-1.37 (9H, s), 1.49 (1H, q), 1.70 (1H, d), 1.75-1.9 (6H, m), 2.04-2.16 (1H, m), 2.58-2.68 (1H, m), 2.90 (2H, s), 3.58-3.67 (1H, m), 3.75 (1H, q), 3.89 (1H, q), 3.95 (2H, s), 4.17 (1H, dd), 7.60 (1H, d), 8.00 (1H, s), 8.26 (1H, s), 8.35 (1H, s), 10.55 (1H, s). m/z: ES+ [M+H]+ 486.

Example 47: (1S,3R)-3-acetamido-N-(4-(5,5-dimethyl-5,6-dihydro-4H-pyrrolo[1,2-b]pyrazol-3-yl)-5-methylpyridin-2-yl)cyclohexanecarboxamide

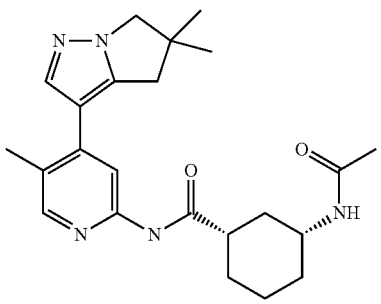 [SMILES: CC(=O)N[C@@H]1CCC[C@H](C(=O)Nc2cc(-c3cnn4c3CC(C)(C)C4)c(C)cn2)C1]

5,5-Dimethyl-3-(4,4,5,5-tetramethyl-1,3,2-dioxaborolan-2-yl)-5,6-dihydro-4H-pyrrolo[1,2-b]pyrazole (94 mg, 0.26 mmol; prepared according to Example 23) was added to a solution of (1S,3R)-3-acetamido-N-(4-iodo-5-methylpyridin-2-yl)cyclohexanecarboxamide (100 mg, 0.25 mmol) in 1,4-dioxane (2.1 mL) and water (0.4 mL) to give a colorless solution. The solution was purged with nitrogen for 10 min, and then cesium carbonate (244 mg, 0.75 mmol) and 2nd Generation XPhos Precatalyst (19.6 mg, 0.02 mmol) were added. The reaction was heated at 85° C. for 7 hr and then cooled to r.t. The reaction was diluted with EtAOc (50 mL) and then washed with water and saturated aqueous sodium chloride. The organic layer was concentrated under reduced pressure, and the resulting residue was adsorbed onto silica gel and purified by flash silica chromatography, eluting with 0 to 10% MeOH in DCM, to afford (1S,3R)-3-acetamido-N-(4-(5,5-dimethyl-5,6-dihydro-4H-pyrrolo[1,2-b]pyrazol-3-yl)-5-methylpyridin-2-yl)cyclohexanecarboxamide (37 mg, 36%) as a white solid. $^1$H NMR (300 MHz, DMSO-d$_6$, 27° C.) 1.00-1.16 (1H, m), 1.27 (9H, s), 1.78 (6H, s), 1.85-1.96 (1H, m), 2.33 (3H, s), 2.55-2.65 (1H, m), 2.86 (2H, s), 3.88-3.97 (2H, m), 7.75 (1H, d), 7.82 (1H, s), 7.98 (1H, s), 8.13 (1H, s), 10.45 (1H, br s). m/z: ES+ [M+H]+ 410.

Optical Rotation:
Concentration: 0.1 g/dL
Lamp: Sodium
Wavelength: 589 nm
Temperature: 25° C.
Path length: 10 cm
Cell volume: 1 mL
Solvent: DMSO
[α]=+39.7

Procedures used to prepare the starting material (1S,3R)-3-acetamido-N-(4-iodo-5-methylpyridin-2-yl)cyclohexanecarboxamide are described below:

Preparation of 4-iodo-5-methylpyridin-2-amine

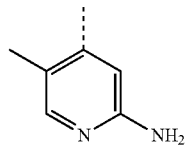

A white suspension of 2-fluoro-4-iodo-5-methylpyridine (3.00 g, 12.7 mmol) and concentrated aqueous ammonium hydroxide (3.5 mL, 90 mmol) in DMSO (17 mL) was subjected to microwave conditions (140° C., 4 h) and then cooled. The reaction was diluted with EtOAc and water, and the layers were separated. The aqueous layer was extracted with EtOAc (3×50 mL), and the combined organic layers were concentrated under reduced pressure. The resulting residue was adsorbed onto silica gel and purified by flash silica chromatography, elution gradient 0 to 10% MeOH in DCM, to afford 4-iodo-5-methylpyridin-2-amine (800 mg, 27%) as a white solid. $^1$H NMR (300 MHz, DMSO-d$_6$, 27° C.) 2.13 (s, 3H) 5.81 (s, 2H) 6.99 (s, 1H) 7.75 (s, 1H). m/z: ES+ [M+H]+ 235.

Preparation of Tert-butyl ((1R,3S)-3-((4-iodo-5-methylpyridin-2-yl)carbamoyl)cyclohexyl)carbamate

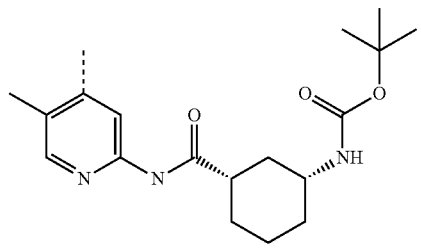

1-Chloro-N,N,2-trimethylprop-1-en-1-amine (0.24 mL, 1.8 mmol) was added to a solution of (1S,3R)-3-((tert-butoxycarbonyl)amino)cyclohexanecarboxylic acid (321 mg, 1.32 mmol; prepared according to Example 2) in DCM (2.8 mL) to give a colorless solution. The solution was stirred at r.t. for 2 h and then added a solution of 4-iodo-5-methylpyridin-2-amine (281 mg, 1.2 mmol) and pyridine (0.24 mL, 3.0 mmol) in DCM (2.8 mL) at 0° C. The reaction was allowed to warm to r.t. and stirred under these conditions 3 h before being diluted with DCM and washed with saturated aqueous NaHCO₃, water, and saturated aqueous sodium chloride. The organic layer was dried over sodium sulfate, filtered, and concentrated under reduced pressure. The resulting residue was adsorbed onto silica gel and purified by flash silica chromatography, elution gradient 0 to 10% MeOH in DCM, to afford tert-butyl ((1R,3S)-3-((4-iodo-5-methylpyridin-2-yl)carbamoyl)cyclohexyl)carbamate (530 mg, 96%) as a white solid. ¹H NMR (300 MHz, DMSO-d₆, 27° C.) 1.02-1.13 (1H, m), 1.44-1.53 (3H, m), 1.38 (9H, s), 1.65-1.80 (3H, m), 1.87 (1H, br d), 2.29 (3H, s), 2.52-2.61 (1H, m), 3.19-3.34 (1H, m), 6.78 (1H, br d), 8.16 (1H, s), 8.61 (1H, s), 10.43 (1H, s). m/z: ES+ [M+H]+ 460.

Preparation of (1S,3R)-3-acetamido-N-(4-iodo-5-methylpyridin-2-yl)cyclohexanecarboxamide

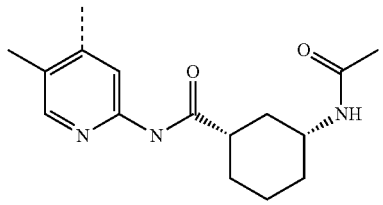

Hydrochloric acid dioxane (4 M; 2.1 mL, 8.6 mmol) was added to tert-butyl ((1R,3S)-3-((4-iodo-5-methylpyridin-2-yl)carbamoyl)cyclohexyl)carbamate (393 mg, 0.86 mmol) in MeOH (4.3 mL) to give a colorless solution. The reaction was stirred at r.t. for 4 h, resulting in a white mixture. The reaction was concentrated under reduced pressure to afford a white solid. TEA (0.60 mL, 4.3 mmol) and acetic anhydride (0.16 mL, 1.7 mmol) were added, and the reaction was stirred at r.t. for 1 hour. The mixture was then diluted with DCM, and washed with water and saturated aqueous sodium chloride. The organic layer was concentrated under reduced pressure, and the resulting residue was adsorbed onto silica gel and purified by flash silica chromatography, elution gradient 0 to 10% MeOH in DCM to afford (1S,3R)-3-acetamido-N-(4-iodo-5-methylpyridin-2-yl)cyclohexanecarboxamide (100 mg, 29%) as a clear oil. ¹H NMR (300 MHz, DMSO-d₆, 27° C.) 1.04-1.13 (1H, m), 1.19-1.39 (3H, m), 1.69-1.81 (6H, m), 1.86 (1H, br d), 2.29 (3H, s), 2.55-2.61 (1H, m), 3.41-3.62 (1H, m), 7.75 (1H, br d), 8.16 (1H, s), 8.61 (1H, s), 10.45 (1H, s). m/z: ES+ [M+H]+ 402.

Example 48: (1S,3R)-3-acetamido-N-(5-chloro-4-(5,5-dimethyl-5,6-dihydro-4H-pyrrolo[1,2-b]pyrazol-3-yl)pyridin-2-yl)cyclopentanecarboxamide

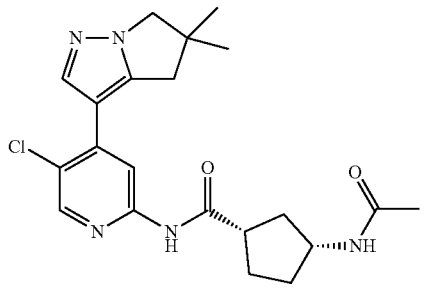 [SMILES: CC(=O)N[C@@H]1CC[C@H](C(=O)Nc2cc(-c3cnn4c3CC(C)(C)C4)c(Cl)cn2)C1]

Acetic anhydride (0.25 mL, 2.67 mmol) was added to (1S,3R)-3-amino-N-(5-chloro-4-(5,5-dimethyl-5,6-dihydro-4H-pyrrolo[1,2-b]pyrazol-3-yl)pyridin-2-yl)cyclopentanecarboxamide (500 mg, 1.34 mmol) and TEA (0.64 mL, 4.6 mmol) in DCM (10 mL) and MeOH (2 mL) under nitrogen. The resulting suspension was stirred at r.t. for 6 h. The reaction mixture was then diluted with DCM and washed sequentially with saturated aqueous ammonium chloride and water before being dried over magnesium sulfate, filtered, and concentrated under reduced pressure. The resulting residue was purified by preparative HPLC (Waters SunFire column, 5µ silica, 30 mm diameter, 100 mm length), using decreasingly polar mixtures of water (containing 0.1% formic acid) and MeCN as eluents. Fractions containing the desired compound were concentrated under reduced pressure to afford (1S,3R)-3-acetamido-N-(5-chloro-4-(5,5-dimethyl-5,6-dihydro-4H-pyrrolo[1,2-b]pyrazol-3-yl)pyridin-2-yl)cyclopentanecarboxamide (340 mg, 61%) as a solid. ¹H NMR (500 MHz, DMSO, 30° C.) 1.28 (6H, s), 1.45-1.51 (1H, m), 1.62 (1H, dt), 1.79 (3H, s), 1.81-1.89 (3H, m), 2.15 (1H, dt), 2.90 (2H, s), 3.00 (1H, dq), 3.95 (2H, s), 4.04 (1H, dq), 7.90 (1H, d), 8.00 (1H, s), 8.28 (1H, s), 8.35 (1H, s), 10.58 (1H, s). m/z: ES+ [M+H]+ 416.

Procedures used to prepare the starting material (1S,3R)-3-amino-N-(5-chloro-4-(5,5-dimethyl-5,6-dihydro-4H-pyrrolo[1,2-b]pyrazol-3-yl)pyridin-2-yl)cyclopentanecarboxamide are described below:

Preparation of Tert-butyl ((1R,3S)-3-((5-chloro-4-iodopyridin-2-yl)carbamoyl)cyclopentyl)carbamate

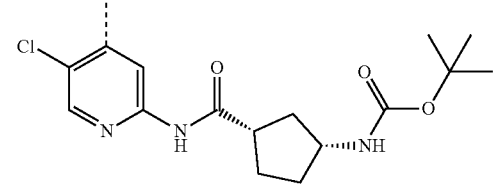

T₃P (≥50 wt % in ethyl acetate; 2.60 mL, 4.36 mmol) was added to a solution of 5-chloro-4-iodopyridin-2-amine (694 mg, 2.18 mmol; prepared according to Example 2), (1S,3R)-3-((tert-butoxycarbonyl)amino)cyclopentanecarboxylic acid (500 mg, 2.18 mmol) and pyridine (0.71 mL, 8.7 mmol) in EtOAc (10 mL). The resulting solution was stirred at r.t. for 24 h. The reaction mixture was diluted with saturated aqueous ammonium chloride (25 mL) and extracted with EtOAc (50 mL). The organic layer was dried over MgSO₄, filtered, and concentrated under reduced pressure to afford tert-butyl ((1R,3S)-3-((5-chloro-4-iodopyridin-2-yl)carbamoyl)cyclopentyl)carbamate (650 mg, 64%). ¹H NMR (400 MHz, DMSO-d₆, 30° C.) 1.39 (9H, s), 1.46-1.63 (2H, m), 1.74-183 (3H, m), 2.04-2.17 (1H, m), 2.90-3.00 (1H, m), 3.70-3.84 (1H, m), 6.73-6.82 (1H, m), 8.39 (1H, s), 8.73 (1H, s), 10.68 (1H, s). m/z: ES+ [M+H]+ 466.

Preparation of Tert-butyl ((1R,3S)-3-((5-chloro-4-(5,5-dimethyl-5,6-dihydro-4H-pyrrolo[1,2-b]pyrazol-3-yl)pyridin-2-yl)carbamoyl)cyclopentyl)carbamate

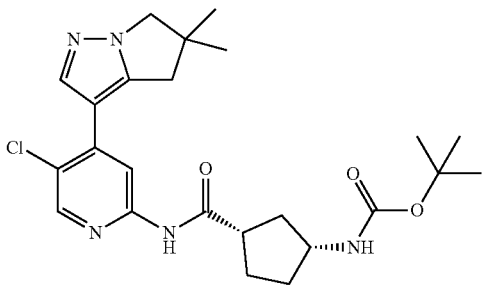 [SMILES: CC1(C)Cc2c(-c3cc(NC(=O)[C@H]4CC[C@@H](NC(=O)OC(C)(C)C)C4)ncc3Cl)cnn2C1]

5,5-Dimethyl-3-(4,4,5,5-tetramethyl-1,3,2-dioxaborolan-2-yl)-5,6-dihydro-4H-pyrrolo[1,2-b]pyrazole (665 mg, 1.95 mmol; prepared according to Example 23) was added to tert-butyl ((1R,3S)-3-((5-chloro-4-iodopyridin-2-yl)carbamoyl)cyclopentyl)carbamate (650 mg, 1.40 mmol), 2nd Generation XPhos Precatalyst (110 mg, 0.14 mmol) and potassium phosphate, dibasic (729 mg, 4.19 mmol) in 1,4-dioxane (20 mL) and water (4 mL) under nitrogen. The resulting suspension was stirred at 85° C. for 20 h. The reaction mixture was diluted with EtOAc (50 mL), and washed sequentially with water (2×25 mL) and saturated aqueous sodium chloride (25 mL). The organic layer was dried over MgSO$_4$, filtered, and concentrated under reduced pressure. The resulting residue was purified by flash silica chromatography, eluting with 25 to 70% EtOAc in heptane. Pure fractions were evaporated to dryness to afford tert-butyl ((1R,3S)-3-((5-chloro-4-(5,5-dimethyl-5,6-dihydro-4H-pyrrolo[1,2-b]pyrazol-3-yl)pyridin-2-yl)carbamoyl)cyclopentyl)carbamate (600 mg, 91%) as a white solid. m/z: ES+ [M+H]+ 474.

Preparation of (1S,3R)-3-amino-N-(5-chloro-4-(5,5-dimethyl-5,6-dihydro-4H-pyrrolo[1,2-b]pyrazol-3-yl)pyridin-2-yl)cyclopentanecarboxamide

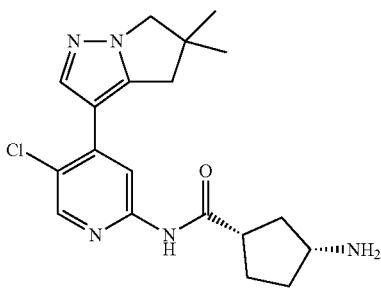 [SMILES: CC1(C)Cc2c(-c3cc(NC(=O)[C@H]4CC[C@@H](N)C4)ncc3Cl)cnn2C1]

Hydrochloric acid in dioxane (4 M; 1.6 mL, 6.3 mmol) was added slowly to tert-butyl ((1R,3S)-3-((5-chloro-4-(5,5-dimethyl-5,6-dihydro-4H-pyrrolo[1,2-b]pyrazol-3-yl)pyridin-2-yl)carbamoyl)cyclopentyl)carbamate (600 mg, 1.27 mmol) in DCM (10 mL) under nitrogen. The resulting suspension was stirred at r.t. for 4 h and then stored in the fridge for a 72 hour period. The reaction mixture was then diluted with DCM (10 mL) and MeOH (2 mL), and hydrochloric acid in dioxane (4 M; 1.6 mL, 6.3 mmol) was added under nitrogen. The resulting suspension was stirred at r.t. for an additional 18 h and then concentrated under reduced pressure. The resulting residue was purified by ion exchange chromatography using an SCX column. The desired product was eluted from the column using 1 M NH$_3$ in MeOH, and product fractions were concentrated under reduced pressure to afford (1S,3R)-3-amino-N-(5-chloro-4-(5,5-dimethyl-5,6-dihydro-4H-pyrrolo[1,2-b]pyrazol-3-yl)pyridin-2-yl)cyclopentanecarboxamide (473 mg, 99%) as a yellow oil. $^1$H NMR (500 MHz, DMSO-d$_6$, 27° C.) 1.28 (6H, s), 1.49 (1H, dd), 1.59 (1H, dd), 1.73 (1H, dd), 1.91 (2H, q), 2.04 (1H, td), 2.89-2.93 (3H, m), 3.78-3.83 (1H, m), 3.95 (2H, s), 8.00 (1H, s), 8.27 (1H, s), 8.34 (1H, s). Amide NH not observed; NH$_2$ signal assumed to be under broad water peak. m/z: ES+ [M+H]+ 374.

Example 49: (1S,3R)-3-acetamido-N-(5-chloro-4-(4,5,6,7-tetrahydro-[1,2,3]triazolo[1,5-a]pyridin-3-yl)pyridin-2-yl)cyclohexanecarboxamide

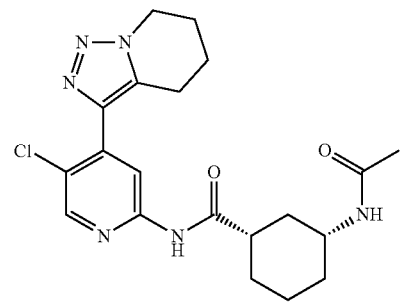 [SMILES: CC(=O)N[C@@H]1CCC[C@H](C(=O)Nc2cc(-c3nnn4c3CCCC4)c(Cl)cn2)C1]

Methoxy(cyclooctadiene)iridium(I) dimer (54 mg, 0.08 mmol) was added to 4,5,6,7-tetrahydro-[1,2,3]triazolo[1,5-a]pyridine (100 mg, 0.81 mmol), 4,4,5,5-tetramethyl-1,3,2-dioxaborolane (312 mg, 2.44 mmol), and 4,4'-di-tert-butyl-2,2'-dipyridyl (44 mg, 0.16 mmol) in THF (2 mL) under nitrogen. The resulting mixture was stirred at 90° C. for 3 h. Upon cooling, approximately 2.3 mL of reaction mixture containing crude 3-(4,4,5,5-tetramethyl-1,3,2-dioxaborolan-2-yl)-4,5,6,7-tetrahydro-[1,2,3]triazolo[1,5-a]pyridine was obtained as a suspension. m/z: ES+ [M+3H−(C(CH$_3$)$_2$)$_2$]$^+$ 168.

Crude 3-(4,4,5,5-tetramethyl-1,3,2-dioxaborolan-2-yl)-4,5,6,7-tetrahydro-[1,2,3]triazolo[1,5-a]pyridine (approximately 0.3 mL of the reaction suspension above) was added to a mixture of (1S,3R)-3-acetamido-N-(5-chloro-4-iodopyridin-2-yl)cyclohexanecarboxamide (10 mg, 0.02 mmol; prepared according to Example 12), Cs$_2$CO$_3$ (15 mg, 0.05 mmol) and 2nd Generation XPhos Precatalyst (1.9 mg, 2.4 μmol) in 1,4-dioxane (2 mL) and water (0.5 mL) under nitrogen. The resulting mixture was warmed to 60° C. and maintained under these conditions for 45 minutes. This reaction was then allowed to cool to r.t.

In a separate flask the remaining suspension mixture containing crude 3-(4,4,5,5-tetramethyl-1,3,2-dioxaborolan-2-yl)-4,5,6,7-tetrahydro-[1,2,3]triazolo[1,5-a]pyridine (approximately 2.0 mL) was added to a mixture of (1S,3R)-3-acetamido-N-(5-chloro-4-iodopyridin-2-yl)cyclohexanecarboxamide (70 mg, 0.17 mmol; prepared according to Example 12), Cs$_2$CO$_3$ (325 mg, 1.00 mmol) and 2nd Generation XPhos Precatalyst (26 mg, 0.03 mmol) in 1,4-dioxane (16 mL) and water (4 mL) under nitrogen. The resulting mixture was stirred at 60° C. for 45 minutes. This reaction was then allowed to cool to r.t.

Both cooled reaction mixtures were combined and then diluted with saturated aqueous sodium chloride (100 mL). The resulting mixture was extracted with EtOAc (3×100 mL), and the combined organic layers were dried over Na₂SO₄, filtered, and concentrated under reduced pressure. The resulting residue was purified by flash silica chromatography, using an elution gradient of 0 to 100% EtOAc in petroleum ether followed by an elution gradient of 0 to 20% MeOH in EtOAc. Pure fractions were concentrated under reduced pressure. The resulting residue was further purified by preparative HPLC (XBridge Prep C18 OBD column, 5μ silica, 19 mm diameter, 150 mm length), using decreasingly polar mixtures of water (containing 0.8% NH₄HCO₃) and MeCN as eluents. Fractions containing the desired compound were concentrated under reduced pressure to afford (1S,3R)-3-acetamido-N-(5-chloro-4-(4,5,6,7-tetrahydro-[1,2,3]triazolo[1,5-a]pyridin-3-yl)pyridin-2-yl)cyclohexanecarboxamide (20 mg, 25%) as a white solid. ¹H NMR (DMSO-d₆, 400 MHz, 21° C.) 1.00-1.14 (1H, m), 1.19-1.37 (3H, m), 1.68-1.81 (6H, m), 1.81-1.92 (3H, m), 1.99-2.10 (2H, m), 2.56-2.70 (1H, m), 2.82 (2H, t), 3.51-3.63 (1H, m), 4.42 (2H, t), 7.80 (1H, d), 8.26 (1H, s), 8.48 (1H, s), 10.73 (1H, s). m/z: ES+ [M+H]+ 417.

Example 50: (1S,3R)-3-acetamido-N-(4-(6,6-dimethyl-6,7-dihydro-5H-pyrrolo[1,2-a]imidazol-3-yl)-5-fluoropyridin-2-yl)cyclohexanecarboxamide

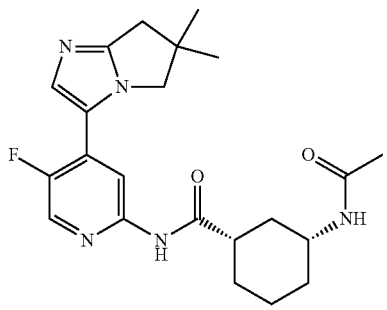 [SMILES: CC(=O)N[C@@H]1CCC[C@H](C(=O)Nc2cc(-c3cnc4n3CC(C)(C)C4)c(F)cn2)C1]

Acetic anhydride (0.024 mL, 0.26 mmol) was added dropwise to (1S,3R)-3-amino-N-(4-(6,6-dimethyl-6,7-dihydro-5H-pyrrolo[1,2-a]imidazol-3-yl)-5-fluoropyridin-2-yl)cyclohexanecarboxamide (0.080 g, 0.22 mmol), 4-dimethylaminopyridine (1 mg, 11 μmol) and triethylamine (0.093 mL, 0.67 mmol) in DCM (2 mL) at r.t. under nitrogen. The resulting solution was stirred at r.t. for 4 h. The reaction mixture was quenched with saturated aqueous ammonium chloride (10 mL), extracted with DCM (2×10 mL), and the combined organic layers were dried over MgSO₄, filtered, and concentrated under reduced pressure. The resulting residue was purified by preparative HPLC (Waters)(Bridge Prep C18 OBD column, 5μ silica, 30 mm diameter, 100 mm length), using decreasingly polar mixtures of water (containing 1% NH₃) and MeCN as eluents. Fractions containing the desired compound were concentrated under reduced pressure to afford (1S,3R)-3-acetamido-N-(4-(6,6-dimethyl-6,7-dihydro-5H-pyrrolo[1,2-a]imidazol-3-yl)-5-fluoropyridin-2-yl)cyclohexanecarboxamide (0.070 g, 79%). ¹H NMR (500 MHz, DMSO-d₆, 30° C.) 1.02-1.21 (1H, m), 1.22-1.38 (9H, m), 1.70-1.82 (6H, m), 1.91 (1H, br d), 2.54-2.65 (1H, m), 2.71 (2H, s), 3.58 (1H, dt), 4.00 (2H, s), 7.44 (1H, d), 7.76 (1H, d), 8.34 (1H, d), 8.38 (1H, d), 10.56 (1H, s). m/z: ES+ [M+H]+ 414.

Procedures used to prepare the starting material to (1S,3R)-3-amino-N-(4-(6,6-dimethyl-6,7-dihydro-5H-pyrrolo[1,2-a]imidazol-3-yl)-5-fluoropyridin-2-yl)cyclohexanecarboxamide are described below:

Preparation of 3-(2-chloro-5-fluoropyridin-4-yl)-6,6-dimethyl-6,7-dihydro-5H-pyrrolo[1,2-a]imidazole

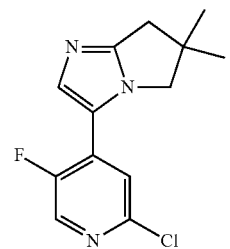 [SMILES: CC1(C)Cc2ncc(-c3cc(Cl)ncc3F)n2C1]

6,6-Dimethyl-6,7-dihydro-5H-pyrrolo[1,2-a]imidazole (0.180 g, 1.32 mmol; prepared according to Example 22), 2-chloro-5-fluoro-4-iodopyridine (0.476 g, 1.85 mmol), cesium carbonate (0.474 g, 1.45 mmol), triethylamine (0.368 mL, 2.64 mmol), triphenylphosphine (0.055 g, 0.21 mmol) and diacetoxypalladium (0.024 g, 0.11 mmol) were suspended in 1,4-dioxane (5 mL) and sealed into a microwave tube. The reaction was subjected to microwave conditions (100° C., 16 h) and cooled to r.t. The reaction mixture was diluted with DCM (20 mL) and washed with water (3×25 mL). The organic layer was then dried over MgSO₄, filtered, and concentrated under reduced pressure. The resulting residue was purified by flash silica chromatography, elution gradient 0 to 50% EtOAc in heptane. Pure fractions were concentrated under reduced pressure to afford 3-(2-chloro-5-fluoropyridin-4-yl)-6,6-dimethyl-6,7-dihydro-5H-pyrrolo[1,2-a]imidazole (0.185 g, 53%) as an orange solid. ¹H NMR (500 MHz, CDCl₃, 27° C.) 1.34 (6H, s), 2.80 (2H, s), 3.93 (2H, s), 7.32 (1H, d), 7.59 (1H, d), 8.26 (1H, d). m/z: ES+ [M+H]+ 266.

Preparation of Tert-butyl ((1R,3S)-3-((4-(6,6-dimethyl-6,7-dihydro-5H-pyrrolo[1,2-a]imidazol-3-yl)-5-fluoropyridin-2-yl)carbamoyl)cyclohexyl)carbamate

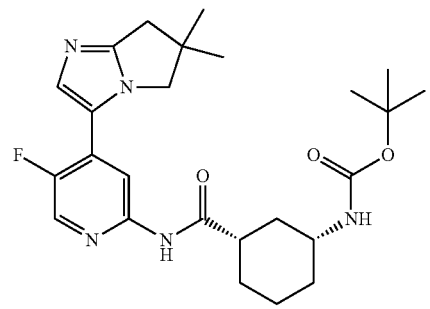 [SMILES: CC1(C)Cc2ncc(-c3cc(NC(=O)[C@H]4CCC[C@@H](NC(=O)OC(C)(C)C)C4)ncc3F)n2C1]

Tetrakis(triphenylphosphine)palladium(0) (43 mg, 0.04 mmol) was added to 3-(2-chloro-5-fluoropyridin-4-yl)-6,6-dimethyl-6,7-dihydro-5H-pyrrolo[1,2-a]imidazole (100 mg, 0.38 mmol), tert-butyl ((1R,3S)-3-carbamoylcyclohexyl)carbamate (109 mg, 0.45 mmol; prepared according to Example 25), 9,9-dimethyl-4,5-bis(diphenylphosphino)xanthene (44 mg, 0.08 mmol) and cesium carbonate (368 mg, 1.13 mmol) in 1,4-dioxane (6 mL). The mixture was degassed for 5 minutes under nitrogen, and the resulting suspension was subjected to microwave conditions (120° C., 3 h). The reaction mixture was partitioned between water (20 mL) and DCM (40 mL). The layers were separated using a phase separation cartridge, and the organic layer was adsorbed onto silica and purified by flash silica chromatography, elution gradient 0 to 60% EtOAc in heptane. Pure fractions were concentrated under reduced pressure to afford tert-butyl ((1R,3S)-3-((4-(6,6-dimethyl-6,7-dihydro-5H-pyrrolo[1,2-a]imidazol-3-yl)-5-fluoropyridin-2-yl)carbamoyl)cyclohexyl)carbamate (142 mg, 80%). m/z: ES+ [M+H]+ 472.

Preparation of (1S,3R)-3-amino-N-(4-(6,6-dimethyl-6,7-dihydro-5H-pyrrolo[1,2-a]imidazol-3-yl)-5-fluoropyridin-2-yl)cyclohexanecarboxamide

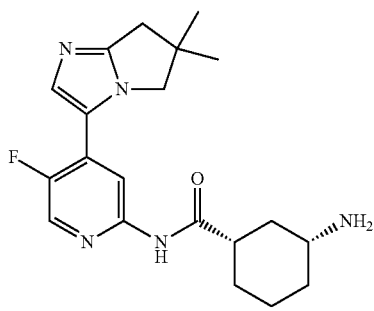 [SMILES: CC1(C)Cc2ncc(-c3cc(NC(=O)[C@H]4CCC[C@@H](N)C4)ncc3F)n2C1]

Tert-butyl ((1R,3S)-3-((4-(6,6-dimethyl-6,7-dihydro-5H-pyrrolo[1,2-a]imidazol-3-yl)-5-fluoropyridin-2-yl)carbamoyl)cyclohexyl)carbamate (0.100 g, 0.21 mmol) was dissolved in DCM (5 mL) and trifluoroacetic acid (0.16 mL, 2.1 mmol) was added. The reaction mixture was stirred at r.t. for 30 min and then purified by ion exchange chromatography using an SCX column. The desired product was eluted from the column using 1 M NH₃ in MeOH, and pure fractions were concentrated under reduced pressure to afford semi-pure (1S,3R)-3-amino-N-(4-(6,6-dimethyl-6,7-dihydro-5H-pyrrolo[1,2-a]imidazol-3-yl)-5-fluoropyridin-2-yl)cyclohexanecarboxamide as a colourless gum (100 mg). This gum was used in next step without further purification. m/z: ES+ [M+H]+ 372.

Example 51: (1S,3R)-3-acetamido-N-(4-(5,5-dimethyl-4,5,6,7-tetrahydropyrazolo[1,5-a]pyridin-3-yl)-5-fluoropyridin-2-yl)cyclohexanecarboxamide

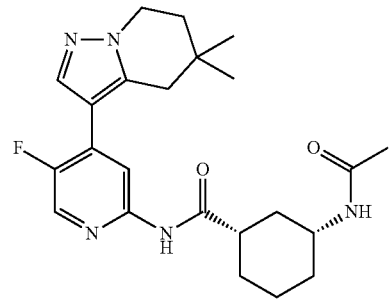 [SMILES: CC(=O)N[C@@H]1CCC[C@H](C(=O)Nc2cc(-c3cnn4c3CC(C)(C)CC4)c(F)cn2)C1]

Acetic anhydride (0.088 mL, 0.93 mmol) was added to a stirred solution of (1S,3R)-3-amino-N-(4-(5,5-dimethyl-4,5,6,7-tetrahydropyrazolo[1,5-a]pyridin-3-yl)-5-fluoropyridin-2-yl)cyclohexanecarboxamide (300 mg, 0.78 mmol; described in Example 51a), triethylamine (0.23 mL, 1.6 mmol) and DCM (10 mL). The reaction mixture was stirred at ambient temperature for 4 h. Silica was added, and the volatiles were removed by concentration under reduced pressure. The resulting residue purified by flash silica chromatography, eluting with 0.5% methanol in ethyl acetate, to afford (1S,3R)-3-acetamido-N-(4-(5,5-dimethyl-4,5,6,7-tetrahydropyrazolo[1,5-a]pyridin-3-yl)-5-fluoropyridin-2-yl)cyclohexanecarboxamide (300 mg, 90%) as a white solid. ¹H NMR (400 MHz, DMSO-d₆, 30° C.) 1.03 (6H, s), 1.02-1.14 (1H, m), 1.24-1.38 (3H, m), 1.72-1.81 (6H, m), 1.86-1.91 (3H, m), 2.55-2.64 (1H, m), 2.69 (2H, s), 3.52-3.64 (1H, m), 4.16 (2H, t), 7.64-7.81 (2H, m), 8.19 (1H, d), 8.29 (1H, d), 10.45 (1H, s). m/z: ES+ [M+H]+ 428.

Example 51a: (1S,3R)-3-amino-N-(4-(5,5-dimethyl-4,5,6,7-tetrahydropyrazolo[1,5-a]pyridin-3-yl)-5-fluoropyridin-2-yl)cyclohexanecarboxamide

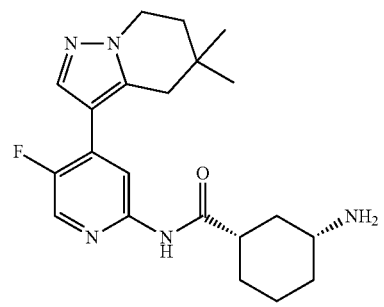 [SMILES: CC1(C)CCn2ncc(-c3cc(NC(=O)[C@H]4CCC[C@@H](N)C4)ncc3F)c2C1]

TFA (2 mL) was added to a solution of tert-butyl ((1R,3S)-3-((4-(5,5-dimethyl-4,5,6,7-tetrahydropyrazolo[1,5-a]pyridin-3-yl)-5-fluoropyridin-2-yl)carbamoyl)cyclohexyl)carbamate (1.1 g, 2.27 mmol) in DCM (20 mL). The resulting mixture was stirred at ambient temperature for 24 h, and then the reaction was concentrated under reduced pressure. The resulting residue was purified by ion exchange chromatography using an SCX column. The desired product was eluted from the column using 7N NH₃ in MeOH. Pure product fractions were concentrated under reduced pressure to afford (1S,3R)-3-amino-N-(4-(5,5-dimethyl-4,5,6,7-tetrahydropyrazolo[1,5-a]pyridin-3-yl)-5-fluoropyridin-2-yl)cyclohexanecarboxamide (0.87 g, 100%) as a solid. ¹H NMR (400 MHz, CDCl₃, 22° C.) 1.01-1.12 (7H, m), 1.31-1.49 (3H, m), 1.83-1.99 (5H, m), 2.14 (1H, d), 2.35 (1H, td), 2.66-2.85 (3H, m), 4.23 (2H, t), 7.85 (1H, d), 7.99-8.18 (2H, m), 8.29 (1H, d). NH₂ signal not observed and is assumed to be under broad water peak at 1.66 ppm. m/z: ES+ [M+H]+ 386.

Procedures for preparing the starting material of tert-butyl ((1R,3S)-3-((4-(5,5-dimethyl-4,5,6,7-tetrahydropyrazolo[1,5-a]pyridin-3-yl)-5-fluoropyridin-2-yl)carbamoyl)cyclohexyl)carbamate are described below:

Preparation of 5,5-dimethyl-3-(4,4,5,5-tetramethyl-1,3,2-dioxaborolan-2-yl)-4,5,6,7-tetrahydropyrazolo[1,5-a]pyridine

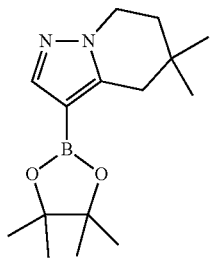

Isopropylmagnesium chloride lithium chloride complex in THF (1.3 M; 9.1 mL, 12 mmol) was added dropwise to 3-iodo-5,5-dimethyl-4,5,6,7-tetrahydropyrazolo[1,5-a]pyridine (2.5 g, 9.1 mmol; prepared according to Example 44) in THF (20 mL) under nitrogen at 0° C. The resulting mixture was stirred at 0° C. for 30 minutes. Then 2-isopropoxy-4,4,5,5-tetramethyl-1,3,2-dioxaborolane (2.8 mL, 14 mmol) was added dropwise, and the ice bath was removed. The reaction was maintained under these conditions for 18 h and then diluted with Et₂O (20 mL). This new mixture was washed sequentially with saturated aqueous ammonium chloride (20 mL), water (20 mL), and saturated aqueous sodium chloride (10 mL). The organic layer was dried over MgSO₄, filtered, and concentrated under reduced pressure to afford crude 5,5-dimethyl-3-(4,4,5,5-tetramethyl-1,3,2-dioxaborolan-2-yl)-4,5,6,7-tetrahydropyrazolo[1,5-a]pyridine (2.5 g, 100%) as an oil. ¹H NMR (400 MHz, CDCl₃, 30° C.) 1.06 (6H, s), 1.29 (12H, s), 1.79 (2H, t), 2.74 (2H, s), 4.16 (2H, t), 7.72 (1H, s).

Preparation of 3-(2-chloro-5-fluoropyridin-4-yl)-5,5-dimethyl-4,5,6,7-tetrahydropyrazolo[1,5-a]pyridine

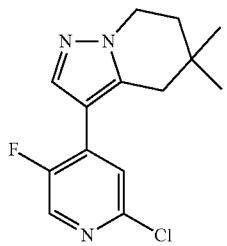 [SMILES: CC1(C)CCn2ncc(-c3cc(Cl)ncc3F)c2C1]

2-Chloro-5-fluoro-4-iodopyridine (1.55 g, 6.03 mmol), 5,5-dimethyl-3-(4,4,5,5-tetramethyl-1,3,2-dioxaborolan-2-yl)-4,5,6,7-tetrahydropyrazolo[1,5-a]pyridine (2.0 g, 7.2 mmol), 2nd Generation XPhos Precatalyst (0.48 g, 0.60 mmol) and potassium phosphate, dibasic (3.15 g, 18.1 mmol) were dissolved in degassed dioxane (20 mL) and water (1 mL) at 21° C. The mixture was stirred at 90° C. for 24 h and then allowed to cool to r.t. The mixture was diluted with EtOAc (30 mL), washed with water (10 mL), and the organic layer was concentrated under reduced pressure. The resulting residue was purified by flash silica chromatography, elution gradient 0 to 50% EtOAc in heptane. Pure fractions were concentrated under reduced pressure to afford 3-(2-chloro-5-fluoropyridin-4-yl)-5,5-dimethyl-4,5,6,7-tetrahydropyrazolo[1,5-a]pyridine (1.3 g, 77%) as a white solid. ¹H NMR (400 MHz, CDCl₃, 30° C.) 1.10 (6H, s), 1.89 (2H, m), 2.68 (2H, s), 4.26 (2H, t), 7.27 (1H, d), 7.80 (1H, d), 8.23 (1H, d). m/z: ES+ [M+H]+ 280.

Preparation of Tert-butyl ((1R,3S)-3-((4-(5,5-dimethyl-4,5,6,7-tetrahydropyrazolo[1,5-a]pyridin-3-yl)-5-fluoropyridin-2-yl)carbamoyl)cyclohexyl)carbamate

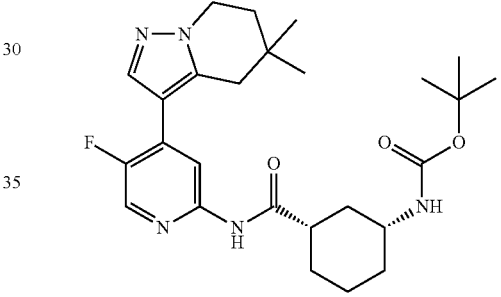

Tetrakis(triphenylphosphine)palladium(0) (0.496 g, 0.43 mmol) was added to 3-(2-chloro-5-fluoropyridin-4-yl)-5,5-dimethyl-4,5,6,7-tetrahydropyrazolo[1,5-a]pyridine (1.2 g, 4.29 mmol), tert-butyl ((1R,3S)-3-carbamoylcyclohexyl)carbamate (1.04 g, 4.29 mmol; prepared according to Example 25), 9,9-dimethyl-4,5-bis(diphenylphosphino)xanthene (0.496 g, 0.86 mmol) and cesium carbonate (4.19 g, 12.9 mmol) in 1,4-dioxane (10 mL). The resulting mixture was degassed for 5 mins under nitrogen and then subjected to microwave conditions (120° C.; 17 h). The reaction mixture was diluted with water (20 mL) and ethyl acetate (100 mL) before being filtered. The layers were separated, and the organic layer was adsorbed onto silica and purified by flash silica chromatography, eluting with isocratic 50% EtOAc in heptane. Pure fractions were concentrated under reduced pressure to afford tert-butyl ((1R,3S)-3-((4-(5,5-dimethyl-4,5,6,7-tetrahydropyrazolo[1,5-a]pyridin-3-yl)-5-fluoropyridin-2-yl)carbamoyl)cyclohexyl)carbamate (1.1 g, 53%) as a white solid. ¹H NMR (400 MHz, DMSO-d₆, 30° C.) 1.03 (6H, s), 1.02-1.14 (1H, m), 1.20-1.35 (3H, m), 1.39 (9H, s), 1.70-1.79 (3H, br m), 1.82-1.92 (3H, m), 2.54-2.63 (1H, m), 2.68 (2H, s), 4.16 (2H, t), 6.76 (1H, br d), 7.76 (1H, d), 8.19 (1H, d), 8.29 (1H, d), 10.43 (1H, s). 1H multiplet under water peak. m/z: ES+ [M+H]+ 486.

Example 52: (1S,3R)—N-(5-chloro-4-(5,5-dimethyl-5,6-dihydro-4H-pyrrolo[1,2-b]pyrazol-3-yl)pyridin-2-yl)-3-(3-hydroxypropanamido)cyclohexanecarboxamide

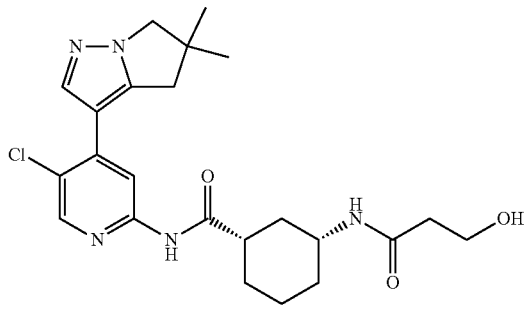 [SMILES: CC1(C)Cc2c(-c3cc(NC(=O)[C@H]4CCC[C@@H](NC(=O)CCO)C4)ncc3Cl)cnn2C1]

Trifluoroacetic acid (6.5 μL, 0.080 mmol) was added to (1S,3R)—N-(5-chloro-4-(5,5-dimethyl-5,6-dihydro-4H-pyrrolo[1,2-b]pyrazol-3-yl)pyridin-2-yl)-3-(3-((tetrahydro-2H-pyran-2-yl)oxy)propanamido)cyclohexanecarboxamide (0.046 g, 0.080 mmol) in DCM (2 mL) at r.t. The resulting solution was stirred at r.t. for 1 hour. The crude product was purified by ion exchange chromatography, using an SCX column. The desired product was eluted from the column using 1 M $NH_3$ in MeOH and pure fractions were concentrated under reduced pressure to afford (1S,3R)—N-(5-chloro-4-(5,5-dimethyl-5,6-dihydro-4H-pyrrolo[1,2-b]pyrazol-3-yl)pyridin-2-yl)-3-(3-hydroxypropanamido)cyclohexanecarboxamide (0.032 g, 82%) as a colourless solid. $^1$H NMR (400 MHz, $CDCl_3$, 30° C.) 1.08-1.21 (1H, m), 1.34 (6H, s), 1.35-1.49 (3H, m), 1.88-1.93 (3H, m), 2.10-2.37 (2H, m), 2.36-2.49 (2H, m), 2.48-2.57 (1H, m), 2.95 (2H, s), 3.79-3.92 (3H, m), 3.95 (2H, s), 6.56 (1H, br d), 8.09 (1H, s), 8.21 (1H, s), 8.26 (1H, s), 8.89 (1H, s).m/z: ES+ [M+H]+ 460.

Procedures for preparing the starting material (1S,3R)—N-(5-chloro-4-(5,5-dimethyl-5,6-dihydro-4H-pyrrolo[1,2-b]pyrazol-3-yl)pyridin-2-yl)-3-(3-((tetrahydro-2H-pyran-2-yl)oxy)propanamido)cyclohexanecarboxamide are described below:

Preparation of Methyl 3-hydroxypropanoate

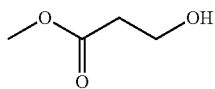

Oxetan-2-one (22 mL, 350 mmol) was added dropwise to a stirred solution of MeOH (300 mL) and sulfuric acid (5.6 mL, 104 mmol) at 0° C. After 18 h, the reaction was recooled to 10° C., and sodium bicarbonate (18.1 g, 215 mmol) was added portionwise (pH=7 after addition). The resulting suspension was left to stir at r.t. for 30 minutes. The mixture was then filtered, and the filtrate was concentrated under reduced pressure. The resulting residue was diluted with DCM and filtered a second time. The new filtrate was evaporated to dryness to afford methyl 3-hydroxypropanoate (35 g, 97%) as a colorless liquid. $^1$H NMR (500 MHz, $CDCl_3$, 24° C.) 2.41-2.45 (1H, m), 2.58 (2H, t), 3.72 (3H, s), 3.89 (2H, t).

Preparation of Methyl 3-(tetrahydro-2H-pyran-2-yloxy)propanoate

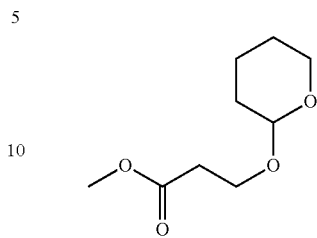

Pyridine 4-methylbenzenesulfonate (4.22 g, 16.8 mmol) was added to a solution of methyl 3-hydroxypropanoate (35 g, 336 mmol) and 3,4-dihydro-2H-pyran (43 mL, 470 mmol) in DCM (500 ml) under nitrogen. The solution was stirred at r.t. for 2.5 days. The mixture was then washed with a saturated aqueous sodium bicarbonate, and the organic layer was dried over magnesium sulfate and concentrated under reduced pressure. The resulting oil was purified by flash silica chromatography, eluting with isocratic 15% ethyl acetate in heptane, to afford methyl 3-(tetrahydro-2H-pyran-2-yloxy)propanoate (26 g, 41%) as a colorless oil. $^1$H NMR (500 MHz, DMSO-$d_6$, 24° C.) 1.37-1.46 (4H, m), 1.54-1.59 (2H, m), 2.56 (2H, t), 3.39-3.42 (1H, m), 3.53-3.63 (4H, m), 3.68-3.75 (1H, m), 3.81-3.87 (1H, m), 4.57 (1H, t).

Preparation of 3-(tetrahydro-2H-pyran-2-yloxy)propanoic Acid

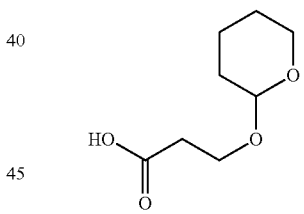

Aqueous sodium hydroxide (2N; 134 mL, 268 mmol) was added to a solution of methyl 3-(tetrahydro-2H-pyran-2-yloxy)propanoate (26 g, 138 mmol) in THF (300 mL). The mixture was stirred at r.t. for 5 h and then concentrated under reduced pressure. Ethyl acetate (100 mL) was added, and the layers were separated. The aqueous layer was cooled to 0° C., and aqueous HCl (1N) was cautiously added dropwise until a pH of 3.5 was achieved. The aqueous layer was then extracted with ethyl acetate (2×250 mL). The combined organic layers were dried over magnesium sulfate, filtered and concentrated under reduced pressure to afford 3-(tetrahydro-2H-pyran-2-yloxy)propanoic acid (24 g, 98%) as a colorless oil. $^1$H NMR (500 MHz, $CDCl_3$, 24° C.) 1.45-1.62 (4H, m), 1.63-1.85 (2H, m), 2.64-2.68 (2H, m), 3.52-3.56, (1H, m), 3.70-3.74, (1H, m), 3.85-3.89 (1H, m), 3.99-4.03 (1H, m), 4.62-4.66 (1H, m), 11.2 (1H, br s).

151

Preparation of (1S,3R)—N-(5-chloro-4-(5,5-dimethyl-5,6-dihydro-4H-pyrrolo[1,2-b]pyrazol-3-yl)pyridin-2-yl)-3-(3-((tetrahydro-2H-pyran-2-yl)oxy)propanamido)cyclohexanecarboxamide

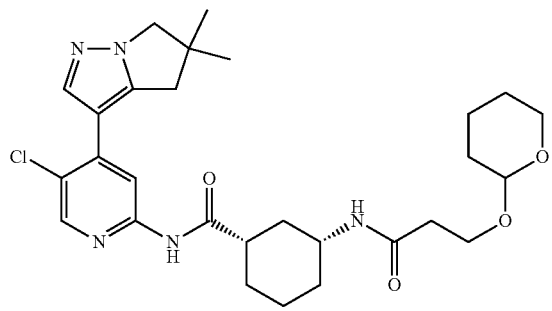 [SMILES: CC1(C)Cc2c(-c3cc(NC(=O)[C@H]4CCC[C@@H](NC(=O)CCOC5CCCCO5)C4)ncc3Cl)cnn2C1]

HATU (118 mg, 0.31 mmol) was added to a solution of 3-((tetrahydro-2H-pyran-2-yl)oxy)propanoic acid (54 mg, 0.31 mmol), (1S,3R)-3-amino-N-(5-chloro-4-(5,5-dimethyl-5,6-dihydro-4H-pyrrolo[1,2-b]pyrazol-3-yl)pyridin-2-yl)cyclohexanecarboxamide (100 mg, 0.26 mmol; prepared according to Example 14), and triethylamine (0.11 mL, 0.77 mmol) in DMA (2 mL). The resulting mixture was stirred at ambient temperature for 16 h before HCl in dioxane (4 M; 0.52 mL, 2.1 mmol) was added. This new mixture was stirred at r.t. for 2 h before being basified with saturated aqueous $Na_2CO_3$. The resulting mixture was diluted with water (20 mL) and extracted with DCM (50 mL). The organic layer was washed with saturated aqueous sodium chloride (50 mL) before being passed through a phase separation cartridge. The organic fractions were dried over $MgSO_4$ and concentrated under reduced pressure. The resulting residue was purified by preparative HPLC (Waters) (Bridge Prep C18 OBD column, 5μ silica, 30 mm diameter, 100 mm length), using decreasingly polar mixtures of water (containing 1% $NH_3$) and MeCN as eluents. Fractions containing the desired compound were concentrated under reduced pressure to afford (1S,3R)—N-(5-chloro-4-(5,5-dimethyl-5,6-dihydro-4H-pyrrolo[1,2-b]pyrazol-3-yl)pyridin-2-yl)-3-(3-((tetrahydro-2H-pyran-2-yl)oxy)propanamido)cyclohexanecarboxamide (46 mg, 33%) as a white solid. $^1$H NMR (500 MHz, DMSO-$d_6$, 30° C.) 1.05-1.2 (1H, m), 1.24-1.51 (13H, m), 1.52-1.63 (1H, m), 1.64-1.71 (1H, m), 1.72-1.83 (3H, m), 1.88-1.93 (1H, m), 2.25-2.35 (2H, m), 2.57-2.7 (1H, m), 2.90 (2H, s), 3.38-3.44 (1H, m), 3.48-3.58 (1H, m), 3.59-3.64 (1H, m), 3.74 (1H, ddd), 3.81 (1H, ddt), 3.95 (2H, s), 4.55 (1H, d), 7.78 (1H, d), 8.00 (1H, s), 8.25 (1H, s), 8.36 (1H, s), 10.56 (1H, s). m/z: ES+ [M+H]+ 544.

152

Example 53: (1S,3R)—N-(5-chloro-4-(5,5-dimethyl-5,6-dihydro-4H-pyrrolo[1,2-b]pyrazol-3-yl)pyridin-2-yl)-3-(cis-3-hydroxycyclobutanecarboxamido)cyclohexanecarboxamide

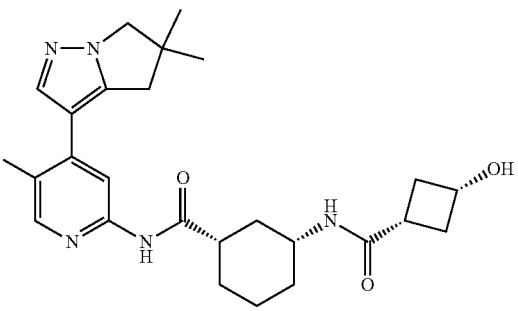

HATU (118 mg, 0.31 mmol) was added to a solution of cis-3-((tert-butyldimethylsilyl)oxy)cyclobutanecarboxylic acid (71 mg, 0.31 mmol; prepared according to Example 4), (1S,3R)-3-amino-N-(5-chloro-4-(5,5-dimethyl-5,6-dihydro-4H-pyrrolo[1,2-b]pyrazol-3-yl)pyridin-2-yl)cyclohexanecarboxamide (100 mg, 0.26 mmol; prepared according to Example 14), and triethylamine (0.11 mL, 0.77 mmol) in DMA (2 mL). The resulting mixture was stirred at r.t. for 16 h before a solution of tetrabutylammonium fluoride in THF (1 M; 1.0 mL, 1.0 mmol) was added. The mixture was stirred at r.t. for 2 h before being quenched with water (20 mL). The mixture was extracted with DCM (50 mL) and washed with saturated aqueous sodium chloride (50 mL) before being passed through a phase separation cartridge. The organic fractions were dried over $MgSO_4$ and concentrated under reduced pressure. The resulting residue was purified by preparative HPLC (Waters)(Bridge Prep C18 OBD column, 5μ silica, 30 mm diameter, 100 mm length), using decreasingly polar mixtures of water (containing 1% $NH_3$) and MeCN as eluents. Product fractions were concentrated under reduced pressure, and the resulting residue was further purified by flash silica chromatography, elution gradient 0 to 10% MeOH in EtOAc. Pure fractions were concentrated under reduced pressure to afford (1S,3R)—N-(5-chloro-4-(5,5-dimethyl-5,6-dihydro-4H-pyrrolo[1,2-b]pyrazol-3-yl)pyridin-2-yl)-3-((ci s)-3-hydroxycyclobutanecarboxamido)cyclohexanecarboxamide (0.037 g, 53%) as a white solid. $^1$H NMR (400 MHz, CDCl$_3$, 30° C.) 1.34 (6H, s), 1.47-1.49 (3H, m), 1.85-1.99 (5H, m), 2.10-2.30 (4H, m), 2.39-2.62 (4H, m), 2.96 (2H, s), 3.79-3.86 (1H, m), 3.95 (2H, s), 5.90 (1H, br d), 8.09 (1H, s), 8.22 (1H, s), 8.26 (1H, s), 8.69 (1H, s). m/z: ES+ [M+H]+ 486.

Example 54: (1S,3R)-3-amino-N-(4-(5,5-dimethyl-5,6-dihydro-4H-pyrrolo[1,2-b]pyrazol-3-yl)-5-fluoropyridin-2-yl)cyclohexane-1-carboxamide

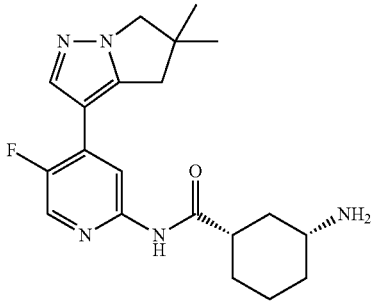 [SMILES: CC1(C)Cc2c(-c3cc(NC(=O)[C@H]4CCC[C@@H](N)C4)ncc3F)cnn2C1]

Hydrochloric acid in dioxane (4 M; 3.2 mL, 13 mmol) was added to a solution of tert-butyl ((1R,3S)-3-((4-(5,5-dimethyl-5,6-dihydro-4H-pyrrolo[1,2-b]pyrazol-3-yl)-5-fluoropyridin-2-yl)carbamoyl)cyclohexyl)carbamate (600 mg, 1.27 mmol) in DCM (9.5 mL) to give a yellow suspension. Methanol (~5 mL) was added, which afforded a clear yellow solution. The reaction was stirred for 18 h at r.t. and then concentrated under reduced pressure to afford (1S,3R)-3-amino-N-(4-(5,5-dimethyl-5,6-dihydro-4H-pyrrolo[1,2-b]pyrazol-3-yl)-5-fluoropyridin-2-yl)cyclohexane-1-carboxamide as a dihydrochloride salt (488 mg, 87%) and an off-white solid. $^1$H NMR (300 MHz, DMSO-$d_6$, 27° C.) 1.23-1.36 (9H, m), 1.50 (1H, q), 1.77-1.89 (2H, m), 1.89-2.01 (1H, m), 2.01-2.09 (1H, m), 2.56-2.68 (1H, m), 2.94 (2H, s), 2.97-3.09 (1H, m), 3.95 (2H, s), 7.85-7.93 (1H, m), 7.98-8.14 (3H, m), 8.26-8.32 (2H, m), 10.56 (1H, s). 1 HCl equivalent assumed to be incorporated into broad singlet at 5.4 ppm. m/z: ES+ [M+H]+ 372.

Procedures used to prepare the starting material tert-butyl ((1R,3S)-3-((4-(5,5-dimethyl-5,6-dihydro-4H-pyrrolo[1,2-b]pyrazol-3-yl)-5-fluoropyridin-2-yl)carbamoyl)cyclohexyl)carbamate are described below:

Preparation of 5-fluoro-4-iodopyridin-2-amine

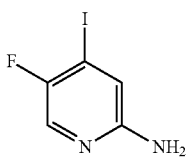

Concentrated aqueous ammonium hydroxide (26 wt %; 7.0 mL, 45 mmol) was added dropwise (slight exotherm) to a solution of 2,5-difluoro-4-iodopyridine (2.0 g, 8.30 mmol) in DMSO (2 mL) to give a white suspension. The suspension was heated in the microwave at 140° C. for 4 h. The reaction was partitioned between EtOAc and water, and the aqueous layer was extracted with EtOAc (3×50 mL). The combined organics were concentrated under reduced pressure, and the resulting residue was adsorbed onto silica gel before being purified by flash silica chromatography (0 to 10% methanol in DCM) to afford 5-fluoro-4-iodopyridin-2-amine (1.3 g, 66%) as a white solid. $^1$H NMR (300 MHz, DMSO-$d_6$, 27° C.) 5.96 (1H, br s) 5.96 (1H, s) 6.92 (1H, d) 7.77-7.84 (1H, m). m/z: ES+ [M+H]+ 239.

Tert-butyl ((1R,3S)-34(5-fluoro-4-iodopyridin-2-yl)carbamoyl)cyclohexyl)carbamate

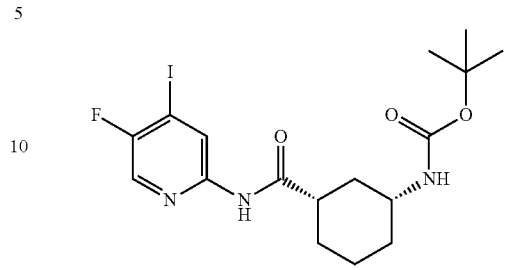

1-Chloro-N,N,2-trimethylprop-1-en-1-amine (0.62 mL, 4.7 mmol) was added to a solution of (1S,3R)-3-((tert-butoxycarbonyl)amino)cyclohexanecarboxylic acid (843 mg, 3.47 mmol; prepared according to Example 2) in DCM (15 mL). The colorless solution was stirred at r.t. for 1.5 h. Then a solution of 5-fluoro-4-iodopyridin-2-amine (750 mg, 3.15 mmol) and pyridine (0.51 mL, 6.3 mmol) in DCM (15 mL) was added. The resulting reaction was stirred at r.t. for 18 h before being diluted with DCM (200 mL) and washed with water and saturated aqueous sodium chloride. The organic layer was dried over sodium sulfate, filtered and concentrated under reduced pressure. The resulting residue was adsorbed onto silica gel and purified by flash silica chromatography, elution gradient 0 to 10% methanol in DCM, to afford tert-butyl ((1R,3S)-3-((5-fluoro-4-iodopyridin-2-yl)carbamoyl)cyclohexyl)carbamate (827 mg, 57%) as a white solid. $^1$H NMR (300 MHz, DMSO-$d_6$, 27° C.) 1.01-1.19 (1H, m), 1.18-1.31 (3H, m), 1.38 (9H, s), 1.61-1.81 (m, 3H), 1.87 (1H, d), 2.53-2.62 (1H, m), 3.16-3.26 (1H, m), 6.78 (1H, br d), 8.26 (1H, s), 8.60 (1H, d), 10.61 (1H, s). m/z: ES+ [M+Na+]+ 486.

Preparation of Tert-butyl ((1R,3S)-3-((4-(5,5-dimethyl-5,6-dihydro-4H-pyrrolo[1,2-b]pyrazol-3-yl)-5-fluoropyridin-2-yl)carbamoyl)cyclohexyl)carbamate

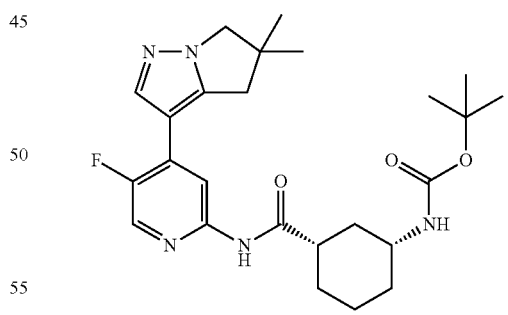

Cesium carbonate (2.81 g, 8.61 mmol) and 2nd Generation XPhos Precatalyst (0.090 g, 0.11 mmol) were added to a degassed mixture of 5,5-dimethyl-3-(4,4,5,5-tetramethyl-1,3,2-dioxaborolan-2-yl)-5,6-dihydro-4H-pyrrolo[1,2-b]pyrazole (0.828 g, 3.16 mmol; prepared according to Example 23), tert-butyl ((1R,3S)-3-((5-fluoro-4-iodopyridin-2-yl)carbamoyl)cyclohexyl)carbamate (1.33 g, 2.87 mmol), dioxane (24 mL), and water (5 mL). The reaction was heated to 95° C. and maintained under these conditions for 18 h. The reaction was then diluted with EtOAc (250

Example 55: (1S,3R)—N-(4-(5,5-dimethyl-5,6-dihydro-4H-pyrrolo[1,2-b]pyrazol-3-yl)-5-fluoropyridin-2-yl)-3-(1-hydroxycyclopropanecarboxamido)cyclohexanecarboxamide

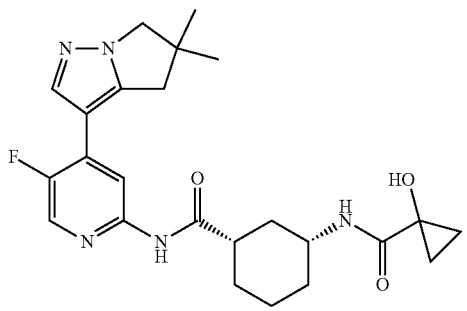 [SMILES: CC1(C)Cc2c(-c3cc(NC(=O)[C@H]4CCC[C@@H](NC(=O)C5(O)CC5)C4)ncc3F)cnn2C1]

HATU (98 mg, 0.26 mmol) was added to a solution of 1-hydroxycyclopropanecarboxylic acid (32 mg, 0.31 mmol), (1S,3R)-3-amino-N-(4-(5,5-dimethyl-5,6-dihydro-4H-pyrrolo[1,2-b]pyrazol-3-yl)-5-fluoropyridin-2-yl)cyclohexanecarboxamide dihydrochloride (96 mg, 0.22 mmol; prepared according to Example 54), and triethylamine (0.11 mL, 0.77 mmol) in DMF (1.5 mL). The reaction mixture was heated at 50° C. for 1.75 h and then allowed to cool to r.t. After 18 h, the resulting mixture was purified by preparative HPLC (Waters)(Bridge Prep C18 OBD column, 5μ silica, 30 mm diameter, 100 mm length) using decreasingly polar mixtures of water (containing 1% NH₃) and MeCN as eluents. Fractions containing the desired compound were evaporated to dryness to afford (1S,3R)—N-(4-(5,5-dimethyl-5,6-dihydro-4H-pyrrolo[1,2-b]pyrazol-3-yl)-5-fluoropyridin-2-yl)-3-(1-hydroxycyclopropanecarboxamido)cyclohexanecarboxamide (33 mg, 33%) as a white solid. ¹H NMR (500 MHz, DMSO-d₆, 30° C.) 0.76-0.84 (2H, m), 0.98-1.04 (2H, m), 1.29 (6H, s), 1.30-1.37 (3H, m), 1.52 (1H, q), 1.7-1.84 (3H, m), 1.88 (1H, d), 2.58-2.67 (1H, m), 2.94 (2H, s), 3.63-3.73 (1H, m), 3.95 (2H, s), 6.14 (1H, br s), 7.65 (1H, d), 7.89 (1H, d), 8.28 (1H, d), 8.32 (1H, d), 10.46 (1H, s). m/z: ES+ [M+H]+ 456.

Example 56: (1S,3R)—N-(5-chloro-4-(6,6-dimethyl-6,7-dihydro-5H-pyrrolo[1,2-a]imidazol-3-yl)pyridin-2-yl)-3-(1-hydroxycyclopropanecarboxamido)cyclohexanecarboxamide

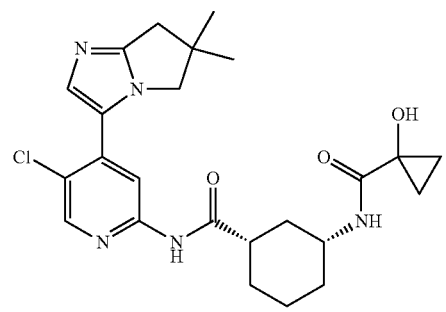 [SMILES: CC1(C)Cc2ncc(-c3cc(NC(=O)[C@H]4CCC[C@@H](NC(=O)C5(O)CC5)C4)ncc3Cl)n2C1]

HATU (118 mg, 0.31 mmol) was added to a solution of 1-hydroxycyclopropanecarboxylic acid (31.6 mg, 0.31 mmol), (1S,3R)-3-amino-N-(5-chloro-4-(6,6-dimethyl-6,7-dihydro-5H-pyrrolo[1,2-a]imidazol-3-yl)pyridin-2-yl)cyclohexanecarboxamide (100 mg, 0.26 mmol), and triethylamine (0.11 mL, 0.77 mmol) in DMA (2 mL). The reaction was stirred overnight at r.t. and was then purified by preparative HPLC (Waters)(Bridge Prep C18 OBD column, 5μ silica, 30 mm diameter, 100 mm length), using decreasingly polar mixtures of water (containing 1% NH₃) and MeCN as eluents. Fractions containing the desired compound were concentrated under reduced pressure to afford (1S,3R)—N-(5-chloro-4-(6,6-dimethyl-6,7-dihydro-5H-pyrrolo[1,2-a]imidazol-3-yl)pyridin-2-yl)-3-(1-hydroxycyclopropanecarboxamido)cyclohexanecarboxamide (27 mg, 22%) as a white solid. ¹H NMR (500 MHz, DMSO-d₆, 30° C.) 0.75-0.82 (2H, m), 0.93-1.09 (2H, m), 1.25 (6H, s), 1.27-1.38 (3H, m), 1.52 (1H, q), 1.65-1.93 (4H, m), 2.53-2.70 (1H, m), 2.71 (2H, s), 3.60-3.71 (1H, m), 3.91 (2H, s), 6.15 (1H, s), 7.51 (1H, s), 7.65 (1H, d), 8.29 (1H, s), 8.42 (1H, s), 10.65 (1H, s). m/z: ES+ [M+H]+ 472.

Procedures used to prepare the starting material (1S,3R)-3-amino-N-(5-chloro-4-(6,6-dimethyl-6,7-dihydro-5H-pyrrolo[1,2-a]imidazol-3-yl)pyridin-2-yl)cyclohexanecarboxamide are described below:

Preparation of Tert-butyl ((1R,3S)-3-((5-chloro-4-(6,6-dimethyl-6,7-dihydro-5H-pyrrolo[1,2-a]imidazol-3-yl)pyridin-2-yl)carbamoyl)cyclohexyl)carbamate

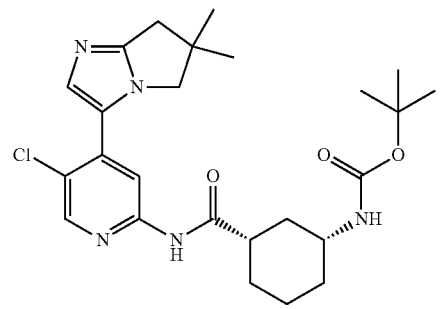 [SMILES: CC1(C)Cc2ncc(-c3cc(NC(=O)[C@H]4CCC[C@@H](NC(=O)OC(C)(C)C)C4)ncc3Cl)n2C1]

Tert-butyl ((1R,3S)-3-((5-chloro-4-iodopyridin-2-yl)carbamoyl)cyclohexyl)carbamate (0.40 g, 0.83 mmol; prepared according to Example 10), 6,6-dimethyl-6,7-dihydro-5H-pyrrolo[1,2-a]imidazole (0.200 g, 1.25 mmol; prepared according to Example 22), potassium acetate (0.163 g, 1.66 mmol) and palladium acetate (0.337 g, 0.33 mmol) were suspended in DMA (10 mL) and sealed into a microwave tube. The tube was evacuated and purged with nitrogen (3×) and then heated at 150° C. for 16 h. The reaction mixture was purified by ion exchange chromatography using an SCX column. The desired product was eluted from the column using 1 M NH₃ in MeOH, and pure fractions were concentrated under reduced pressure. The resulting residue was purified by flash silica chromatography, elution gradient 0 to 100% EtOAc in heptane. Pure fractions were concentrated under reduced pressure to afford tert-butyl ((1R,3S)-3-((5-chloro-4-(6,6-dimethyl-6,7-dihydro-5H-pyrrolo[1,2-a]imidazol-3-yl)pyridin-2-yl)carbamoyl)cyclohexyl)carbamate (0.20 g, 49%) as an orange gum. ¹H NMR (400 MHz, CDCl₃, 21° C.) 1.05-1.19 (1H, m), 1.33 (6H, s), 1.40-1.46 (12H, m), 1.9-2.05 (3H, m), 2.20-2.47 (2H, m), 2.78 (2H, s), 3.46-3.52 (1H, m), 3.93 (2H, s), 4.44-4.52 (1H, m), 7.67 (1H, s), 8.06 (1H, br s), 8.28 (1H, s), 8.29 (1H, s). m/z: ES+ [M+H]+ 488.

Preparation of (1S,3R)-3-amino-N-(5-chloro-4-(6,6-dimethyl-6,7-dihydro-5H-pyrrolo[1,2-a]imidazol-3-yl)pyridin-2-yl)cyclohexanecarboxamide

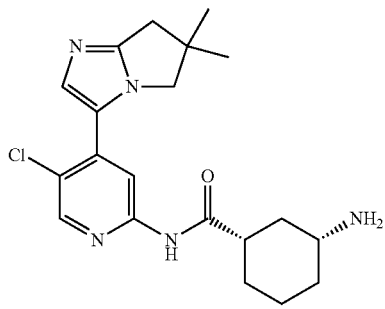 [SMILES: CC1(C)Cc2ncc(-c3cc(NC(=O)[C@H]4CCC[C@@H](N)C4)ncc3Cl)n2C1]

Tert-butyl ((1R,3S)-3-((5-chloro-4-(6,6-dimethyl-6,7-dihydro-5H-pyrrolo[1,2-a]imidazol-3-yl)pyridin-2-yl)carbamoyl)cyclohexyl)carbamate (0.25 g, 0.51 mmol) was dissolved in DCM (5 mL). Trifluoroacetic acid (0.39 mL, 5.1 mmol) was added, and the reaction mixture stirred at r.t. for 30 min. The reaction mixture was then purified by ion exchange chromatography using an SCX column. The desired product was eluted from the column using 1 M NH₃ in MeOH, and pure fractions were concentrated under reduced pressure to afford (1S,3R)-3-amino-N-(5-chloro-4-(6,6-dimethyl-6,7-dihydro-5H-pyrrolo[1,2-a]imidazol-3-yl)pyridin-2-yl)cyclohexanecarboxamide (0.19 g, 96%) as an orange gum. This gum was used in the next step without further purification. m/z: ES+ [M+H]+ 388.

Example 57: N-((1R,3S)-3-((5-chloro-4-(6,6-dimethyl-6,7-dihydro-5H-pyrrolo[1,2-a]imidazol-3-yl)pyridin-2-yl)carbamoyl)cyclohexyl)oxetane-3-carboxamide

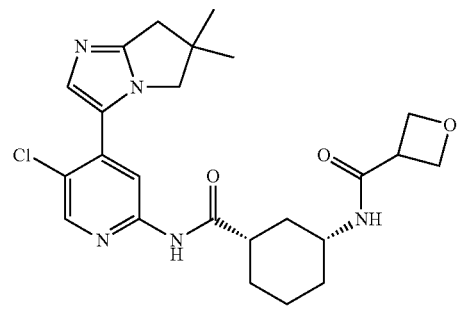 [SMILES: CC1(C)Cc2ncc(-c3cc(NC(=O)[C@H]4CCC[C@@H](NC(=O)C5COC5)C4)ncc3Cl)n2C1]

HATU (118 mg, 0.31 mmol) was added to a solution of oxetane-3-carboxylic acid (32 mg, 0.31 mmol), (1S,3R)-3-amino-N-(5-chloro-4-(6,6-dimethyl-6,7-dihydro-5H-pyrrolo[1,2-a]imidazol-3-yl)pyridin-2-yl)cyclohexanecarboxamide (100 mg, 0.26 mmol; prepared according to Example 56) and triethylamine (0.11 mL, 0.77 mmol) in DMA (2 mL). The reaction mixture was purified by preparative HPLC (Waters)(Bridge Prep C18 OBD column, 5µ silica, 30 mm diameter, 100 mm length), using decreasingly polar mixtures of water (containing 1% NH₃) and MeCN as eluents. Fractions containing the desired compound were concentrated under reduced pressure to afford semipure product. This material was further purified by flash silica chromatography, elution gradient 0 to 10% MeOH in EtOAc. Pure fractions were concentrated under reduced pressure to afford N-((1R,3S)-3-((5-chloro-4-(6,6-dimethyl-6,7-dihydro-5H-pyrrolo[1,2-a]imidazol-3-yl)pyridin-2-yl)carbamoyl)cyclohexyl)oxetane-3-carboxamide (13 mg, 11%) as a white solid. ¹H NMR (400 MHz, CDCl₃, 30° C.) 1.11-1.29 (1H, m), 1.32 (6H, s), 1.36-1.6 (3H, m), 1.9-2.02 (3H, m), 2.22-2.31 (1H, br d), 2.41-2.55 (1H, m), 2.78 (2H, s), 3.67 (1H, ddd), 3.82-3.96 (3H, m), 4.74-4.9 (4H, m), 5.75 (1H, d), 7.64 (1H, s), 8.27 (3H, d). m/z: ES+ [M+H]+ 472.

Example 58: cis-N-(5-chloro-4-(6,6-dimethyl-6,7-dihydro-5H-pyrrolo[1,2-a]imidazol-3-yl)pyridin-2-yl)-3-hydroxycyclobutanecarboxamide

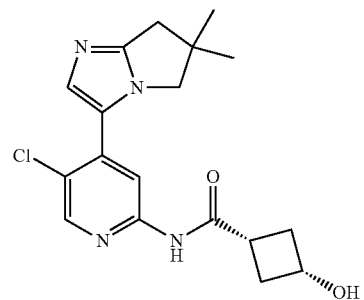 [SMILES: CC1(C)Cc2ncc(-c3cc(NC(=O)[C@H]4C[C@@H](O)C4)ncc3Cl)n2C1]

Cis-3-((tert-butyldimethylsilyl)oxy)-N-(5-chloro-4-iodopyridin-2-yl)cyclobutanecarboxamide (0.194 g, 0.42 mmol; prepared according to Example 27), 6,6-dimethyl-6,7-dihydro-5H-pyrrolo[1,2-a]imidazole (0.100 g, 0.62 mmol;

prepared according Example 22), potassium acetate (0.082 g, 0.83 mmol) and palladium acetate (0.168 g, 0.17 mmol) were suspended in DMA (10 mL) and sealed into a microwave tube. The tube was evacuated and purged with nitrogen (3×) and then heated at 150° C. for 16 h. The reaction mixture was diluted with water (20 mL) and washed with DCM (3×20 mL). The combined organic layers were dried over MgSO$_4$, filtered, and concentrated under reduced pressure. The resulting residue was purified by preparative HPLC (Waters)(Bridge Prep C18 OBD column, 5µ silica, 19 mm diameter, 100 mm length), using decreasingly polar mixtures of water (containing 1% NH$_3$) and MeCN as eluents. Product fractions were concentrated under reduced pressure, and the resulting residue was repurified by preparative HPLC (Waters SunFire column, 5µ silica, 19 mm diameter, 100 mm length), using decreasingly polar mixtures of water (containing 0.1% formic acid) and MeCN as eluents. Fractions containing the desired compound were concentrated under reduced pressure to afford cis-N-(5-chloro-4-(6,6-dimethyl-6,7-dihydro-5H-pyrrolo[1,2-a]imidazol-3-yl)pyridin-2-yl)-3-hydroxycyclobutanecarboxamide (0.016 g, 11%) as a white solid. $^1$H NMR (500 MHz, DMSO-d$_6$, 30° C.) 1.26 (6H, s), 1.98-2.09 (2H, m), 2.30-2.40 (2H, m), 2.72 (2H, s), 2.74-2.83 (1H, m), 3.93 (2H, s), 3.95-4.00 (1H, m), 5.15 (1H, s), 7.53 (1H, s), 8.32 (1H, s), 8.41 (1H, s), 10.61 (1H, s). m/z: ES+ [M+H]+ 361.

Example 59 and 60: Isomer 1 and Isomer 2 of trans-3-acetamido-N-(5-chloro-4-(5,5-dimethyl-5,6-dihydro-4H-pyrrolo[1,2-b]pyrazol-3-yl)pyridin-2-yl)cyclohexanecarboxamide

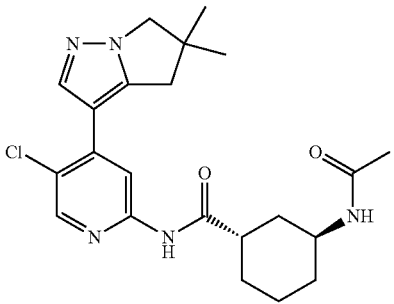

Example 59, Isomer 1

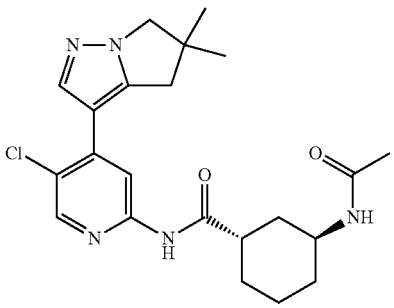

Example 60, Isomer 2

Examples 59 and 60 are pure enantiomers with relative trans configurations. The absolute configurations of Examples 59 and 60 are unknown but are opposite from one another.

Acetic anhydride (0.049 mL, 0.52 mmol) was added dropwise to trans-3-amino-N-(5-chloro-4-(5,5-dimethyl-5,6-dihydro-4H-pyrrolo[1,2-b]pyrazol-3-yl)pyridin-2-yl)cyclohexanecarboxamide (0.167 g, 0.43 mmol), 4-dimethylaminopyridine (2.6 mg, 0.02 mmol) and triethylamine (0.19 mL, 1.3 mmol) in DCM (2 mL) at r.t. under nitrogen. The resulting solution was stirred at r.t. for 4 h. The reaction mixture was quenched with saturated aqueous ammonium chloride (10 mL), extracted with DCM (2×10 mL), and the combined organic layers were dried over MgSO$_4$, filtered, and concentrated under reduced pressure. The resulting residue was purified by preparative HPLC (Chiral Technologies IE column, 20 µm silica, 50 mm diameter, 250 mm length) eluting with isocratic 30% heptane in acetone at 120 mL/min with detection at 210 nm. Fractions containing the desired compounds were concentrated under reduced pressure to afford faster eluting isomer 1 of trans-3-acetamido-N-(5-chloro-4-(5,5-dimethyl-5,6-dihydro-4H-pyrrolo[1,2-b]pyrazol-3-yl)pyridin-2-yl)cyclohexanecarboxamide (0.059 g, 32%) and slower eluting isomer 2 of trans-3-acetamido-N-(5-chloro-4-(5,5-dimethyl-5,6-dihydro-4H-pyrrolo[1,2-b]pyrazol-3-yl)pyridin-2-yl)cyclohexanecarboxamide (0.052 g, 28%) as white solids.

Example 59, Isomer 1

$^1$H NMR (400 MHz, CDCl$_3$, 30° C.) 1.34 (6H, s), 1.56-2.00 (8H, m), 2.01 (3H, s), 2.48-2.56 (1H, m), 2.96 (2H, s), 3.95 (2H, s), 4.17-4.24 (1H, m), 5.42-5.49 (1H, m), 7.96 (1H, br s), 8.10 (1H, s), 8.24 (1H, s), 8.26 (1H, s). m/z: ES+ [M+H]+ 430.

Example 60, Isomer 2

$^1$H NMR (400 MHz, CDCl$_3$, 30° C.) 1.34 (6H, s), 1.48-1.55 (1H, m), 1.62-1.78 (4H, m), 1.82-1.90 (1H, m), 1.94-1.98 (2H, m), 2.01 (3H, s), 2.46-2.58 (1H, m), 2.96 (2H, s), 3.95 (2H, s), 4.17-4.26 (1H, m), 5.45-5.54 (1H, br d), 8.01 (1H, s), 8.10 (1H, s), 8.23 (1H, s), 8.26 (1H, s). m/z: ES+ [M+H]+ 430.

Analytical Reverse Phase Chiral Conditions:
Column: Chiral Technologies IE column
Column Dimensions: 5 µm, 4.6 mm diameter, 250 mm length
Mobile Phase A: Acetonitrile
Mobile Phase B: MeOH
Gradient: Isocratic 10% Mobile Phase B
Flow Rate: 1 mL/min over 30 min
Retention Time: 4.9 min, Example 59
6.3 min, Example 60
e.e. >98%, Example 59
>98%, Example 60

Procedures used to prepare the starting material to trans-3-amino-N-(5-chloro-4-(5,5-dimethyl-5,6-dihydro-4H-pyrrolo[1,2-b]pyrazol-3-yl)pyridin-2-yl)cyclohexanecarboxamide are described below:

Preparation of Tert-butyl trans-3-((5-chloro-4-iodopyridin-2-yl)carbamoyl)cyclohexyl)carbamate

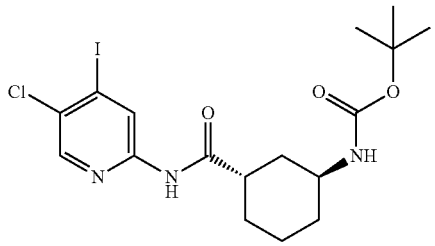 [SMILES: CC(C)(C)OC(=O)N[C@H]1CCC[C@H](C(=O)Nc2cc(I)c(Cl)cn2)C1]

trans racemic

1-Chloro-N,N,2-trimethylprop-1-en-1-amine (1.1 mL, 8.2 mmol) was added to trans-3-((tert-butoxycarbonyl)amino)cyclohexanecarboxylic acid (1.34 g, 5.50 mmol) in DCM (20 mL) at 0° C. under nitrogen. The resulting solution was stirred at 20° C. for 1.5 h, and then 5-chloro-4-iodopyridin-2-amine (1.40 g, 5.50 mmol; prepared according to Example 2) and pyridine (0.67 mL, 8.2 mmol) were added dropwise over 2 minutes. The resulting solution was stirred for 70 h. The reaction mixture was then quenched with saturated aqueous sodium hydrogencarbonate (300 mL), extracted with DCM (3×30 mL), and the combined organic layers were dried over MgSO₄, filtered, and concentrated under reduced pressure to afford a cream-colored solid. This solid was purified by preparative HPLC (Waters) (Bridge Prep C18 OBD column, 5μ silica, 30 mm diameter, 100 mm length), using decreasingly polar mixtures of water (containing 1% NH₃) and MeCN as eluents. Fractions containing the desired compound were concentrated under reduced pressure to afford tert-butyl (trans-3-((5-chloro-4-iodopyridin-2-yl)carbamoyl)cyclohexyl)carbamate (0.99 g, 37%) as a pink solid. $^1$H NMR (500 MHz, CDCl₃, 27° C.) 1.46 (9H, s), 1.49-1.55 (1H, m), 1.61-1.72 (4H, m), 1.82-1.93 (3H, m), 2.47-2.52 (1H, m), 3.89-3.99 (1H, br s), 4.55-4.59 (1H, br s), 7.84 (1H, br s), 8.19 (1H, s), 8.83 (1H, s). m/z: ES+ [M+H]+ 480.

Preparation of Tert-butyl (trans-34(5-chloro-4-(5,5-dimethyl-5,6-dihydro-4H-pyrrolo[1,2-b]pyrazol-3-yl)pyridin-2-yl)carbamoyl)cyclohexyl)carbamate

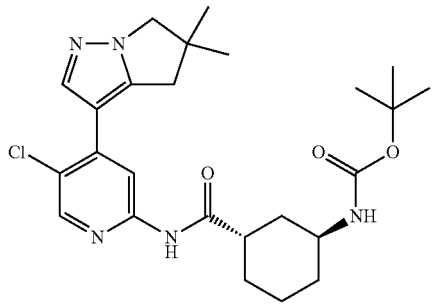

trans racemic

2nd Generation)(Phos Precatalyst (0.049 g, 0.06 mmol) was added to a degassed mixture of 5,5-dimethyl-3-(4,4,5,5-tetramethyl-1,3,2-dioxaborolan-2-yl)-5,6-dihydro-4H-pyrrolo[1,2-b]pyrazole (0.219 g, 0.75 mmol; prepared according to Example 23), tert-butyl (trans-3-((5-chloro-4-iodopyridin-2-yl)carbamoyl)cyclohexyl)carbamate (0.30 g, 0.63 mmol) and potassium phosphate, tribasic, (0.327 g, 1.88 mmol) in 1,4-dioxane (8 mL) and water (1.6 mL). The mixture was degassed and stirred at 90° C. for 2 h under nitrogen. The reaction mixture was then concentrated under reduced pressure and taken up in water (20 mL). The resulting mixture was extracted sequentially with EtOAc (2×20 mL) and DCM (20 mL). The combined organic layers were dried over MgSO₄, filtered, and concentrated under reduced pressure. The resulting residue was purified by flash silica chromatography, elution gradient 0 to 70% EtOAc in heptane. Product fractions were concentrated under reduced pressure to afford tert-butyl (trans-3-((5-chloro-4-(5,5-dimethyl-5,6-dihydro-4H-pyrrolo[1,2-b]pyrazol-3-yl)pyridin-2-yl)carbamoyl)cyclohexyl)carbamate (0.26 g, 86%) as a cream-colored solid. m/z: ES+ [M+H]+ 488.

Preparation of trans-3-amino-N-(5-chloro-4-(5,5-dimethyl-5,6-dihydro-4H-pyrrolo[1,2-b]pyrazol-3-yl)pyridin-2-yl)cyclohexanecarboxamide

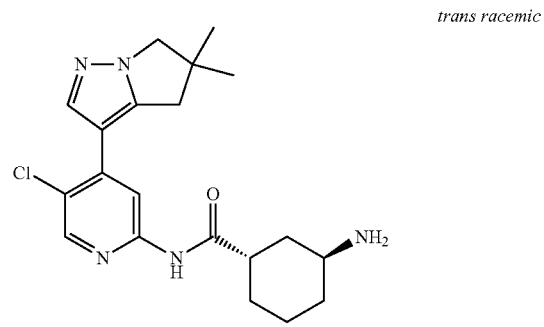 [SMILES: CC1(C)Cc2c(-c3cc(NC(=O)[C@H]4CCC[C@H](N)C4)ncc3Cl)cnn2C1]

trans racemic

Tert-butyl (trans-3-((5-chloro-4-(5,5-dimethyl-5,6-dihydro-4H-pyrrolo[1,2-b]pyrazol-3-yl)pyridin-2-yl)carbamoyl)cyclohexyl)carbamate (0.263 g, 0.54 mmol) was dissolved in DCM (5 mL). Trifluoroacetic acid (0.41 mL, 5.4 mmol) was added, and the reaction mixture was stirred at r.t. for 18 h. The reaction was then purified by ion exchange chromatography, using an SCX column. The desired product was eluted from the column using 1 M NH₃ in MeOH, and product fractions were concentrated under reduced pressure to afford trans-3-amino-N-(5-chloro-4-(5,5-dimethyl-5,6-dihydro-4H-pyrrolo[1,2-b]pyrazol-3-yl)pyridin-2-yl)cyclohexanecarboxamide as a white solid. m/z: ES+ [M+H]+ 388.

Examples 61 and 62: Isomer 1 and Isomer 2 of trans-3-acetamido-N-(5-chloro-4-(4,5,6,7-tetrahydropyrazolo[1,5-a]pyridin-3-yl)pyridin-2-yl)cyclohexanecarboxamide Example 61, Isomer 1

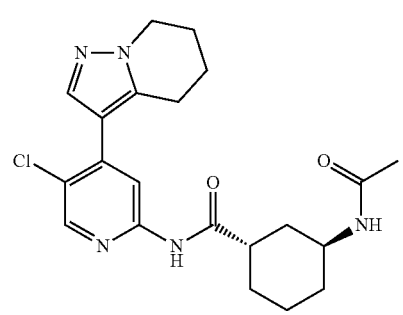

Example 62, Isomer 2

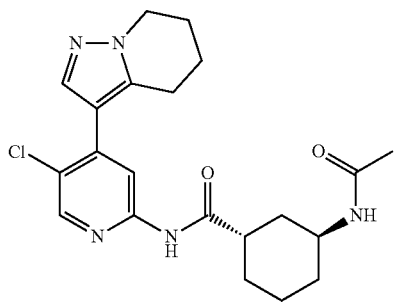

Examples 61 and 62 are pure enantiomers with relative trans configurations. The absolute configurations of Examples 61 and 62 are unknown but are opposite from one another.

Acetic anhydride (0.036 mL, 0.38 mmol) was added dropwise to trans-3-amino-N-(5-chloro-4-(4,5,6,7-tetrahydropyrazolo[1,5-a]pyridin-3-yl)pyridin-2-yl)cyclohexanecarboxamide (0.119 g, 0.32 mmol), 4-dimethylaminopyridine (1.9 mg, 0.02 mmol), and triethylamine (0.14 mL, 1.0 mmol) in DCM (2 mL) at r.t. under nitrogen. The resulting solution was stirred at r.t. for 4 h. The reaction mixture was quenched with saturated aqueous ammonium chloride (10 mL), extracted with DCM (2×10 mL), the combined organic layers were dried over MgSO$_4$, filtered, and concentrated under reduced pressure. The resulting residue was purified by preparative HPLC (Chiral Technologies IE column, 20 μm silica, 50 mm diameter, 250 mm length), using a 30/70 mixture of heptane/acetone as eluents, a flow rate of 120 mL/min, and a detection trigger at 210 nm. Fractions containing the desired compounds were concentrated under reduced pressure to afford faster eluting isomer 1 of trans-3-acetamido-N-(5-chloro-4-(4,5,6,7-tetrahydropyrazolo[1,5-a]pyridin-3-yl)pyridin-2-yl)cyclohexanecarboxamide (0.076 g, 57%) and slower eluting isomer 2 of trans-3-acetamido-N-(5-chloro-4-(4,5,6,7-tetrahydropyrazolo[1,5-a]pyridin-3-yl)pyridin-2-yl)cyclohexanecarboxamide (0.056 g, 42%).

Example 61, Isomer 1

$^1$H NMR (400 MHz, CDCl$_3$, 31° C.) 1.57-1.96 (7H, m), 2.01 (3H, s), 2.04-2.16 (2H, m), 2.49-2.56 (1H, m), 2.92 (2H, t), 4.16-4.23 (3H, m), 5.46-5.52 (1H, m), 7.87 (1H, s), 8.05 (1H, br s), 8.21 (1H, s), 8.27 (1H, s). 3H at 1.50 to 1.62 ppm obscured by water signal. m/z: ES+ [M+H]+ 416.

Example 62, Isomer 2

$^1$H NMR (400 MHz, CDCl$_3$, 30° C.) 1.45-1.96 (10H, m), 2.01 (3H, s), 2.04-2.13 (2H, m), 2.49-2.58 (1H, m), 2.92 (2H, t), 4.16-4.24 (3H, m), 5.52-5.57 (1H, m), 7.87 (1H, s), 8.12 (1H, br s), 8.21 (1H, s), 8.26 (1H, s). m/z: ES+ [M+H]+ 416.

Analytical Reverse Phase Chiral Conditions:
Column: Chiral Technologies IE column
Column Dimensions: 5 μm, 4.6 mm diameter, 250 mm length
Mobile Phase A: Acetonitrile
Mobile Phase B: MeOH
Gradient: Isocratic 10% Mobile Phase B
Flow Rate: 1 mL/min over 30 min Retention Time: 5.2 min, Example 61
6.8 min, Example 62
e. e. >98%, Example 61
>98%, Example 62

Procedures used to prepare the starting material trans-3-amino-N-(5-chloro-4-(4,5,6,7-tetrahydropyrazolo[1,5-a]pyridin-3-yl)pyridin-2-yl)cyclohexanecarboxamide are described below:

Preparation of Tert-butyl (trans-34(5-chloro-4-(4,5,6,7-tetrahydropyrazolo[1,5-a]pyridin-3-yl)pyridin-2-yl)carbamoyl)cyclohexyl)carbamate

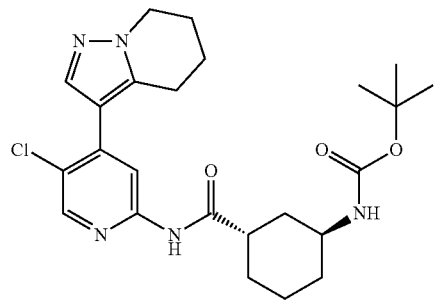

*trans racemic*

2nd Generation XPhos Precatalyst (0.049 g, 0.06 mmol) was added to a degassed mixture of 3-(4,4,5,5-tetramethyl-1,3,2-dioxaborolan-2-yl)-4,5,6,7-tetrahydropyrazolo[1,5-a]pyridine (0.186 g, 0.75 mmol), tert-butyl (trans-3-((5-chloro-4-iodopyridin-2-yl)carbamoyl)cyclohexyl)carbamate (0.30 g, 0.63 mmol; prepared according to Examples 59 and 60, Intermediates) and tribasic potassium phosphate (0.327 g, 1.88 mmol) in 1,4-dioxane (10 mL) and water (2 mL). The reaction mixture was degassed and then stirred at 90° C. for 2 h under nitrogen. The reaction mixture was concentrated under reduced pressure and taken up in water (20 mL). The resulting mixture was extracted sequentially with EtOAc (2×20 mL) and DCM (20 mL). The combined organic layers were dried over MgSO$_4$, filtered, and concentrated under reduced pressure. The resulting residue was purified by flash silica chromatography, elution gradient 0 to 70% EtOAc in heptane. Pure fractions were concentrated under reduced pressure to afford tert-butyl (trans-3-((5-chloro-4-(4,5,6,7-tetrahydropyrazolo[1,5-a]pyridin-3-yl)pyridin-2-yl)carbamoyl)cyclohexyl)carbamate (0.163 g, 55%) as a cream-colored solid. $^1$H NMR (500 MHz, CDCl$_3$, 27° C.) 1.46 (9H, s), 1.48-1.54 (1H, m), 1.61-1.74 (4H, m), 1.82-1.97 (5H, m), 2.05-2.13 (2H, m), 2.46-2.57 (1H, m), 2.92 (2H, t), 3.98 (1H, br s), 4.21 (2H, t), 4.60 (1H, br s), 7.87 (2H, s), 8.21 (1H, s), 8.27 (1H, s). m/z: ES+ [M+H]+ 474.

Preparation of trans-3-amino-N-(5-chloro-4-(4,5,6,7-tetrahydropyrazolo[1,5-a]pyridin-3-yl)pyridin-2-yl)cyclohexanecarboxamide

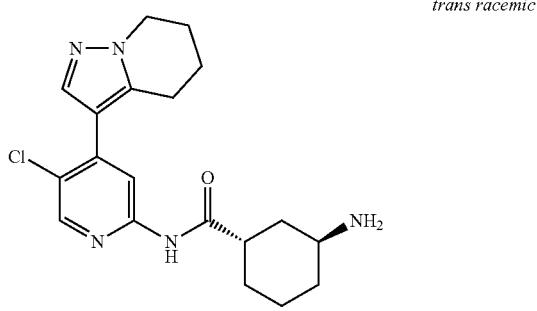 [SMILES: N[C@H]1CCC[C@H](C(=O)Nc2cc(-c3cnn4c3CCCC4)c(Cl)cn2)C1]

*trans racemic*

Tert-butyl (trans-3-((5-chloro-4-(4,5,6,7-tetrahydropyrazolo[1,5-a]pyridin-3-yl)pyridin-2-yl)carbamoyl)cyclohexyl)carbamate (0.16 g, 0.34 mmol) was dissolved in DCM (5 mL). Trifluoroacetic acid (0.26 mL, 3.4 mmol) was added, and the reaction mixture was stirred at r.t. for 18 h. The reaction mixture was then purified by ion exchange chromatography, using an SCX column. The desired product was eluted from the column using 1 M $NH_3$ in MeOH, and product fractions were concentrated under reduced pressure to afford trans-3-amino-N-(5-chloro-4-(4,5,6,7-tetrahydropyrazolo[1,5-a]pyridin-3-yl)pyridin-2-yl)cyclohexanecarboxamide as a yellow gum. m/z: ES+ [M+H]+ 374.

Example 63: (1S,3R)-3-acetamido-N-(5-fluoro-4-(4,5,6,7-tetrahydropyrazolo[1,5-a]pyridin-3-yl)pyridin-2-yl)cyclohexanecarboxamide

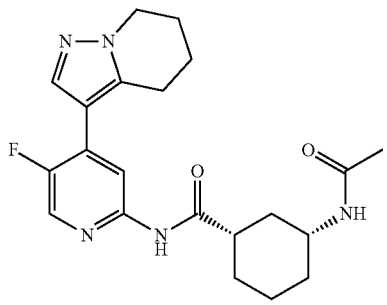 [SMILES: CC(=O)N[C@@H]1CCC[C@H](C(=O)Nc2cc(-c3cnn4c3CCCC4)c(F)cn2)C1]

Acetic anhydride (0.032 mL, 0.34 mmol) was added to (1S,3R)-3-amino-N-(5-fluoro-4-(4,5,6,7-tetrahydropyrazolo[1,5-a]pyridin-3-yl)pyridin-2-yl)cyclohexanecarboxamide (0.10 g, 0.28 mmol), triethylamine (0.12 mL, 0.84 mmol) and N,N-dimethylpyridin-4-amine (2 mg, 0.01 mmol) in DCM (5 mL) at r.t. under air. The resulting solution was stirred at r.t. for 2 h. The reaction mixture was quenched with saturated aqueous ammonium chloride (20 mL) and extracted with DCM (2×20 mL). The combined organic layers were dried over $MgSO_4$, filtered, and concentrated under reduced pressure. The resulting residue was purified by preparative HPLC (Waters)(Bridge Prep C18 OBD column, 5μ silica, 30 mm diameter, 100 mm length), using decreasingly polar mixtures of water (containing 1% $NH_3$) and MeCN as eluents. Fractions containing the desired compound were concentrated under reduced pressure to afford (1S,3R)-3-acetamido-N-(5-fluoro-4-(4,5,6,7-tetrahydropyrazolo[1,5-a]pyridin-3-yl)pyridin-2-yl)cyclohexanecarboxamide (0.047 g, 42%) as a gum. $^1$H NMR (500 MHz, DMSO-$d_6$, 30° C.) 1.03-1.15 (1H, m), 1.23-1.37 (3H, m), 1.74-1.82 (6H, m), 1.83-1.94 (3H, m), 2.00-2.08 (2H, m), 2.56-2.68 (1H, m), 2.91 (2H, t), 3.58-3.61 (1H, m), 4.15 (2H, t), 7.73-7.78 (2H, m), 8.26 (1H, d), 8.30 (1H, d), 10.48 (1H, s). m/z: ES+ [M+H]+ 400.

Procedures for preparing the starting material (1S,3R)-3-amino-N-(5-fluoro-4-(4,5,6,7-tetrahydropyrazolo[1,5-a]pyridin-3-yl)pyridin-2-yl)cyclohexanecarboxamide are described below:

Preparation of 3-(2-chloro-5-fluoropyridin-4-yl)-4,5,6,7-tetrahydropyrazolo[1,5-a]pyridine

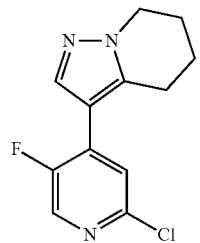 [SMILES: Fc1cnc(Cl)cc1-c1cnn2c1CCCC2]

2nd Generation XPhos Precatalyst (0.092 g, 0.12 mmol) was added to a degassed mixture of 3-(4,4,5,5-tetramethyl-1,3,2-dioxaborolan-2-yl)-4,5,6,7-tetrahydropyrazolo[1,5-a]pyridine (0.347 g, 1.40 mmol), 2-chloro-5-fluoro-4-iodopyridine (0.300 g, 1.17 mmol) and potassium phosphate, tribasic (0.609 g, 3.50 mmol) in 1,4-dioxane (10 mL) and water (2 mL). The mixture was degassed and stirred at 90° C. for 2 h under nitrogen. The reaction mixture was concentrated under reduced pressure, and the resulting residue was taken up in water (20 mL). The resulting mixture was extracted sequentially with DCM (3×20 mL). The organic layer was dried over $MgSO_4$, filtered, and concentrated under reduced pressure. The resulting residue was purified by flash silica chromatography, elution gradient 0 to 60% EtOAc in heptane. Pure fractions were concentrated under reduced pressure to afford 3-(2-chloro-5-fluoropyridin-4-yl)-4,5,6,7-tetrahydropyrazolo[1,5-a]pyridine (200 mg, 68%) as a yellow gum. m/z: ES+ [M+H]+ 252.

Preparation of Tert-butyl ((1R,3S)-3-((5-fluoro-4-(4,5,6,7-tetrahydropyrazolo[1,5-a]pyridin-3-yl)pyridin-2-yl)carbamoyl)cyclohexyl)carbamate

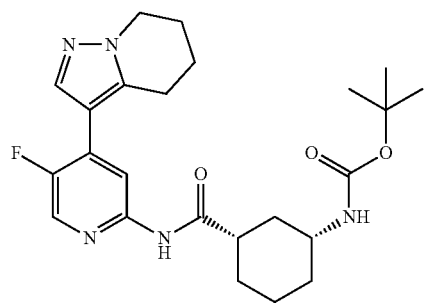 [SMILES: CC(C)(C)OC(=O)N[C@@H]1CCC[C@H](C(=O)Nc2cc(-c3cnn4c3CCCC4)c(F)cn2)C1]

Tetrakis(triphenylphosphine)palladium(0) (0.092 g, 0.080 mmol) was added to a mixture of 3-(2-chloro-5-fluoropyridin-4-yl)-4,5,6,7-tetrahydropyrazolo[1,5-a]pyridine (0.20 g, 0.79 mmol), tert-butyl ((1R,3S)-3-carbamoylcyclohexyl)carbamate (0.231 g, 0.95 mmol; prepared according to Example 25), 9,9-dimethyl-4,5-bis(diphenylphosphino)xanthene (0.092 g, 0.16 mmol), and cesium carbonate (0.777 g, 2.38 mmol) in 1,4-dioxane (6 mL). The mixture was degassed (vacuum), backfilled with nitrogen, and the resulting suspension was stirred at 120° C. for 2 h in the microwave reactor. The reaction mixture was partitioned between water (20 mL) and DCM (40 mL) and separated using a phase separation cartridge. The organics were adsorbed onto silica and purified by flash silica chromatography, elution gradient 0 to 60% EtOAc in heptane. Fractions containing product were concentrated under reduced pressure to afford tert-butyl ((1R,3S)-3-((5-fluoro-4-(4,5,6,7-tetrahydropyrazolo[1,5-a]pyridin-3-yl)pyridin-2-yl)carbamoyl)cyclohexyl)carbamate (136 mg). This material was used directly in the next step without further purification. m/z: ES+ [M+H]+ 458.

Preparation of (1S,3R)-3-amino-N-(5-fluoro-4-(4,5,6,7-tetrahydropyrazolo[1,5-a]pyridin-3-yl)pyridin-2-yl)cyclohexanecarboxamide

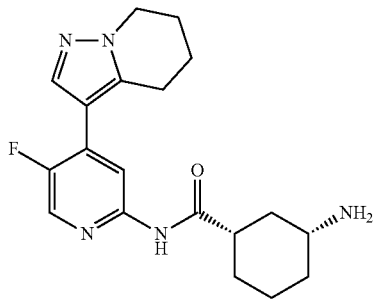 [SMILES: N[C@@H]1CCC[C@H](C(=O)Nc2cc(-c3cnn4c3CCCC4)c(F)cn2)C1]

Trifluoroacetic acid (0.17 mL, 2.2 mmol) was added to tert-butyl ((1R,3S)-3-((5-fluoro-4-(4,5,6,7-tetrahydropyrazolo[1,5-a]pyridin-3-yl)pyridin-2-yl)carbamoyl)cyclohexyl)carbamate (0.10 g, 0.22 mmol) in DCM (5 mL). The resulting solution was stirred at r.t. for 1 h. The crude product was purified by ion exchange chromatography using an SCX column. The desired product was eluted from the column using 1 M NH₃ in MeOH, and pure fractions were concentrated under reduced pressure to afford (1S,3R)-3-amino-N-(5-fluoro-4-(4,5,6,7-tetrahydropyrazolo[1,5-a]pyridin-3-yl)pyridin-2-yl)cyclohexanecarboxamide as a yellow gum. This material was used directly in the next step without further purification. m/z: ES+ [M+H]+ 358.

Example 64 and 65: Preparation of Isomer 1 and Isomer 2 of (1S,3R)-3-acetamido-N-(5-chloro-4-(5-methyl-4,5,6,7-tetrahydropyrazolo[1,5-a]pyridin-3-yl)pyridin-2-yl)cyclohexanecarboxamide

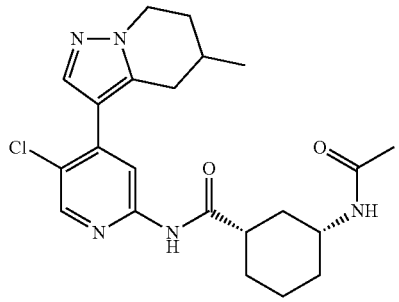

Example 64, isomer 1

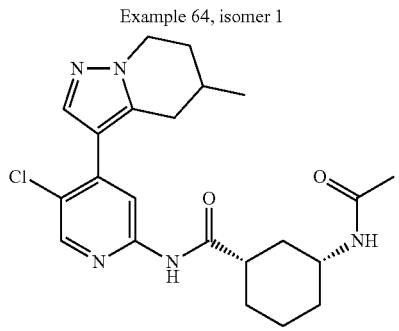

Example 65, isomer 1

Pure enantiomers. The configuration of the methyl is unknown for Example 64 and 65 but is opposite in Example 64 vs Example 65.

2nd Generation XPhos precatalyst (0.056 g, 0.07 mmol) was added to a mixture of 5-methyl-3-(4,4,5,5-tetramethyl-1,3,2-dioxaborolan-2-yl)-4,5,6,7-tetrahydropyrazolo[1,5-a]pyridine (0.56 g, 0.85 mmol), (1S,3R)-3-acetamido-N-(5-chloro-4-iodopyridin-2-yl)cyclohexanecarboxamide (0.30 g, 0.71 mmol; prepared according to Example 12) and Cs₂CO₃ (0.695 g, 2.13 mmol) in dioxane (10 mL) and water (2.0 mL) under nitrogen. The resulting mixture was stirred at 100° C. for 30 minutes. The reaction mixture was then concentrated under reduced pressure, and the resulting residue was diluted with DCM (100 mL) before being washed sequentially with water (100 mL) and saturated aqueous sodium chloride (100 mL). The organic layer was dried over Na₂SO₄, filtered, and concentrated under reduced pressure. The resulting residue was purified by flash silica chromatography, elution gradient 0 to 10% MeOH in DCM. Product fractions were concentrated under reduced pressure, and the resulting residue was further purified by preparative HPLC (Waters)(Bridge Prep C18 OBD column, 5µ silica, 19 mm diameter, 150 mm length), using decreasingly polar mixtures of water (containing 0.1% NH₄HCO₃) and MeCN as eluents. Product fractions were concentrated under reduced pressure to afford (1S,3R)-3-acetamido-N-(5-chloro-4-(5-methyl-4,5,6,7-tetrahydropyrazolo[1,5-a]pyridin-3-yl)pyridin-2-yl)cyclohexanecarboxamide (0.120 g, 39%; mixture of Examples 64 and 65, ratio unknown) as a white solid. m/z: ES+ [M+H]+ 430.

This material was resolved by preparative HPLC (Chiralpak® IA-3 column, 5 µm silica, 20 mm diameter, 250 mm length), using an isocratic mixture of 30% isopropanol in hexane (containing 0.1% diethylamine) as eluents over 23 min at a flow rate of 20 mL/min. Product fractions were concentrated under reduced pressure to afford faster eluting isomer 1 (14.3 min) of (1S,3R)-3-acetamido-N-(5-chloro-4-(5-methyl-4,5,6,7-tetrahydropyrazolo[1,5-a]pyridin-3-yl)pyridin-2-yl)cyclohexanecarboxamide (0.045 g, 38%, Example 64) as a white solid and slower eluting isomer 2 (18.8 min) of (1S,3R)-3-acetamido-N-(5-chloro-4-(5-methyl-4,5,6,7-tetrahydropyrazolo[1,5-a]pyridin-3-yl)pyridin-2-yl)cyclohexanecarboxamide (0.045 g, 38%, Example 65) as a white solid.

Example 64, Isomer 1

$^1$H NMR (400 MHz, DMSO-$d_6$, 21° C.) 1.00-1.14 (4H, m), 1.19-1.36 (3H, m), 1.69-1.84 (7H, m), 1.85-2.10 (3H, m), 2.37-2.49 (1H, m), 2.56-2.66 (1H, m), 2.79-2.90 (1H, m), 3.49-3.63 (1H, m), 4.01-4.13 (1H, m), 4.19-4.30 (1H, m), 7.75 (1H, s), 7.79 (1H, d), 8.12 (1H, s), 8.39 (1H, s), 10.61 (1H, s). m/z: ES+ [M+H]+ 430.

Example 65, Isomer 2

$^1$H NMR (400 MHz, DMSO-$d_6$, 21° C.) 1.01-1.14 (4H, m), 1.21-1.35 (3H, m), 1.70-1.83 (7H, m), 1.83-2.09 (3H, m), 2.37-2.49 (1H, m), 2.56-2.63 (1H, m), 2.79-2.89 (1H, m), 3.49-3.62 (1H, m), 4.01-4.14 (1H, m), 4.19-4.30 (1H, m), 7.74 (1H, s), 7.78 (1H, d), 8.12 (1H, s), 8.39 (1H, s), 10.61 (1H, s). m/z: ES+ [M+H]+ 430.
Analytical Reverse Phase Chiral Conditions:
Column: Chiralpak® IA-3 column,
Column Dimensions: 3 µm, 4.6 mm diameter, 50 mm length,
Mobile Phase A: Hexane containing 0.1% diethylamine
Mobile Phase B: Isopropanol
Gradient: Isocratic 30% Mobile Phase B
Flow Rate: 1 mL/min over 7 min
Retention Time: 2.93 min, Example 64
3.67 min, Example 65
e.e. 100%, Isomer 1
98.7%, Isomer 2
Procedures for preparing the starting material 5-methyl-3-(4,4,5,5-tetramethyl-1,3,2-dioxaborolan-2-yl)-4,5,6,7-tetrahydropyrazolo[1,5-a]pyridine are described below:

Preparation of 5-methylpyrazolo[1,5-a]pyridine

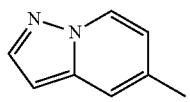

Palladium(II) acetate (0.114 g, 0.51 mmol) was added to 5-bromopyrazolo[1,5-a]pyridine (1.00 g, 5.08 mmol), 2,4,6-trimethyl-1,3,5,2,4,6-trioxatriborinane (0.765 g, 6.09 mmol), potassium carbonate (2.10 g, 15.2 mmol), 1,4-dioxane (10 mL), and water (1 mL) under nitrogen. The resulting mixture was stirred at 80° C. for 1 hour. This reaction was repeated in a separate flask, and both reactions were then combined, diluted with EtOAc (100 mL), and washed sequentially with water (75 mL) and saturated aqueous sodium chloride (75 mL). The organic layer was dried over Na$_2$SO$_4$, filtered, and concentrated under reduced pressure. The resulting residue was purified by flash silica chromatography, elution gradient 0 to 20% EtOAc in petroleum ether. Pure fractions were concentrated under reduced pressure to afford 5-methylpyrazolo[1,5-a]pyridine (1.1 g, 82%) as a brown oil. $^1$H NMR (400 MHz, DMSO-$d_6$, 20° C.) 2.33 (3H, s), 6.45 (1H, d), 6.71 (1H, dd), 7.44 (1H, s), 7.92 (1H, d), 8.55 (1H, d). m/z: ES+ [M+H]+ 133.

Preparation of 5-methyl-4,5,6,7-tetrahydropyrazolo[1,5-a]pyridine

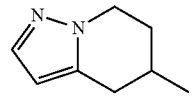

5-Methylpyrazolo[1,5-a]pyridine (500 mg, 3.78 mmol), palladium on carbon (10 wt %; 250 mg) and acetic acid (0.217 mL, 3.78 mmol) in MeOH (20 mL) were stirred under an atmosphere of hydrogen at 20 atm and 80° C. for 50 h. This reaction was then repeated in a separate flask. Upon cooling both reactions were filtered through Celite, and the filtrates were combined concentrated under reduced pressure to afford crude 5-methyl-4,5,6,7-tetrahydropyrazolo[1,5-a]pyridine (1.05 g, 98%) as a brown oil. This product was used in the next step directly without further purification. $^1$H NMR (400 MHz, DMSO-$d_6$, 20° C.) 1.06 (3H, d), 1.57-1.72 (1H, m), 1.84-2.04 (2H, m), 2.24-2.36 (1H, mf), 2.81-2.93 (1H, m), 3.90-4.07 (1H, m), 4.11-4.19 (1H, m), 5.95 (1H, s), 7.33 (1H, s).

Preparation of 3-iodo-5-methyl-4,5,6,7-tetrahydropyrazolo[1,5-a]pyridine

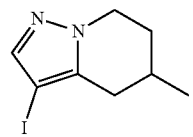

NIS (1.98 g, 8.81 mmol) was added to 5-methyl-4,5,6,7-tetrahydropyrazolo[1,5-a]pyridine (1.05 g, 7.34 mmol) in acetonitrile (2 mL). The resulting mixture was stirred at r.t. for 3 h before being concentrated under reduced pressure. The resulting residue was then diluted with EtOAc (100 mL) and washed sequentially with water (75 mL) and saturated aqueous sodium chloride (2×75 mL). The organic layer was dried over Na$_2$SO$_4$, filtered, and concentrated under reduced pressure. The resulting residue was purified by flash silica chromatography, elution gradient 0 to 30% EtOAc in petroleum ether. Product fractions were concentrated under reduced pressure to afford 3-iodo-5-methyl-4,5,6,7-tetrahydropyrazolo[1,5-a]pyridine (1.0 g, 52%) as a brown solid. $^1$H NMR (400 MHz, DMSO-$d_6$, 20° C.) 1.08 (3H, d), 1.58-1.72 (1H, m), 1.87-2.01 (2H, m), 2.07-2.22 (1H, m), 2.64-2.71 (1H, m), 3.93-4.06 (1H, m), 4.10-4.22 (1H, m), 7.47 (1H, s).

Preparation of 5-methyl-3-(4,4,5,5-tetramethyl-1,3,2-dioxaborolan-2-yl)-4,5,6,7-tetrahydropyrazolo[1,5-a]pyridine

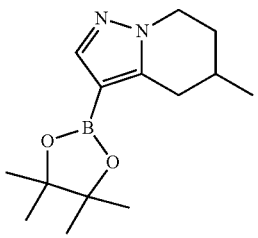

n-BuLi in hexane (2.5 M; 0.916 mL, 2.29 mmol) was added dropwise to 3-iodo-5-methyl-4,5,6,7-tetrahydropyrazolo[1,5-a]pyridine (0.50 g, 1.91 mmol), 2-isopropoxy-4,4,5,5-tetramethyl-1,3,2-dioxaborolane (0.532 g, 2.86 mmol), and TMEDA (0.40 mL, 2.7 mmol) in THF (20 mL) at −78° C. under nitrogen. The resulting mixture was stirred at −78° C. for 1 hour. The reaction mixture was quenched with saturated aqueous ammonium chloride (5 mL) and extracted with EtOAc (3×20 mL). The combined organic layers were washed with saturated aqueous sodium chloride (50 mL), dried over Na$_2$SO$_4$, filtered, and concentrated under reduced pressure to afford 5-methyl-3-(4,4,5,5-tetramethyl-1,3,2-dioxaborolan-2-yl)-4,5,6,7-tetrahydropyrazolo[1,5-a]pyridine (0.60 g, 79%) contaminated with ~23 mol % 5-methyl-4,5,6,7-tetrahydropyrazolo[1,5-a]pyridine based on NMR analysis as a yellow gum. m/z: ES+ [M+CH$_3$CN+H]+ 304.

Example 66: (1S,3R)-3-acetamido-N-(5-chloro-4-(5,6,7,8-tetrahydro-4H-pyrazolo[1,5-a]azepin-3-yl)pyridin-2-yl)cyclohexanecarboxamide

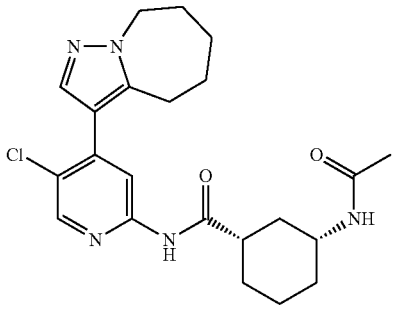 [SMILES: CC(=O)N[C@@H]1CCC[C@H](C(=O)Nc2cc(-c3cnn4c3CCCCC4)c(Cl)cn2)C1]

Acetic anhydride (0.13 mL, 1.4 mmol) was added to a stirred solution of (1S,3R)-3-amino-N-(5-chloro-4-(5,6,7,8-tetrahydro-4H-pyrazolo[1,5-a]azepin-3-yl)pyridin-2-yl)cyclohexanecarboxamide (450 mg, 1.16 mmol), triethylamine (0.34 mL, 2.4 mmol) and DCM (10 mL). The reaction mixture was stirred at r.t. for 4 h. Silica was added, and the mixture was concentrated under reduced pressure. The resulting residue was purified by flash silica chromatography, eluting with 0.5% methanol in ethyl acetate, to give (1S,3R)-3-acetamido-N-(5-chloro-4-(5,6,7,8-tetrahydro-4H-pyrazolo[1,5-a]azepin-3-yl)pyridin-2-yl)cyclohexanecarboxamide (260 mg, 52%) as a white solid. $^1$H NMR (400 MHz, DMSO-d$_6$, 30° C.) 1.05-1.12 (1H, m), 1.17-1.37 (3H, m), 1.57-1.66 (2H, m), 1.69-1.95 (11H, m), 2.56-2.65 (1H, m), 2.70-2.77 (2H, m), 3.50-3.61 (1H, m), 4.21-4.45 (2H, m), 7.48 (1H, s), 7.73 (1H, d), 8.05 (1H, s), 8.40 (1H, s), 10.58 (1H, s). m/z: ES+ [M+H]+ 430.

Procedures for preparing the starting material (1S,3R)-3-amino-N-(5-chloro-4-(5,6,7,8-tetrahydro-4H-pyrazolo[1,5-a]azepin-3-yl)pyridin-2-yl)cyclohexanecarboxamide are described below:

Preparation of Ethyl 1-(5-methoxy-5-oxopentyl)-1H-pyrazole-5-carboxylate

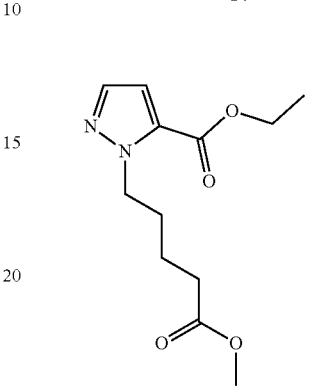

Ethyl 1H-pyrazole-5-carboxylate (9.9 g, 71 mmol) and potassium carbonate (12 g, 85 mmol) were stirred in DMF (70 mL), and methyl 5-bromopentanoate (14 g, 71 mmol) was added. The mixture was stirred at ambient temperature for 24 h. Water was added and the mixture was extracted with ether (3×). The combined organic layers were combined and washed with water (2×), dried over magnesium sulfate, and concentrated under reduced pressure. The resulting residue was purified by flash silica chromatography, eluting with 20% ethyl acetate in pentane to give ethyl 1-(5-methoxy-5-oxopentyl)-1H-pyrazole-5-carboxylate (9 g, 50.1%). $^1$H NMR (400 MHz, CDCl$_3$, 30° C.) 1.38 (3H, t), 1.54-1.75 (2H, m), 1.8-1.95 (2H, m), 2.34 (2H, t), 3.65 (3H, s), 4.34 (2H, q), 4.58 (2H, t), 6.83 (1H, d), 7.46 (1H, d). m/z: ES+ [M+H]+ 255. Also isolated was ethyl 1-(5-methoxy-5-oxopentyl)-1H-pyrazole-3-carboxylate (7.70 g, 43%).

Preparation of Methyl 4-oxo-5,6,7,8-tetrahydro-4H-pyrazolo[1,5-a]azepine-5-carboxylate

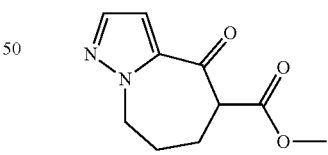

Potassium tert-butoxide (6.29 g, 56.0 mmol) was added to ethyl 1-(5-methoxy-5-oxopentyl)-1H-pyrazole-5-carboxylate (9.5 g, 37 mmol) in toluene (200 mL). The mixture was stirred for 10 minutes then warmed to 110° C., resulting in a thick precipitate. The mixture was heated for 30 minutes and then allowed to cool to r.t. The mixture was neutralized to pH 7 with dilute aqueous HCl (2N) and extracted with ethyl acetate (3×). The combined organic layers were dried over magnesium sulfate and concentrated under reduced pressure to afford methyl 4-oxo-5,6,7,8-tetrahydro-4H-pyrazolo[1,5-a]azepine-5-carboxylate (8.00 g, 103%) contaminated with the ethyl ester analog This material was used directly in the next step without further purification. m/z: ES+ [M+H]+ 209 (Me ester) & 223 (Et ester).

Preparation of 5,6,7,8-tetrahydro-4H-pyrazolo[1,5-a]azepin-4-one

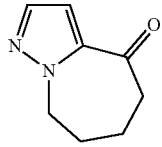 [SMILES: O=C1CCCCn2nccc21]

Lithium chloride (2.60 g, 61.2 mmol) was added to a solution of methyl 4-oxo-5,6,7,8-tetrahydro-4H-pyrazolo[1,5-a]azepine-5-carboxylate (8.50 g, 40.8 mmol, contaminated with the ethyl ester analog) in DMSO (50 mL). The mixture was heated at 120° C. for 24 h and then cooled to r.t. Water was added, and the mixture was extracted with ethyl acetate (3×). The combined organic layers were concentrated under reduced pressure. The resulting residue was purified by flash silica chromatography, eluting with 30% ethyl acetate in heptane to give 5,6,7,8-tetrahydro-4H-pyrazolo[1,5-a]azepin-4-one (3.50 g, 57%) as an oil. $^1$H NMR (400 MHz, CDCl$_3$, 30° C.) 1.91-2.08 (2H, m), 2.08-2.28 (2H, m), 2.76-2.93 (2H, m), 4.49-4.64 (2H, m), 6.86 (1H, d), 7.44 (1H, d).

Preparation 5,6,7,8-tetrahydro-4H-pyrazolo[1,5-a]azepine

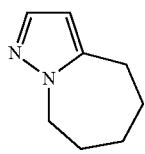

Hydrazine hydrate (5.65 mL, 117 mmol) was added to a stirred solution of 5,6,7,8-tetrahydro-4H-pyrazolo[1,5-a]azepin-4-one (3.5 g, 23 mmol) dissolved in diethylene glycol (66 mL). The resulting solution was stirred at 170° C. for 1 hour. The reaction was then removed from heat, and potassium hydroxide (4.58 g, 81.6 mmol) was carefully added to the mixture. The resulting suspension was stirred at 170° C. for 2 h and then cooled to r.t. The reaction mixture was then diluted water, acidified to pH 5 with dilute aqueous hydrochloric acid (2N), and extracted with Et$_2$O (5×50 mL). The combined ether layers were washed with water (2×20 mL), dried over magnesium sulfate, filtered, and concentrated under reduced pressure to give 5,6,7,8-tetrahydro-4H-pyrazolo[1,5-a]azepine (2.10 g, 66%) as a solid. $^1$H NMR (400 MHz, CDCl$_3$, 30° C.) 1.61-1.67 (2H, m), 1.71-1.79 (2H, m), 1.80-1.87 (2H, m), 2.62-2.83 (2H, m), 4.17-4.3 (2H, m), 5.98 (1H, d), 7.26 (1H, d).

Preparation of 3-iodo-5,6,7,8-tetrahydro-4H-pyrazolo[1,5-a]azepine

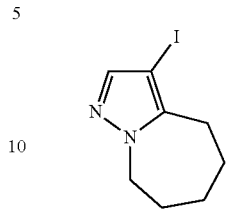

NIS (3.47 g, 15.4 mmol) was added to a stirred solution of 5,6,7,8-tetrahydro-4H-pyrazolo[1,5-a]azepine (2.10 g, 15.4 mmol) dissolved in acetonitrile (30 mL) at r.t. The resulting mixture was stirred at r.t. for 16 h. The reaction mixture was then diluted with ether (50 mL), and washed sequentially with water (2×20 mL) and saturated aqueous sodium chloride (20 mL). The organic layer was dried over MgSO$_4$, filtered, and concentrated under reduced pressure to afford 3-iodo-5,6,7,8-tetrahydro-4H-pyrazolo[1,5-a]azepine (3.3 g, 82%) as an orange oil which solidified on standing. This material was used directly in the next step without further purification. $^1$H NMR (400 MHz, CDCl$_3$, 30° C.) 1.6-1.72 (2H, m), 1.73-1.82 (2H, m), 1.82-1.92 (2H, m), 2.74-2.83 (2H, m), 4.25-4.35 (2H, m), 7.32 (1H, s).

Preparation of 3-(4,4,5,5-tetramethyl-1,3,2-dioxaborolan-2-yl)-5,6,7,8-tetrahydro-4H-pyrazolo[1,5-a]azepine

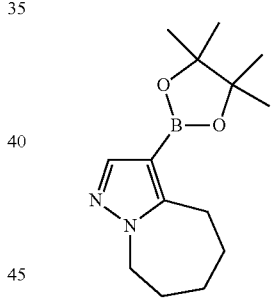

Isopropylmagnesium chloride lithium chloride complex in THF (1.3 M; 12.6 mL, 16.4 mmol) was added dropwise over 5 minutes to 3-iodo-5,6,7,8-tetrahydro-4H-pyrazolo[1,5-a]azepine (3.30 g, 12.6 mmol) in THF (20 mL) at 0° C. under nitrogen. The resulting mixture was stirred at 0° C. for 30 minutes. 2-Isopropoxy-4,4,5,5-tetramethyl-1,3,2-dioxaborolane (3.85 mL, 18.9 mmol) was added dropwise at 0° C., and the reaction mixture was then allowed to warm to r.t. overnight. The reaction mixture was diluted with ether (20 mL) and washed sequentially with saturated aqueous ammonium chloride (20 mL), water (20 mL), and saturated aqueous sodium chloride (10 mL). The organic layer was dried over MgSO$_4$, filtered, and concentrated under reduced pressure. The resulting oil was taken up in heptane, resulting in formation of a white mixture. This mixture was filtered to afford 3-(4,4,5,5-tetramethyl-1,3,2-dioxaborolan-2-yl)-5,6,7,8-tetrahydro-4H-pyrazolo[1,5-a]azepine (2.00 g, 61%) as a white solid. $^1$H NMR (400 MHz, CDCl$_3$, 30° C.) 1.29 (12H, s), 1.63-1.72 (2H, m), 1.72-1.8 (2H, m), 1.80-1.87 (2H, m), 2.88-3.09 (2H, m), 4.20-4.33 (2H, m), 7.56 (1H, s).

Preparation of Tert-butyl ((1R,3S)-3-((5-chloro-4-(5,6,7,8-tetrahydro-4H-pyrazolo[1,5-a]azepin-3-yl)pyridin-2-yl)carbamoyl)cyclohexyl)carbamate

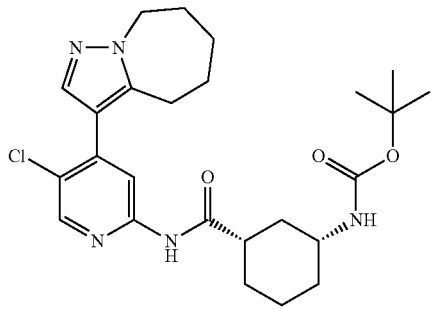 [SMILES: CC(C)(C)OC(=O)N[C@@H]1CCC[C@H](C(=O)Nc2cc(-c3cnn4c3CCCCC4)c(Cl)cn2)C1]

2nd Generation XPhos Precatalyst (0.16 g, 0.21 mmol) was added to a degassed mixture of 3-(4,4,5,5-tetramethyl-1,3,2-dioxaborolan-2-yl)-5,6,7,8-tetrahydro-4H-pyrazolo[1,5-a]azepine (0.656 g, 2.50 mmol), tert-butyl (1R,3S)-3-((5-chloro-4-iodopyridin-2-ylcarbamoyl)cyclohexyl)carbamate (1.00 g, 2.08 mmol; prepared according to Example 10) and potassium phosphate, tribasic, (1.09 g, 6.25 mmol) in 1,4-dioxane (20 mL) and water (2 mL). The mixture was again degassed and was stirred at 85° C. for 24 h under nitrogen. The reaction mixture was allowed to cool, and silica was added. This new mixture was concentrated under reduced pressure, and the resulting residue was purified by flash silica chromatography, eluting with 50% ethyl acetate in heptane to give tert-butyl ((1R,3S)-3-((5-chloro-4-(5,6,7,8-tetrahydro-4H-pyrazolo[1,5-a]azepin-3-yl)pyridin-2-yl)carbamoyl)cyclohexyl)carbamate (0.70 g, 69%) as a solid. This material was carried on to the next step without further purification. m/z: ES+ [M+H]+ 488.

Preparation of (1S,3R)-3-amino-N-(5-chloro-4-(5,6,7,8-tetrahydro-4H-pyrazolo[1,5-a]azepin-3-yl)pyridin-2-yl)cyclohexanecarboxamide

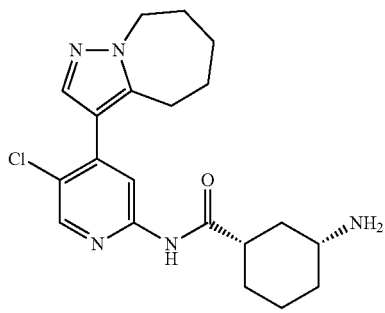 [SMILES: N[C@@H]1CCC[C@H](C(=O)Nc2cc(-c3cnn4c3CCCCC4)c(Cl)cn2)C1]

TFA (2 mL) was added to a stirred solution of tert-butyl ((1R,3S)-3-((5-chloro-4-(5,6,7,8-tetrahydro-4H-pyrazolo[1,5-a]azepin-3-yl)pyridin-2-yl)carbamoyl)cyclohexyl)carbamate (700 mg, 1.43 mmol) in DCM (10 mL). The reaction was stirred at r.t. for 24 h, the volatiles removed under vacuum, and the resulting residue was purified by ion exchange chromatography using an SCX column, eluting with 7N ammonia in methanol. Product fractions were concentrated under reduced pressure to afford (1S,3R)-3-amino-N-(5-chloro-4-(5,6,7,8-tetrahydro-4H-pyrazolo[1,5-a]azepin-3-yl)pyridin-2-yl)cyclohexanecarboxamide (550 mg, 99%) as a solid. m/z: ES+ [M+H]+ 388.

Example 67: N-((1R,3S)-3-((5-chloro-4-(4,5,6,7-tetrahydropyrazolo[1,5-a]pyridin-3-yl)pyridin-2-yl)carbamoyl)cyclohexyl)oxetane-3-carboxamide

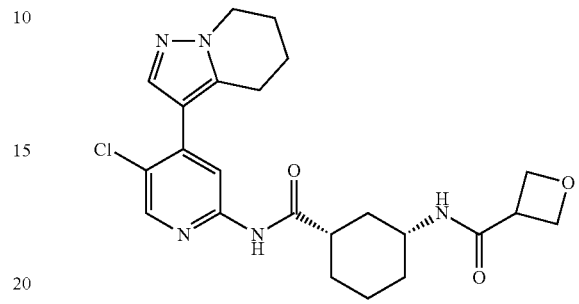

HATU (166 mg, 0.44 mmol) and DIPEA (0.18 mL, 1.0 mmol) were added sequentially to a solution of (1S,3R)-3-amino-N-(5-chloro-4-(4,5,6,7-tetrahydropyrazolo[1,5-a]pyridin-3-yl)pyridin-2-yl)cyclohexanecarboxamide dihydrochloride (150 mg, 0.34 mmol; prepared according to Example 31b) and oxetane-3-carboxylic acid (45 mg, 0.44 mmol) in DMF (1.2 mL). The reaction was stirred at r.t. for 3 h before being diluted with saturated aqueous sodium hydrogencarbonate and extracted with EtOAc (3×). The combined organic layers were dried over sodium sulfate, filtered, and concentrated under reduced pressure. The resulting crude gum was purified by preparative HPLC (Waters)(Bridge Prep Phenyl OBD column, 5μ silica, 19 mm diameter, 150 mm length) using decreasingly polar mixtures of water (containing 0.2% ammonium hydroxide, pH 10) and MeCN as eluents to afford N-((1R,3S)-3-((5-chloro-4-(4,5,6,7-tetrahydropyrazolo[1,5-a]pyridin-3-yl)pyridin-2-yl)carbamoyl)cyclohexyl)-oxetane-3-carboxamide (20 mg).

A second reaction was set up as follows: HATU (140 mg, 0.37 mmol) was added to a solution of (1S,3R)-3-amino-N-(5-chloro-4-(4,5,6,7-tetrahydropyrazolo[1,5-a]pyridin-3-yl)pyridin-2-yl)cyclohexanecarboxamide dihydrochloride (150 mg, 0.34 mmol), oxetane-3-carboxylic acid (45 mg, 0.44 mmol), DIPEA (0.18 mL, 1.0 mmol) and DMF (1.2 mL). The reaction was stirred at r.t. for 3 h. The reaction was diluted with EtOAc and washed with saturated NaHCO₃ and saturated aqueous sodium chloride. The organic layer was dried over sodium sulfate, filtered and concentrated under reduced pressure. The resulting residue was purified by flash silica chromatography, eluting with gradient 80 to 100% EtOAc in hexane, to afford N-((1R,3S)-3-((5-chloro-4-(4,5,6,7-tetrahydropyrazolo[1,5-a]pyridin-3-yl)pyridin-2-yl)carbamoyl)cyclohexyl)oxetane-3-carboxamide (50 mg) as a white solid. This residue was combined with the product from the first reaction and repurified by preparative HPLC (Waters) (Bridge Prep Phenyl OBD column, 5μ silica, 19 mm diameter, 150 mm length) to afford N-((1R,3S)-3-((5-chloro-4-(4,5,6,7-tetrahydropyrazolo[1,5-a]pyridin-3-yl)pyridin-2-yl)carbamoyl)cyclohexyl)oxetane-3-carboxamide (54 mg, 17%) as a white solid. $^1$H NMR (300 MHz, CDCl₃, 27° C.) 1.10-1.26 (1H, m), 1.37-1.68 (3H, m), 2.17-1.84 (7H, m), 2.37-2.22 (1H, m), 2.57-2.43 (1H, m), 2.95 (2H, t), 3.67 (1H, tt), 3.85-4.00 (1H, m), 4.24 (2H, t), 4.89-4.78 (4H, m), 5.52 (1H, br d), 7.93 (1H, s), 8.27 (1H, s), 8.28 (1H, s), 8.60 (1H, br s). m/z: ES+ [M+H]+ 458.

Examples 68 and 69: Isomer 1 and Isomer 2 of (1S,3R)-3-acetamido-N-(5-chloro-4-(6-methyl-4,5,6,7-tetrahydropyrazolo[1,5-a]pyridin-3-yl)pyridin-2-yl)cyclohexanecarboxamide Example 68, Isomer 1

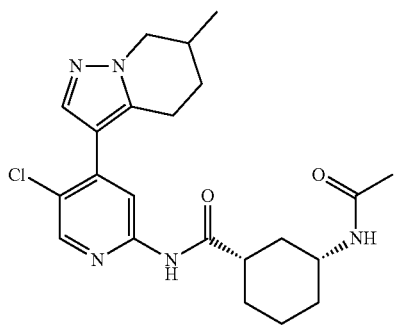

Example 69, Isomer 2

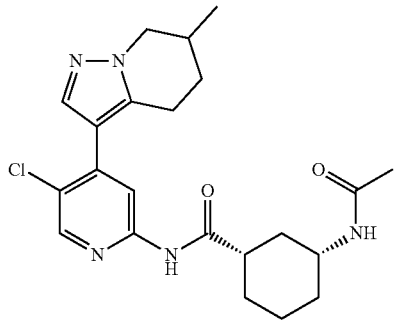

Pure enantiomers. The configuration of the methyl is unknown for Example 68 and 69 but is opposite in Example 68 vs 69.

(1S,3R)-3-Acetamido-N-(5-chloro-4-(6-methyl-4,5,6,7-tetrahydropyrazolo[1,5-a]pyridin-3-yl)pyridin-2-yl)cyclohexanecarboxamide (163 g, 0.379 mmol; mixture of Examples 68 and 69, unknown ratio) was separated using SFC conditions (Column: Chiralpak AS, 5 μm, 21.2 mm diameter, 250 mm length, 20 mL/min flow rate over 7 min), eluting with 25% methanol in CO$_2$, to afford Isomer 1 (3.10 min) of (1S,3R)-3-acetamido-N-(5-chloro-4-(6-methyl-4,5,6,7-tetrahydropyrazolo[1,5-a]pyridin-3-yl)pyridin-2-yl)cyclohexanecarboxamide (65 mg, 28%, Example 68) and Isomer 2 (4.09 min) of (1S,3R)-3-acetamido-N-(5-chloro-4-(6-methyl-4,5,6,7-tetrahydropyrazolo[1,5-a]pyridin-3-yl)pyridin-2-yl)cyclohexanecarboxamide (68, 29%, Example 69) as white solids.

Example 68, Isomer 1

$^1$H NMR (300 MHz, CDCl$_3$, 27° C.) 1.05-1.25 (4H, m), 1.65-1.33 (4H, m), 1.85-2.09 (7H, m), 2.15-2.32 (2H, m), 2.38-2.53 (1H, m), 2.86-3.03 (2H, m), 3.70 (1H, dd), 3.82-3.97 (1H, m), 4.33 (1H, dd), 5.47 (1H, br d), 7.89 (1H, s), 8.12 (1H, br s), 8.22 (1H, s), 8.27 (1H, s). m/z: ES+ [M+H]+ 430.

Example 69, Isomer 2

$^1$H NMR (300 MHz, CDCl$_3$, 27° C.) 1.09-1.24 (4H, d), 1.34-1.58 (4H, m), 1.86-2.08 (7H, m), 2.15-2.32 (1H, m), 2.41-2.51 (1H, m), 2.86-3.03 (1H, m), 3.64-3.75 (1H, m), 3.81-3.95 (1H, m), 4.33 (1H, dd), 5.52 (1H, br d), 7.88 (1H, s), 8.15-8.21 (2H, m), 8.27 (1H, s). m/z: ES+ [M+H]+ 430.

Analytical SFC Conditions:
Column: Chiralpak AS
Column Dimensions: 5 μm, 4.6 mm diameter, 50 mm length,
Mobile Phase A: CO$_2$ (100%)
Mobile Phase B: Methanol
Gradient: Isocratic 25% Mobile Phase B
Flow Rate: 1 mL/min over 2 min
Retention Time: 1.05 min, Example 68, Isomer 1
1.44 min, Example 69, Isomer 2
e.e. >98%, Example 68, Isomer 1
>98%, Example 69, Isomer 2

Procedures used to prepare the starting material (1S,3R)-3-acetamido-N-(5-chloro-4-(6-methyl-4,5,6,7-tetrahydropyrazolo[1,5-a]pyridin-3-yl)pyridin-2-yl)cyclohexanecarboxamide are described below:

Preparation of 6-methylpyrazolo[1,5-a]pyridine

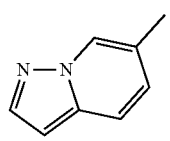

Dioxane (32 mL) and water (6.0 mL) were added to potassium carbonate (1.82 g, 13.2 mmol), 2,4,6-trimethyl-1,3,5,2,4,6-trioxatriborinane (1.9 mL, 13 mmol) and 6-bromopyrazolo[1,5-a]pyridine (1.3 g, 6.60 mmol). The reaction suspension was degassed with nitrogen. 3rd Generation RuPhos Precatalyst (0.27 g, 0.33 mmol) was added, and the reaction was immersed in an oil bath that had been preheated to 100° C. The reaction was maintained under these conditions for 4 h and then cooled to r.t. The resulting mixture was filtered, and the filtrate was washed with saturated aqueous sodium chloride. The organic layer was dried over sodium sulfate, filtered and concentrated under reduced pressure. The resulting oil was purified by flash silica chromatography, elution gradient 5 to 40% ethyl acetate in hexane to give 6-methylpyrazolo[1,5-a]pyridine (0.680 g, 78%) as a white solid. $^1$H NMR (300 MHz, CDCl$_3$, 27° C.) 2.29 (3H, s), 6.53 (1H, dd), 7.07 (1H, dd), 7.60 (1H, d), 7.90 (1H, d), 8.49-8.52 (1H, m). m/z: ES+ [M+H]+ 133.

Preparation of 6-methyl-4,5,6,7-tetrahydropyrazolo[1,5-a]pyridine

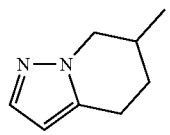

Methanol (45 mL) and acetic acid (0.5 mL) were added to a flask charged with 6-methylpyrazolo[1,5-a]pyridine (0.71 g, 5.4 mmol) and platinum(IV) oxide (0.12 g, 0.54 mmol). The flask was purged with nitrogen, evacuated, and then subjected to a hydrogen atmosphere (balloon). The reaction was stirred at 35° C. for 18 h and then filtered through a bed of Celite®. The filtrate was concentrated under reduced pressure and then diluted with diethyl ether. The mixture was washed with saturated aqueous sodium hydrogencarbonate and saturated aqueous sodium chloride. The organic layer was dried over sodium sulfate, filtered and concentrated under reduced pressure to give crude 6-methyl-4,5,6,7-tetrahydropyrazolo[1,5-a]pyridine (0.71 g, 97%) as an off-white solid. $^1$H NMR (300 MHz, CDCl$_3$, 27° C.) 1.1 (3H, d), 1.50 (1H, dtd), 1.92-2.01 (1H, m), 2.08-2.27 (1H, m), 2.64-2.80 (1H, m), 2.87-2.96 (1H, m), 3.64 (1H, dd), 4.27 (1H, ddd), 5.99 (1H, s), 7.39 (1H, d). m/z: ES+ [M+H]+ 137.

Preparation of 3-iodo-6-methyl-4,5,6,7-tetrahydropyrazolo[1,5-a]pyridine

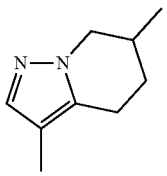

NIS (1.16 g, 5.14 mmol) was added to a solution of 6-methyl-4,5,6,7-tetrahydropyrazolo[1,5-a]pyridine (0.70 g, 5.14 mmol) in acetonitrile (12 mL) at r.t. The reaction was stirred under these conditions for 18 h and then diluted with EtOAc. The resulting mixture was washed with water, and the aqueous layer was extracted with EtOAc (4×100 mL). The combined organic layers were washed with saturated aqueous sodium chloride and concentrated under reduced pressure. The resulting crude gum was purified by flash silica chromatography, elution gradient 5 to 50% ethyl acetate in hexanes, to give 3-iodo-6-methyl-4,5,6,7-tetrahydropyrazolo[1,5-a]pyridine (1.10 g, 82%) as a white solid. $^1$H NMR (300 MHz, CDCl$_3$, 27° C.) 1.15 (3H, d), 1.42-1.61 (1H, m), 1.90-2.07 (1H, m), 2.08-2.22 (1H, m), 2.52-2.60 (1H, m), 2.75-2.86 (1H, m), 3.65 (1H, dd), 4.26 (1H, dd), 7.49 (1H, s). m/z: ES+ [M+H]+ 263.

Preparation of 6-methyl-3-(4,4,5,5-tetramethyl-1,3,2-dioxaborolan-2-yl)-4,5,6,7-tetrahydropyrazolo[1,5-a]pyridine

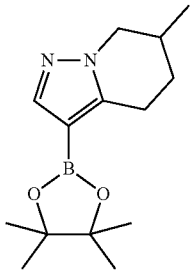

Tetrahydrofuran (3 mL) was added to a flask charged with 3-iodo-6-methyl-4,5,6,7-tetrahydropyrazolo[1,5-a]pyridine (0.40 g, 1.53 mmol). The reaction was immersed in an ice-bath, and isopropylmagnesium chloride lithium chloride complex in THF (1.3 M; 1.5 mL, 2.0 mmol) was added dropwise. The reaction was maintained between 0 and 3° C.

for 30 min. Then 2-isopropoxy-4,4,5,5-tetramethyl-1,3,2-dioxaborolane (0.426 g, 2.29 mmol) was added via syringe, and the ice bath was removed. The reaction was maintained under these conditions for 18 h and then diluted with saturated aqueous ammonium chloride. The mixture was extracted in EtOAc (3×), and the combined organic layers were dried over sodium sulfate, filtered and concentrated under reduced pressure to afford 6-methyl-3-(4,4,5,5-tetramethyl-1,3,2-dioxaborolan-2-yl)-4,5,6,7-tetrahydropyrazolo[1,5-a]pyridine (0.186 g). This material was used in the next step without further purification. m/z: ES+ [M+H]+ 263.

Preparation of (1S,3R)-3-acetamido-N-(5-chloro-4-(6-methyl-4,5,6,7-tetrahydropyrazolo[1,5-a]pyridin-3-yl)pyridin-2-yl)cyclohexanecarboxamide

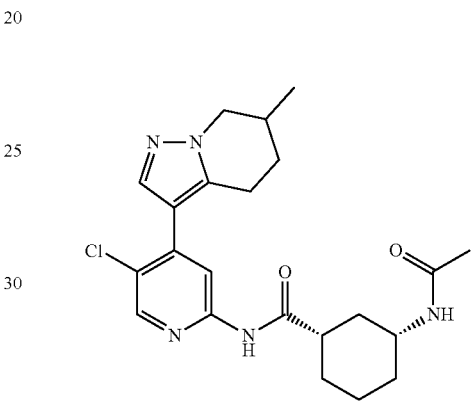

Mixture of Examples 68 and 69, ratio unknown 1,4-Dioxane (5 mL) and water (0.63 mL) were added to a flask charged with (1S,3R)-3-acetamido-N-(5-chloro-4-iodopyridin-2-yl)cyclohexanecarboxamide (0.23 g, 0.55 mmol; prepared according to Example 12) and 6-methyl-3-(4,4,5,5-tetramethyl-1,3,2-dioxaborolan-2-yl)-4,5,6,7-tetrahydropyrazolo[1,5-a]pyridine (0.19 g, 0.71 mmol). The reaction mixture was evacuated and purged with nitrogen. Then cesium carbonate (0.444 g, 1.36 mmol) and PdCl$_2$(dppf) (0.040 g, 0.05 mmol) were added. The reaction was set in an oil bath preheated to 95° C., and the reaction was maintained under these conditions for 2 h. The reaction was then cooled to r.t. and filtered through Celite® using an ethyl acetate wash. The filtrate was washed with saturated aqueous sodium chloride, and the organic layer was dried over sodium sulfate, filtered and concentrated under reduced pressure. The resulting gray solid was purified by flash silica chromatography, elution gradient 1 to 10% methanol in ethyl acetate, to afford (1S,3R)-3-acetamido-N-(5-chloro-4-(6-methyl-4,5,6,7-tetrahydropyrazolo[1,5-a]pyridin-3-yl)pyridin-2-yl)cyclohexanecarboxamide (0.16 g, 69%). $^1$H NMR (300 MHz, DMSO-d$_6$, 27° C.) 0.99-1.15 (4H, m), 1.20-1.33 (3H, m), 1.37-1.48 (1H, m), 1.68-1.77 (6H, m), 1.81-1.92 (2H, m), 2.10-2.20 (1H, m), 2.54-2.62 (1H, m), 2.79-2.87 (2H, m), 3.48-3.61 (1H, m), 3.65 (1H, dd), 4.26 (1H, dd), 7.73 (1H, br d), 7.76 (1H, s), 8.15 (1H, s), 8.38 (1H, s), 10.58 (1H, s). m/z: ES+ [M+H]+ 430.

Example 70 and Example 71: Preparation of Isomer 1 and Isomer 2 of (1S,3R)-3-acetamido-N-(5-chloro-4-(6-methoxy-4,5,6,7-tetrahydropyrazolo[1,5-a]pyridin-3-yl)pyridin-2-yl)cyclohexanecarboxamide

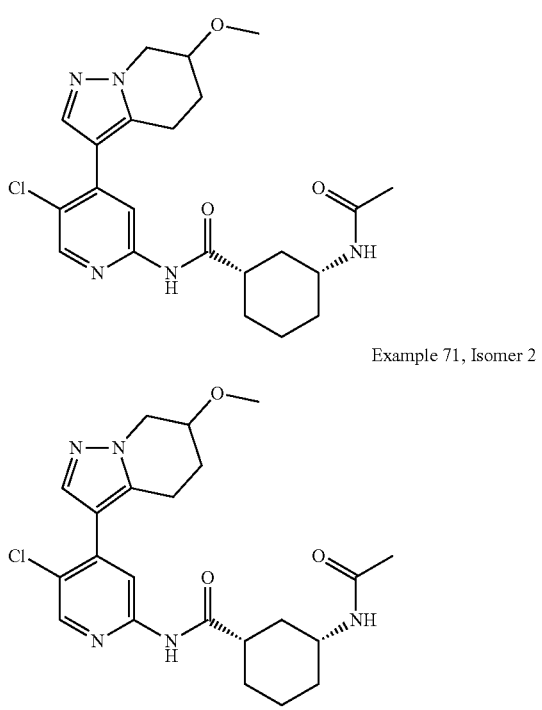

Example 70, Isomer 1

Example 71, Isomer 2

Pure enantiomers. The configuration of the methoxy is unknown for Examples 70 and 71 but is opposite in Example 70 vs Example 71.

(1S,3R)-3-acetamido-N-(5-chloro-4-(6-methoxy-4,5,6,7-tetrahydropyrazolo[1,5-a]pyridin-3-yl)pyridin-2-yl)cyclohexanecarboxamide (100 mg, 0.22 mmol) was resolved by preparative HPLC conditions (Chiralpak IA column, 5 μm, 20 mm diameter, 250 mm length, 25° C. column temperature, 15 mL/min flow rate), eluting with isocratic 50% ethanol in hexane over 22 min to afford faster eluting (10.8 min) isomer 1 of (1S,3R)-3-acetamido-N-(5-chloro-4-(6-methoxy-4,5,6,7-tetrahydropyrazolo[1,5-a]pyridin-3-yl)pyridin-2-yl)cyclohexanecarboxamide (0.030 g, 30%) and slower eluting (17.9 min) isomer 2 of (1S,3R)-3-acetamido-N-(5-chloro-4-(6-methoxy-4,5,6,7-tetrahydropyrazolo[1,5-a]pyridin-3-yl)pyridin-2-yl)cyclohexanecarboxamide (0.030 g, 30%) as white solids.

Example 70, Isomer 1

$^1$H NMR (400 MHz, DMSO-$d_6$, 19° C.) 1.00-1.14 (1H, m), 1.20-1.34 (3H, m), 1.72-1.80 (6H, m), 1.84-1.97 (2H, m), 2.07-2.19 (1H, m), 2.56-2.66 (1H, m), 2.70-2.92 (2H, m), 3.36 (3H, s), 3.48-3.63 (1H, m), 3.93-4.02 (1H, m), 4.23 (2H, d), 7.76-7.83 (2H, m), 8.15 (1H, s), 8.39 (1H, s), 10.64 (1H, s). m/z: ES+ [M+H]+ 446.

Example 71, Isomer 2

$^1$H NMR (400 MHz, DMSO-$d_6$, 19° C.) 1.00-1.17 (1H, m), 1.19-1.35 (3H, m), 1.72-1.80 (6H, m), 1.85-1.97 (2H, m), 2.06-2.19 (1H, m), 2.55-2.63 (1H, m), 2.71-2.92 (2H, m), 3.36 (3H, s), 3.50-3.62 (1H, m), 3.93-4.02 (1H, m), 4.23 (2H, d), 7.76-7.83 (2H, m), 8.16 (1H, s), 8.39 (1H, s), 10.64 (1H, s). m/z: ES+ [M+H]+ 446.

Analytical SFC Conditions:
Column: Chiralpak IA-3 column,
Column Dimensions: 3 μm, 4.6 mm diameter, 50 mm length,
Column Temperature: 25° C.
Mobile Phase A: Hexane containing 0.1% diethylamine
Mobile Phase B: Ethanol
Gradient: Isocratic 50% Mobile Phase B
Flow Rate: 1.5 mL/min over 10 min
Retention Time: 1.31 min, Example 70, Isomer 1
2.04 min, Example 71, Isomer 2
e.e. 100%, Example 70, Isomer 1
100%, Example 71, Isomer 2

Procedures used to prepare the starting material (1S,3R)-3-acetamido-N-(5-chloro-4-(6-methoxy-4,5,6,7-tetrahydropyrazolo[1,5-a]pyridin-3-yl)pyridin-2-yl)cyclohexanecarboxamide are described below:

Preparation of 6-methoxypyrazolo[1,5-a]pyridine

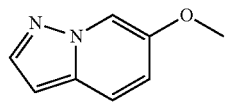

Cesium carbonate (3.31 g, 10.2 mmol) was added to 6-bromopyrazolo[1,5-a]pyridine (1.00 g, 5.08 mmol), MeOH (0.41 mL, 10 mmol), palladium acetate (0.057 g, 0.25 mmol) and 2-(di-1-adamantylphosphino)-3,6-dimethoxy-2',4'6'-triisopropyl-1,1'-biphenyl (AdBrettPhos; 0.14 g, 0.25 mmol) in toluene (10 mL). The resulting mixture was stirred at 90° C. for 2 h. The above reaction was repeated in a separate reaction. Once both reactions were cooled, they were combined, filtered, and concentrated under reduced pressure. The resulting residue was purified by flash silica chromatography, elution gradient 0 to 20% EtOAc in petroleum ether. Pure fractions were concentrated under reduced pressure to afford 6-methoxypyrazolo[1,5-a]pyridine (0.83 g, 55%) as a colourless oil. $^1$H NMR (400 MHz, DMSO-$d_6$, 27° C.) 3.82 (3H, s), 6.54 (1H, s), 7.01 (1H, d), 7.61 (1H, d), 7.87 (1H, s), 8.38 (1H, s).

Preparation of 6-methoxy-4,5,6,7-tetrahydropyrazolo[1,5-a]pyridine

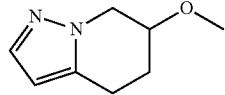

6-Methoxypyrazolo[1,5-a]pyridine (0.36 g, 2.4 mmol) and palladium on carbon (10 wt %; 0.078 g, 0.73 mmol) in MeOH (50 mL) was stirred under an atmosphere of hydrogen at 20 atm and 80° C. for 16 h. The mixture was filtered through a Celite® pad, and the filtrate was concentrated under reduced pressure. The resulting residue was diluted with EtOAc (25 mL) and washed sequentially with saturated saturated aqueous sodium hydrogencarbonate (25 mL) and saturated aqueous sodium chloride (25 mL). The organic layer was dried over sodium sulfate, filtered and concentrated under reduced pressure to afford 6-methoxy-4,5,6,7-tetrahydropyrazolo[1,5-a]pyridine (0.30 g, 81%) as a yellow waxy solid. $^1$H NMR (400 MHz, DMSO, 20° C.) 1.85-1.94 (1H, m), 1.98-2.09 (1H, m), 2.71-2.78 (2H, m), 3.32 (3H, s), 3.89 (1H, m), 4.02-4.18 (2H, m), 5.97 (1H, d), 7.34 (1H, d).

Preparation of 3-iodo-5-methoxy-4,5,6,7-tetrahydropyrazolo[1,5-a]pyridine

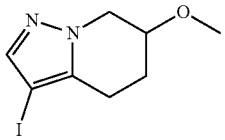

NIS (0.559 g, 2.48 mmol) was added to 5-methoxy-4,5,6,7-tetrahydropyrazolo[1,5-a]pyridine (0.27 g, 1.77 mmol) in acetonitrile (10 mL). The resulting mixture was stirred at r.t. for 30 minutes. The reaction mixture was concentrated under reduced pressure, and the resulting residue was diluted with EtOAc (25 mL). This new mixture was washed sequentially with water (25 mL) and saturated aqueous sodium chloride (25 mL). The organic layer was dried over sodium sulfate, filtered and concentrated under reduced pressure. The resulting residue was purified by flash silica chromatography, elution gradient 0 to 30% EtOAc in petroleum ether. Product fractions were concentrated under reduced pressure to afford 3-iodo-5-methoxy-4,5,6,7-tetrahydropyrazolo[1,5-a]pyridine (0.40 g, 81%) as a yellow oil. $^1$H NMR (400 MHz, DMSO-d$_6$, 21° C.) 1.78-1.99 (1H, m), 2.02-2.23 (1H, m), 2.53-2.60 (2H, m), 3.34 (3H, s), 3.82-3.96 (1H, m), 4.07-4.26 (2H, m), 7.48 (1H, s).

Preparation of 6-methoxy-3-(4,4,5,5-tetramethyl-1,3,2-dioxaborolan-2-yl)-4,5,6,7-tetrahydropyrazolo[1,5-a]pyridine

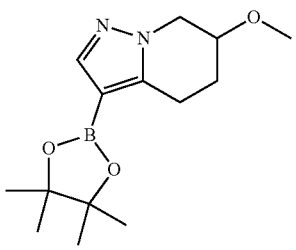

n-BuLi (0.805 mL, 2.01 mmol) was added to 3-iodo-6-methoxy-4,5,6,7-tetrahydropyrazolo[1,5-a]pyridine (0.4 g, 1.44 mmol), 2-isopropoxy-4,4,5,5-tetramethyl-1,3,2-dioxaborolane (0.401 g, 2.16 mmol), and TMEDA (0.30 mL, 2.0 mmol) in THF (20 mL) cooled to −78° C. under nitrogen. The resulting mixture was maintained at −78° C. for 1 hour. The reaction mixture was then quenched with saturated aqueous ammonium chloride (200 mL), extracted with EtOAc (3×150 mL), the organic layer was dried over sodium sulfate, filtered and concentrated under reduced pressure to afford 6-methoxy-3-(4,4,5,5-tetramethyl-1,3,2-dioxaborolan-2-yl)-4,5,6,7-tetrahydropyrazolo[1,5-a]pyridine (0.400 g, 100%) as a colourless gum, contaminated with 14 wt % des-iodo starting material (NMR analysis). This material was carried on to the next step without further purification.

Preparation of Tert-butyl ((1R,3S)-3-((5-chloro-4-(6-methoxy-4,5,6,7-tetrahydropyrazolo pyridin-3-yl)pyridin-2-yl)carbamoyl)cyclohexyl)carbamate

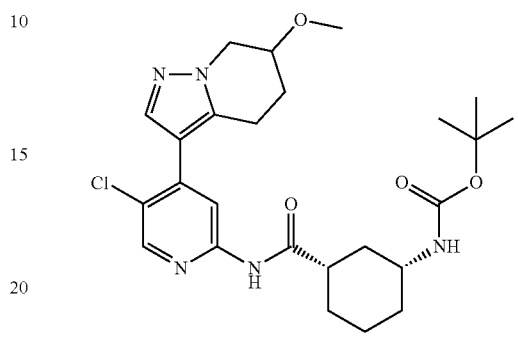

2nd Generation XPhos Precatalyst (0.049 g, 0.06 mmol) was added to 6-methoxy-3-(4,4,5,5-tetramethyl-1,3,2-dioxaborolan-2-yl)-4,5,6,7-tetrahydropyrazolo[1,5-a]pyridine (0.387 g, 1.25 mmol), tert-butyl ((1R,3S)-3-((5-chloro-4-iodopyridin-2-yl)carbamoyl)cyclohexyl)carbamate (0.3 g, 0.63 mmol; prepared according to Example 10) and cesium carbonate (0.611 g, 1.88 mmol) in dioxane (10 mL) and water (1 mL) under nitrogen. The resulting mixture was stirred at 100° C. for 1 hour, and the reaction mixture was then cooled and diluted with EtOAc (200 mL). The resulting mixture was washed sequentially with water (200 mL) and saturated aqueous sodium chloride (200 mL). The organic layer was dried over sodium sulfate, filtered and concentrated under reduced pressure. The resulting residue was purified by flash silica chromatography, elution gradient 0 to 60% EtOAc in petroleum ether. Pure fractions were concentrated under reduced pressure to afford tert-butyl ((1R,3S)-3-((5-chloro-4-(6-methoxy-4,5,6,7-tetrahydropyrazolo[1,5-a]pyridin-3-yl)pyridin-2-yl)carbamoyl)cyclohexyl)carbamate (0.14 g, 44%) as a white solid. m/z: ES+ [M+H]+ 504.

Preparation of (1S,3R)-3-amino-N-(5-chloro-4-(6-methoxy-4,5,6,7-tetrahydropyrazolo[1,5-a]pyridin-3-yl)pyridin-2-yl)cyclohexanecarboxamide

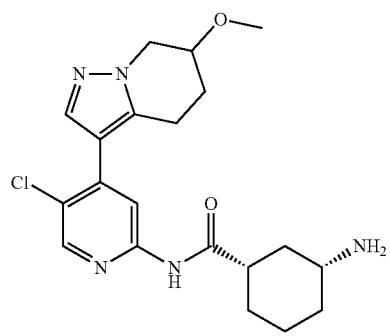 [SMILES: COC1CCc2c(-c3cc(NC(=O)[C@H]4CCC[C@@H](N)C4)ncc3Cl)cnn2C1]

TFA (4 mL, 51.92 mmol) was added to tert-butyl ((1R,3S)-3-((5-chloro-4-(6-methoxy-4,5,6,7-tetrahydropyrazolo

[1,5-a]pyridin-3-yl)pyridin-2-yl)carbamoyl)cyclohexyl)carbamate (0.14 g, 0.28 mmol) in DCM (10 mL). The resulting mixture was stirred at r.t. for 1 hour. The reaction mixture was concentrated under reduced pressure to afford crude (1S,3R)-3-amino-N-(5-chloro-4-(6-methoxy-4,5,6,7-tetrahydropyrazolo[1,5-a]pyridin-3-yl)pyridin-2-yl)cyclohexanecarboxamide as the di-trifluoroacetic acid salt (0.15 g, 98%) and a yellow gum. m/z: ES+ [M+H]+ 404.

Preparation of (1S,3R)-3-acetamido-N-(5-chloro-4-(6-methoxy-4,5,6,7-tetrahydropyrazolo[1,5-a]pyridin-3-yl)pyridin-2-yl)cyclohexanecarboxamide

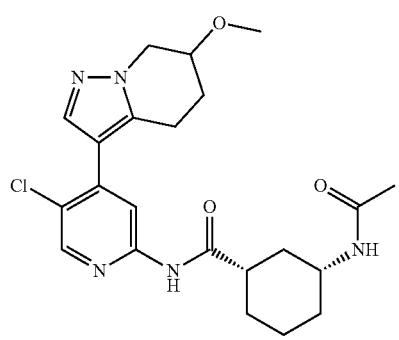 [SMILES: COC1CCc2c(-c3cc(NC(=O)[C@H]4CCC[C@@H](NC(C)=O)C4)ncc3Cl)cnn2C1]

Mixture of Examples 70 and 71, ratio unknown.

Acetic anhydride (0.023 mL, 0.25 mmol) was added to (1S,3R)-3-amino-N-(5-chloro-4-(6-methoxy-4,5,6,7-tetrahydropyrazolo[1,5-a]pyridin-3-yl)pyridin-2-yl)cyclohexanecarboxamide (di-trifluoroacetic acid salt; 0.15 g, 0.25 mmol) and TEA (0.17 mL, 1.2 mmol) in DCM (5 mL). The resulting mixture was stirred at r.t. for 16 h. The reaction was then concentrated under reduced pressure, and the crude product was purified by preparative HPLC (XBridge Prep C18 OBD column, 21.2 mm diameter, 250 mm length), using decreasingly polar mixtures of water (containing 0.1% NH$_4$HCO$_3$) and MeCN as eluents. Fractions containing the desired compound were concentrated under reduced pressure to afford (1S,3R)-3-acetamido-N-(5-chloro-4-(6-methoxy-4,5,6,7-tetrahydropyrazolo[1,5-a]pyridin-3-yl)pyridin-2-yl)cyclohexanecarboxamide (0.100 g, 91%; mixture of Examples 70 and 71) as a white solid. m/z: ES+ [M+H]+ 446.

Example 72 and Example 73: Preparation of Isomer 1 and Isomer 2 of (1S,3R)-3-acetamido-N-(5-chloro-4-(5-methoxy-4,5,6,7-tetrahydropyrazolo[1,5-a]pyridin-3-yl)pyridin-2-yl)cyclohexanecarboxamide Example 72, Isomer 1

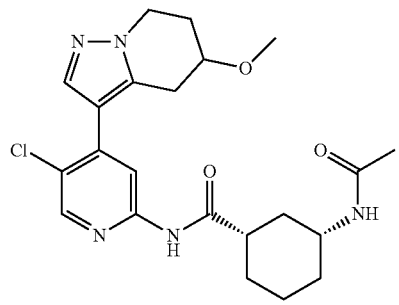

Example 73, Isomer 2

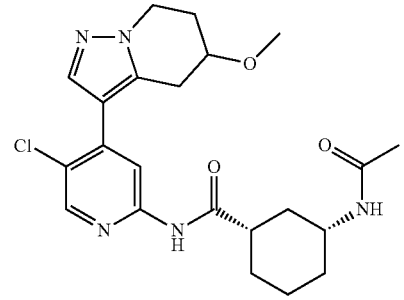

Pure enantiomers. The configuration of the methoxy is unknown for Examples 72 and 73 but is opposite in Example 72 vs Example 73

(1S,3R)-3-acetamido-N-(5-chloro-4-(5-methoxy-4,5,6,7-tetrahydropyrazolo[1,5-a]pyridin-3-yl)pyridin-2-yl)cyclohexanecarboxamide (120 mg, 0.270 mmol; prepared according to the procedures of Examples 70 and 71 substituting 5-bromopyrazolo[1,5-a]pyridine for 6-bromopyrazolo[1,5-a]pyridine) was resolved by preparative HPLC conditions (Chiralpak ID column, 5 μm, 20 mm diameter, 250 mm length, 25° C. column temperature, 15 mL/min flow rate), eluting with isocratic 50% ethanol in hexane over 31 min to afford faster eluting (16.0 min) isomer 1 of (1S,3R)-3-acetamido-N-(5-chloro-4-(6-methoxy-4,5,6,7-tetrahydropyrazolo[1,5-a]pyridin-3-yl)pyridin-2-yl)cyclohexanecarboxamide (0.040 g, 33.3%) and slower eluting (24.8 min) isomer 2 of (1S,3R)-3-acetamido-N-(5-chloro-4-(6-methoxy-4,5,6,7-tetrahydropyrazolo[1,5-a]pyridin-3-yl)pyridin-2-yl)cyclohexanecarboxamide (0.040 g, 33.3%) as white solids.

Example 72, Isomer 1

$^1$H NMR (400 MHz, DMSO-d$_6$, 19° C.) δ 1.03-1.14 (1H, m), 1.19-1.35 (3H, m), 1.65-1.84 (6H, m), 1.84-1.94 (1H, m), 2.16-2.25 (2H, m), 2.56-2.66 (1H, m), 2.83-2.94 (1H, m), 2.97-3.08 (1H, m), 3.29 (3H, s), 3.50-3.63 (1H, m), 3.82-3.91 (1H, m), 4.06-4.24 (2H, m), 7.77 (1H, s), 7.80 (1H, d), 8.13 (1H, s), 8.39 (1H, s), 10.64 (1H, s). m/z: ES+ [M+H]+ 446.

Example 73, Isomer 2

$^1$H NMR (400 MHz, DMSO-d$_6$, 19° C.) δ 1.00-1.14 (1H, m), 1.19-1.35 (3H, m), 1.72-1.81 (6H, m), 1.84-1.92 (1H, m), 2.16-2.25 (2H, m), 2.56-2.66 (1H, m), 2.83-2.93 (1H, m), 3.03 (1H, m), 3.29 (3H, s), 3.48-3.62 (1H, m), 3.82-3.91 (1H, m), 4.06-4.24 (2H, m), 7.77 (1H, s), 7.80 (1H, d), 8.13 (1H, s), 8.39 (1H, s), 10.64 (1H, s). m/z: ES+ [M+H]+ 446.

Analytical SFC Conditions:
Column: Chiralpak ID-3 column,
Column Dimensions: 3 μm, 4.6 mm diameter, 50 mm length,
Column Temperature: 25° C.
Mobile Phase A: Hexane containing 0.1% diethylamine
Mobile Phase B: Ethanol
Gradient: Isocratic 50% Mobile Phase B
Flow Rate: 1.5 mL/min over 10 min
Retention Time: 1.57 min, Example 72, Isomer 1
2.54 min, Example 73, Isomer 2
e.e. 99.9%, Example 72, Isomer 1

>99%, Example 73, Isomer 2

Example 74: Preparation of (1S,3R)-3-acetamido-N-(5-fluoro-4-(5,6,7,8-tetrahydro-4H-pyrazolo[1,5-a]azepin-3-yl)pyridin-2-yl)cyclohexanecarboxamide

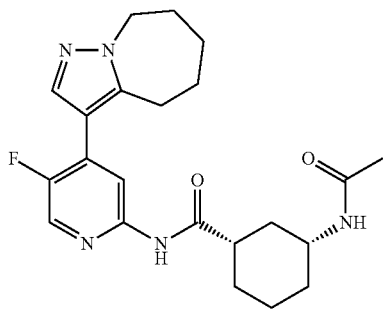 [SMILES: CC(=O)N[C@@H]1CCC[C@H](C(=O)Nc2cc(-c3cnn4c3CCCCC4)c(F)cn2)C1]

Acetic anhydride (0.11 mL, 1.1 mmol) was added to a stirred solution of (1S,3R)-3-amino-N-(5-fluoro-4-(5,6,7,8-tetrahydro-4H-pyrazolo[1,5-a]azepin-3-yl)pyridin-2-yl)cyclohexanecarboxamidee (350 mg, 0.94 mmol), triethylamine (0.28 mL, 2.0 mmol) and DCM (10 mL). The reaction mixture was stirred at r.t. for 4 h. Silica was added, and the resulting mixture was concentrated under reduced pressure. The resulting adsorbed residue was purified by flash silica chromatography, eluting with 0.5% methanol in ethyl acetate, to afford (1S,3R)-3-acetamido-N-(5-fluoro-4-(5,6,7,8-tetrahydro-4H-pyrazolo[1,5-a]azepin-3-yl)pyridin-2-yl)cyclohexanecarboxamide (200 mg, 51%) as an off-white solid. $^1$H NMR (400 MHz, DMSO-$d_6$, 30° C.) 1.03-1.07 (1H, m), 1.30 (3H, m), 1.57-1.96 (13H, m), 2.56-2.62 (1H, m), 2.68-2.93 (2H, m), 3.47-3.66 (1H, m), 4.19-4.4 (2H, m), 7.49 (1H, d), 7.73 (1H, d), 8.09 (1H, d), 8.32 (1H, d), 10.48 (1H, s). m/z: ES+ [M+H]+ 414.

Procedures used to prepare the starting material (1S,3R)-3-amino-N-(5-fluoro-4-(5,6,7,8-tetrahydro-4H-pyrazolo[1,5-a]azepin-3-yl)pyridin-2-yl)cyclohexanecarboxamide are described below:

Preparation of 3-(2-chloro-5-fluoropyridin-4-yl)-5,6,7,8-tetrahydro-4H-pyrazolo[1,5-a]azepine

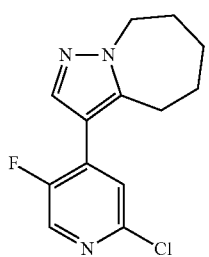 [SMILES: Fc1cnc(Cl)cc1-c1cnn2c1CCCCC2]

2-Chloro-5-fluoro-4-iodopyridine (1.064 g, 4.13 mmol) 3-(4,4,5,5-tetramethyl-1,3,2-dioxaborolan-2-yl)-5,6,7,8-tetrahydro-4H-pyrazolo[1,5-a]azepine (1.30 g, 4.96 mmol; prepared according to Example 66), 2nd Generation XPhos Precatalyst (0.325 g, 0.41 mmol) and potassium phosphate, dibasic, (2.16 g, 12.4 mmol) were dissolved in degassed dioxane (20 mL) and water (1 mL) at 21° C. The mixture was stirred at 90° C. for 24 h and then cooled. The mixture was diluted with EtOAc (30 mL), washed with water (10 mL), and then concentrated under reduced pressure. The resulting residue was purified by flash silica chromatography, elution gradient 0 to 50% EtOAc in heptane. Product fractions were evaporated to dryness to afford 3-(2-chloro-5-fluoropyridin-4-yl)-5,6,7,8-tetrahydro-4H-pyrazolo[1,5-a]azepine (0.650 g, 59%) as an oil. $^1$H NMR (400 MHz, CDCl$_3$, 30° C.) 1.62-1.94 (6H, m), 2.77-2.88 (2H, m), 4.29-4.4 (2H, m), 7.22 (1H, d), 7.50 (1H, d), 8.25 (1H, d). m/z: ES+ [M+H]+ 266.

Preparation of Tert-butyl ((1R,3S)-3-((5-fluoro-4-(5,6,7,8-tetrahydro-4H-pyrazolo[1,5-a]azepin-3-yl)pyridin-2-yl)carbamoyl)cyclohexyl)carbamate

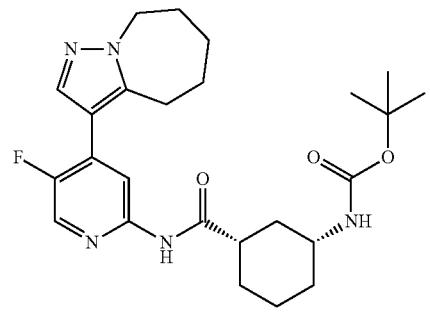 [SMILES: CC(C)(C)OC(=O)N[C@@H]1CCC[C@H](C(=O)Nc2cc(-c3cnn4c3CCCCC4)c(F)cn2)C1]

Tetrakis(triphenylphosphine)palladium(0) (0.30 g, 0.26 mmol) was added to a degassed mixture of 3-(2-chloro-5-fluoropyridin-4-yl)-5,6,7,8-tetrahydro-4H-pyrazolo[1,5-a]azepine (0.700 g, 2.63 mmol), tert-butyl ((1R,3S)-3-carbamoylcyclohexyl)carbamate (0.638 g, 2.63 mmol; prepared according to Example 25), 9,9-dimethyl-4,5-bis(diphenylphosphino)xanthene (0.305 g, 0.53 mmol) and cesium carbonate (2.58 g, 7.90 mmol) in 1,4-dioxane (10 mL). The resulting mixture was purged for 5 mins under nitrogen, and the resulting suspension was subjected to microwave conditions (120° C., 17 h). The reaction mixture was cooled and partitioned between water (20 mL) and ethyl acetate (100 mL) before being filtered. The layers were separated, and the organic layer concentrated under reduced pressure, adsorbed onto silica, and purified by flash silica chromatography, eluting with 50% EtOAc in heptane. Product fractions were concentrated under reduced pressure to afford crude tert-butyl ((1R,3S)-3-((5-fluoro-4-(5,6,7,8-tetrahydro-4H-pyrazolo[1,5-a]azepin-3-yl)pyridin-2-yl)carbamoyl)cyclohexyl)carbamate (0.90 g, 72%) as a white solid. m/z: ES+ [M+H]+ 472.

Preparation of (1S,3R)-3-amino-N-(5-fluoro-4-(5,6,7,8-tetrahydro-4H-pyrazolo[1,5-a]azepin-3-yl)pyridin-2-yl)cyclohexanecarboxamide

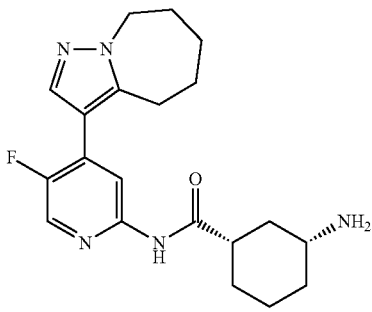 [SMILES: N[C@@H]1CCC[C@H](C(=O)Nc2cc(-c3cnn4c3CCCCC4)c(F)cn2)C1]

TFA (1 mL) was added to a solution of tert-butyl ((1R,3S)-3-((5-fluoro-4-(5,6,7,8-tetrahydro-4H-pyrazolo[1,5-a]azepin-3-yl)pyridin-2-yl)carbamoyl)cyclohexyl)carbamate (600 mg, 1.27 mmol) in DCM (10 mL). The mixture was stirred at r.t. for 24 h, and then the reaction was concentrated under reduced pressure. The resulting residue was purified by ion-exchange chromatography, using an SCX column and eluting with 7N ammonia in methanol. Product fractions were concentrated under reduced pressure to afford (1S,3R)-3-amino-N-(5-fluoro-4-(5,6,7,8-tetrahydro-4H-pyrazolo[1,5-a]azepin-3-yl)pyridin-2-yl)cyclohexanecarboxamide (350 mg, 74%) as a white solid. m/z: ES+ [M+H]+ 372.

Example 75: Preparation of (1S,3R)—N-(4-(5,5-dimethyl-5,6-dihydro-4H-pyrrolo[1,2-b]pyrazol-3-yl)-5-methylpyridin-2-yl)-3-(2-hydroxyacetamido)cyclohexanecarboxamide

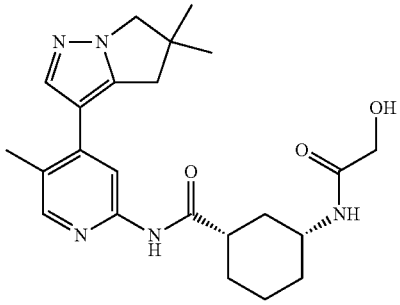 [SMILES: Cc1cnc(NC(=O)[C@H]2CCC[C@@H](NC(=O)CO)C2)cc1-c1cnn2c1CC(C)(C)C2]

Cesium carbonate (436 mg, 1.34 mmol) and 2nd Generation XPhos Precatalyst (35 mg, 0.04 mmol) were added to a degassed mixture of 5,5-dimethyl-3-(4,4,5,5-tetramethyl-1,3,2-dioxaborolan-2-yl)-5,6-dihydro-4H-pyrrolo[1,2-b]pyrazole (168 mg, 0.470 mmol; prepared according to Example 23) and (1S,3R)-3-(2-hydroxyacetamido)-N-(4-iodo-5-methylpyridin-2-yl)cyclohexanecarboxamide (186 mg, 0.45 mmol) in 1,4-dioxane (3.7 mL) and water (0.7 mL) to give a colorless solution. The reaction was stirred at 85° C. for 18 h and then cooled and diluted with EtOAc (50 mL). This new mixture was washed with water and saturated aqueous sodium chloride. The aqueous layers were extracted with EtOAc (2×50 mL). The combined organic layers were dried over magnesium sulfate, filtered, and concentrated under reduced pressure. The resulting residue was adsorbed onto silica gel and purified by flash silica chromatography, eluting with 10% MeOH in DCM, to afford (1S,3R)—N-(4-(5,5-dimethyl-5,6-dihydro-4H-pyrrolo[1,2-b]pyrazol-3-yl)-5-methylpyridin-2-yl)-3-(2-hydroxyacetamido)cyclohexanecarboxamide (78 mg, 41%) as a white solid. $^1$H NMR (300 MHz, DMSO-$d_6$, 27° C.) 1.18-1.38 (9H, m), 1.46 (1H, q), 1.65-1.92 (4H, m), 2.32 (3H, s), 2.57-2.67 (1H, m), 2.85 (2H, s), 3.58-3.72 (1H, m), 3.78 (1H, d), 3.93 (2H, s), 5.36 (1H, t), 7.54 (1H, d), 7.77 (1H, s), 8.07 (1H, s), 8.13 (1H, 2), 10.27 (1H, s). m/z: ES+ [M+H]+ 426.

Optical Rotation:
Concentration: 0.1 g/dL
Lamp: Sodium
Wavelength: 589 nm
Temperature: 25° C.
Path length: 10 cm
Cell volume: 1 mL
Solvent: DMSO
[α]=+82

Procedures used to prepare the starting material (1S,3R)-3-(2-hydroxyacetamido)-N-(4-iodo-5-methylpyridin-2-yl)cyclohexanecarboxamide are described below:

Preparation of (1S,3R)-3-amino-N-(4-iodo-5-methylpyridin-2-yl)cyclohexanecarboxamide

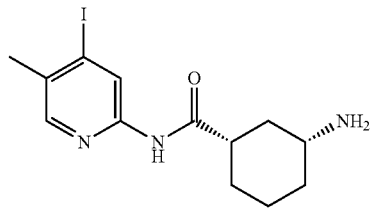 [SMILES: Cc1cnc(NC(=O)[C@H]2CCC[C@@H](N)C2)cc1I]

Hydrochloric acid in dioxane (4M; 2 mL, 8 mmol) was added to tert-butyl ((1R,3S)-3-((4-iodo-5-methylpyridin-2-yl)carbamoyl)cyclohexyl)carbamate (530 mg, 1.15 mmol; prepared according to Example 47) in MeOH (11 mL) to give a colorless solution. The reaction was stirred for 2 h at r.t. and then concentrated under reduced pressure to afford (1S,3R)-3-amino-N-(4-iodo-5-methylpyridin-2-yl)cyclohexanecarboxamide (550 mg) as the dihydrochloride salt, a white solid. This solid was carried on to the next step without further purification. $^1$H NMR (300 MHz, DMSO-$d_6$, 27° C.) 1.11-1.36 (3H, m), 1.49 (1H, q), 1.76-1.88 (2H, m), 1.88-1.89 (1H, m) 2.04 (1H, d), 2.30 (3H, s), 2.54-2.67 (1H, m), 2.94-3.07 (1H, m), 8.03 (3H, br. s), 8.17 (1H, s), 8.61 (1H, s), 10.58 (1H, br. s). One HCl equivalent detected, second assumed to be buried under broad HOD peak at 5.9 ppm. m/z: ES+ [M+H]+ 360.

Preparation of (1S,3R)-3-(2-hydroxyacetamido)-N-(4-iodo-5-methylpyridin-2-yl)cyclohexanecarboxamide

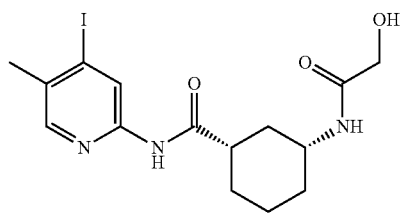 [SMILES: Cc1cnc(NC(=O)[C@H]2CCC[C@@H](NC(=O)CO)C2)cc1I]

HATU (328 mg, 0.86 mmol) was added to a mixture of (1S,3R)-3-amino-N-(4-iodo-5-methylpyridin-2-yl)cyclohexanecarboxamide dihydrochloride (228 mg, 0.53 mmol), 2-hydroxyacetic acid (66 mg, 0.86 mmol), TEA (0.24 mL, 1.7 mmol), DMF (2.8 mL), and DCM (2.8 mL). The reaction was stirred at r.t. under nitrogen for 5 h and then concentrated under reduced pressure. The resulting residue was taken up in DCM and washed with water (4×25 mL) and saturated aqueous sodium chloride. The organic layer was dried over sodium sulfate, filtered and concentrated under reduced pressure. The resulting residue was adsorbed onto silica gel and purified by flash silica chromatography, eluting with 0 to 10% methanol in DCM, to afford (1S,3R)-3-(2-hydroxyacetamido)-N-(4-iodo-5-m ethylpyridin-2-yl)cyclohexanecarboxamide (186 mg, 52%) as a white solid. $^1$H NMR (300 MHz, DMSO-d$_6$, 27° C.) 1.17-1.34 (3H, m) 1.43 (1H, q) 1.60-1.91 (4H, m) 2.28 (3H, s), 2.54-2.69 (1H, m), 3.56-3.72 (1H, m), 3.78 (2H, d), 5.36 (1H, t) 7.55 (1H, d) 8.16 (1H, s) 8.61 (1H, s) 10.45 (1H, s). m/z: ES+ [M+H]+ 418.

Example 76: Preparation of N-((1R,3S)-3-((4-(5,5-dimethyl-5,6-dihydro-4H-pyrrolo[1,2-b]pyrazol-3-yl)-5-methylpyridin-2-yl)carbamoyl)cyclohexyl)oxetane-3-carboxamide

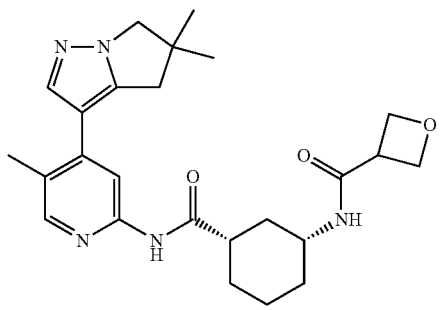 [SMILES: Cc1cnc(NC(=O)[C@H]2CCC[C@@H](NC(=O)C3COC3)C2)cc1-c1cnn2c1CC(C)(C)C2]

Cesium carbonate (247 mg, 0.76 mmol) and 2nd Generation XPhos Precatalyst (20 mg, 0.03 mmol) were added to a degassed mixture of 5,5-dimethyl-3-(4,4,5,5-tetramethyl-1,3,2-dioxaborolan-2-yl)-5,6-dihydro-4H-pyrrolo[1,2-b]pyrazole (90 mg, 0.25 mmol; prepared according to Example 23) and N-((1R,3S)-3-((4-iodo-5-methylpyridin-2-yl)carbamoyl)cyclohexyl)oxetane-3-carboxamide (112 mg, 0.25 mmol) in 1,4-dioxane (2.1 mL) and water (0.4 mL). The reaction was stirred at 85° C. for 18 h, cooled to r.t., and then diluted with EtOAc (50 mL). The mixture was washed with water and saturated aqueous sodium chloride. The combined aqueous layers were extracted with EtOAc (2×50 mL), and the combined organic layers were dried over magnesium sulfate, filtered, and concentrated under reduced pressure. The resulting residue was adsorbed onto silica gel and purified by flash silica chromatography, eluting with 10% MeOH in DCM, to afford an off-white solid (72 mg). This material was repurified by flash silica chromatography, 0 to 10% methanol in DCM, to afford N-((1R,3S)-3-((4-(5,5-dimethyl-5,6-dihydro-4H-pyrrolo[1,2-b]pyrazol-3-yl)-5-methylpyridin-2yl)carbamoyl)cyclohexyl)oxetane-3-carboxamide (50 mg, 44%) as a white solid. $^1$H NMR (300 MHz, DMSO-d$_6$, 27° C.) 1.00-1.17 (1H, m), 1.21-1.37 (9H, m) 1.68-1.84 (3H, m), 1.89 (1H, br d), 2.33 (3H, s), 2.55-2.67 (1H, m), 2.84 (2H, s), 3.53-3.74 (2H, m), 3.93 (2H, s), 4.54-4.65 (4H, m), 7.73-7.84 (2H, m), 8.07 (1H, s), 8.14 (1H, s), 10.28 (1H, s). m/z: ES+ [M+H]+ 452.

Optical Rotation:

Concentration: 0.1 g/dL

Lamp: Sodium

Wavelength: 589 nm

Temperature: 25° C.

Path length: 10 cm

Cell volume: 1 mL

Solvent: DMSO

[α]=+70.5

Procedures to prepare the starting material N-((1R,3S)-3-((4-iodo-5-methylpyridin-2-yl)carbamoyl)cyclohexyl)oxetane-3-carboxamide are described below:

Preparation of N-((1R,3S)-3-((4-iodo-5-methylpyridin-2-yl)carbamoyl)cyclohexyl)oxetane-3-carboxamide

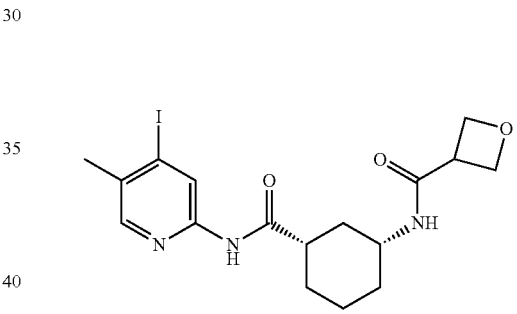

HATU (219 mg, 0.58 mmol) was added to a solution of (1S,3R)-3-amino-N-(4-iodo-5-methylpyridin-2-yl)cyclohexanecarboxamide dihydrochloride (228 mg, 0.53 mmol; prepared according to Example 75), oxetane-3-carboxylic acid (59 mg, 0.58 mmol), TEA (0.24 mL, 1.7 mmol), DCM (2.8 mL) and DMF (2.8 mL) to give a colorless solution. The reaction turned yellow over time; after 4 h at r.t., the reaction was concentrated under reduced pressure and then diluted with DCM. The mixture was washed with water (3×50 mL), dried over sodium sulfate, filtered, concentrated under reduced pressure. The resulting residue was adsorbed onto silica gel and purified by flash column chromatography, eluting with 0 to 10% MeOH and DCM to afford N-((1R,3S)-3-((4-iodo-5-methylpyridin-2-yl)carbamoyl)cyclohexyl)oxetane-3-carboxamide (112 mg, 47%) as a white solid. $^1$H NMR (300 MHz, DMSO-d$_6$, 27° C.) 0.99-1.17 (1H, m), 1.20-1.37 (3H, m), 1.70-1.83 (3H, m), 1.84-1.94 (1H, m), 2.29 (3H, s), 2.54-2.64 (1H, m), 3.55-3.73 (2H, m), 4.54-4.64 (4H, m), 7.81 (1H, d), 8.16 (1H, s), 8.61 (1H, s), 10.45 (1H, s). m/z: ES+ [M+H]+ 444.

Example 77: (1S,3R)-3-acetamido-N-(5-methyl-4-(4,5,6,7-tetrahydropyrazolo[1,5-a]pyridin-3-yl)pyridin-2-yl)cyclohexanecarboxamide

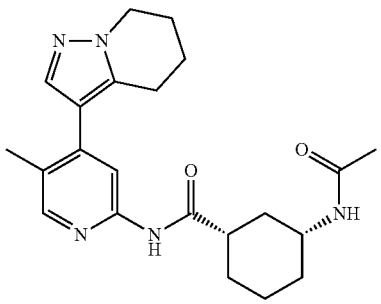 [SMILES: CC(=O)N[C@@H]1CCC[C@H](C(=O)Nc2cc(-c3cnn4c3CCCC4)c(C)cn2)C1]

To a stirred solution of (1S,3R)-3-amino-N-(5-methyl-4-(4,5,6,7-tetrahydropyrazolo[1,5-a]pyridin-3-yl)pyridin-2-yl)cyclohexanecarboxamide (150 mg, 0.42 mmol), triethylamine (0.12 mL, 0.89 mmol) in DCM (10 mL) was added acetic anhydride (0.048 mL, 0.51 mmol). The reaction mixture was stirred at r.t. for 4 h. Silica was added and the volatiles removed under vacuum. The residue was purified by flash silica chromatography, eluting with 0.5% methanol in ethyl acetate to afford (1S,3R)-3-acetamido-N-(5-methyl-4-(4,5,6,7-tetrahydropyrazolo[1,5-a]pyridin-3-yl)pyridin-2-yl)cyclohexanecarboxamide (140 mg, 83%) as an off-white solid. $^1$H NMR (400 MHz, DMSO-$d_6$, 30° C.) 1.04-1.11 (1H, m), 1.22-1.35 (3H, m), 1.7-1.94 (9H, m), 1.99-2.08 (2H, m), 2.23 (3H, s), 2.55-2.63 (1H, m), 2.75 (2H, t), 3.51-3.61 (1H, m), 4.13 (2H, t), 7.62 (1H, s), 7.72 (1H, d), 7.96 (1H, s), 8.16 (1H, s), 10.27 (1H, s). m/z: ES+ [M+H]+ 396.

Procedures used to prepare the starting material (1S,3R)-3-amino-N-(5-methyl-4-(4,5,6,7-tetrahydropyrazolo[1,5-a]pyridin-3-yl)pyridin-2-yl)cyclohexanecarboxamide are described below:

Preparation of Tert-butyl ((1R,3S)-3-((5-methyl-4-(4,5,6,7-tetrahydropyrazolo[1,5-a]pyridin-3-yl)pyridin-2-yl)carbamoyl)cyclohexyl)carbamate

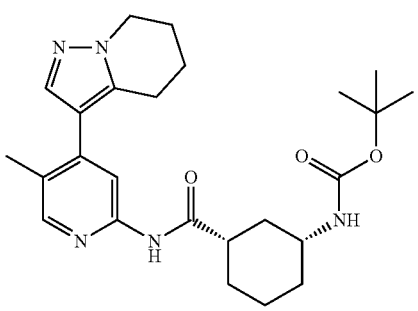 [SMILES: Cc1cnc(NC(=O)[C@H]2CCC[C@@H](NC(=O)OC(C)(C)C)C2)cc1-c1cnn2c1CCCC2]

2nd Generation XPhos Precatalyst (86 mg, 0.11 mmol) was added to a degassed mixture of 3-(4,4,5,5-tetramethyl-1,3,2-dioxaborolan-2-yl)-4,5,6,7-tetrahydropyrazolo[1,5-a]pyridine (324 mg, 1.31 mmol), tert-butyl ((1R,3S)-3-((4-iodo-5-methylpyridin-2-yl)carbamoyl)cyclohexyl)carbamate (500 mg, 1.09 mmol, prepared according to Example 47, Intermediate) and potassium phosphate, tribasic, (569 mg, 3.27 mmol) in 1,4-dioxane (10 mL) and water (1 mL). The mixture was degassed and was stirred at 85° C. for 24 h under nitrogen. The reaction mixture was cooled and silica was added. The mixture was concentrated under reduced pressure, and the resulting residue was purified by flash silica chromatography, eluting with isocratic 60% ethyl acetate in heptane, to afford tert-butyl ((1R,3S)-3-((5-methyl-4-(4,5,6,7-tetrahydropyrazolo[1,5-a]pyridin-3-yl)pyridin-2-yl)carbamoyl)cyclohexyl)carbamate (220 mg, 45%) as a solid. $^1$H NMR (400 MHz, DMSO, 30° C.) 1.05-1.14 (1H, m), 1.21-1.31 (3H, m), 1.38 (9H, s), 1.69-1.94 (7H, m), 1.96-2.08 (2H, m), 2.23 (3H, s), 2.54-2.61 (1H, m), 2.75 (2H, t), 4.13 (2H, t), 6.75 (1H, br d), 7.62 (1H, s), 7.96 (1H, s), 8.16 (1H, s), 10.25 (1H, s). m/z: ES+ [M+H]+ 454.

Preparation of (1S,3R)-3-amino-N-(5-methyl-4-(4,5,6,7-tetrahydropyrazolo[1,5-a]pyridin-2-yl)cyclohexanecarboxamide

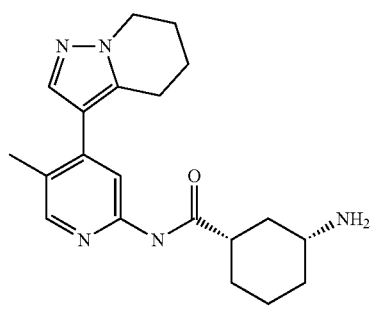 [SMILES: Cc1cnc(NC(=O)[C@H]2CCC[C@@H](N)C2)cc1-c1cnn2c1CCCC2]

TFA (1 mL) was added to tert-butyl ((1R,3S)-3-((5-methyl-4-(4,5,6,7-tetrahydropyrazolo[1,5-a]pyridin-3-yl)pyridin-2-yl)carbamoyl)cyclohexyl)carbamate (200 mg, 0.44 mmol) in DCM (10 mL). The mixture was stirred at r.t. for 24 h, and the volatiles were removed under reduced pressure. The resulting residue was purified by ion-exchange chromatography using an SCX column, eluting with 7N ammonia in methanol. Product fractions were concentrated under reduced pressure to afford (1S,3R)-3-amino-N-(5-methyl-4-(4,5,6,7-tetrahydropyrazolo[1,5-a]pyridin-3-yl)pyridin-2-yl)cyclohexanecarboxamide (150 mg, 96%) as a white solid. This material was used directly in the next step without further purification. m/z: ES+ [M+H]+ 354.

Example 78: (1S,3R)-3-acetamido-N-(5-chloro-4-(7-hydroxy-4,5,6,7-tetrahydropyrazolo[1,5-a]pyridin-3-yl)pyridin-2-yl)cyclohexanecarboxamide

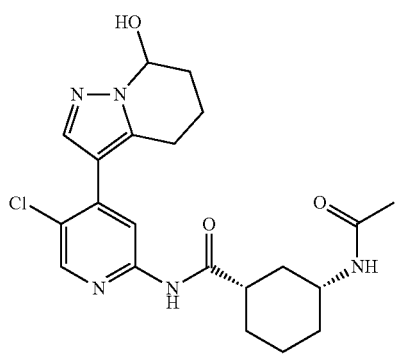 [SMILES: CC(=O)N[C@@H]1CCC[C@H](C(=O)Nc2cc(-c3cnn4c3CCCC4O)c(Cl)cn2)C1]

Unknown mixture of diastereomers as the hydroxy configuration is unknown.

Pyridine sulfur trioxide (40 mg, 0.25 mmol) was added to a solution of (1S,3R)-3-acetamido-N-(5-chloro-4-(5-(4-hydroxybutyl)-1H-pyrazol-4-yl)pyridin-2-yl)cyclohexanecarboxamide (100 mg, 0.23 mmol, prepared in Example 78a) in 2:1 DCM:DMSO (4 mL) at 0° C. After 2 h at 0° C. the reaction mixture was diluted with water and extracted with ethyl acetate (3×). The combined organic layers were dried over sodium sulfate, filtered, concentrated under reduced pressure. The resulting residue was purified by flash silica chromatography, elution gradient 0 to 15% MeOH in DCM containing 0.2% triethylamine, to afford a white solid. This solid was triturated with 10% DCM in hexanes to afford (1S,3R)-3-acetamido-N-(5-chloro-4-(7-hydroxy-4,5,6,7-tetrahydropyrazolo[1,5-a]pyridin-3-yl)pyridin-2-yl)cyclohexanecarboxamide (74 mg, 74%) as white foam solid. $^1$H NMR (300 MHz, DMSO-$d_6$, 27° C.) 0.98-1.11 (1H, m), 1.18-1.41 (3H, m), 1.70-1.81 (6H, m), 1.85-2.18 (4H, m), 2.56-2.66 (1H, m), 2.67-2.91 (2H, m), 3.49-3.67 (1H, m), 4.23-4.40 (1H, m), 5.54-5.73 (1H, m), 6.87 (1H, d), 7.75 (1H, d), 7.81 (1H, s), 8.15 (1H, s), 8.39 (1H, s), 10.59 (1H, s). m/z: ES+ [M+H]+ 432.

Example 78a: Preparation of (1S,3R)-3-acetamido-N-(5-chloro-4-(5-(4-hydroxybutyl)-1H-pyrazol-4-yl)pyridin-2-yl)cyclohexanecarboxamide

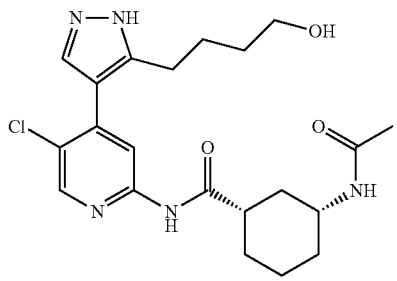 [SMILES: CC(=O)N[C@@H]1CCC[C@H](C(=O)Nc2cc(-c3cn[nH]c3CCCCO)c(Cl)cn2)C1]

Hydrochloric acid in dioxane (4 M; 2.2 mL, 8.8 mmol) was added to a solution of (1S,3R)-3-acetamido-N-(4-(5-(4-((tert-butyldimethylsilyl)oxy)butyl)-1-((2-(trimethyl silyl)ethoxy)methyl)-1H-pyrazol-4-yl)-5-chloropyridin-2-yl)cyclohexanecarboxamide (300 mg, 0.44 mmol) in methanol (3 mL). The reaction was stirred for 2 h at r.t. and then concentrated under reduced pressure. The resulting residue was diluted with water (40 mL) and basified with sodium bicarbonate. The mixture was then, saturated with sodium chloride and extracted with ethyl acetate (5×). The combined organic layers were dried over sodium sulfate, filtered, and concentrated under reduced pressure. The resulting residue was purified by flash silica chromatography, elution gradient 0 to 30% methanol in DCM, to afford crude (1S,3R)-3-acetamido-N-(5-chloro-4-(5-(4-hydroxybutyl)-1H-pyrazol-4-yl)pyridin-2-yl)cyclohexanecarboxamide (163 mg, 83%) as a gum. $^1$H NMR (300 MHz, DMSO-$d_6$, 27° C.) 1.02-1.23 (1H, m), 1.24-1.47 (5H, m), 1.52-1.66 (2H, m), 1.75-1.88 (6H, m), 1.88-1.97 (1H, m), 2.59-2.76 (3H, m), 3.35-3.43 (2H, m), 3.54-3.68 (1H, m), 4.25-4.39 (1H, m), 7.66 (0.6H, s), 7.79 (1H, d), 7.92-8.02 (0.4H, m), 8.12-8.21 (1H, m), 8.43 (1H, s), 10.62 (1H, s), 12.91 (0.4H, br s), 12.98 (0.6H, br s) −2:3 ratio of pyrazole tautomers. m/z: ES+ [M+H]+ 434.

(1S,3R)-3-acetamido-N-(4-(5-(4-((tert-butyldimethylsilyl)oxy)butyl)-1-((2-(trimethylsilyl)ethoxy)methyl)-1H-pyrazol-4-yl)-5-chloropyridin-2-yl)cyclohexanecarboxamide used as starting material was prepared as follows:

Preparation of 1-((2-(trimethylsilyl)ethoxy)methyl)-1H-pyrazole

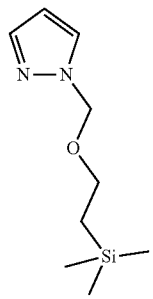

NaH (60% wt in mineral oil; 1.85 g, 46.3 mmol) was added portionwise to 1H-pyrazole (3.0 g, 44.1 mmol) in THF (30 mL) at 5° C. over a period of 10 minutes under nitrogen. The resulting mixture was stirred at 5° C. for 30 minutes. SEM-Cl (8.2 mL, 46 mmol) was then added dropwise to the reaction. The resulting mixture was stirred at 5° C. for 1 hour. The reaction mixture was then diluted with water (50 mL) and washed sequentially with Et$_2$O (3×50 mL). The combined organic layers were dried over magnesium sulfate, filtered and concentrated under reduced pressure to afford 1-((2-(trimethylsilyl)ethoxy)methyl)-1H-pyrazole (6.5 g, 78%) as a faint yellow oil. $^1$H NMR (300 MHz, DMSO-$d_6$, 27° C.) 0.00 (s, 9H), 0.79-0.95 (2H, m), 3.48-3.62 (2H, m), 5.45 (2H, s), 6.36 (1H, t), 7.56 (1H, d), 7.91 (1H, d).

Preparation of 5-bromo-1-((2-(trimethylsilyl)ethoxy)methyl)-1H-pyrazole

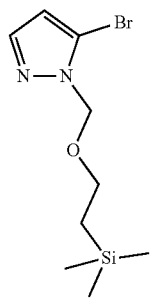

Lithium magnesium 2,2,6,6-tetramethylpiperidin-1-ide dichloride (25.2 mL, 27.7 mmol) was added dropwise to 1-((2-(trimethylsilyl)ethoxy)methyl)-1H-pyrazole (5 g, 25 mmol) in THF (30 mL) at 21° C. under nitrogen. The resulting suspension was stirred at 21° C. for 1 hour. After 1.5 h the reaction was cooled to 0° C., and then 1,2-dibromo-1,1,2,2-tetrachloroethane (8.21 g, 25.2 mmol) was added. The ice bath was removed, and the mixture was allowed to warm to r.t.; after 18 h, the reaction mixture was quenched with saturated aqueous sodium chloride and extracted with ethyl acetate (2×). The combined organic layers were dried over sodium sulfate, filtered, and concentrated under reduced pressure. The resulting residue was purified by flash silica chromatography, elution gradient 0 to 40% ethyl acetate in hexanes, to afford 5-bromo-1-((2-(trimethylsilyl)ethoxy)methyl)-1H-pyrazole (4.2 g, 60%) as a brown oil. $^1$H NMR (DMSO-$d_6$, 27° C.) 0.00 (9H, s), 0.88-0.96 (2H, m), 3.61 (2H, t), 5.49 (2H, s), 6.58 (1H, d), 7.67 (1H, d).

Preparation of 5-(pent-4-en-1-yl)-1-((2-(trimethylsilyl)ethoxy)methyl)-1H-pyrazole

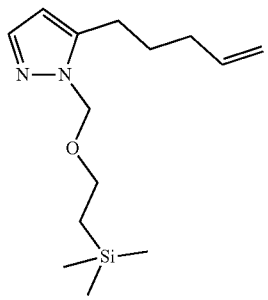 [SMILES: C=CCCCc1ccnn1COCC[Si](C)(C)C]

3$^{rd}$ Generation RuPhos Precatalyst (0.247 g, 0.30 mmol) was added to a degassed mixture of 5-bromo-1-((2-(trimethylsilyl)ethoxy)methyl)-1H-pyrazole (4.1 g, 15 mmol), pent-4-en-1-ylboronic acid (2.19 g, 19.2 mmol) and cesium carbonate (9.64 g, 29.6 mmol) in 1,4-dioxane (120 mL), and the reaction was stirred at 90° C. for 18 h. The reaction mixture was cooled to r.t. and then diluted with water. Aqueous sodium bicarbonate was added, and the resulting mixture was extracted with ethyl acetate (3×). The combined organic layers were dried over sodium sulfate, filtered, and concentrated under reduced pressure. The resulting residue was purified by flash silica chromatography, elution gradient 0 to 50% ethyl acetate in hexanes, to afford 5-(pent-4-en-1-yl)-1-((2-(trimethylsilyl)ethoxy)methyl)-1H-pyrazole (2.2 g, 55%) as light yellow oil. $^1$H NMR (DMSO-$d_6$, 27° C.) 0.00 (9H, s), 0.75-0.93 (2H, m), 1.66-1.88 (2H, m), 2.15 (2H, q), 2.61-2.85 (2H, m), 3.44-3.61 (2H, m), 4.92-5.22 (2H, m), 5.43 (2H, s), 5.89 (1H, ddt), 6.18 (1H, d), 7.42 (1H, d).

Preparation of 4-(1((2-(trimethylsilyl)ethoxy)methyl)-1H-pyrazol-5-yl)butanal

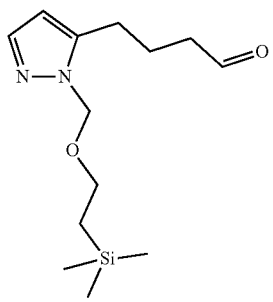 [SMILES: C[Si](C)(C)CCOCn1nccc1CCCC=O]

5-(Pent-4-en-1-yl)-1-((2-(trimethylsilyl)ethoxy)methyl)-1H-pyrazole (2.14 g, 8.03 mmol) was dissolved in DCM (40 mL) and cooled to −78° C. Ozone was bubbled through the solution for 12 minutes. The reaction was then purged of ozone using a stream of nitrogen, and triphenylphosphine (2.11 g, 8.03 mmol) was added. The reaction was allowed to warm to r.t. and was maintained under these conditions for 18 h before being concentrated under reduced pressure. The resulting residue was purified by flash silica chromatography, elution gradient 0 to 50% ethyl acetate in hexane, to afford 4-(1-((2-(trimethylsilyl)ethoxy)methyl)-1H-pyrazol-5-yl)butanal (1.34 g, 62%) as an oil. $^1$H NMR (DMSO-$d_6$, 27° C.) 0.00 (9H, s), 0.76-0.94 (2H, m), 1.81-2.01 (2H, m), 2.57-2.60 (2H, m), 2.73 (2H, t), 3.42-3.64 (2H, m), 5.43 (2H, s), 6.20 (1H, d), 7.43 (1H, d), 9.74 (1H, t).

Preparation of 4-(1-((2-(trimethylsilyl)ethoxy)methyl)-1H-pyrazol-5-yl)butan-1-ol

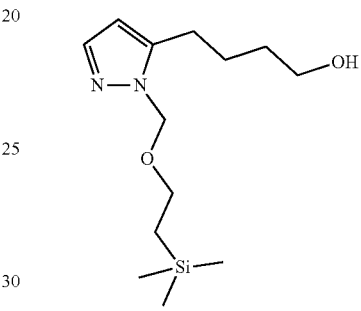

Sodium borohydride (0.372 g, 9.84 mmol) was added to a stirred solution of 4414(2-(trimethylsilyl)ethoxy)methyl)-1H-pyrazol-5-yl)butanal (1.32 g, 4.92 mmol) in methanol (20 mL) at 0° C. The resulting mixture was stirred for 1 h under these conditions. The reaction was then diluted with water and extracted with ethyl acetate (2×). The combined organic layers were dried over sodium sulfate, filtered, and concentrated under reduced pressure. The resulting crude residue was filtered through a plug of silica eluting with ethyl acetate. The filtrate was concentrated under reduced pressure to afford 4-(1-((2-(trimethylsilyl)ethoxy)methyl)-1H-pyrazol-5-yl)butan-1-ol (1.1 g, 85%) as a light brown oil. $^1$H NMR (DMSO-$d_6$, 27° C.) 0.00 (9H, s), 0.86 (2H, t), 1.43-1.59 (2H, m), 1.61-1.79 (2H, m), 2.72 (2H, t), 3.39-3.64 (4H, m), 4.43 (1H, t), 5.42 (2H, s), 6.16 (1H, d), 7.42 (1H, d). m/z: ES+ [M+H]+ 271.

Preparation of 5-(4-((tert-butyldimethylsilyl)oxy)butyl)-1-((2-(trimethylsilyl)ethoxy)methyl)-1H-pyrazole

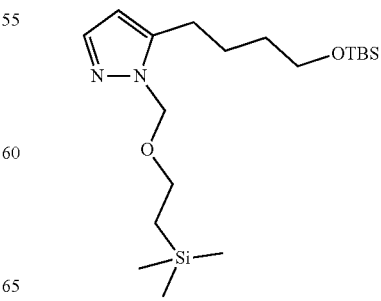

TBS-Cl (0.94 g, 6.2 mmol) was added to a stirred solution of 4-(1-((2-(trimethylsilyl)ethoxy)methyl)-1H-pyrazol-5-yl)butan-1-ol (1.1 g, 4.1 mmol) and imidazole (0.85 g, 12 mmol) in DCM (20 mL) at 0° C., and the reaction was stirred at r.t. for 18 h. The reaction mixture was diluted with water and extracted with EtOAc. The organic layer as dried over sodium sulfate, filtered, and concentrated under reduced pressure. The resulting residue was purified by flash silica chromatography, elution gradient 0 to 40% ethyl acetate in hexane, to give 5-(4-((tert-butyldimethylsilyl)oxy)butyl)-1-((2-(trimethylsilyl)ethoxy)methyl)-1H-pyrazole (1.5 g, 96%) as an oil. $^1$H NMR (DMSO-$d_6$, 27° C.) 0.00 (9H, s), 0.09 (6H, s), 0.81-0.89 (2H, m), 0.92 (9H, s), 1.49-1.62 (2H, m), 1.65-1.80 (2H, m), 2.73 (2H, t), 3.47-3.61 (2H, m), 3.67 (2H, t), 5.43 (2H, s), 6.15 (1H, d), 7.42 (1H, d). m/z: ES+ [M+H]+ 385.

Preparation of 5-(4-((tert-butyldimethylsilyl)oxy)butyl)-4-iodo-1-((2-(trimethylsilyl)ethoxy)methyl)-1H-pyrazole

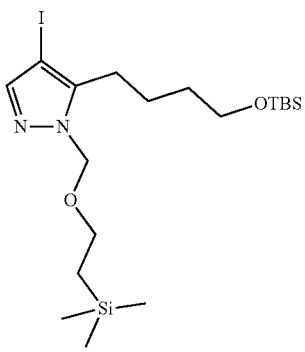 [SMILES: CC(C)(C)[Si](C)(C)OCCCCc1c(I)cnn1COCC[Si](C)(C)C]

NIS (0.89 g, 4.0 mmol) was added to a stirred solution of 5-(4-((tert-butyldimethylsilyl)oxy)butyl)-142-(trimethylsilyl)ethoxy)methyl)-1H-pyrazole (1.5 g, 4.0 mmol) in DCM (25 mL) at 0° C. The ice bath was removed, and the reaction was stirred for 18 h under these conditions. The reaction mixture was diluted with water and extracted with EtOAc. The organic layer was dried over sodium sulfate, filtered, and concentrated under reduced pressure. The resulting residue was purified by flash silica chromatography, elution gradient 0 to 50% ethyl acetate in hexane, to give 5-(4-((tert-butyldimethylsilyl)oxy)butyl)-4-iodo-1-((2-(trimethylsilyl)ethoxy)methyl)-1H-pyrazole (1.7 g, 85%) as a gum.

$^1$H NMR (DMSO-$d_6$, 27° C.) 0.00 (9H, s), 0.07 (6H, s), 0.82-0.88 (2H, m), 0.91 (9H, s), 1.45-1.74 (4H, m), 2.75 (2H, t), 3.48-3.60 (2H, m), 3.64 (2H, t), 5.48 (2H, s), 7.55 (1H, s).

Preparation of 5-(4-((tert-butyldimethylsilyl)oxy)butyl)-4-(4,4,5,5-tetramethyl-1,3,2-dioxaborolan-2-yl)-14(2-(trimethylsilyl)ethoxy)methyl)-1H-pyrazole

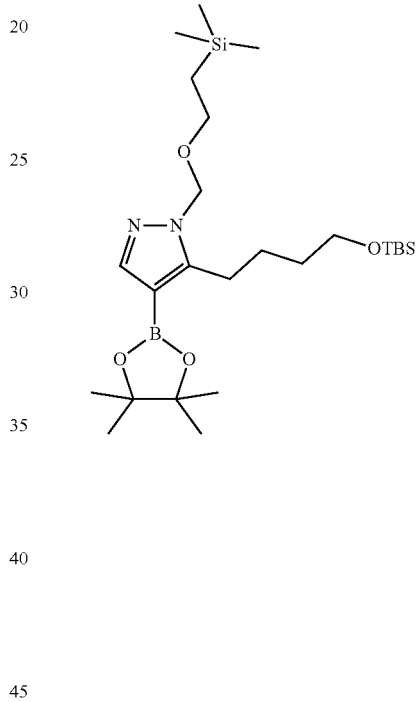

THF (16 mL) was added to 5-(4-((tert-butyldimethylsilyl)oxy)butyl)-4-iodo-1-((2-(trimethylsilyl)ethoxy)methyl)-1H-pyrazole (800 mg, 1.57 mmol). The reaction was cooled to 0° C., and isopropylmagnesium chloride lithium chloride complex in THF (1.3 M; 1.57 mL, 2.04 mmol) was added dropwise. The reaction was maintained under these conditions for 30 minutes. Then 2-isopropoxy-4,4,5,5-tetramethyl-1,3,2-dioxaborolane (0.48 mL, 2.3 mmol) was added dropwise. The reaction was allowed to warm to r.t. and was then stirred under these conditions for 18 h. The reaction was diluted with water and extracted with ethyl acetate (2×). The combined organic layers were dried over sodium sulphate, filtered, and concentrated under reduced pressure. The resulting residue was carried on to the next step without purification. $^1$H NMR (300 MHz, DMSO-$d_6$) 0.00 (9H, s), 0.05 (6H, s), 0.83-0.91 (11H, m), 1.30 (12H, s), 1.45-1.55 (2H, m), 1.55-1.69 (2H, m), 2.89 (2H, t), 3.48-3.69 (4H, m), 5.44 (2H, s), 7.54 (1H, s).

Preparation of (1S,3R)-3-acetamido-N-(4-(5-(4-((tert-butyldimethylsilyl)oxy)butyl)-1-((2-(trimethylsilyl)ethoxy)methyl)-1H-pyrazol-4-yl)-5-chloropyridin-2-yl)cyclohexanecarboxamide

Examples 79 and 80: Isomer 1 and Isomer 2 of (1S,3R)-3-acetamido-N-(5-chloro-4-(4-hydroxy-5,5-dimethyl-5,6-dihydro-4H-pyrrolo[1,2-b]pyrazol-3-yl)pyridin-2-yl)cyclohexanecarboxamide

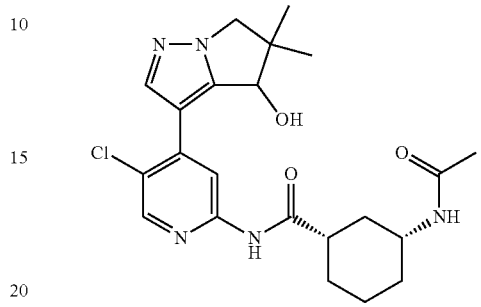

Example 79, Isomer 1

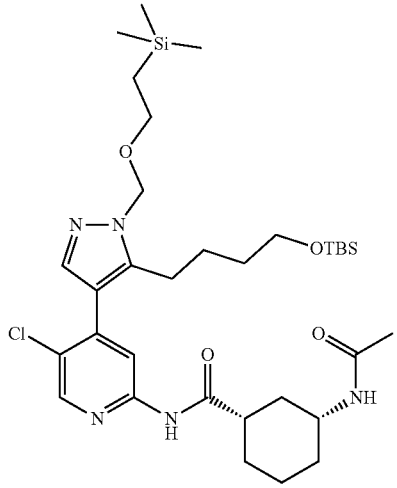 [SMILES: CC(=O)N[C@@H]1CCC[C@H](C(=O)Nc2cc(-c3cnn(COCC[Si](C)(C)C)c3CCCCO[Si](C)(C)C(C)(C)C)c(Cl)cn2)C1]

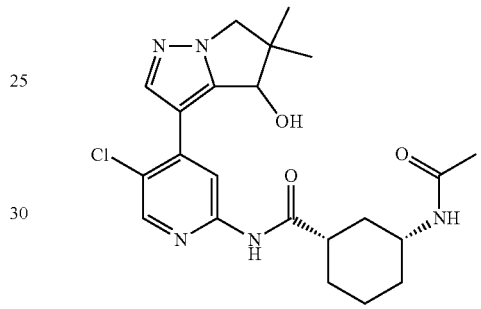

Example 80, Isomer 2

Pure enantiomers. The configuration of the hydroxy is unknown for Example 79 and 80 but is opposite in Example 79 vs Example 80

(1S,3R)-3-Acetamido-N-(4-(4-((tert-butyldimethylsilyl)oxy)-5,5-dimethyl-5,6-dihydro-4H-pyrrolo[1,2-b]pyrazol-3-yl)-5-chloropyridin-2-yl)cyclohexanecarboxamide (180 mg, 0.32 mmol) was resolved into diastereomeric components using SFC conditions (Column: Chiralpak AS, 5 μm, 21.2 mm diameter, 250 mm length, 75 mL/min flow rate over 8 min), eluting with 20% isopropanol in CO₂, to afford faster eluting isomer 1 of (1S,3R)-3-acetamido-N-(4-(4-((tert-butyldimethylsilyl)oxy)-5,5-dimethyl-5,6-dihydro-4H-pyrrolo[1,2-b]pyrazol-3-yl)-5-chloropyridin-2-yl)cyclohexanecarboxamide (49 mg, 27%) as a clear film and slower eluting isomer 2 of afford (1S,3R)-3-acetamido-N-(4-(4-((tert-butyldimethylsilyl)oxy)-5,5-dimethyl-5,6-dihydro-4H-pyrrolo[1,2-b]pyrazol-3-yl)-5-chloropyridin-2-yl)cyclohexanecarboxamide (42 mg, 22%) as a clear film.

Each isomer was then deprotected as follows: Hydrochloric acid in dioxane (4 M; 0.500 mL, 14.40 mmol) was added dropwise to a solution of either isomer 1 (49 mg) or isomer 2 (42 mg) of (1S,3R)-3-acetamido-N-(4-(4-((tert-butyldimethylsilyl)oxy)-5,5-dimethyl-5,6-dihydro-4H-pyrrolo[1,2-b]pyrazol-3-yl)-5-chloropyridin-2-yl)cyclohexanecarboxamide in THF (2 mL). The resulting colorless solution was stirred at r.t. for 18 h and then diluted with EtOAc (10 mL). The resulting mixture was washed with saturated aqueous sodium bicarbonate and extracted with EtOAc (3×). The combined organic layers were concentrated under reduced pressure, and the resulting residue was adsorbed onto silica gel before being purified by flash silica chromatography, elution gradient 0 to 10% methanol in DCM, to afford either 2nd Generation XPhos Precatalyst (28 mg, 0.04 mmol) was added to a degassed mixture of (1S,3R)-3-acetamido-N-(5-chloro-4-iodopyridin-2-yl)cyclohexanecarboxamide (300 mg, 0.71 mmol; prepared according to Example 12), 5-(4-((tert-butyldimethylsilyl)oxy)butyl)-4-(4,4,5,5-tetramethyl-1,3,2-dioxaborolan-2-yl)-1-((2-(trimethylsilyl)ethoxy)methyl)-1H-pyrazole (472 mg, 0.92 mmol) and Cs₂CO₃ (695 mg, 2.13 mmol) in 1,4-dioxane (4 mL) and water (1 mL). The reaction mixture was stirred at 90° C. for 3 h and then cooled and diluted with saturated aqueous sodium chloride. The mixture was extracted with ethyl acetate (2×) and the combined organic layers were dried over sodium sulfate, filtered, and concentrated under reduced pressure. The resulting residue was, purified by flash silica chromatography, elution gradient 0 to 10% methanol in DCM, to afford (1S,3R)-3-acetamido-N-(4-(5-(4-((tert-butyldimethylsilyl)oxy)butyl)-1-((2-(trimethylsilyl)ethoxy)methyl)-1H-pyrazol-4-yl)-5-chloropyridin-2-yl)cyclohexanecarboxamide (423 mg, 88%) as a light yellow gum (HPLC purity: 91%). ¹H NMR (DMSO-d₆, 27° C.) −0.08 (6H, s), −0.05-−0.02 (9H, m), 0.75-0.79 (9H, m), 0.80-0.88 (2H, m), 1.04-1.16 (1H, m), 1.20-1.40 (5H, m), 1.42-1.62 (2H, m), 1.76 (6H, s), 1.90 (1H, d), 2.54-2.67 (1H, m), 2.76 (2H, t), 3.40-3.48 (2H, m), 3.51-3.62 (3H, m), 5.48 (2H, s), 7.62 (1H, s), 7.74 (1H, d), 8.12 (1H, s), 8.40 (1H, s), 10.62 (1H, s). The multiplet at 1.04-1.16 ppm is partially obscured by pinacol impurities. m/z: ES+ [M+H]+ 678.

isomer 1 (26 mg, 67%) or isomer 2 (16 mg, 48%) of (1S,3R)-3-acetamido-N-(5-chloro-4-(4-hydroxy-5,5-dimethyl-5,6-dihydro-4H-pyrrolo[1,2-b]pyrazol-3-yl)pyridin-2-yl)cyclohexanecarboxamide as a white solid.

Example 79, Isomer 1

$^1$H NMR (300 MHz, DMSO-d$_6$, 27° C.) 1.01-1.20 (7H, m), 1.20-1.34 (3H, m), 1.67-1.85 (6H, m), 1.90 (1H, d), 2.58-2.66 (1H, m), 3.51-3.63 (1H, m), 3.88 (1H, d), 4.00 (1H, d), 4.68 (1H, d), 5.53 (1H, d) 7.75 (1H, d), 7.93 (1H, s), 8.37 (2H, d), 10.52 (1H, s). m/z: ES+ [M+H]+ 446.

Example 80, Isomer 2

$^1$H NMR (300 MHz, DMSO-d$_6$) 1.16 (7H, m), 1.22-1.38 (3H, m), 1.72-1.83 (6H, m), 1.89 (1H, br d), 2.56-2.68 (1H, m), 3.47-3.66 (1H, m), 3.88 (1H, d), 4.00 (1H, d), 4.68 (1H, d) 5.53 (1H, d) 7.75 (1H, br d), 7.93 (1H, s), 8.37 (2H, s), 10.52 (1H, s). m/z: ES+ [M+H]+ 446.

Analytical SFC Conditions:
Column: Chiralpak AS
Column Dimensions: 5 μm, 4.6 mm diameter, 50 mm length,
Mobile Phase A: CO$_2$ (100%)
Mobile Phase B: Isopropanol
Gradient: 10 to 60% Mobile Phase B
Flow Rate: 2.8 mL/min over 5 min
Column Temperature: 40° C. (100 bar)
Retention Time: 1.66 min, Example 79, Isomer 1
1.90 min, Example 80, Isomer 2
e.e. >96.4%, Example 79, Isomer 1
>98%, Example 80, Isomer 2

Procedures used to prepare the starting material (1S,3R)-3-acetamido-N-(4-(4-((tert-butyldimethylsilyl)oxy)-5,5-dimethyl-5,6-dihydro-4H-pyrrolo[1,2-b]pyrazol-3-yl)-5-chloropyridin-2-yl)cyclohexanecarboxamide are described below:

Preparation of 5,5-dimethyl-5,6-dihydro-4H-pyrrolo[1,2-b]pyrazol-4-ol

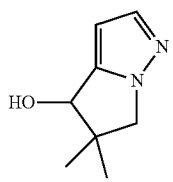

NaBH$_4$ (202 mg, 5.33 mmol) was added to a solution of 5,5-dimethyl-5,6-dihydro-4H-pyrrolo[1,2-b]pyrazol-4-one (400 mg, 2.66 mmol; prepared according to Example 14) in MeOH (12 mL) to give a white mixture. The reaction was stirred under these conditions for 1 hour and then quenched with water. The resulting mixture was extracted with DCM (25 mL) and then further extracted with 25% IPA in chloroform (50 mL). The combined organic layers were dried over sodium sulfate, filtered, concentrated under reduced pressure (405 mg, quantitative) to afford a clear oil. $^1$H NMR (500 MHz, DMSO-d$_6$, 27° C.) 1.11 (6H, s), 3.75 (1H, d), 3.91 (1H, d), 4.48 (1H, d), 5.49 (1H, d), 6.11 (1H, d), 7.42 (1H, s). m/z: ES+ [M+H]+ 153.

Preparation of 4-((tert-butyldimethylsilyl)oxy)-5,5-dimethyl-5,6-dihydro-4H-pyrrolo[1,2-b]pyrazole

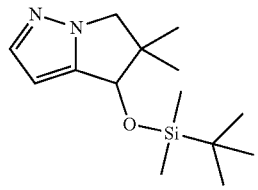 [SMILES: CC1(C)Cn2nccc2C1O[Si](C)(C)C(C)(C)C]

TBS-Cl (501 mg, 3.33 mmol) was added to a solution of 5,5-dimethyl-5,6-dihydro-4H-pyrrolo[1,2-b]pyrazol-4-ol (405 mg, 2.66 mmol), imidazole (362 mg, 5.32 mmol), and DCM (12 mL) to give a white suspension. The reaction was stirred at r.t. for 18 h and then diluted with DCM (100 mL) and washed with water and saturated aqueous sodium chloride. The organic layer was dried over sodium sulfate, filtered, and concentrated under reduced pressure before being adsorbed onto silica gel and purified by flash silica chromatography, elution gradient 0 to 10% MeOH in DCM to afford 4-((tert-butyldimethylsilyl)oxy)-5,5-dimethyl-5,6-dihydro-4H-pyrrolo[1,2-b]pyrazole (391 mg, 55%) as a clear oil. m/z: ES+ [M+H]+ 267.

Preparation of 4-((tert-butyldimethylsilyl)oxy)-3-iodo-5,5-dimethyl-5,6-dihydro-4H-pyrrolo[1,2-b]pyrazole

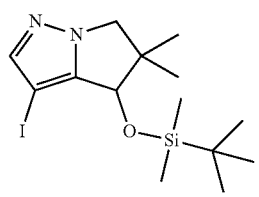 [SMILES: CC1(C)Cn2ncc(I)c2C1O[Si](C)(C)C(C)(C)C]

NIS (330 mg, 1.47 mmol) was added to a solution of 4-((tert-butyldimethylsilyl)oxy)-5,5-dimethyl-5,6-dihydro-4H-pyrrolo[1,2-b]pyrazole (391 mg, 1.47 mmol) in DCM (3 mL) to give a red solution. The reaction was stirred at r.t. under nitrogen for 18 h. The reaction was then diluted with DCM (50 mL) and washed with water and saturated aqueous sodium chloride. The organic layer was dried over sodium sulfate, filtered, and concentrated under reduced pressure. The resulting residue was purified by flash silica chromatography, elution gradient 0 to 10% methanol in DCM, to afford 4-((tert-butyldimethylsilyl)oxy)-3-iodo-5,5-dimethyl-5,6-dihydro-4H-pyrrolo[1,2-b]pyrazole (350 mg, 61%) as a red foam $^1$H NMR (300 MHz, DMSO-d$_6$, 27° C.) 0.19 (3H, s), 0.23 (3H, s) 0.87 (9H, s) 1.03 (3H, s) 1.12 (3H, s) 3.81 (1H, d) 3.96 (1H, d) 4.52-4.63 (1H, s) 7.47 (1H, s). m/z: ES+ [M+H]+ 393.

Preparation of 4-((tert-butyldimethylsilyl)oxy)-5,5-dimethyl-3-(4,4,5,5-tetramethyl-1,3,2-dioxaborolan-2-yl)-5,6-dihydro-4H-pyrrolo[1,2-b]pyrazole

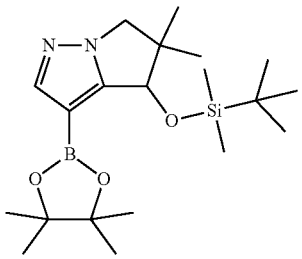 [SMILES: CC1(C)Cn2ncc(B3OC(C)(C)C(C)(C)O3)c2C1O[Si](C)(C)C(C)(C)C]

Isopropylmagnesium chloride lithium chloride complex in THF (1.3 M; 0.89 mL, 1.2 mmol) was added dropwise to a solution of 4-((tert-butyldimethylsilyl)oxy)-3-iodo-5,5-dimethyl-5,6-dihydro-4H-pyrrolo[1,2-b]pyrazole (350 mg, 0.89 mmol) in THF (2.2 mL) at 0° C. Then 2-isopropoxy-4,4,5,5-tetramethyl-1,3,2-dioxaborolane (0.273 mL, 1.34 mmol) was added dropwise. The reaction was allowed to warm to r.t. and maintained under these conditions for 18 h. The reaction was then diluted with EtOAc (25 mL) and washed with saturated aqueous ammonium chloride and saturated aqueous sodium chloride. The organic layer was dried over sodium sulfate, filtered, and concentrated under reduced pressure to afford crude 4-((tert-butyldimethylsilyl)oxy)-5,5-dimethyl-3-(4,4,5,5-tetramethyl-1,3,2-dioxaborolan-2-yl)-5,6-dihydro-4H-pyrrolo[1,2-b]pyrazole (290 mg, 83%) as a yellow foam solid. $^1$H NMR (300 MHz, DMSO-d$_6$, 27° C.) 0.00 (3H, s), 0.19 (3H, s), 0.81 (9H, s), 0.92 (3H, s), 1.17 (3H, s), 1.22 (6H, s), 1.24 (6H, s), 3.70 (1H, d), 3.91 (1H, d), 4.47 (1H, s), 7.55 (1H, s). m/z: ES+ [M+H]+ 393.

Preparation of (1S,3R)-3-acetamido-N-(4-(4-((tert-butyldimethylsilyl)oxy)-5,5-dimethyl-5,6-dihydro-4H-pyrrolo[1,2-b]pyrazol-3-yl)-5-chloropyridin-2-yl)cyclohexanecarboxamide

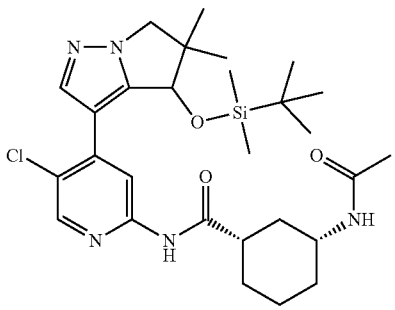 [SMILES: CC(=O)N[C@@H]1CCC[C@H](C(=O)Nc2cc(-c3cnn4c3C(O[Si](C)(C)C(C)(C)C)C(C)(C)C4)c(Cl)cn2)C1]

Cesium carbonate (641 mg, 1.97 mmol) and 2nd Generation XPhos Precatalyst (52 mg, 0.07 mmol) were added to a degassed mixture of 4-((tert-butyldimethylsilyl)oxy)-5,5-dimethyl-3-(4,4,5,5-tetramethyl-1,3,2-dioxaborolan-2-yl)-5,6-dihydro-4H-pyrrolo[1,2-b]pyrazole (270 mg, 0.69 mmol) and (1S,3R)-3-acetamido-N-(5-chloro-4-iodopyridin-2-yl)cyclohexanecarboxamide (276 mg, 0.66 mmol; prepared according to Example 12) in 1,4-dioxane (5.4 mL) and water (1.1 mL). The reaction was then warmed to 85° C. and maintained under these conditions for 18 h before being diluted with EtOAc, washed with water, brine, concentrated under reduced pressure. The resulting residue was adsorbed onto silica gel and purified by flash silica chromatography, elution gradient 0 to 10% MeOH in DCM to afford (1S,3R)-3-acetamido-N-(4-(4-((tert-butyldimethylsilyl)oxy)-5,5-dimethyl-5,6-dihydro-4H-pyrrolo[1,2-b]pyrazol-3-yl)-5-chloropyridin-2-yl)cyclohexanecarboxamide (180 mg, 49%) as a yellow solid. $^1$H NMR (300 MHz, DMSO-d$_6$, 27° C.) −0.38 (3H, d), 0.00 (3H, s), 0.71 (9H, s), 1.03-1.47 (10H, m), 1.76-2.01 (7H, m), 2.61-2.75 (1H, m), 3.51-3.72 (1H, m), 3.96 (1H, d), 4.06 (1H, d), 4.87 (1H, s), 7.79-7.87 (2H, m), 8.32 (1H, s), 8.46 (1H, s), 10.67 (1H, br s).
m/z: ES+ [M+H]+ 560.

Example 81: (1R,3S)-3-acetamido-N-(4-(5,5-dimethyl-5,6-dihydro-4H-pyrrolo[1,2-b]pyrazol-3-yl)-5-fluoropyridin-2-yl)cyclohexanecarboxamide

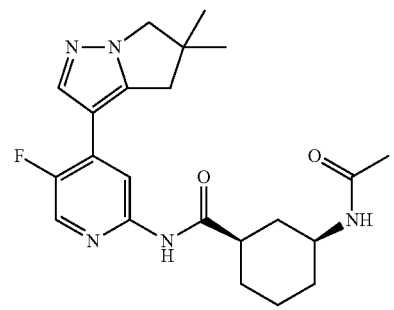 [SMILES: CC(=O)N[C@H]1CCC[C@@H](C(=O)Nc2cc(-c3cnn4c3CC(C)(C)C4)c(F)cn2)C1]

Cesium carbonate (482 mg, 1.48 mmol) and 2nd Generation XPhos Precatalyst (15 mg, 0.02 mmol) were added to a degassed mixture of 5,5-dimethyl-3-(4,4,5,5-tetramethyl-1,3,2-dioxaborolan-2-yl)-5,6-dihydro-4H-pyrrolo[1,2-b]pyrazole (142 mg, 0.54 mmol; prepared according to Example 23), (1R,3S)-3-acetamido-N-(5-fluoro-4-iodopyridin-2-yl)cyclohexanecarboxamide (200 mg, 0.49 mmol), dioxane (4.1 mL), and water (0.8 mL). The reaction was maintained at 95° C.; after 4 h, additional 5,5-dimethyl-3-(4,4,5,5-tetramethyl-1,3,2-dioxaborolan-2-yl)-5,6-dihydro-4H-pyrrolo[1,2-b]pyrazole (100 mg) was added. The reaction was maintained under these conditions for another 18 h, cooled, and then diluted with EtOAc (150 mL) and washed with water and saturated aqueous sodium chloride. The organic layer was then dried over sodium sulfate, filtered, and concentrated under reduced pressure. The resulting residue was adsorbed onto silica gel and purified by flash silica chromatography, elution gradient 0 to 100% ethyl acetate in hexanes followed by 0 to 10% MeOH in EtOAc, to afford a beige solid. $^1$H NMR (300 MHz, DMSO-d$_6$, 27° C.) 0.98-1.19 (1H, t), 1.19-1.41 (9H, m), 1.73-1.83 (6H, m), 1.90 (1H, br d), 2.56-2.69 (1H, m), 2.93 (3H, s), 3.50-3.64 (1H, m), 3.94 (2H, s), 7.75 (1H, d), 7.88 (1H, d), 8.28 (1H, d)), 8.30 (1H, d), 10.46 (1H, s). m/z: ES+ [M+H]+ 414.

Optical Rotation:
Concentration: 0.1 g/dL
Lamp: Sodium
Wavelength: 589 nm
Temperature: 25° C.
Path length: 10 cm
Cell volume: 1 mL
Solvent: MeOH
[α]=−101

Procedures used to prepare the starting material (1R,3S)-3-acetamido-N-(5-fluoro-4-iodopyridin-2-yl)cyclohexanecarboxamide are described below:

Preparation of Tert-butyl ((1S,3R)-3-((5-fluoro-4-iodopyridin-2-yl)carbamoyl)cyclohexyl)carbamate

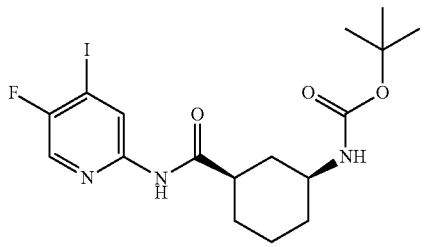 [SMILES: CC(C)(C)OC(=O)N[C@H]1CCC[C@@H](C(=O)Nc2cc(I)c(F)cn2)C1]

1-Chloro-N,N,2-trimethylprop-1-en-1-amine (489 µL, 3.70 mmol) was added dropwise to a solution of (1R,3S)-3-((tert-butoxycarbonyl)amino)cyclohexanecarboxylic acid (660 mg, 2.7 mmol; prepared according to Example 25 substituting (1R,3S)-benzyl 3-((tert-butoxycarbonyl)amino) cyclohexanecarboxylate for (1S,3R)-benzyl 3-((tert-butoxycarbonyl)amino)cyclohexanecarboxylate) in DCM (6.3 mL). After 1 hour, a solution of 5-fluoro-4-iodopyridin-2-amine (587 mg, 2.47 mmol; prepared according to Example 54) and pyridine (400 µL, 4.9 mmol) in DCM (6 mL) was added. After 18 h, the reaction was diluted with DCM (200 mL) and washed with water and saturated aqueous sodium chloride. The organic layer was dried over sodium sulfate, filtered, and concentrated under reduced pressure. The resulting residue was adsorbed onto silica and purified by flash silica chromatography, elution gradient 0 to 10% methanol in DCM, to afford tert-butyl ((1S,3R)-3-(5-fluoro-4-iodopyridin-2-yl)carbamoyl)cyclohexyl)carbamate (1.10 g, 96%) as a white solid. $^1$H NMR (300 MHz, DMSO-d$_6$, 27° C.) 1.02-1.18 (1H, m), 1.19-1.35 (3H, m), 1.38 (10H, s), 1.62-1.81 (3H, m), 1.82-1.94 (1H, m), 2.56-2.71 (1H, m), 3.48-3.59 (1H, m), 6.78 (1H, d), 8.25 (1H, s), 8.60 (1H, d), 10.59 (1H, s). m/z: ES+ [M+Na]+486.

Preparation of (1R,3S)-3-acetamido-N-(5-fluoro-4-iodopyridin-2-yl)cyclohexanecarboxamide

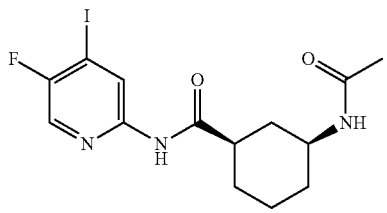 [SMILES: CC(=O)N[C@H]1CCC[C@@H](C(=O)Nc2cc(I)c(F)cn2)C1]

Hydrochloric acid in dioxane (4 M; 2.7 mL, 11 mmol) was added to a solution of tert-butyl ((1S,3R)-3-((5-fluoro-4-iodopyridin-2-yl)carbamoyl)cyclohexyl)carbamate (500 mg, 1.08 mmol) in methanol (8.97 mL) at r.t. After stirring under these conditions for 19 h, the reaction was concentrated under reduced pressure. Triethylamine (750 µL, 5.4 mmol) and acetic anhydride (200 µL, 2.2 mmol) were added to the resulting residue. The reaction was stirred under these conditions for 1 hour and then diluted with DCM (100 mL). The resulting mixture was washed with 1N aqueous HCl, water, and saturated aqueous sodium chloride. The organic layer was then dried over sodium sulfate, filtered, and concentrated under reduced pressure. The resulting residue was adsorbed onto silica gel and purified by flash silica chromatography, elution gradient 0 to 100% ethyl acetate in hexane followed by 0 to 10% methanol in ethyl acetate, to afford (1R,3S)-3-acetamido-N-(5-fluoro-4-iodopyridin-2-yl)cyclohexanecarboxamide (200 mg, 46%) as a white solid. $^1$H NMR (300 MHz, DMSO-d$_6$, 27° C.) 1.00-1.17 (1H, m), 1.20-1.40 (3H, m), 1.71-1.82 (6H, m), 1.83-1.92 (1H, m) 2.54-2.64 (1H, m) 3.48-3.58 (1H, m) 7.76 (1H, d) 8.25 (1H, s) 8.61 (1H, d) 10.61 (1H, s). m/z: ES+ [M+H]+ 406.

Example 82a: Preparation of (1S,3R)-3-acetamido-N-(5-chloro-4-(5-(3-hydroxy-2,2-dimethylpropyl)-1H-pyrazol-4-yl)pyridin-2-yl)cyclohexane-1-carboxamide

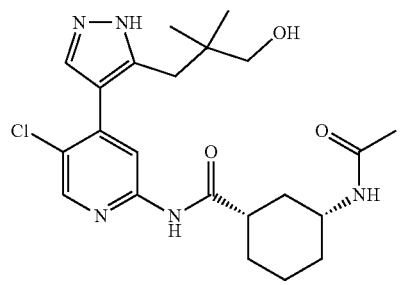 [SMILES: CC(=O)N[C@@H]1CCC[C@H](C(=O)Nc2cc(-c3cn[nH]c3CC(C)(C)CO)c(Cl)cn2)C1]

Hydrochloric acid in dioxane (4 M, 0.27 mL, 1.09 mmol) was added to a solution containing a 7:3 ratio of unidentified pyrazole isomers of (1S,3R)-3-acetamido-N-(4-(3-(3-((tert-butyldimethylsilyl)oxy)-2,2-dimethylpropyl)-1-((2-(trimethyl silyl)ethoxy)methyl)-1H-pyrazol-4-yl)-5-chloropyridin-2-yl)cyclohexane-1-carboxamide and (1S,3R)-3-acetamido-N-(4-(5-(3-((tert-butyldimethylsilyl)oxy)-2,2-dimethylpropyl)-1-((2-(trimethyl silyl)ethoxy)methyl)-1H-pyrazol-4-yl)-5-chloropyridin-2-yl)cyclohexane-1-carboxamide (0.75 g, 1.1 mmol) in methanol (2 mL). After 4 h the reaction was stored in the freezer for 6 days, and then concentrated under reduced pressure. The resulting residue was basified with saturated aqueous sodium bicarbonate and the resulting mixture was extracted with ethyl acetate (×2). The combined organic layers were dried over sodium sulfate, filtered, and concentrated under reduced pressure. The resulting residue was purified by flash silica chromatography, elution gradient 0 to 40% methanol in ethyl acetate, to afford (1S,3R)-3-acetamido-N-(5-chloro-4-(5-(3-hydroxy-2,2-dimethylpropyl)-1H-pyrazol-4-yl)pyridin-2-yl)cyclohexane-1-carboxamide (0.48 g, 98%) as a white solid. $^1$H NMR (DMSO-d$_6$, 27° C.) 0.49-0.66 (m, 6H), 0.97-1.13 (1H, m), 1.27 (3H, d), 1.71-1.83 (6H, m), 1.89 (1H, d), 2.54-2.70 (3H, m), 2.93-3.06 (2H, m), 3.45-3.66 (1H, m), 4.34 (0.3H, br s), 4.45-4.64 (0.7H, m), 7.54 (0.7H, br s), 7.74 (1H, d), 7.87 (0.3H, br s), 8.08 (1H, s), 8.39 (1H, s), 10.55 (1H, s), 12.77 (0.7H, br s), 12.89 (0.3H, br s). m/z: ES+ [M+H]+ 448.

Optical Rotation:
Concentration: 0.1 g/dL
Lamp: Sodium
Wavelength: 589 nm
Temperature: 25° C.
Path length: 10 cm Cell volume: 1 mL
Solvent: DMSO
[α]=+72

Procedures to prepare the starting material mixture of (1S,3R)-3-acetamido-N-(4-(3-(3-((tert-butyldimethylsilyl)oxy)-2,2-dimethylpropyl)-1-((2-(trimethylsilyl)ethoxy)methyl)-1H-pyrazol-4-yl)-5-chloropyridin-2-yl)cyclohexane-1-carboxamide and (1S,3R)-3-acetamido-N-(4-(5-(3-((tert-butyldimethylsilyl)oxy)-2,2-dimethylpropyl)-1-((2-(trimethylsilyl)ethoxy)methyl)-1H-pyrazol-4-yl)-5-chloropyridin-2-yl)cyclohexane-1-carboxamide are described below:

Preparation of Ethyl 1-benzyl-1H-pyrazole-3-carboxylate

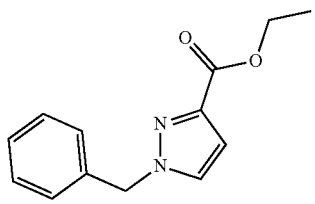 [SMILES: CCOC(=O)c1ccn(Cc2ccccc2)n1]

Sodium hydride (60 wt % in mineral oil; 3.14 g, 78.5 mmol) was added to a solution of ethyl 1H-pyrazole-3-carboxylate (10 g, 71.4 mmol), benzyl bromide (12.7 mL, 107 mmol), and DMF (100 mL) at 0° C. portionwise over 3 min with vigorous stirring. The mixture was allowed to warm to r.t. over 18 h and then diluted with ethyl acetate. The resulting mixture was washed with water (×3) and saturated aqueous sodium chloride. The organic layer was then dried over sodium sulfate, filtered and concentrated under reduced pressure. The resulting residue was purified by flash column chromatography, elution gradient 0 to 50% ethyl acetate in hexanes, to afford ethyl 1-benzyl-1H-pyrazole-3-carboxylate (11.3 g, 69%) as a slower eluting amber oil. Also isolated was ethyl 1-benzyl-1H-pyrazole-5-carboxylate (2.69 g, 16.4%) as a light amber oil.

Ethyl 1-benzyl-1H-pyrazole-3-carboxylate $^1$H NMR (DMSO-d$_6$ 27° C.) 1.28 (3H, t), 4.25 (2H, q), 5.43 (2H, s), 6.77 (1H, d), 7.23-7.42 (5H, m), 7.97 (1H, d). m/z: ES+ [M+H]+ 231.

Preparation of 1-benzyl-1H-pyrazole-3-carboxylic Acid

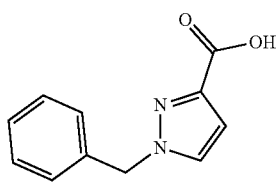 [SMILES: O=C(O)c1ccn(Cc2ccccc2)n1]

Lithium hydroxide (1.3 g, 56 mmol) was added to a solution of ethyl 1-benzyl-1H-pyrazole-3-carboxylate (11.3 g, 49.1 mmol) in tetrahydrofuran (55 mL), water (19 mL), and methanol (19 mL). After stirring under these conditions for 1.5 h, the reaction was poured into ethyl acetate and quenched with aqueous hydrochloric acid (1N; 57 mL, 57 mmol). The mixture was washed with saturated aqueous sodium chloride, and the organic layer was dried over sodium sulfate, filtered, and concentrated under reduced pressure to afford an oily white solid. This solid was taken up in minimal DCM and then diluted with 50% ether in hexanes. After stirring vigorously for 15 min the mixture was filtered to afford 1-benzyl-1H-pyrazole-3-carboxylic acid (3.78 g, 38%) as a white crystalline solid.

Additional aqueous hydrochloric acid (1N) was added to the combined aqueous layers until the mixture was at pH 5. Then the combined aqueous layers were extracted with ethyl acetate (×3), and the combined organic layers were dried over sodium sulfate, filtered, and concentrated under reduced pressure. The resulting solid was taken up in hexanes and stirred vigorously for 10 min. Upon filtration, the resulting crystalline white solid was dried under vacuum to afford additional 1-benzyl-1H-pyrazole-3-carboxylic acid (5.3 g, 53%) as a white crystalline solid. $^1$H NMR (DMSO-d$_6$, 27° C.) 5.40 (2H, s), 6.69 (1H, d), 7.22-7.41 (5H, m), 7.92 (1H, d), 12.07-13.22 (1H, br s). m/z: ES+ [M+H]+ 203.

Preparation of 1-bromo-3-methylbut-2-ene Lithium Chloride

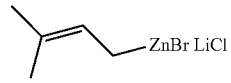

Following the procedures of Samann & Knochel (*Synthesis*, 2013, 45, 1870), lithium chloride (1.78 g, 42.0 mmol) in a flame dried flask was dried under vacuum with a heat gun for 5 min. Upon cooling, zinc powder (5.0 g, 77 mmol) was added followed by THF (37 mL). After stirring vigorously for 5 min, 1,2-dibromoethane (0.19 mL, 2.2 mmol) and then TMS-Cl (0.39 mL, 3.1 mmol) were added. The resulting mixture was allowed to stir at r.t. for 2 min and then immersed in a water bath. A light brown solution of 1-bromo-3-methylbut-2-ene (4 mL, 35 mmol) in THF (37 mL) was added dropwise over 30 min, and the water bath was removed. The black mixture was maintained under these conditions for 1.5 h and then stirring was stopped. The mixture was allowed to settle over 18 h and then used directly without further purification.

Preparation 1-benzyl-1H-pyrazole-3-carbonyl Chloride

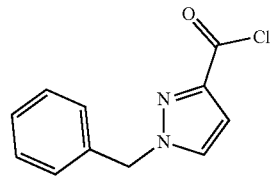 [SMILES: O=C(Cl)c1ccn(Cc2ccccc2)n1]

Two drops of DMF were added to a mixture of 1-benzyl-1H-pyrazole-3-carboxylic acid (5.26 g, 26.0 mmol) and oxalyl chloride (3.4 mL, 39 mmol) in DCM (100 mL). After 4 h, the now clear light yellow solution was concentrated under reduced pressure, and the resulting yellow-orange oil was dried under vacuum with heating (heat gun) to remove excess oxalyl chloride. The now dark orange/amber oil was used directly without further purification.

Preparation of 1-(1-benzyl-1H-pyrazol-3-yl)-2,2-dimethylbut-3-en-1-one

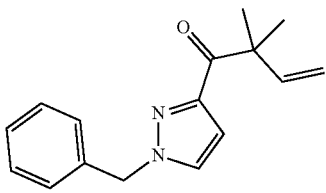 [SMILES: C=CC(C)(C)C(=O)c1ccn(Cc2ccccc2)n1]

(3-Methylbut-2-en-1-yl)zinc(II) bromide lithium chloride (77 mL, 32.5 mmol) in THF (as described above) was added dropwise to a yellow solution of 1-benzyl-1H-pyrazole-3-carbonyl chloride (5.74 g, 26.0 mmol) in tetrahydrofuran (53 mL) at −78° C. After 45 min the reaction was quenched with 50% saturated aqueous sodium chloride, and the layers were separated. The aqueous layer was extracted with ethyl acetate, and the combined organic layers were dried over sodium sulfate, filtered, and concentrated under reduced pressure. The resulting residue was purified by flash column chromatography, elution gradient 0 to 50% ethyl acetate in hexanes, to afford 1-(1-benzyl-1H-pyrazol-3-yl)-2,2-dimethylbut-3-en-1-one (5.2 g, 79%) as a clear faint amber oil. Impure product fractions were concentrated under reduced pressure and repurified using the same conditions to afford additional 1-(1-benzyl-1H-pyrazol-3-yl)-2,2-dimethylbut-3-en-1-one (0.81 g, 12%) as a faint amber oil. $^1$H NMR (DMSO-d$_6$, 27° C.) 1.40 (6H, s), 5.02 (1H, dd), 5.07 (1H, dd), 5.43 (2H, s), 6.44 (1H, dd), 6.71 (1H, d), 7.25-7.40 (5H, m), 7.89 (1H, d). m/z: ES+ [M+H]+ 255.

Preparation of 1-benzyl-3-(2,2-dimethylbut-3-en-1-yl)-1H-pyrazole

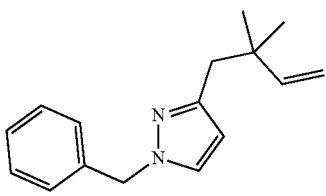 [SMILES: C=CC(C)(C)Cc1ccn(Cc2ccccc2)n1]

Hydrazine monohydrate (5.1 mL, 67 mmol) was added to a solution of 1-(1-benzyl-1H-pyrazol-3-yl)-2,2-dimethylbut-3-en-1-one (3.42 g, 13.45 mmol) and 2,2'-oxybis(ethan-1-ol) (35 mL, 369 mmol) at 120° C. The reaction was then warmed to 180° C. and aqueous potassium hydroxide (3.8 ml, 67 mmol) was added cautiously and followed by 8 KOH chips. After 1 hour, another 4 KOH chips were added. The reaction was maintained under these conditions for another 2 h and then cooled to r.t. and diluted with water. The mixture was extracted with ether (×3). The combined organic layers were dried over sodium sulfate, filtered, and concentrated under reduced pressure. The resulting residue was purified by column chromatography, elution gradient 0 to 30% ethyl acetate in hexanes, to afford 1-benzyl-3-(2,2-dimethylbut-3-en-1-yl)-1H-pyrazole (2.72 g, 84%) as a clear colorless oil. $^1$H NMR (DMSO-d$_6$, 27° C.) 0.96 (6H, s), 4.85 (1H, s), 4.88-4.93 (1H, m), 5.26 (2H, s), 5.83-5.94 (1H, m), 6.02 (1H, d), 7.12-7.17 (2H, m), 7.22-7.35 (3H, m), 7.64 (1H, d). A 2H multiplet is buried under the DMSO signal. m/z: ES+ [M+H]+ 241.

Preparation of 3-(1-benzyl-1H-pyrazol-3-yl)-2,2-dimethylpropan-1-ol

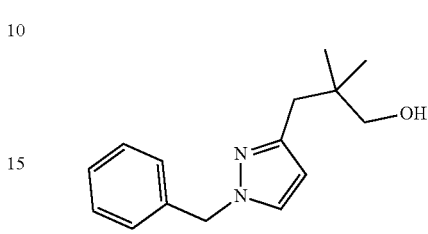

Ozone was bubbled through a solution of 1-benzyl-3-(2,2-dimethylbut-3-en-1-yl)-1H-pyrazole (2.7 g, 11 mmol) in methanol (45 mL) at −78° C. for 30 min, resulting in a light yellow-green solution. Then sodium borohydride (1.1 g, 28 mmol) was added, and the reaction was allowed to warm to r.t. After 15 min, another 200 mg of sodium borohydride were added, and the reaction was maintained under these conditions for a further 20 min. Then the reaction was concentrated under reduced pressure and quenched with concentrated aqueous HCl (4.5 mL). The resulting white mixture was diluted with water and ethyl acetate and basified with potassium carbonate until pH 8. The layers were separated, and the aqueous layer was extracted with ethyl acetate (×3). The combined organic layers were washed with saturated aqueous sodium chloride and dried over sodium sulfate, filtered, and concentrated under reduced pressure. The resulting residue was taken up in DCM and purified by flash silica chromatography, elution gradient 0 to 100% ethyl acetate in hexanes) to afford 3-(1-benzyl-1H-pyrazol-3-yl)-2,2-dimethylpropan-1-ol (2.14 g, 78%) as a clear colorless oil. $^1$H NMR (DMSO-d$_6$, 27° C.) 0.78 (6H, s), 2.42 (2H, s), 3.11 (2H, d), 4.44 (1H, t), 5.26 (2H, s), 6.04 (1H, d), 7.12-7.19 (2H, m), 7.23-7.36 (3H, m), 7.65 (1H, d). m/z: ES+ [M+H]+ 245.

Preparation of 2,2-dimethyl-3-(1H-pyrazol-3-yl)propan-1-ol

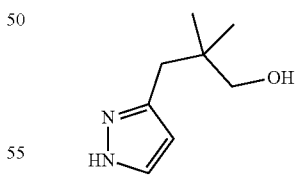

A degassed mixture of 3-(1-benzyl-1H-pyrazol-3-yl)-2,2-dimethylpropan-1-ol (2.10 g, 8.59 mmol), aqueous hydrochloric acid (1N; 3.9 mL, 3.9 mmol), and 20 wt % Pd(OH)$_2$ on carbon (0.151 g, 0.21 mmol) was subjected to a hydrogen atmosphere and warmed to 50° C. After 2 h, the reaction was filtered while still warm with a methanol wash. The clear colorless filtrate was concentrated under reduced pressure to a light yellow oil, which was then reconcentrated from toluene (×3). This afforded a light yellow gum (0.45 equiv HCl salt) which was used in the next step without further purification. ¹H NMR (DMSO-d₆, 27° C.) 0.79 (6H, s), 2.55 (2H, s), 3.11 (2H, s), 6.18 (1H, d), 7.70 (1H, d), 9.63 (1H, br s). OH and HCl signals not observed. m/z: ES+ [M+H]+ 155.

Preparation of 3-(3-((tert-butyldimethylsilyl)oxy)-2,2-dimethylpropyl)-1H-pyrazole

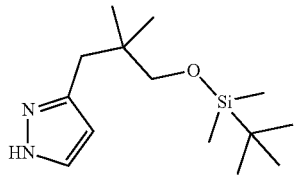 [SMILES: CC(C)(CO[Si](C)(C)C(C)(C)C)Cc1cc[nH]n1]

TBS-Cl (50 wt % in toluene; 4.5 mL, 13 mmol) was added dropwise to a solution of crude 2,2-dimethyl-3-(1H-pyrazol-3-yl)propan-1-ol (0.45 molar HCl salt; 1.47 g, 8.59 mmol) and imidazole (1.75 g, 25.8 mmol) in DCM (81 mL) at r.t. After 15 min, another 1 mL of TBS-Cl in toluene was added. The white mixture was maintained under these conditions for 1.5 h and then poured into saturated aqueous sodium bicarbonate. The layers were separated, and the aqueous layer was extracted with DCM (2×). The combined organic layers were washed with saturated aqueous sodium chloride, dried over sodium sulfate, filtered, and concentrated under reduced pressure. The resulting clear colorless oil was purified by flash silica chromatography, elution gradient 0 to 60% ethyl acetate in hexane, to afford 3-(3-((tert-butyldimethylsilyl)oxy)-2,2-dimethylpropyl)-1H-pyrazole (2.13 g, 92%) as a clear faint yellow oil. ¹H NMR (DMSO-d₆, 27° C.) 0.00 (s, 6H), 0.75 (6H, s), 0.86 (9H, s), 3.22 (2H, s), 5.92 (1H, br s), 7.08-7.67 (1H, m), 12.35 (1H, br s). m/z: ES+ [M+H]+ 269.

Preparation of 3-(3-((tert-butyldimethylsilyl)oxy)-2,2-dimethylpropyl)-14(2-(trimethylsilyl)ethoxy)methyl)-1H-pyrazole compound and 5-(3-((tert-butyldimethylsilyl)oxy)-2,2-dimethylpropyl)-1-((2-(trimethylsilyl)ethoxy)methyl)-1H-pyrazole

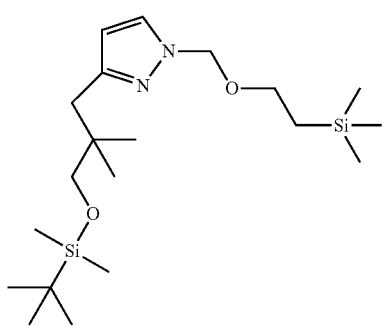

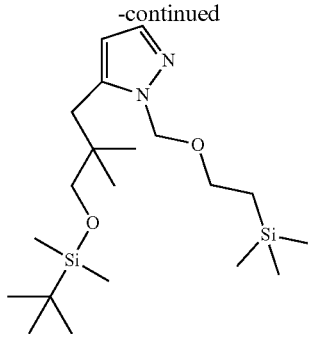

Isolated as a 2:3 ratio of unidentified SEM-protected isomers

Sodium hydride (60 wt % in mineral oil; 0.381 g, 9.52 mmol) was added in one portion to a solution of 3-(3-((tert-butyldimethylsilyl)oxy)-2,2-dimethylpropyl)-1H-pyrazole (2.13 g, 7.93 mmol) in DMF (11 mL) at 0° C. After 5 min, (2-(chloromethoxy)ethyl)trimethylsilane (SEM-Cl; 1.8 mL, 9.5 mmol) was added dropwise. After 10 min, another 100 µL of SEM-Cl were added along with 20 mg of NaH (60 wt % suspension in mineral oil). After a final 15 min, the reaction was quenched with saturated aqueous sodium bicarbonate and diluted with ethyl acetate. The layers were separated, and the organic layer was washed with 50% saturated aqueous sodium chloride (×2) and then saturated aqueous sodium chloride. The organic layer was dried over sodium sulfate, filtered, and concentrated under reduced pressure to a clear colorless oil. This oil was purified by flash silica chromatography, elution gradient 0 to 20% ethyl acetate in hexanes, to afford an unseparated mixture of 3-(3-((tert-butyldimethylsilyl)oxy)-2,2-dimethylpropyl)-1-((2-(trimethyl silyl)ethoxy)methyl)-1H-pyrazole and 5-(3-((tert-butyldimethylsilyl)oxy)-2,2-dimethylpropyl)-1-((2-(trimethylsilyl)ethoxy)methyl)-1H-pyrazole (2.58 g, 81.6%) as a 2:3 ratio of unidentified SEM-protected isomers and a clear colorless oil. ¹H NMR (DMSO-d₆, 27° C.) −0.09-(−0.05) (9H, m), 0.02-0.07 (6H, m), 0.77-0.84 (8H, m), 0.89 (9H, s), 2.44 (1.2H, s), 2.65 (0.8H, s), 3.23 (0.8H, m), 3.27 (1.2H, m), 3.48 (2H, t), 5.31 (1.2H, s), 5.40 (0.8H, s), 6.05 (0.6H, d), 6.09 (0.4H, d), 7.40 (0.4H, d), 7.71 (0.6H, d). m/z: ES+ [M+H]+ 399

Preparation of 3-(3-((tert-butyldimethylsilyl)oxy)-2,2-dimethylpropyl)-4-iodo-14(2-(trimethylsilyl)ethoxy)methyl)-1H-pyrazole compound and 5-(3-((tert-butyldimethylsilyl)oxy)-2,2-dimethylpropyl)-4-iodo-1-((2-(trimethylsilyl)ethoxy)methyl)-1H-pyrazole

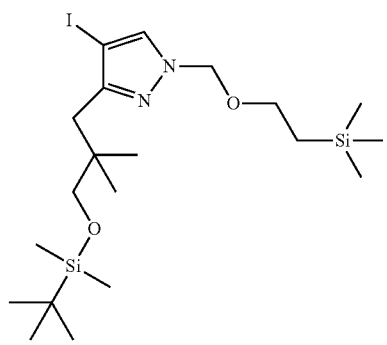

-continued

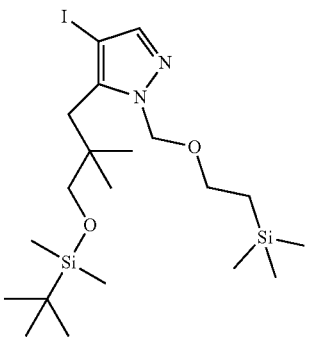

Isolated as a 2:3 ratio of unidentified SEM-protected isomers

NIS (1.78 g, 7.91 mmol) was added to a solution of an unidentified 2:3 mixture of 3-(3-((tert-butyldimethylsilyl)oxy)-2,2-dimethylpropyl)-1-((2-(trimethylsilyl)ethoxy)methyl)-1H-pyrazole compound and 5-(3-((tert-butyldimethylsilyl)oxy)-2,2-dimethylpropyl)-1-((2-(trimethylsilyl)ethoxy)methyl)-1H-pyrazole (2.58 g, 6.48 mmol) in acetonitrile (34 mL). After 18 h, another 1.8 g of NIS was added, and the reaction was warmed to 50° C. After 4 h, another 400 mg of NIS was added. After another 4 h, the reaction was allowed to cool to r.t. and was maintained under these conditions for 18 h. The reaction was then poured into 50% saturated aqueous sodium chloride and titrated with sodium thiosulfate until all dark red-amber color disappeared. The layers were separated, and the organic layer was washed with saturated aqueous sodium chloride. The organic layer was then dried over sodium sulfate, filtered, and concentrated under reduced pressure. The resulting residue was purified by flash column chromatography, elution gradient 0 to 15% ethyl acetate in hexanes, to afford 3-(3-((tert-butyldimethylsilyl)oxy)-2,2-dimethylpropyl)-4-iodo-1-((2-(trimethylsilyl)ethoxy)methyl)-1H-pyrazole compound and 5-(3-((tert-butyldimethylsilyl)oxy)-2,2-dimethylpropyl)-4-iodo-1-((2-(trimethyl silyl)ethoxy)methyl)-1H-pyrazole (2.93 g, 86%) as a 2:3 mixture of unidentified SEM-protected isomers and a light yellow oil. $^1$H NMR (DMSO-d$_6$, 27° C.) −0.09-(−0.05) (9H, m), 0.02-0.06 (6H, m), 0.76-0.92 (17H, m), 2.45 (1.2H, s), 2.71 (0.8H, s), 3.29-3.32 (0.8H, m), 3.34-3.37 (1.2H, m), 3.50 (2H, td), 5.33 (1.2H, s), 5.47 (0.8H, s), 7.56 (s, 0.4H), 7.96 (0.6H, s). m/z: ES+ [M+H]+ 525.

Preparation of 3-(3-((tert-butyldimethylsilyl)oxy)-2,2-dimethylpropyl)-4-(4,4,5,5-tetramethyl-1,3,2-dioxaborolan-2-yl)-1-((2-(trimethylsilyl)ethoxy)methyl)-1H-pyrazole Compound and 5-(3-((tert-butyldimethylsilyl)oxy)-2,2-dimethylpropyl)-4-(4,4,5,5-tetramethyl-1,3,2-dioxaborolan-2-yl)-14(2-(trimethylsilyl)ethoxy)methyl)-1H-pyrazole

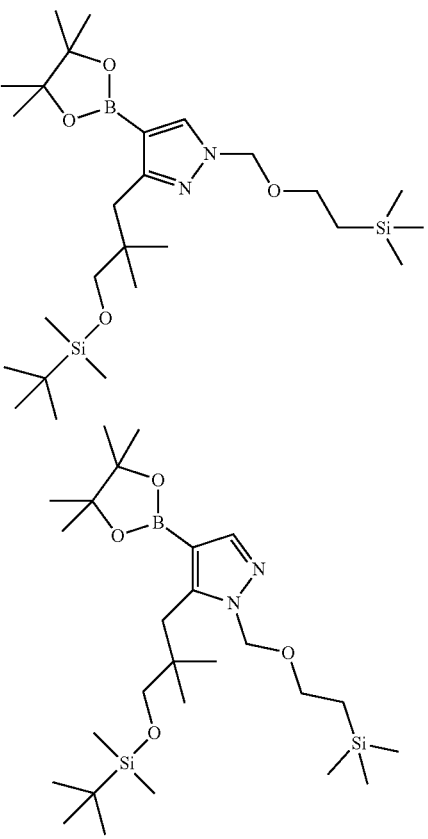

Isolated as an 3:2 ratio of SEM-protected isomers as shown

Isopropylmagnesium chloride lithium chloride complex in THF (1.3 M; 6.45 mL, 8.39 mmol) was added dropwise to a solution of a 2:3 unidentified mixture of 3-(3-((tert-butyldimethylsilyl)oxy)-2,2-dimethylpropyl)-4-iodo-1-((2-(trimethylsilyl)ethoxy)methyl)-1H-pyrazole compound and 5-(3-((tert-butyldimethylsilyl)oxy)-2,2-dimethylpropyl)-4-iodo-1-((2-(trimethylsilyl)ethoxy)methyl)-1H-pyrazole (2.93 g, 5.59 mmol) in THF (40 mL) at −78° C. After 1 hour, 2-isopropoxy-4,4,5,5-tetramethyl-1,3,2-dioxaborolane (1.8 mL, 8.9 mmol) was added dropwise, and the reaction was allowed to stir under these conditions for 2 h. Then the reaction was immersed in an ice bath (0° C.). After another 2 h, the reaction was poured into saturated aqueous ammonium chloride. The mixture was extracted with ethyl acetate (3×), and the combined organic layers were dried over sodium sulfate, filtered, and concentrated under reduced pressure. The resulting residue was purified by flash silica chromatography, elution gradient 0 to 10% ethyl acetate in hexanes over 20 min) to afford an identified 3:2 mixture of 3-(3-((tert-butyldimethylsilyl)oxy)-2,2-dimethylpropyl)-4-(4,4,5,5-tetramethyl-1,3,2-dioxaborolan-2-yl)-1-((2-(trimethyl silyl)ethoxy)methyl)-1H-pyrazole and 5-(3-((tert-butyldimethylsilyl)oxy)-2,2-dimethylpropyl)-4-(4,4,5,5-tetramethyl-1,3,2-dioxaborolan-2-yl)-1-((2-(trimethyl silyl)ethoxy)methyl)-1H-pyrazole (2.37 g, 80%) as a clear colorless oil. $^1$H NMR (DMSO-d$_6$, 27° C.) −0.09-(−0.05) (9H, m), 0.01-0.06 (6H, m), 0.73-0.84 (8H, m), 0.87-0.92 (9H, m), 1.24 (12H, s), 2.63 (1.2H, s), 2.85 (0.6H, s), 3.26 (0.8H, s), 3.33 (1.2H, s), 3.50 (2H, t), 5.33 (1.2H, s), 5.43 (8H, s), 7.54 (4H, s), 7.91 (0.6H, s). m/z: ES+ [M+H]+ 525.

Preparation of (1S,3R)-3-acetamido-N-(4-(3-(3-((tert-butyldimethylsilyloxy)-2,2-dimethylpropyl)-14 (2-(trimethylsilyl)ethoxy)methyl)-1H-pyrazol-4-yl)-5-chloropyridin-2-yl)cyclohexane-1-carboxamide and (1S,3R)-3-acetamido-N-(4-(5-(3-((tert-butyldimethylsilyl)oxy)-2,2-dimethylpropyl)-1-((2-(trimethylsilyl)ethoxy)methyl)-1H-pyrazol-4-yl)-5-chloropyridin-2-yl)cyclohexane-1-carboxamide

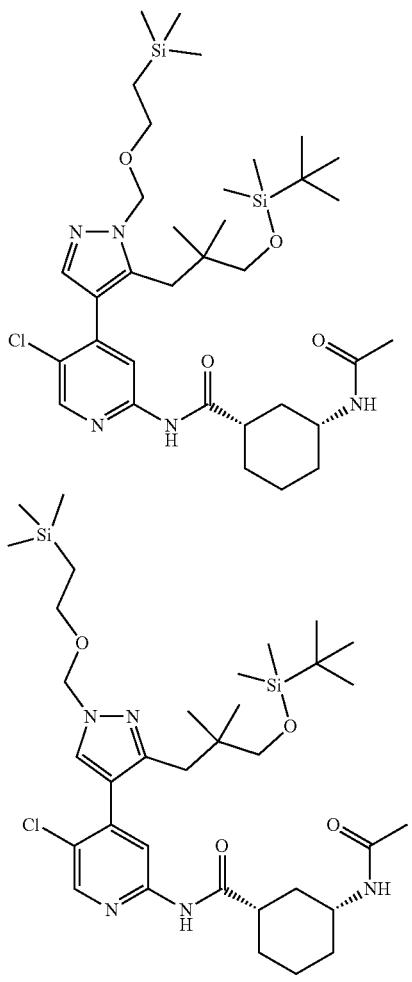

Isolated as a 3:7 ratio of SEM-protected isomers

PdCl$_2$(dppf) (DCM adduct; 0.061 g, 0.07 mmol) and cesium carbonate (1.45 g, 4.46 mmol) were added to a degassed mixture of (1S,3R)-3-acetamido-N-(5-chloro-4-iodopyridin-2-yl)cyclohexane-1-carboxamide (0.74 g, 1.49 mmol; prepared according to Example 12), a 3:2 mixture of 3-(3-((tert-butyldimethylsilyl)oxy)-2,2-dimethylpropyl)-4-(4,4,5,5-tetramethyl-1,3,2-dioxaborolan-2-yl)-1-((2-(trimethylsilyl)ethoxy)methyl)-1H-pyrazole and 5-(3-((tert-butyldimethylsilyl)oxy)-2,2-dimethylpropyl)-4-(4,4,5,5-tetramethyl-1,3,2-dioxaborolan-2-yl)-1-((2-(trimethylsilyl)ethoxy)methyl)-1H-pyrazole (0.813 g, 1.55 mmol), 1,4-dioxane (12 mL), and water (2.5 mL). The mixture was warmed to 93° C. and maintained under these conditions for 18 h. The reaction was then cooled, diluted with ethyl acetate, and washed with saturated aqueous sodium chloride. The organic layer was dried over sodium sulfate, filtered, and concentrated under reduced pressure. The resulting black-green residue was purified by flash silica chromatography, elution gradient 50 to 100% ethyl acetate in hexane then 0 to 10% methanol in ethyl acetate, to afford (1S,3R)-3-acetamido-N-(4-(3-(3-((tert-butyldimethylsilyl)oxy)-2,2-dimethylpropyl)-1-((2-(trimethylsilyl)ethoxy)methyl)-1H-pyrazol-4-yl)-5-chloropyridin-2-yl)cyclohexane-1-carboxamide and (1S,3R)-3-acetamido-N-(4-(5-(3-((tert-butyldimethylsilyl)oxy)-2,2-dimethylpropyl)-1-((2-(trimethyl silyl)ethoxy)methyl)-1H-pyrazol-4-yl)-5-chloropyridin-2-yl)cyclohexane-1-carboxamide (0.75 g, 73%) in a 3:7 ratio of unidentified SEM-protected isomers as a light amber glass. $^1$H NMR (DMSO-d$_6$, 27° C.) −0.06-0.02 (15H, m), 0.61 (1.7H, s), 0.72 (4.3H, s), 0.81 (6.3H, s), 0.84-0.93 (4.7H, m), 1.04-1.22 (1H, m), 1.22-1.40 (3H, m), 1.71-1.87 (6H, m), 1.88-1.98 (1H, m), 2.58-2.73 (2.4H, m), 2.91 (0.6H, s), 3.12 (0.6H, s), 3.19 (1.4H, s), 3.55-3.67 (3H, m), 5.46 (1.3H, s), 5.57 (0.7H, s), 7.66 (0.3H, s), 7.78 (1H, d), 8.09 (0.7H, s), 8.12-8.15 (0.3H, s), 8.15-8.17 (0.7H, s), 8.42-8.44 (0.7H, s), 8.46 (0.3H, s), 10.64 (1H, s). m/z: ES+ [M+H]+ 692.

Example 82: Preparation of (1S,3R)-3-acetamido-N-(5-chloro-4-(6-hydroxy-5,5-dimethyl-5,6-dihydro-4H-pyrrolo[1,2-b]pyrazol-3-yl)pyridin-2-yl)cyclohexane-1-carboxamide

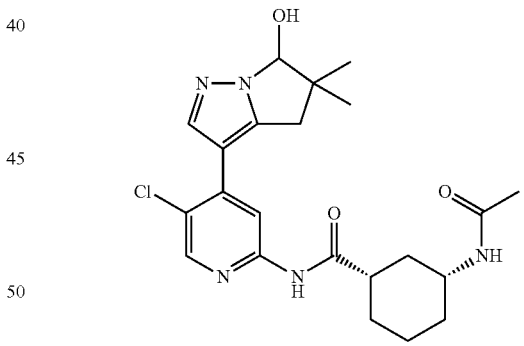

Unknown mixture of diastereomers as the hydroxy configuration is unknown

Pyridine sulfur trioxide (0.30 g, 1.9 mmol) was added to a solution of (1S,3R)-3-acetamido-N-(5-chloro-4-(5-(3-hydroxy-2,2-dimethylpropyl)-1H-pyrazol-4-yl)pyridin-2-yl)cyclohexane-1-carboxamide (0.48 g, 1.1 mmol, prepared in Example 82a) in DCM (6.8 mL) and dimethylsulfoxide (3.4 mL) at 0° C. The resulting solution was maintained under these conditions for 15 minutes and then poured into ethyl acetate and saturated aqueous ammonium chloride. The layers were separated and the organic layer was washed with 50% saturated aqueous sodium chloride and then 100% saturated aqueous sodium chloride. The organic layer was dried over sodium sulfate, filtered, and concentrated under reduced pressure. The resulting turbid residue was taken up in DCM and purified by flash silica chromatography, elution gradient 0 to 40% methanol in ethyl acetate, to afford a white foam solid (460 mg). This solid was further purified by preparative HPLC (Waters)(Bridge Phenyl Prep column, 5μ silica, 19 mm diameter, 100 mm length), using decreasingly polar mixtures of water (containing 0.2% NH$_4$OH, pH 10) and methanol as eluents. Fractions containing the desired compound were concentrated under reduced pressure to afford (1S,3R)-3-acetamido-N-(5-chloro-4-(6-hydroxy-5,5-dimethyl-5,6-dihydro-4H-pyrrolo[1,2-b]pyrazol-3-yl)pyridin-2-yl)cyclohexane-1-carboxamide (255 mg, 53%) as a white foam solid. $^1$H NMR (DMSO-d$_6$, 27° C.) 0.99-1.16 (4H, m), 1.20 (3H, s), 1.23-1.40 (3H, m), 1.73-1.83 (6H, m), 1.89 (1H, d), 2.56-2.68 (1H, m), 2.75 (1H, d), 2.95 (1H, d), 3.50-3.63 (1H, m), 5.25 (1H, s), 6.92 (1H, br s), 7.75 (1H, d), 8.04 (1H, s), 8.25 (1H, s), 8.36 (1H, s), 10.56 (1H, s). m/z: ES+ [M+H]+ 446.

Examples 83 and 84: Preparation of (1R,3R)-3-acetamido-N-(4-(5,5-dimethyl-5,6-dihydro-4H-pyrrolo[1,2-b]pyrazol-3-yl)-5-fluoropyridin-2-yl)cyclohexane-1-carboxamide and (1S,3S)-3-acetamido-N-(4-(5,5-dimethyl-5,6-dihydro-4H-pyrrolo[1,2-b]pyrazol-3-yl)-5-fluoropyridin-2-yl)cyclohexane-1-carboxamide Example 83, Isomer 1

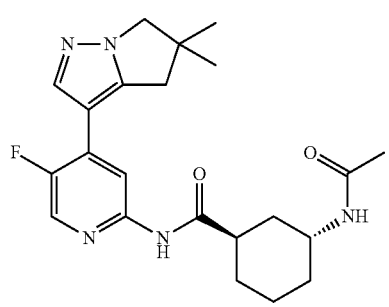

Example 84, Isomer 2

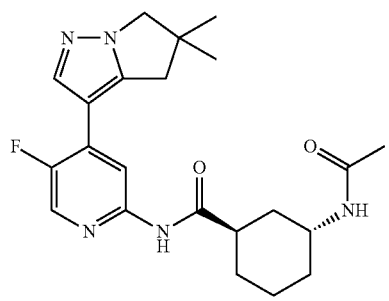

Examples 83 and 84 are pure enantiomers. The absolute configuration for Examples 83 and 84 are unknown, but are opposite from one another. Relative configuration is trans for both Examples 83 and 84.

Triethylamine (0.29 mL, 2.1 mmol) and acetic anhydride (0.066 mL, 0.70 mmol) were added to racemic trans-3-amino-N-(4-(5,5-dimethyl-5,6-dihydro-4H-pyrrolo[1,2-b]pyrazol-3-yl)-5-fluoropyridin-2-yl)cyclohexane-1-carboxamide (0.24 g, 0.64 mmol) in DCM (4 mL). After stirring at r.t. for 1 hour, the mixture was washed with water and concentrated under reduced pressure. The resulting residue was purified by flash silica chromatography, elution gradient 0 to 10% MeOH in DCM, to afford racemic trans-3-acetamido-N-(4-(5,5-dimethyl-5,6-dihydro-4H-pyrrolo[1,2-b]pyrazol-3-yl)-5-fluoropyridin-2-yl)cyclohexane-1-carboxamide (0.270 g) as a colourless oil. The racemic material was resolved by preparative HPLC (Phenomonex Lux C4 column, 20 μm silica, 50 mm diameter, 250 mm length), using a 70/30 mixture of Heptane/IPA as eluent at 120 mL/min. Fractions containing isomer 1 (faster eluting) and isomer 2 (slower eluting) were evaporated to dryness. Isomer 1 (114 mg) was repurified by preparative HPLC (Waters) (Bridge Prep C18 OBD column, 5μ silica, 30 mm diameter, 100 mm length), using decreasingly polar mixtures of water (containing 1% NH$_3$) and MeCN as eluents to afford isomer 1 of trans-3-acetamido-N-(4-(5,5-dimethyl-5,6-dihydro-4H-pyrrolo[1,2-b]pyrazol-3-yl)-5-fluoropyridin-2-yl)cyclohexane-1-carboxamide (0.081 g, 31%).

Isomer 2 of trans-3-acetamido-N-(4-(5,5-dimethyl-5,6-dihydro-4H-pyrrolo[1,2-b]pyrazol-3-yl)-5-fluoropyridin-2-yl)cyclohexane-1-carboxamide (0.090 g, 34%) was isolated from the first chiral preparative purification.

Example 83, Isomer 1

$^1$H NMR (400 MHz, DMSO-d$_6$, 30° C.) 1.29 (6H, s), 1.45-1.83 (9H, m), 1.86 (3H, s), 2.71-2.84 (1H, m), 2.94 (2H, s), 3.94 (2H, s), 7.54 (1H, d), 7.89 (1H, d), 8.22-8.34 (2H, m), 10.30 (1H, s). m/z: ES+ [M+H]+ 414.

Example 84, Isomer 2

$^1$H NMR (400 MHz, CDCl$_3$, 30° C.) 1.35 (6H, s), 1.44-1.92 (7H, m), 1.95-2.04 (4H, m), 2.54 (1H, s), 3.02 (2H, s), 3.94 (2H, s), 4.17-4.35 (1H, m), 5.57 (1H, d), 8.01 (1H, d), 8.08 (2H, d), 8.34 (1H, d). m/z: ES+ [M+H]+ 414.

Analytical Chiral Conditions:
Column: Chiralpak IA column ID-2
Column Dimensions: 5 μm, 4.6 mm diameter, 250 mm length,
Mobile Phase A: Heptane
Mobile Phase B: Isopropanol
Gradient: Isocratic 30% Mobile Phase B
Flow Rate: 2 mL/min over 15 min
Retention Time: 6.34 min, Example 83, Isomer 1
8.93 min, Example 84, Isomer 2
e.e. >98% (both isomers)

Procedures used to prepare racemic trans-3-amino-N-(4-(5,5-dimethyl-5,6-dihydro-4H-pyrrolo[1,2-b]pyrazol-3-yl)-5-fluoropyridin-2-yl)cyclohexane-1-carboxamide are described below:

Preparation of Racemic trans-3-((tert-butoxycarbonyl)amino)cyclohexane-1-carboxylic acid

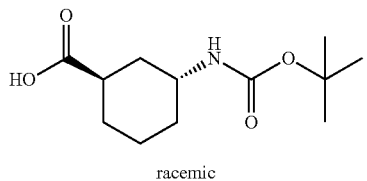 [SMILES: CC(C)(C)OC(=O)N[C@@H]1CCC[C@@H](C(=O)O)C1]

racemic

A solution of racemic trans-3-aminocyclohexanecarboxylic acid hydrochloride (2.00 g, 11.1 mmol) and N-ethyl-N-isopropylpropan-2-amine (7.9 mL, 44 mmol) in 1,4- dioxane (16 mL) and water (16 mL) was cooled to 0° C. Di-tert-butyl dicarbonate (2.67 g, 12.25 mmol) was then added portionwise to the reaction mixture, which was allowed to warm to r.t. after the final portion was added. The reaction mixture was then cooled to 0° C., and 2 M aqueous hydrochloric acid was added to adjust the pH to 2. The reaction mixture was extracted with EtOAc (2×200 mL), and the combined organic layers were washed with water (100 mL) and dried over Na$_2$SO$_4$. The resulting mixture was filtered, and the filtrate was concentrated under reduced pressure. The resulting white solid was dried under vacuum for 18 h to afford racemic trans-3-((tert-butoxycarbonyl)amino)cyclohexane-1-carboxylic acid (2.73 g, 101%). $^1$H NMR (400 MHz, DMSO-d$_6$, 30° C.) 1.25-1.33 (1H, m), 1.39 (9H, s), 1.45-1.61 (6H, m), 1.71-1.81 (1H, m), 2.58-2.69 (1H, m), 3.55 (1H, br s), 6.71 (1H, br s), 12.03 (1H, br s).

Preparation of Racemic Tert-butyl trans-(-3-carbamoylcyclohexyl)carbamate

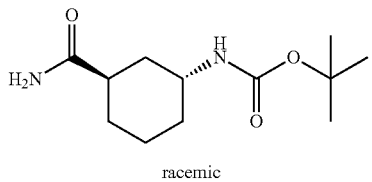 [SMILES: CC(C)(C)OC(=O)N[C@@H]1CCC[C@@H](C(N)=O)C1]

racemic

CDI (3.14 g, 19.39 mmol) was added to a solution of racemic trans-3-((tert-butoxycarbonyl)amino)cyclohexanecarboxylic acid (1.73 g, 7.11 mmol) in DMF (15 mL) at 40 CC. The resulting mixture was maintained under these conditions for 4 h. The reaction mixture was then cooled to 0° C. and acetic acid ammonia salt (3.49 g, 45.3 mmol) was added. The reaction mixture was allowed to warm to r.t. and stirred for a further 60 h. The reaction mixture was poured into ice water, and the resulting mixture was filtered. The collected precipitate was dried under vacuum to give racemic tert-butyl trans-(3-carbamoylcyclohexyl)carbamate (0.95 g, 61%). $^1$H NMR (400 MHz, CDCl$_3$, 30° C.) 1.45 (9H, s), 1.48-1.56 (2H, m), 1.62-1.78 (4H, m), 1.79-1.92 (2H, m), 2.45 (1H, dt), 3.84 (1H, s), 4.57 (1H, s), 5.35 (1H, br s), 5.66 (1H, br s).

Preparation of Racemic Tert-butyl (trans-34(4-(5,5-dimethyl-5,6-dihydro-4H-pyrrolo[1,2-b]pyrazol-3-yl)-5-fluoropyridin-2-yl)carbamoyl)cyclohexyl)carbamate

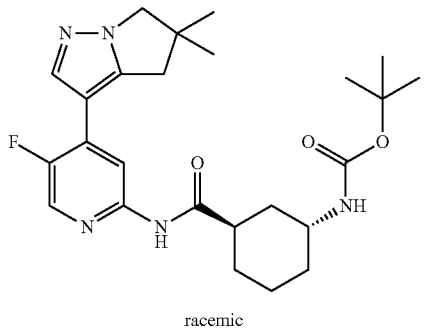 [SMILES: CC1(C)Cc2c(-c3cc(NC(=O)[C@@H]4CCC[C@@H](NC(=O)OC(C)(C)C)C4)ncc3F)cnn2C1]

racemic

Tetrakis(triphenylphosphine)palladium(0) (0.094 g, 0.08 mmol) was added to racemic tert-butyl (trans-3-carbamoyl cyclohexyl)carbamate (0.235 g, 0.97 mmol), 3-(2-chloro-5-fluoropyridin-4-yl)-5,5-dimethyl-5,6-dihydro-4H-pyrrolo[1,2-b]pyrazole (0.215 g, 0.81 mmol, prepared according to Example 25), (9,9-dimethyl-9H-xanthene-4,5-diyl)bis(diphenylphosphane) (0.094 g, 0.16 mmol) and cesium carbonate (0.791 g, 2.43 mmol) in 1,4-dioxane (6 mL) and water (1.2 mL). The resulting suspension was degassed for 10 minutes under nitrogen and then stirred at 100° C. for 48 h. The mixture was cooled, diluted with water (40 mL), and extracted with EtOAc (3×20 mL). The combined organics were evaporated to crude material. The crude product was purified by flash silica chromatography, elution gradient 0 to 60% ethyl acetate in heptane. Pure fractions were evaporated to dryness to afford racemic tert-butyl (trans-3-((4-(5,5-dimethyl-5,6-dihydro-4H-pyrrolo[1,2-b]pyrazol-3-yl)-5-fluoropyridin-2-yl)carbamoyl)cyclohexyl)carbamate (0.322 g, 84%) as a white foam solid. m/z: ES+ [M+H]+ 472.

Preparation of Racemic trans-3-amino-N-(4-(5,5-dimethyl-5,6-dihydro-4H-pyrrolo[1,2-b]pyrazol-3-yl)-5-fluoropyridin-2-yl)cyclohexane-1-carboxamide

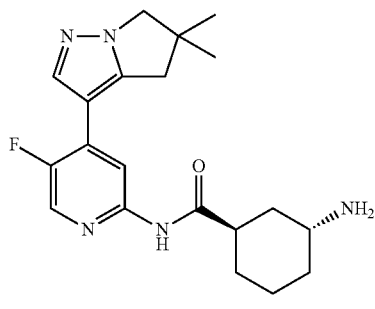

racemic

Trifluoroacetic acid (2.3 g, 20 mmol) was added to a solution of racemic tert-butyl (trans-3-((4-(5,5-dimethyl-5,6-dihydro-4H-pyrrolo[1,2-b]pyrazol-3-yl)-5-fluoropyridin-2-yl)carbamoyl)cyclohexyl)carbamate (0.322 g, 0.68 mmol) in DCM (10 mL). After 15 min, the reaction was purified by ion exchange chromatography using an SCX column. The desired product was eluted from the column using 1M NH$_3$ in MeOH and pure fractions were concentrated under reduced pressure to afford racemic trans-3-amino-N-(4-(5,5-dimethyl-5,6-dihydro-4H-pyrrolo[1,2-b]pyrazol-3-yl)-5-fluoropyridin-2-yl)cyclohexane-1-carboxamide (0.237 g, 93%) as a white dry film. m/z: ES+ [M+H]+ 372.

Example 85: Preparation of (1S,3R)-3-acetamido-N-(5-chloro-4-(5,5-dimethyl-5,6-dihydro-4H-pyrrolo[1,2-b]pyrazol-3-yl)pyridin-2-yl)cyclohexane-1-carboxamide

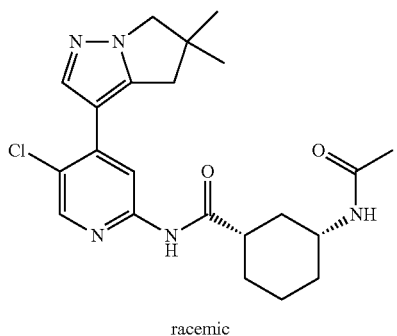 [SMILES: CC(=O)N[C@@H]1CCC[C@H](C(=O)Nc2cc(-c3cnn4c3CC(C)(C)C4)c(Cl)cn2)C1]

racemic

5-Chloro-4-(5,5-dimethyl-5,6-dihydro-4H-pyrrolo[1,2-b]pyrazol-3-yl)pyridin-2-amine (56.7 g, 215.7 mmol) and pyridine (0.073 L, 863 mmol) were added to a fine suspension of (1S,3R)-3-acetamidocyclohexane-1-carboxylic acid (49.9 g, 84% w/w, 227 mmol) in EtOAc (1 L) under a nitrogen atmosphere. Then 1-propanephosphonic anhydride ($T_3P$, ≥50 wt % in EtOAc; 206 g, 324 mmol) was added slowly over 1 hour. After an additional 20 h of stirring, water (400 mL) was added, and the biphasic mixture was stirred for an additional 10 minutes. The organic layer was washed with saturated aqueous sodium carbonate (300 mL) and water (300 mL). The organic layer was concentrated under reduced pressure, and the resulting solid was taken up in acetonitrile (300 mL) and reconcentrated under reduced pressure. Acetonitrile (450 mL) was again added, and the resulting suspension was heated to 70° C. Seed crystals were added, and the thick suspension was stirred at 50° C. for 3 h. The mixture was then cooled to 20° C. and maintained under these conditions for 3 days. The suspension was filtered, and the isolated precipitate was washed with acetonitrile (3×100 mL) and then dried under reduced pressure at 45° C. This yielded (1S,3R)-3-acetamido-N-(5-chloro-4-(5,5-dimethyl-5,6-dihydro-4H-pyrrolo[1,2-b]pyrazol-3-yl)pyridin-2-yl)cyclohexane-1-carboxamide as an off-white crystalline solid (83.2 g, 90%). $^1$H NMR (400 MHz, CDCl$_3$, 23° C.) 1.08-1.23 (1H, m), 1.33 (6H, s), 1.37-1.57 (3H, m), 1.86-2.04 (6H, m), 2.26 (1H, d), 2.38-2.52 (1H, m), 2.95 (2H, s), 3.79-3.92 (1H, m), 3.94 (2H, s), 5.51 (1H, d), 8.09 (1H, s), 8.12 (1H, s), 8.22 (1H, s), 8.24 (1H, s). m/z: ES+ [M+H]+ 430. Characterisation consistent with Example 14.

The crystals obtained from Example 85 were analyzed by XRPD, confirming that the solid contains exclusively Form A, previously characterized in Example 14.

Procedures used to prepare the starting materials 5-chloro-4-(5,5-dimethyl-5,6-dihydro-4H-pyrrolo[1,2-b]pyrazol-3-yl)pyridin-2-amine and (1S,3R)-3-acetamidocyclohexane-1-carboxylic acid are described below:

Preparation of cis-3-(isopropoxycarbonyl)cyclohexanaminium Chloride

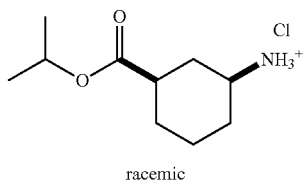

racemic

Hydrochloric acid (5 to 6 M in 2-propanol; 16 mL) was added to a suspension of 3-aminobenzoic acid (10 g, 73 mmol) in 2-propanol (100 mL). Then rhodium (5% on Al$_2$O$_3$; 0.75 g, 0.36 mmol) was added, and the mixture was subjected to a hydrogen atmosphere (8 bar) at 100° C. for 3 days. Additional hydrochloric acid (5 to 6 M in 2-propanol; 5 mL) was added, and the mixture was stirred at 70° C. in a sealed steel vessel for an additional 2 days. The mixture was then filtered through Celite® using 2-propanol (2×10 mL) and water (2×20 mL) washes. The filtrate was concentrated under reduced pressure to afford a white solid. This solid was treated with 2-propanol (50 mL) and reconcentrated under reduced pressure before being suspended in 100 mL of hot (70° C.) isopropyl acetate. The mixture was slowly cooled to 20° C. and then stirred for an additional 15 minutes. The mixture was filtered, and the solid collected was washed with isopropyl acetate (3×30 mL) and dried under reduced pressure to afford cis-3-(isopropoxycarbonyl)cyclohexanaminium chloride (7.5 g, 46%) as a white solid. $^1$H NMR (400 MHz, D$_2$O, 23° C.) 1.27 (6H, d), 1.30-1.57 (4H, m), 1.90-2.14 (3H, m), 2.28 (1H, d), 2.52 (1H, tt), 3.20-3.36 (1H, m), 5.01 (1H, hept).

Preparation of cis-isopropyl 3-aminocyclohexanecarboxylate racemic

A solution of sodium hydroxide (2.72 g, 68.1 mmol) in water (20 mL) was slowly added to a mixture of cis-3-(isopropoxycarbonyl)cyclohexanaminium chloride (14.0 g, 62 mmol) in water (50 mL) and i-Pr acetate (150 mL) at 20° C. until a pH of 10.9 was obtained. The aqueous layer was extracted with i-Pr acetate (2×50 mL) and the pooled organic layer was concentrated under reduced pressure. The resulting residue was reconcentrated from isopropyl acetate (2×20 mL) to afford cis-isopropyl 3-aminocyclohexanecarboxylate as a colorless non-viscous oil (11.86 g, 100% yield). $^1$H NMR (400 MHz, CDCl$_3$, 20° C.) 0.83-0.97 (1H, m), 0.82-

1.27 (5H, m), 1.11 (6H, d), 1.67-1.82 (3H, m), 1.93-2.02 (1H, m), 2.18 (1H, tt), 2.56 (1H, tt), 4.88 (1H, hept).

Preparation of (1S,3R)-isopropyl 3-acetamidocyclohexanecarboxylate

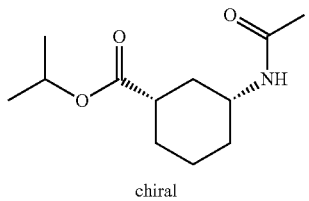 [SMILES: CC(=O)N[C@@H]1CCC[C@H](C(=O)OC(C)C)C1]

chiral

NOVOZYM 435 (3 g, purchased from Novozymes A/S Denmark (activity 10000 PLU/g)) was added to a clear solution of cis-isopropyl 3-aminocyclohexanecarboxylate (59.4 g, 298 mmol) in isopropyl acetate (480 mL). The mixture was stirred at 20° C. for 12 h and then filtered. The collected precipitate was washed with isopropyl acetate (150 mL), and the filtrate was washed with aqueous hydrochloric acid (2 M; 200 mL). The aqueous layer was extracted with isopropyl acetate (3×150 mL), and the combined organic layers were again filtered and concentrated under reduced pressure to a white solid (43 g). This solid was taken up in isopropyl acetate (2×200 mL) and reconcentrated under reduced pressure. The resulting residue was dissolved in isopropyl acetate (400 mL) and washed with saturated aqueous sodium carbonate (50 mL). The aqueous layer was extracted with isopropyl acetate (100 mL), and the combined organic layers were washed with water (50 mL) and concentrated under reduced pressure to a white solid. This solid was taken up in isopropyl acetate (2×100 mL) and again reconcentrated under reduced pressure. The resulting residue was treated with cyclopentylmethylether (70 mL) and cyclohexane (140 mL). This afforded a suspension, which was heated to 70° C. A homogenous solution was obtained, which, upon cooling to 20° C., became a mixture. Seed crystals were added at 50° C. The resulting suspension was stirred for 2 days followed by filtration and washing of the solid with 33% cyclopentylmethyl ether in cyclohexane (2×30 mL). After drying under reduced pressure, (1S,3R)-isopropyl 3-acetamidocyclohexanecarboxylate (26.8 g, 40%) was obtained as a white solid. $^1$H NMR (400 MHz, CDCl$_3$, 20° C.) 1.01-1.13 (1H, m), 1.20 (6H, d), 1.22-1.45 (3H, m), 1.77-1.93 (3H, m), 1.94 (3H, s), 2.12-2.26 (1H, m), 2.37 (1H, tt), 3.70-3.91 (1H, m), 4.96 (1H, p), 5.67 (1H, d).

Analytical SFC Conditions:
Column: Lux C2
Column Dimensions: 3 μm, 4.6 mm diameter, 150 mm length,
Column Temperature: 40° C.
Mobile Phase A: CO$_2$ (100%)
Mobile Phase B: Isopropanol
Gradient: Isocratic 15% Mobile Phase B
Outlet Pressure: 120 bar
Flow Rate: 3.5 mL/min over 5 min
Retention Time:
1.9 min, (1R,3S)-isopropyl 3-acetamidocyclohexanecarboxylate
2.7 min, (1S,3R)-isopropyl 3-acetamidocyclohexanecarboxylate
e. e. 99.9%, (1S,3R)-isopropyl 3-acetamidocyclohexanecarboxylate Preparation of (1S,3R)-3-acetamidocyclohexanecarboxylic Acid

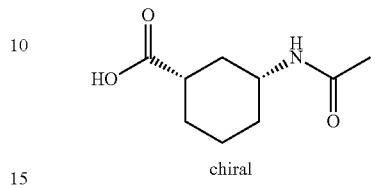

chiral

A solution of aqueous sodium hydroxide (3.8 M; 3.9 mL, 14.8 mmol) was added under an atmosphere of nitrogen to a solution of (1S,3R)-isopropyl 3-acetamidocyclohexanecarboxylate (1.71 g, 7.37 mmol) in MeOH (3 mL). The mixture was stirred at 20° C. for 1 hour and then a solution of aqueous hydrochloric acid (3.8 M; 4.5 mL) was added to the mixture until a pH of 1 was achieved. Ethyl acetate (10 mL) was added, and the layers were separated. The aqueous layer was extracted with ethyl acetate (4×10 mL). The combined organic layers were concentrated under reduced pressure at 40° C. The resulting residue was reconcentrated from ethyl acetate (2×10 mL) to afford (1S,3R)-3-acetamidocyclohexanecarboxylic acid (1.4 g, 94%; 92 wt %) contaminated with sodium chloride as a white solid. $^1$H NMR (400 MHz, CD$_3$OD, 20° C.) 1.08-1.47 (4H, m), 1.78-1.99 (6H, m), 2.12 (1H, d), 2.3-2.45 (1H, m), 3.58-3.74 (1H, m). m/z: ES+ [M+H]+ 186.

3-Bromo-5,5-dimethyl-5,6-dihydro-4H-pyrrolo[1,2-b]pyrazole

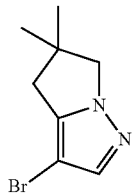

A reactor was charged with 5,5-dimethyl-5,6-dihydro-4H-pyrrolo[1,2-b]pyrazole (79.5 g, 525 mmol; prepared according to Example 14) and CH$_2$Cl$_2$ (800 mL) under a nitrogen atmosphere. NBS (95.4 g, 533 mmol) was added portionwise over 15 minutes. The reaction temperature was kept between 20 and 23° C. during addition. After 0.5 h of stirring at 20° C., a solution of aqueous 8 wt % Na$_2$SO$_3$ (250 mL) was added, and the biphasic mixture was stirred under these conditions for 45 minutes. The organic layer was washed with saturated aqueous sodium carbonate (1×250 mL, 1×200 mL) and water (100 mL). The organic layer was then concentrated under reduced pressure at 30° C. and 400 mbar. The resulting residue was reconcentrated from THF (3×100 mL) to afford 3-bromo-5,5-dimethyl-5,6-dihydro-4H-pyrrolo[1,2-b]pyrazole (138 g, 99%; 81 wt % by NMR strength analysis) as a pale brown oil. This material was used in the next step without further purification. $^1$H NMR (400 MHz, CDCl$_3$, 20° C.) 1.29 (6H, s), 2.64 (2H, s), 3.89 (2H, s), 7.41 (1H, s).

Preparation of 5,5-dimethyl-3-(4,4,5,5-tetramethyl-1,3,2-dioxaborolan-2-yl)-5,6-dihydro-4H-pyrrolo[1,2-b]pyrazole

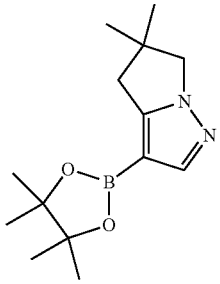 [SMILES: CC1(C)Cc2c(B3OC(C)(C)C(C)(C)O3)cnn2C1]

A solution of butyllithium (2.5 M in hexanes; 0.309 L, 774 mmol) was slowly added to a solution of 3-bromo-5,5-dimethyl-5,6-dihydro-4H-pyrrolo[1,2-b]pyrazole (137 g, 516 mmol; 81 wt %) and triisopropyl borate (0.21 L, 929 mmol) in THF (0.7 L) and toluene (0.7 L) at −70° C. under a nitrogen atmosphere in a 3 L 3-necked flask equipped with a thermometer. The reaction temperature was kept between −65 to −70° C. during addition. After addition was complete a solution of 2,3-dimethylbutane-2,3-diol (91 g, 774 mmol) in toluene (0.5 L) was added over 10 minutes. The mixture was slowly allowed to attain r.t. in the ice-bath and was then stirred for an additional 18 h. The reaction mixture was transferred to a 5 L reactor containing a cold 10° C. solution of saturated aqueous ammonium chloride (2.5 L). The biphasic mixture was stirred for 15 minutes at 20° C., and the organic layer was washed with water (2×500 mL) followed by concentration at 35° C. to afford 5,5-dimethyl-3-(4,4,5,5-tetramethyl-1,3,2-dioxaborolan-2-yl)-5,6-dihydro-4H-pyrrolo[1,2-b]pyrazole as a light yellow solid (194 g, 92%; 64 wt % by NMR strength analysis). This material was used in the next step without further purification. $^1$H NMR (400 MHz, CDCl$_3$, 20° C.) 1.21 (6H, s), 1.26 (12H, s), 2.77 (2H, s), 3.84 (2H, s), 7.74 (1H, s). m/z: ES+ [M+H]+ 263.

Preparation of 5-chloro-4-iodopyridin-2-amine

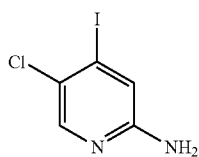

5-Chloro-2-fluoro-4-iodopyridine (90 g, 350 mmol) dissolved in NMP (200 mL) was added to a 10° C. solution of concentration aqueous ammonium hydroxide (aq. 26%; 298 g, 4.54 mol). The reaction temperature was kept below 10° C. during addition. The vessel was sealed and then warmed to 100° C. After 18 h, the mixture was cooled to r.t., after which a suspension was obtained. The crude mixture was combined with that obtained in a small scale experiment carried out under identical conditions starting from 8 g (31 mmol) of 5-chloro-2-fluoro-4-iodopyridine. MTBE (500 mL) and water (200 mL) were added. The layers were separated, and the aqueous layer was extracted with MTBE (2×250 mL). The combined organic layers were washed with water (100 mL) and then concentrated under reduced pressure to a beige solid. This solid was reconcentrated under reduced pressure from MTBE (2×200 mL) to remove residual water. Then the crude mixture was dissolved in hot (65° C.) toluene (400 mL) using a rotary evaporator. The mixture was then slowly allowed to attain 45° C. after which seed crystals were added. The suspension obtained was slowly allowed to cool to 10° C. and was then stirred for an additional 18 h under these conditions. The suspension was filtered and the solid collected was washed with ice-cold toluene (2×70 mL). This yielded 5-chloro-4-iodopyridin-2-amine (63.8 g, 65.9%) as a colorless solid. $^1$H NMR (400 MHz, DMSO-d$_6$, 20° C.) 6.23 (2H, s), 7.04 (1H, s), 7.92 (1H, s).

Preparation of 5-chloro-4-(5,5-dimethyl-5,6-dihydro-4H-pyrrolo[1,2-b]pyrazol-3-yl)pyridin-2-amine

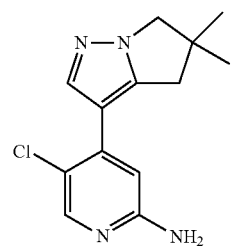 [SMILES: CC1(C)Cc2c(-c3cc(N)ncc3Cl)cnn2C1]

Potassium carbonate (81 g, 582.6 mmol) and Pd(dppf)Cl$_2$ (3.41 g, 4.66 mmol) were added sequentially to a degassed mixture of 5-chloro-4-iodopyridin-2-amine (59.9 g, 233 mmol) and 5,5-dimethyl-3-(4,4,5,5-tetramethyl-1,3,2-dioxaborolan-2-yl)-5,6-dihydro-4H-pyrrolo[1,2-b]pyrazole (64 wt %; 110 g, 268 mmol) in acetonitrile (500 mL) and water (500 mL). The clear pale red biphasic mixture was heated to 50° C. After vigorous stirring for 2 h, additional Pd(dppf)Cl$_2$ (1.0 g, 1.4 mmol) was added, and the mixture was stirred for an additional 20 h under these conditions. The mixture was then cooled to 20° C. and ethyl acetate (450 mL) was added. The layers were separated, and the organic layer was washed with water (200 mL) The Pd-scavenger Silicycle (Sila-MetS)-thiol, (cat #R51030B; 20 g) was then added to the organic layer, and the mixture was further stirred for 2 h at 20° C. The mixture was then filtered and concentrated under reduced pressure to a brown solid. This solid was dissolved in DCM (100 mL), and the solution was then filtered through a short pad of silica gel, eluting with 5% 2-propanol in CH$_2$Cl$_2$. Product fractions were concentrated under reduced pressure to give a brown solid. Methylisobutylketone (MIBK, 250 mL) was added, and the resulting suspension was heated to 70° C. and then slowly cooled to 20° C. The resulting suspension was stirred under these conditions for 18 h and then filtered washed with methyl diisobutylketone (5×30 mL) to afford 5-chloro-4-(5,5-dimethyl-5,6-dihydro-4H-pyrrolo[1,2-b]pyrazol-3-yl)pyridin-2-amine as a faint pink solid (50.7 g, 193 mmol). $^1$H NMR (400 MHz, CDCl$_3$, 20° C.) 1.28 (6H, s), 2.81 (2H, s), 3.91 (2H, s), 4.56 (2H, br s), 6.41 (1H, s), 7.83 (1H, s), 8.03 (1H, s). m/z: ES+ [M+H]+ 263.

Example 86: Preparation of (1S,3R)-3-acetamido-N-(4-(5,5-dimethyl-5,6-dihydro-4H-pyrrolo[1,2-b]pyrazol-3-yl)-5-fluoropyridin-2-yl)cyclohexane-1-carboxamide

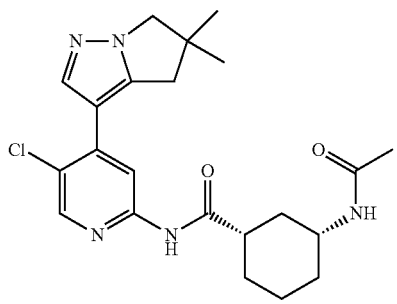 [SMILES: CC(=O)N[C@@H]1CCC[C@H](C(=O)Nc2cc(-c3cnn4c3CC(C)(C)C4)c(Cl)cn2)C1]

4-(5,5-Dimethyl-5,6-dihydro-4H-pyrrolo[1,2-b]pyrazol-3-yl)-5-fluoropyridin-2-amine (31.8 g, 129 mmol) and pyridine (43.9 mL, 517 mmol) were added under an atmosphere of nitrogen at 20° C. to a suspension of (1S,3R)-3-acetamidocyclohexane-1-carboxylic acid (29.9 g, 136 mmol; 84 wt %, prepared according to Example 85) in EtOAc (800 mL). T$_3$P (>50 wt % in EtOAc; 123 g, 194 mmol) was added over 40 minutes, and the resulting mixture was stirred for 21 h under these conditions. Then water (400 mL) was added. The biphasic mixture was stirred for 10 minutes, and the layers were separated. The organic layer was washed with saturated aqueous sodium carbonate (300 mL) and water (300 mL) before being filtered and concentration under reduced pressure to afford a dark brown semi-solid. Acetonitrile (250 mL) was added, and the mixture was warmed to 70° C. after which a homogenous brown solution was obtained. The mixture was allowed to attain 60° C., additional acetonitrile (200 mL) was added, and the slurry was stirred for an additional 2 h under these conditions before being allowed to slowly cool to 20° C. The suspension obtained was stirred for 3 days followed by filtration and washing of the solid with CH$_3$CN (250 mL). After drying under reduced pressure at 48° C. for 20 h, (1S,3R)-3-acetamido-N-(4-(5,5-dimethyl-5,6-dihydro-4H-pyrrolo[1,2-b]pyrazol-3-yl)-5-fluoropyridin-2-yl)cyclohexane-1-carboxamide (49.2 g, 119 mmol) was obtained as an off-white crystalline solid. $^1$H NMR (400 MHz, CDCl$_3$, 20° C.) 1.08-1.23 (1H, m), 1.33 (6H, s), 1.37-1.58 (3H, m), 1.88-1.94 (1H, m), 1.96-2.01 (5H, m), 2.26 (1H, d), 2.38-2.42 (1H, m), 3.00 (2H, s), 3.80-3.91 (1H, m), 3.93 (2H, s), 5.47 (1H, d), 8.00 (1H, d), 8.09-8.17 (2H, m), 8.31 (1H, d). m/z: ES+ [M+H]+ 414. Consistent with characterisation in Example 25

Figure 5:
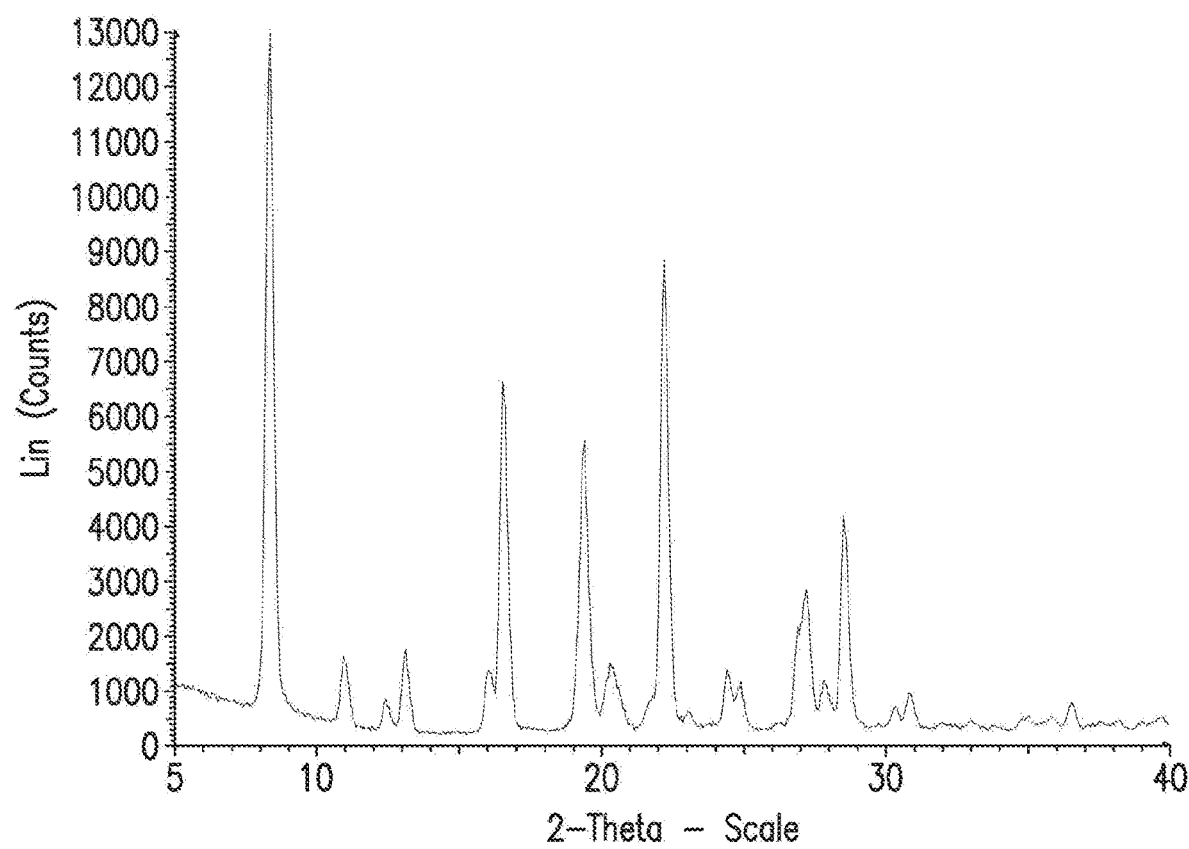
FIG. 5 is a representative X-Ray powder diffractogram of Form B of (1S,3R)-3-acetamido-N-(4-(5,5-dimethyl-5,6-dihydro-4H-pyrrolo[1,2-b]pyrazol-3-yl)-5-fluoropyridin-2-yl)cyclohexane-1-carboxamide (Example 86).

The crystals of (1S,3R)-3-acetamido-N-(4-(5,5-dimethyl-5,6-dihydro-4H-pyrrolo[1,2-b]pyrazol-3-yl)-5-fluoropyridin-2-yl)cyclohexane-1-carboxamide obtained by the procedure described in Example 86 were analyzed by XRPD. The results are tabulated below and are shown in FIG. 5, confirming that the solid contains exclusively Form B.

(1S,3R)-3-acetamido-N-(4-(5,5-dimethyl-5,6-dihydro-4H-pyrrolo[1,2-b]pyrazol-3-yl)-5-fluoropyridin-2-yl)cyclohexane-1-carboxamide, Form B main peaks are shown in Table 3 below:

| Peak | 2θ | Intensity % |
| --- | --- | --- |
| 1 | 8.3 | 100.0 (vs) |
| 2 | 11.0 | 12.6 (s) |
| 3 | 13.1 | 13.5 (s) |
| 4 | 16.6 | 51.0 (vs) |
| 5 | 19.4 | 42.7 (vs) |
| 6 | 20.4 | 11.7 (s) |
| 7 | 22.3 | 68.0 (vs) |
| 8 | 27.0 | 17.1 (s) |
| 9 | 27.2 | 22.0 (s) |
| 10 | 28.6 | 32.1 (vs) |

Figure 6:
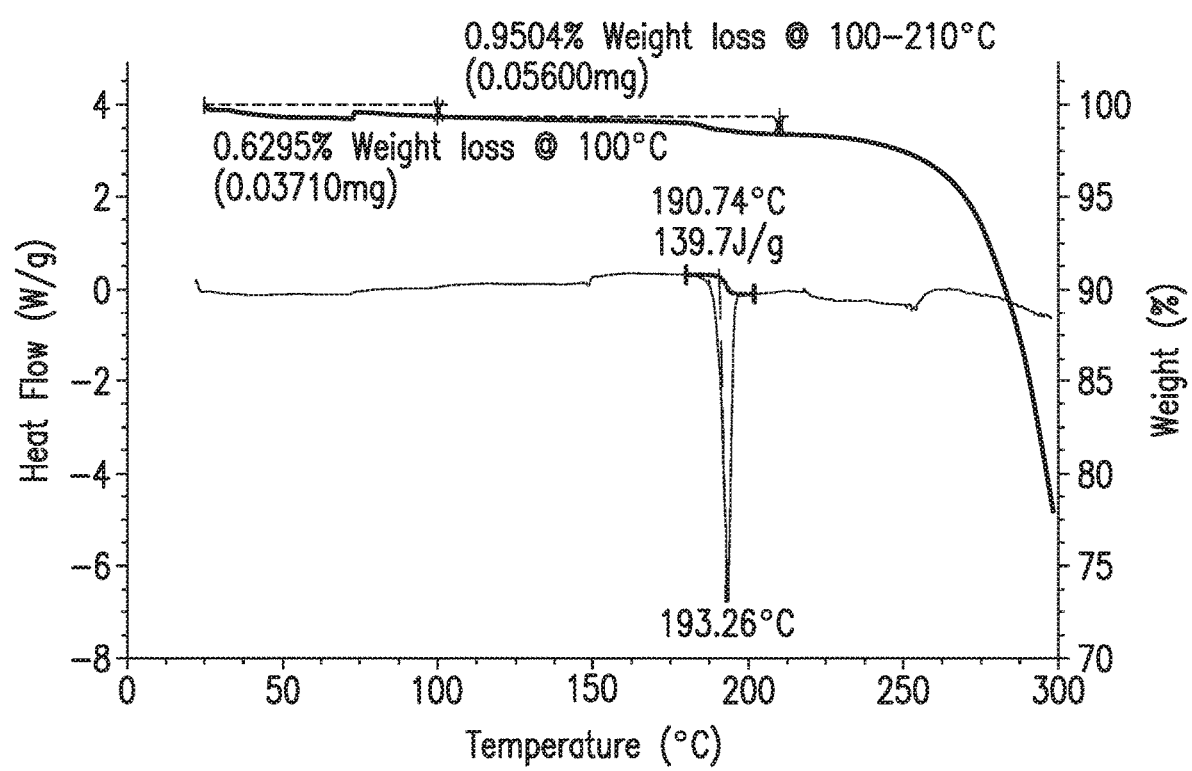
FIG. 6 is a representative DSC/TGA thermograph of Form B of (1S,3R)-3-acetamido-N-(4-(5,5-dimethyl-5,6-dihydro-4H-pyrrolo[1,2-b]pyrazol-3-yl)-5-fluoropyridin-2-yl)cyclohexane-1-carboxamide (Example 86).

According to the present invention there is provided a crystalline form, Form B, which has an X-ray powder diffraction pattern with specific peaks at about 2-theta=8.3, 11.0, 13.1, 16.6, 19.4, 20.4, 22.3, 27.0, 27.2 and 28.6°. DSC analysis indicated the Form B melts with an onset point at 191° C. and a peak at 193° C. TGA indicated that Form B exhibits a mass loss of about 1.6% upon heating from 22° C. to 210° C. A representative DSC/TGA thermogram is shown in FIG. 6.

Conversion of Form A to Form B 100 mg of (1S,3R)-3-acetamido-N-(4-(5,5-dimethyl-5,6-dihydro-4H-pyrrolo[1,2-b]pyrazol-3-yl)-5-fluoropyridin-2-yl)cyclohexane-1-carboxamide, Form A (isolated from Example 25) was added in a 20 mL vial. To the vial, 2.0 mL of acetone was added to obtain a suspension. The resulting slurry was stirred at ambient temperature over the weekend and was then dried in air by evaporation. The resulting white solid obtained was characterized and identified as (1S,3R)-3-acetamido-N-(4-(5,5-dimethyl-5,6-dihydro-4H-pyrrolo[1,2-b]pyrazol-3-yl)-5-fluoropyridin-2-yl)cyclohexane-1-carboxamide, Form B.

Procedures used to prepare the starting material 4-(5,5-dimethyl-5,6-dihydro-4H-pyrrolo[1,2-b]pyrazol-3-yl)-5-fluoropyridin-2-amine are described below:

Preparation of 5-fluoro-4-iodopyridin-2-amine

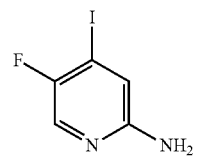

A 5 L steel hydrogenation vessel was charged with aqueous ammonia (26%; 777 g, 11.9 mol) and 2,5-difluoro-4-iodopyridine (220 g, 913 mmol). The mixture was cooled to 5° C., and NMP (500 mL) was added slowly over minutes (gas evolution). The vessel was sealed and the reaction mixture was then heated to 100° C. After 36 h, the reaction temperature was decreased to 90° C., and the reaction was maintained under these conditions for 3.5 days. The mixture was then cooled to 5° C., and MTBE (1 L) and water (500 mL) were added. The aqueous layer was extracted with MTBE (2×500 mL), and the combined organic layers were washed with water (200 mL), filtered, and concentrated under reduced pressure. The resulting pale yellow solid was reconcentrated from MTBE (2×500 mL), and then toluene (400 mL) was added. The resulting mixture was heated to 70° C., and a homogenous brown solution was obtained. Heptane (500 mL) was slowly added. The homogenous solution was then slowly allowed to reach 18° C. in a water bath with seed crystals added once the mixture achieved 42° C. The mixture was stirred overnight under these conditions. The suspension was filtered, and the solid collected was washed with 45% toluene in heptane (200 mL) followed by drying under reduced pressure at 40° C. to afford 5-fluoro-4-iodopyridin-2-amine (111 g, 51%) as a pale grey solid. $^1$H NMR (400 MHz, CDCl$_3$, 20° C.) 4.52 (2H, br s), 6.89 (1H, d), 7.79 (1H, s).

Preparation of 4-(5,5-dimethyl-5,6-dihydro-4H-pyrrolo[1,2-b]pyrazol-3-yl)-5-fluoropyridin-2-amine

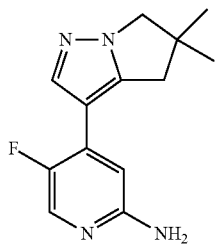 [SMILES: CC1(C)Cc2c(-c3cc(N)ncc3F)cnn2C1]

Potassium carbonate (63.1 g, 457 mmol) and Pd(dppf)Cl$_2$ (2.67 g, 3.66 mmol) were added sequentially under nitrogen to a degassed mixture of 5-fluoro-4-iodopyridin-2-amine (43.5 g, 182.8 mmol) and 5,5-dimethyl-3-(4,4,5,5-tetramethyl-1,3,2-dioxaborolan-2-yl)-5,6-dihydro-4H-pyrrolo[1,2-b]pyrazole (86 g, 210 mmol; 64 wt %, prepared according to Example 85) in acetonitrile (400 mL) and water (400 mL). The pale red biphasic mixture was heated to 50° C. and vigorously stirred for 5 h. The reaction was cooled and then ethyl acetate (400 mL) was added. The layers were separated, and the organic layer was washed with water (200 mL). The Pd-scavenger Silicycle (SilaMetS)-thiol, (cat #R51030B, 10 g) was added to the organic layer, and the mixture was then stirred over night at 20° C. The mixture was filtered, and the filtrate was concentrated under reduced pressure to afford a brown solid. Isopropanol (200 mL) was added, and the mixture was heated to 70° C. which gave a homogenous dark brown solution. The mixture was then slowly allowed to cool to 20° C. and then stirred for 15 h. The suspension obtained was filtered and the solid collected was washed with cold (4° C.) isopropanol (3×30 mL) to afford 4-(5,5-dimethyl-5,6-dihydro-4H-pyrrolo[1,2-b]pyrazol-3-yl)-5-fluoropyridin-2-amine (32 g, 71%) as a pale brown solid. $^1$H NMR (400 MHz, CDCl$_3$, 20° C.) 1.34 (6H, s), 2.91 (2H, s), 3.95 (2H, s), 4.30 (2H, s), 6.51 (1H, d), 7.89 (1H, s), 7.93 (1H, d). m/z: ES+ [M+H]+ 247.

All references cited herein, including patents, patent applications, papers, text books, and the like, and the references cited therein, to the extent that they are not already, are hereby incorporated herein by reference in their entirety for all purposes.

What is claimed is:
1. A compound of Formula I:

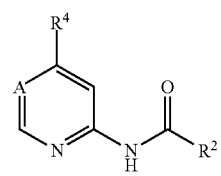

wherein:
A is C(R$^5$) or N;
R$^5$ is H, C$_{1-3}$ alkyl, CN or halogen;
R$^2$ is 3-7 membered heterocycloalkyl or 3-7 membered cycloalkyl;
optionally substituted with one to three substituents independently selected from the group consisting of R$^{10}$, OR$^{10}$, SR$^{10}$, S(O)R$^{10}$, S(O)$_2$R$^{10}$, C(O)R$^{10}$, C(O)OR$^{10}$, OC(O)R$^{10}$, OC(O)OR$^{10}$, NH$_2$, NHR$^{10}$, N(R$^{10}$)$_2$, NHC(O)H, NHC(O)R$^{10}$, NR$^{10}$C(O)H, NR$^{10}$C(O)R$^{10}$, (NHS(O)$_2$R$^{10}$, NR$^{10}$S(O)$_2$R$^{10}$, NHC(O)OR$^{10}$, NR$^{10}$C(O)OR$^{10}$, NHC(O)NH$_2$, NHC(O)NHR$^{10}$, NHC(O)N(R$^{10}$)$_2$, NR$^{10}$C(O)NH$_2$, NR$^{10}$C(O)NHR$^{10}$, NR$^{10}$C(O)N(R$^{10}$)$_2$, C(O)NH$_2$, C(O)NHR$^{10}$, C(O)N(R$^{10}$)$_2$, C(O)NHOH, C(O)NHOR$^{10}$, C(O)NHS(O)$_2$R$^{10}$, C(O)NR$^{10}$S(O)$_2$R$^{10}$, S(O)$_2$NH$_2$, S(O)$_2$NHR$^{10}$, S(O)$_2$N(R$^{10}$)$_2$, S(O)$_2$NHC(O)OR$^{10}$, S(O)$_2$NR$^{10}$C(O)OR$^{10}$, C(O)H, C(O)OH, OH, CN, NO$_2$, F, Cl, Br and I; wherein one or more ring CH$_2$ groups can optionally be replaced by a corresponding number of —C(O) groups, and one or more ring sulfur or nitrogen atoms may be optionally oxidized to form S-oxides or N-oxides;
R$^{10}$, at each occurrence, is independently selected from the group consisting of a 3 to 6 membered cycloalkyl or heterocycloalkyl group, C$_{1-6}$ alkyl, —O—C$_{1-6}$ alkyl, C$_{1-6}$ alkyl-O—C$_{1-6}$ alkyl, NH$_2$, C(O)NH$_2$, C(O)H, C(O)OH, OH, CN, NO$_2$, F, Cl, Br and I; wherein two R$^{10}$ groups together with the atoms to which they are attached may form a 3 to 6 membered cycloalkyl or heterocycloalkyl group; and each aforementioned R$^{10}$ alkyl, cycloalkyl and heterocycloalkyl group may be further substituted with one or two substituents independently selected from CN, OH, halogen, C$_{1-3}$ alkyl, —O—C$_{1-3}$ alkyl, NH$_2$, NH—C$_{1-3}$ alkyl, and NHC(O)—C$_{1-3}$ alkyl;
R$^4$ is

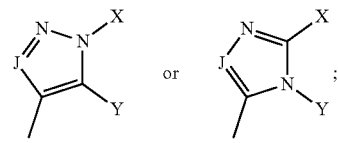

wherein X and Y together with the atoms to which they are attached, form a 5 to 7 membered heterocycloalkyl ring which, in addition to the bridge nitrogen, may contain one or two heteroatoms selected from N, O, and S, which ring may be saturated or partially saturated;
wherein one or two ring CH$_2$ groups can optionally be replaced by a corresponding number of —C(O) groups, one or more ring sulfur or nitrogen atoms may be optionally oxidized to form S-oxides or N-oxides and wherein the ring may be substituted on a ring carbon by one or two $R^{10}$ substituents or on a ring nitrogen by an $R^{12}$ substituent;

J is N or $CR^{11}$; and $R^{11}$ is H, or $C_{1-3}$ alkyl;

$R^{12}$ is at each occurrence independently selected from the group consisting of a 3 to 6 membered cycloalkyl or heterocycloalkyl group, $C_{1-6}$ alkyl, $C_{1-6}$ alkyl-O—$C_{1-6}$ alkyl, $C(O)NH_2$, or $C(O)H$;

wherein $R^{12}$ alkyl, cycloalkyl and heterocycloalkyl group may be further substituted with one or two substituents independently selected from CN, OH, and halogen, $C_{1-3}$ alkyl, $NH_2$, and NH—$C_{1-3}$ alkyl, NHC(O)—$C_{1-3}$ alkyl;

or pharmaceutical acceptable salts thereof.

2. The compound of claim 1 wherein A is $C(R^5)$.

3. The compound of claim 2 wherein $R^5$ is chloro or fluoro.

4. The compound of claim 1 wherein $R^2$ is 3-7 membered cycloalkyl substituted with $NHCOR^{10}$ or $R^{10}$.

5. The compound of claim 4 wherein $R^2$ is selected from cyclopropyl, cyclobutyl, cyclopentyl, cyclohexyl, and cycloheptyl.

6. The compound of claim 5 wherein $R^2$ is selected from cyclopentyl and cyclohexyl.

7. The compound of claim 6 wherein $R^2$ is cyclohexyl substituted with $NHCOR^{10}$.

8. The compound of claim 1 wherein $R_4$ is

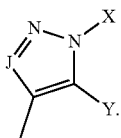

9. The compound of claim 8 wherein J is $C(R^{11})$.

10. The compound of claim 9 wherein $R^{11}$ is H.

11. The compound of claim 1 wherein X and Y together with the atoms to which they are attached form a 5 membered heterocycloalkyl ring.

12. The compound of claim 11 wherein X and Y together with the atoms to which they are attached form a 5 membered heterocycloalkyl ring in which one $CH_2$ is substituted with two methyl groups.

13. The compound of claim 1 wherein

A is $C(R^5)$;

$R^5$ is halogen;

$R^2$ is 3-7 membered cycloalkyl;

$R^4$ is

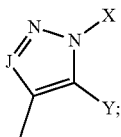

and

X and Y together with the atoms to which they are attached form a 5 membered heterocycloalkyl ring.

14. The compound of claim 1 wherein

A is $C(R^5)$;

$R^5$ is halogen;

$R^2$ is cyclohexyl;

$R^4$ is

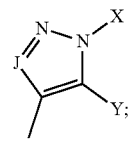

and

X and Y together with the atoms to which they are attached form a 5 membered heterocycloalkyl ring.

15. The compound of claim 14 wherein

A is $C(R^5)$;

$R^5$ is chloro;

$R^2$ is cyclohexyl;

$R^4$ is

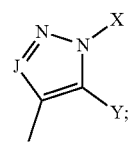

and

X and Y together with the atoms to which they are attached form a 5 membered heterocycloalkyl ring.

16. The compound of claim 1 wherein

A is $C(R^5)$;

$R^5$ is chloro;

$R^2$ is cyclohexyl substituted with $NHC(O)R^{10}$;

$R^4$ is

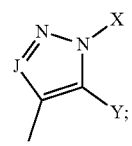

and

X and Y together with the atoms to which they are attached form a 5 membered heterocycloalkyl ring.

17. The compound of claim 1 wherein

A is $C(R^5)$;

$R^5$ is chloro;

$R^2$ is cyclohexyl substituted with $NHC(O)R^{10}$;

$R^{10}$ is $C_{1-6}$ alkyl;

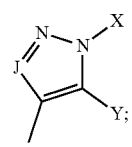

$R^4$ is

J is $C(R^{11})$ and $R^{11}$ is H; and

X and Y together with the atoms to which they are attached form a 5 membered heterocycloalkyl ring.

18. The compound of claim 1 wherein

A is $C(R^5)$;

$R^5$ is chloro;

$R^2$ is cyclohexyl substituted with $NHC(O)R^{10}$;

$R^{10}$ is $C_{1-6}$ alkyl;

$R^4$ is

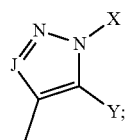
J is $C(R^{11})$ and $R^{11}$ is H; and
X and Y together with the atoms to which they are attached form a pyrrolidinyl wherein one $CH_2$ is substituted with two methyl groups.
19. A pharmaceutical composition containing a compound of claim 1 and at least one pharmaceutically acceptable carrier, diluent, or excipient.
* * * * *